United States Patent
Brodney et al.

(10) Patent No.: US 9,192,612 B2
(45) Date of Patent: Nov. 24, 2015

(54) HETEROARYL-SUBSTITUTED HEXAHYDROPYRANO[3,4-D][1,3]THIAZIN-2-AMINE COMPOUNDS

(71) Applicant: Pfizer Inc., New York, NY (US)

(72) Inventors: Michael Aaron Brodney, Newton, MA (US); Christopher Ryan Butler, Canton, MA (US); Elizabeth Mary Beck, Cambridge, MA (US); Jennifer Elizabeth Davoren, Cambridge, MA (US); Erik Alphie LaChapelle, Johnston, RI (US); Brian Thomas O'Neill, Haddam, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/694,288

(22) Filed: Apr. 23, 2015

(65) Prior Publication Data

US 2015/0224110 A1 Aug. 13, 2015

Related U.S. Application Data

(63) Continuation of application No. 14/464,935, filed on Aug. 21, 2014, now Pat. No. 9,045,499, which is a continuation of application No. 14/178,470, filed on Feb. 12, 2014, now Pat. No. 8,865,706.

(60) Provisional application No. 61/764,185, filed on Feb. 13, 2013.

(51) Int. Cl.
*A61K 31/542* (2006.01)
*C07D 513/04* (2006.01)

(52) U.S. Cl.
CPC ............ *A61K 31/542* (2013.01); *C07D 513/04* (2013.01)

(58) Field of Classification Search
CPC ........................... C07D 513/04; A61K 31/542
USPC ...................................................... 514/224.2
See application file for complete search history.

(56) References Cited

U.S. PATENT DOCUMENTS

| | | | |
|---|---|---|---|
| 5,750,349 A | 5/1998 | Suzuki et al. |
| 7,115,600 B2 | 10/2006 | Wager et al. |
| 7,285,293 B2 | 10/2007 | Castillo et al. |
| 7,975,664 B2 | 7/2011 | Himsel et al. |
| 8,158,620 B2 | 4/2012 | Suzuki et al. |
| 8,198,269 B2 | 6/2012 | Motoki et al. |
| 8,278,441 B2 | 10/2012 | Mergott et al. |
| 8,822,456 B2 | 9/2014 | Brodney et al. |
| 8,865,706 B2 | 10/2014 | Brodney et al. |
| 8,933,221 B2 | 1/2015 | Brodney et al. |
| 8,962,616 B2 | 2/2015 | Brodney et al. |
| 9,045,498 B2 | 6/2015 | Brodney et al. |
| 9,045,499 B2 | 6/2015 | Brodney et al. |
| 2003/0073655 A1 | 4/2003 | Chain |
| 2003/0195205 A1 | 10/2003 | DeNinno et al. |
| 2004/0192898 A1 | 9/2004 | Jia et al. |
| 2004/0220186 A1 | 11/2004 | Bell et al. |
| 2005/0019328 A1 | 1/2005 | Schenk |
| 2005/0043354 A1 | 2/2005 | Wager et al. |
| 2005/0048049 A1 | 3/2005 | Schenk |
| 2005/0256135 A1 | 11/2005 | Lunn et al. |
| 2005/0267095 A1 | 12/2005 | Bernardelli et al. |
| 2005/0267100 A1 | 12/2005 | Elliott et al. |
| 2006/0057701 A1 | 3/2006 | Rosenthal et al. |
| 2006/0106035 A1 | 5/2006 | Hendrix et al. |
| 2006/0111372 A1 | 5/2006 | Hendrix et al. |
| 2006/0178501 A1 | 8/2006 | Summers et al. |
| 2007/0031416 A1 | 2/2007 | Shoji et al. |
| 2007/0160616 A1 | 7/2007 | Rosenthal et al. |
| 2007/0179175 A1 | 8/2007 | Lunn |

(Continued)

FOREIGN PATENT DOCUMENTS

| | | |
|---|---|---|
| EP | 0994728 | 10/1998 |
| EP | 1257584 | 10/2004 |

(Continued)

OTHER PUBLICATIONS

Haan, J., et al., "Amyloid in Central Nervous System Disease", Clinical Neurology and Neurosurgery, 1990, pp. 305-310, 92(4).
Glenner, G., et al., "Amyloidosis of the Nervous System", Journal of Neurological Science, Dec. 1989, pp. 1-28, vol. 94.
Farah, M., et al., "Reduced BACE1 Activity Enhances Clearance of Myelin Debris and Regeneration of Axons in the Injured Peripheral Nervous System", Journal of Neuroscience, Apr. 13, 2011, pp. 5744-5754, 31(15).
Meakin, Paul, et al., "Reduction in BACE1 decreases body weight, protects against diet-induced obesity and enhances insulin sensitivity in mice", Biochemical Journal, Jan. 1, 2012, pp. 285-296, 441(1).
Esterhazy, Daria, et al., "BACE2 is a β Cell-Enriched Protease that Regulates Pancreatic β Cell Function and Mass", Cell Metabolism, Sep. 2011, pp. 365-377, 14(3).

(Continued)

*Primary Examiner* — Kahsay Habte
(74) *Attorney, Agent, or Firm* — John A. Wichtowski

(57) ABSTRACT

The present invention is directed to compounds, tautomers and pharmaceutically acceptable salts of the compounds which are disclosed, wherein the compounds have the structure of Formula I,

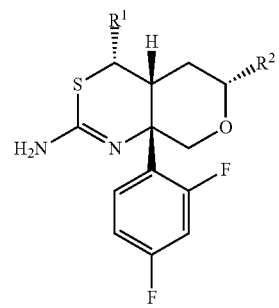

and the variables $R^1$ and $R^2$ are as defined in the specification. Corresponding pharmaceutical compositions, methods of treatment, methods of synthesis, and intermediates are also disclosed.

17 Claims, No Drawings

(56) References Cited

U.S. PATENT DOCUMENTS

| | | | |
|---|---|---|---|
| 2008/0096955 | A1 | 4/2008 | Wager et al. |
| 2008/0176925 | A1 | 7/2008 | Butler et al. |
| 2009/0054482 | A1 | 2/2009 | Chan et al. |
| 2010/0056618 | A1 | 3/2010 | Mascitti et al. |
| 2010/0093999 | A1 | 4/2010 | Motoki et al. |
| 2010/0285145 | A1 | 11/2010 | Darout et al. |
| 2011/0027279 | A1 | 2/2011 | Chain |
| 2011/0038861 | A1 | 2/2011 | Rosenthal |
| 2011/0046122 | A1 | 2/2011 | Andreini et al. |
| 2011/0207723 | A1 | 8/2011 | Motoki et al. |
| 2012/0245155 | A1 | 9/2012 | Yoshida et al. |
| 2013/0296308 | A1 | 11/2013 | Brodney et al. |
| 2015/0087637 | A1 | 3/2015 | Brodney et al. |
| 2015/0133438 | A1 | 5/2015 | Brodney et al. |

FOREIGN PATENT DOCUMENTS

| | | |
|---|---|---|
| EP | 2332943 | 6/2011 |
| EP | 2511269 | 10/2012 |
| WO | 9844955 | 10/1998 |
| WO | 0220521 | 3/2002 |
| WO | 03072197 | 9/2003 |
| WO | 2004032868 | 4/2004 |
| WO | 2005025616 | 3/2005 |
| WO | 2005049616 | 6/2005 |
| WO | 2005116014 | 12/2005 |
| WO | 2006069081 | 6/2006 |
| WO | 2006118959 | 11/2006 |
| WO | 2006120552 | 11/2006 |
| WO | 2006126081 | 11/2006 |
| WO | 2006126082 | 11/2006 |
| WO | 2006126083 | 11/2006 |
| WO | 2006136924 | 12/2006 |
| WO | 2007063385 | 6/2007 |
| WO | 2007069053 | 6/2007 |
| WO | 2007088450 | 8/2007 |
| WO | 2007088462 | 9/2007 |
| WO | 2007099423 | 9/2007 |
| WO | 2007105053 | 9/2007 |
| WO | 2007122466 | 11/2007 |
| WO | 2007122482 | 11/2007 |
| WO | 2007138431 | 12/2007 |
| WO | 2008065508 | 6/2008 |
| WO | 2009016462 | 2/2009 |
| WO | 2009091016 | 7/2009 |
| WO | 2009144554 | 12/2009 |
| WO | 2009144555 | 12/2009 |
| WO | 2010013161 | 2/2010 |
| WO | 2010038686 | 4/2010 |
| WO | 2010086820 | 8/2010 |
| WO | 2010103437 | 9/2010 |
| WO | 2010103438 | 9/2010 |
| WO | 2010106457 | 9/2010 |
| WO | 2010140092 | 12/2010 |
| WO | 2011005611 | 1/2011 |
| WO | 2011071109 | 6/2011 |
| WO | 2012098461 | 7/2012 |
| WO | 2012162334 | 11/2012 |
| WO | 2013030713 | 3/2013 |
| WO | 2013164730 | 11/2013 |

OTHER PUBLICATIONS

Zimmet, P.Z. et al., "The Metabolic Syndrome: Perhaps an Etiologic Mystery but Far From a Myth—Where Does the International Diabetes Federation Stand?," Medscape Diabetes & Endocrinology, Oct. 11, 2005, 8 pages, www.medscape.com, 7(2).

Alberti, K.G. et al., "The Metabolic Syndrome—A New Worldwide Definition," Lancet, Sep. 24-30, 2005, pp. 1059-1062, 366(9491).

Haleblian, John K., "Characterization of Habits and Crystalline Modification of Solids and Their Pharmaceutical Applications", Journal Pharmaceutical Sciences, Aug. 1975, pp. 1269-1288, 64(8).

Finnin, Barrie, et al., "Transdermal Penetration Enhancers Applications, Limitations, and Potential", Journal Pharmaceutical Sciences, Oct. 1999, pp. 955-958, 88(10).

Zhang, S. et al., "PTP1B as a Drug Target: Recent Developments in PTP1B Inhibitor Discovery", Drug Discovery Today, May 2007, pp. 373-381, 12(9/10).

Chao, Edward, et al., "SGLT2 Inhibition—A Novel Strategy for Diabetes Treatment", Nature Reviews Drug Discovery, Jul. 2010, pp. 551-559, 9(7).

Demong, D.E. et al., "Chapter 8, Glucagon Receptor Antagonists for Type II Diabetes", Annual Reports in Medicinal Chemistry 2008, pp. 119-137, vol. 43.

Jones, R.M. et al., "Chapter 7, The Emergence of GPR119 Agonists as Anti-Diabetic Agents", Annual Reports in Medicinal Chemistry 2009, pp. 149-170, vol. 44.

Zhong, M., "TGR5 as a Therapeutic Target for Treating Obesity", Current Topics in Medicinal Chemistry, 2010, pp. 386-396, 10(4).

Medina, J.C., et al., "Chapter 5, GPR40 (FFAR1) Modulators", Annual Reports in Medicinal Chemistry 2008, pp. 75-85, vol. 43.

Carpino, P.A., et al., "Diabetes Area Participation Analysis: A Review of Companies and Targets Described in the 2008-2010 Patent Literature", Expert Opinion on Therapeutic Patents, Dec. 2010, pp. 1627-1651, 20(12).

Spek, A.L., "Single-Crystal Structure Validation with the Program PLATON", Journal of Applied Crystallography, Feb. 2003, pp. 7-13, 36(1).

Macrae, Clare, et al., "Mercury: Visualization and Analysis of Crystal Structures", Journal of Applied Crystallography, Jun. 2006, pp. 453-457, 39(3).

Hooft, Rob, et al., "Determination of Absolute Structure Using Bayesian Statistics on Bijvoet differences", Journal of Applied Crystallography, Feb. 2008, , pp. 96-103, 41(1).

Flack, H.D., ", On Enantiomorph-Polarity Estimation", Acta Cryst., 1983, pp. 876-881, vol. A39.

England, et al., "An Improved Synthesis of a Novel α1A Partial Agonist Including a New Two-Step Synthesis of 4-Fluoropyrazole", Tetrahedron Letters, May 26, 2010, pp. 2849-2851, 51(21).

Kharitonenkov, A. et al., "FGF21: A Novel Prospect for the Treatment of Metabolic Diseases", Current Opinion in Investigational Drugs, Apr. 2009, pp. 359-364, 10(4).

Denmark, S.E, et al., "Allylation of Carbonyls: Methodology and Stereochemistry", Modern Carbonyl Chemistry, 2000, Chapter 10, pp. 299-401.

Miyaura, N., et al., "Palladium-Catalyzed Cross-Coupling Reactions of Organoborn Compounds", Chemical Review, Nov. 1995, pp. 2457-2483, 95(7).

Olsen, R., et al., "Secretase Inhibitors and Modulators for the Treatment of Alzheimer's Disease", Annual Reports in Medicinal Chemistry, 2007, pp. 27-47, vol. 42.

International Application No. PCT/IB2012/054198, filed Aug. 17, 2012, International Search Report and Written Opinion, mailed Jan. 23, 2013, 14 pages.

Sheppeck, J.E. II, et al., "A Convenient and Scaleable Procedure for Removing the Fmoc Group in Solution", Tetrahedron Letters, 2000, pp. 5329-5333, vol. 41(28).

Suzuki, Akira, "Recent advances in the cross-coupling reactions of organoboron derivatives with organic electrophiles 1995-1998", Journal Organometallic Chemistry, 1999, pp. 147-168, vol. 576.

International Application No. PCT/IB2013/053178, filed Apr. 22, 2013, International Written Opinion and Search Report, mailed Jul. 3, 2013, 10 pages.

English equivalent U.S. Pat. No. 8,158,620; Suzuki, et al., filed Jan. 16, 2009 for WO 2009091016, published Jun. 23, 2007.

International Application No. PCT/IB2013/058402, filed Sep. 9, 2013, International Search Report, mailed Dec. 16, 2013, 11 pages.

International Patent Application No. PCT/IB2013/060633 application filed Dec. 4, 2013.

International Patent Application No. PCT/IB2013/058402 application filed Sep. 9, 2013.

International Patent Application No. PCT/IB2013/060456 application filed Nov. 27, 2013.

International Patent Application No. PCT/IB2014/058760 application filed Feb. 3, 2014.-

(56) References Cited

OTHER PUBLICATIONS

International Patent Application No. PCT/IB2014/058777 application filed Feb. 4, 2014.
Guidance for Industry, Q3C-Tables and List, U.S. Department of Health and Human Services, Food and Drug Administration, Center for Drug Evaluation and Research (CDER), Center for Biologics Evaluation and Research (CBER), Nov. 2003, ICH, Revision I.
International Application No. PCT/IB2013/060456, filed Nov. 27, 2013, International Search Report, mailed Feb. 21, 2014, 8 pages.
International Application No. PCT/IB2013/060633, filed Dec. 4, 2013, International Preliminary Report on Patentability, mailed Jun. 23, 2015.
International Application No. PCT/IB2013/060633, filed Dec. 4, 2013, International Search Report and Written Opinion, mailed Mar. 24, 2014.
International Application No. PCT/IB2015/052279, filed Mar. 27, 2015, International Search Report and Written Opinion, mailed Jun. 24, 2015, 10 pages.
International Patent Application No. PCT/IB2014/058777, filed Feb. 4, 2014, International Search Report and Written Opinion, mailed Mar. 25, 2014, 11 pages.

HETEROARYL-SUBSTITUTED HEXAHYDROPYRANO[3,4-D][1,3]THIAZIN-2-AMINE COMPOUNDS

This application is a continuation application under 35 U.S.C. §120 of U.S. patent application Ser. No. 14/464,935 filed Aug. 21, 2014 which is a continuation application of U.S. patent application Ser. No. 14/178,470 filed Feb. 12, 2014 which claims the benefit of U.S. Provisional Patent Application No. 61/764,185 filed on Feb. 13, 2013, the disclosures of which are hereby incorporated by reference in their entirety.

FIELD OF THE INVENTION

The present invention relates to small molecule compounds and pharmaceutically acceptable salts thereof that are inhibitors of β-site amyloid precursor protein (APP) Cleaving Enzyme 1 (BACE1) and inhibitors of BACE2. This invention relates to inhibiting the production of A– beta peptides that can contribute to the formation of neurological deposits of amyloid protein. The present invention also relates to the treatment of Alzheimer's Disease (AD) and other neurodegenerative and/or neurological disorders, as well as the treatment of diabetes in mammals, including humans. More particularly, this invention relates to thioamidine compounds and pharmaceutically acceptable salts thereof useful for the treatment of neurodegenerative and/or neurological disorders, such as AD and Down's Syndrome, related to A– beta peptide production.

BACKGROUND OF THE INVENTION

Dementia results from a wide variety of distinctive pathological processes. The most common pathological processes causing dementia are Alzheimer's disease ("AD"), cerebral amyloid angiopathy ("CM") and prion-mediated diseases (see, e.g., Haan et al., Clin. Neurol. Neurosurg., 1990, 92(4): 305-310; Glenner et al., J. Neurol. Sci., 1989, 94:1-28). AD is a progressive, neurodegenerative disorder characterized by memory impairment and cognitive dysfunction. AD affects nearly half of all people past the age of 85, the most rapidly growing portion of the United States population. As such, the number of AD patients in the United States is expected to increase from about 4 million to about 14 million by 2050.

The accumulation of amyloid-β (Aβ peptides) is believed to be one of the underlying causes of Alzheimer's Disease (AD), which is the most common cause of cognitive decline in the elderly (Hardy & Allsop, Trends Pharmacol Sci., 1991; 12(10):383-8; Selkoe, Behay. Brain Res., 2008; 192(1):106-13). Aβ, the major protein constituent of amyloid plaques, is derived from sequential cleavage of the type I integral membrane protein, amyloid precursor protein (APP) by two proteases, β- and γ-secretase. Proteolytic cleavage of APP by the β-site APP cleaving enzymes (BACE1 and BACE2) generates a soluble N-terminal ectodomain of APP (sAPPβ) and the C-terminal fragment C99. Subsequent cleavage of the membrane-bound C99 fragment by the γ-secretase liberates the various Aβ peptide species, of which Aβ40 and Aβ42 are the most predominant forms (Vassar et al., J. Neurosci., 2009; 29(41):12787-94; Marks & Berg, Neurochem. Res., 2010; 35:181-210). Therefore, limiting the generation of Aβ directly through inhibition of BACE1 is one of the most attractive approaches for the treatment of AD, as BACE1 inhibitors could effectively inhibit the formation of all predominant Aβ peptides.

In addition, it has been determined that BACE1 knock-out mice had markedly enhanced clearance of axonal and myelin debris from degenerated fibers, accelerated axonal regeneration, and earlier reinnervation of neuromuscular junctions compared with littermate controls. These data suggest BACE1 inhibition as a therapeutic approach to accelerate regeneration and recovery after peripheral nerve damage. (See Farah et al., J. Neurosci., 2011, 31(15): 5744-5754).

Insulin resistance and impaired glucose homoeostasis are important indicators of Type 2 diabetes and are early risk factors of AD. In particular, there is a higher risk of sporadic AD in patients with Type 2 diabetes and AD patients are more prone to Type 2 diabetes (Butler, Diabetes, 53:474-481, 2004.). Recently, it has also been proposed that AD should be reconsidered as Type 3 diabetes (de la Monte, J. Diabetes Sci. Technol., 2008; 2(6):1101-1113). Of special interest is the fact that AD and Type 2 diabetes share common pathogenic mechanisms and possibly treatments (Park S. A., J. Clin. Neurol., 2011; 7:10-18; Raffa, Br. J. Clin. Pharmacol 2011, 71(3):365-376). Elevated plasma levels of Aβ, the product of BACE activities, were recently associated with hyperglycemia and obesity in humans (see Meakin et al., Biochem J., 2012, 441(1):285-96.; Martins, Journal of Alzheimer's Disease, 8 (2005) 269-282). Moreover, increased Aβ production prompts the onset of glucose intolerance and insulin resistance in mice (Cózar-Castellano, Am. J. Physiol. Endocrinol. Metab., 302:E1373-E1380, 2012; Delibegovic, Diabetologia (2011) 54:2143-2151). Finally, it is also suggested that circulating Aβ could participate in the development of atherosclerosis in both humans and mice (De Meyer, Atherosclerosis 216 (2011) 54-58; Catapano, Atherosclerosis 210 (2010) 78-87; Roher, Biochimica et Biophysica Acta 1812 (2011) 1508-1514).

Therefore, it is believed that BACE1 levels may play a critical role in glucose and lipid homoeostasis in conditions of chronic nutrient excess. Specifically, BACE1 inhibitors may be potentially useful for increasing insulin sensitivity in skeletal muscle and liver as illustrated by the fact that reduction in BACE1 decreases body weight, protects against diet-induced obesity and enhances insulin sensitivity in mice (see Meakin et al., Biochem. J. 2012, 441(1):285-96). Of equal interest is the identification of LRP1 as a BACE1 substrate and the potential link to atherosclerosis (Strickland, Physiol. Rev., 88: 887-918, 2008; Hyman, J. Biol. Chem., Vol. 280, No. 18, 17777-17785, 2005).

Likewise, inhibition of BACE2 is proposed as a treatment of Type 2 diabetes with the potential to preserve and restore β-cell mass and stimulate insulin secretion in pre-diabetic and diabetic patients (WO2011/020806). BACE2 is a β-cell enriched protease that regulates pancreatic β cell function and mass and is a close homologue of BACE1. Pharmacological inhibition of BACE2 increases β-cell mass and function, leading to the stabilization of Tmem27. (See Esterhazy et al., Cell Metabolism 2011, 14(3): 365-377). It is suggested that BACE2 inhibitors are useful in the treatment and/or prevention of diseases associated with the inhibition of BACE2 (e.g., Type 2 diabetes, with the potential to preserve and restore β-cell mass and stimulate insulin secretion in pre-diabetic and diabetic patients) (WO2011/020806).

Aminodihydrothiazine or thioamidine compounds are described in US2009/0082560, WO 2009/091016 and WO 2010/038686 as useful inhibitors of the β-secretase enzyme. Co-pending PCT application, PCT/IB2012/054198, filed by Pfizer Inc on Aug. 17, 2012, also describes aminodihydrothiazine compounds that are useful inhibitors of the β-secretase enzyme. The present invention is directed to novel thioamidine compounds and their use in the treatment of neurodegenerative diseases, including AD, as well as the treatment of metabolic diseases and conditions such as diabetes and obesity.

SUMMARY OF THE INVENTION

A first embodiment of a first aspect of the present invention is a compound of Formula I:

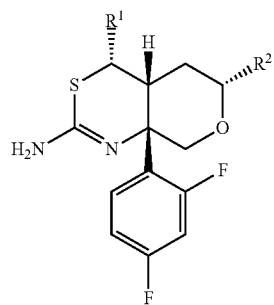

wherein $R^1$ is hydrogen or methyl, wherein said methyl is optionally substituted with one to three fluoro;

$R^2$ is a 5- to 10-membered heteroaryl, having one to four heteroatoms independently selected from N, O or S, wherein at least one of the heteroatoms is N and wherein said N is optionally substituted with $R^4$; and wherein said 5- to 10-membered heteroaryl is optionally substituted on carbon with one to three $R^3$;

$R^3$ at each occurrence is independently selected from the group consisting of halogen, hydroxy, cyano, $C_{1-6}$alkyl, $C_{1-6}$alkoxy, $C_{1-6}$alkoxy-$C_{1-6}$alkyl, $C_{3-6}$cycloalkoxy, $C_{3-6}$cycloalkoxy-$(CR^{5a}R^{5b})_m$—, $C_{3-6}$cycloalkyl-$(CR^{5a}R^{5b})_n$—O—, —$(CR^{5a}R^{5b})_m$—$C_{3-6}$cycloalkyl or —$(CR^{5a}R^{5b})_m$-(4- to 6-membered heterocycloalkyl); wherein said $C_{1-6}$alkyl, $C_{1-6}$alkoxy or $C_{1-6}$alkoxy-$C_{1-6}$alkyl are each optionally substituted with one to three fluoro and wherein said $C_{3-6}$cycloalkyl, $C_{3-6}$cycloalkoxy and (4- to 6-membered heterocycloalkyl) moieties are optionally substituted with one to three substituents independently selected from the group consisting of fluoro, methyl, fluoromethyl, difluoromethyl or trifluoromethyl;

$R^4$ is hydrogen, $C_{1-6}$alkyl, —$(CR^{5a}R^{5b})_m$—$C_{3-6}$cycloalkyl or —$(CR^{5a}R^{5b})_m$-(4- to 6-membered heterocycloalkyl); wherein said $C_{1-6}$alkyl, $C_{3-6}$cycloalkyl and -(4- to 6-membered heterocycloalkyl) moieties are each optionally substituted with one to three substituents independently selected from fluoro, methyl, trifluoromethyl, methoxy or trifluoromethoxy;

$R^{5a}$ and $R^{5b}$ are independently hydrogen, methyl, fluoromethyl, difluoromethyl, trifluoromethyl or methoxy;

m at each occurrence is independently 0, 1 or 2; and n is 1, 2 or 3;

or a tautomer thereof or a pharmaceutically acceptable salt of said compound or tautomer.

Another embodiment of the present invention is a pharmaceutical composition comprising compounds of Formula I, or a tautomer thereof or a pharmaceutically acceptable salt of said compound or tautomer, and a pharmaceutically acceptable vehicle, diluent or carrier. The pharmaceutical compositions described herein can be used for inhibiting production of amyloid-β protein and for inhibiting beta-site amyloid precursor protein cleaving enzyme 1 (BACE1); for treating a neurodegenerative disease and, in particular, Alzheimer's Disease; for inhibiting BACE1 and/or BACE2 activity for the therapeutic and/or prophylactic treatment of diseases and disorders characterized by elevated β-amyloid levels, including diabetes or Type 2 diabetes; for increasing insulin sensitivity in skeletal muscle and liver in a mammal, including humans; and for treating and/or preventing obesity.

The present invention is also directed to methods of treatment employing the compounds of Formula I such as:

(1) Methods of inhibiting BACE enzyme activity, by administering a therapeutically effective amount of a thioamidine compound of any of the embodiments of Formula I or a pharmaceutically acceptable salt thereof, and a pharmaceutically acceptable carrier, to a mammal or a patient in need thereof.

(2) Methods for treating conditions or diseases of the central nervous system and neurological disorders in which the β-secretase enzyme is involved (such as migraine; epilepsy; Alzheimer's disease; Parkinson's disease; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV-associated dementia, Alzheimer's disease, Huntington's disease, Lewy body dementia, vascular dementia, drug-related dementia, tardive dyskinesia, myoclonus, dystonia, delirium, Pick's disease, Creutzfeldt-Jacob disease, HIV disease, Gilles de la Tourette's syndrome, epilepsy, muscular spasms and disorders associated with muscular spasticity or weakness including tremors, and mild cognitive impairment ("MCI"); mental deficiency (including spasticity, Down syndrome and fragile X syndrome); sleep disorders (including hypersomnia, circadian rhythm sleep disorder, insomnia, parasomnia, and sleep deprivation) and psychiatric disorders such as anxiety (including acute stress disorder, generalized anxiety disorder, social anxiety disorder, panic disorder, post-traumatic stress disorder, agoraphobia, and obsessive-compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, seasonal depression, premenstrual syndrome (PMS), premenstrual dysphoric disorder (PDD), and postpartum depression); psychomotor disorder; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, obesity, compulsive eating disorders and pagophagia); sexual dysfunction disorders; urinary incontinence; neuronal damage disorders (including ocular damage, retinopathy or macular degeneration of the eye, tinnitus, hearing impairment and loss, and brain edema), nerve injury treatment (including accelerating regeneration and recovery after peripheral nerve damage) and pediatric psychiatric disorders (including attention deficit disorder, attention deficit/hyperactive disorder, conduct disorder, and autism) in a mammal, preferably a human, comprising administering to said mammal a therapeutically effective amount of a compound of Formula I or pharmaceutically acceptable salt thereof. The compounds of Formula I may also be useful for improving memory (both short-term and long-term) and learning ability. The text revision of the fourth edition of the Diagnostic and Statistical Manual of Mental Disorders (DSM-IV-TR) (2000, American Psychiatric Association, Washington, D.C.) provides a diagnostic tool for identifying many of the disorders described herein. The skilled artisan will recognize that there are alternative nomenclatures, nosologies, and classification systems for disorders described herein, including those as described in the DMS-IV-TR, and that terminology and classification systems evolve with medical scientific progress;

(3) Methods for treating a neurological disorder (such as migraine; epilepsy; Alzheimer's disease; Parkinson's disease; Niemann-Pick type C; brain injury; stroke; cerebrovascular disease; cognitive disorder; sleep disorder) or a psychiatric disorder (such as anxiety; factitious disorder; impulse control disorder; mood disorder; psychomotor disorder; psychotic disorder; drug dependence; eating disorder; and pediatric psychiatric disorder) in a mammal, preferably a human, comprising administering to said mammal a therapeutically effective amount of a compound of Formula I or pharmaceutically acceptable salt thereof;

(4) Methods for the treatment (e.g., delaying the progression or onset) of diabetes or diabetes-related disorders including Type 1 and Type 2 diabetes, impaired glucose tolerance, insulin resistance, hyperglycemia, and diabetic complications such as atherosclerosis, coronary heart disease, stroke, peripheral vascular disease, nephropathy, hypertension, neuropathy, and retinopathy;

(5) Methods for the treatment of obesity co-morbidities, such as metabolic syndrome. Metabolic syndrome includes diseases, conditions or disorders such as dyslipidemia, hypertension, insulin resistance, diabetes (e.g., Type 2 diabetes), coronary artery disease and heart failure. For more detailed information on metabolic syndrome, see, e.g., Zimmet, P. Z. et al., "The Metabolic Syndrome: Perhaps an Etiologic Mystery but Far From a Myth—Where Does the International Diabetes Federation Stand?," Medscape Diabetes & Endocrinology, 7(2), (2005); and Alberti, K. G. et al., "The Metabolic Syndrome—A New Worldwide Definition," Lancet, 366, 1059-62 (2005); and (6) Methods for the treatment of nonalcoholic fatty liver disease (NAFLD) and hepatic insulin resistance;

The present invention is also directed to combination therapies wherein the compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided;

All patents, patent applications and references referred to herein are hereby incorporated by reference in their entirety.

Other features and advantages of this invention will be apparent from this specification and the appendent claims which describe the invention. It is to be understood that both the foregoing and the following detailed description are exemplary only and are not restrictive of the invention as claimed.

DETAILED DESCRIPTION OF THE INVENTION

The present invention may be understood more readily by reference to the following detailed description of exemplary embodiments of the invention and the examples included therein. It is to be understood that this invention is not limited to specific methods of synthesis, which may of course vary. It is also to be understood that the terminology used herein is for the purpose of describing particular embodiments only and is not intended to be limiting.

In this specification and in the claims that follow, reference will be made to a number of terms that shall be defined to have the following meanings:

As used herein, "eating disorders" refer to illnesses in which the patient suffers disturbances in his/her eating behaviors and related thoughts and emotions. Representative examples of obesity-related eating disorders include overeating, bulimia, binge-eating disorder, compulsive dieting, nocturnal sleep-related eating disorder, pica, Prader-Willi syndrome, and night-eating syndrome.

"Patient" refers to warm-blooded animals such as, for example, guinea pigs, mice, rats, gerbils, cats, rabbits, dogs, cattle, goats, sheep, horses, monkeys, chimpanzees, and humans.

The term "pharmaceutically acceptable" means the substance or composition must be compatible, chemically and/or toxicologically, with the other ingredients comprising a formulation, and/or the mammal being treated therewith.

The term "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject. For the avoidance of doubt, reference herein to "treatment" includes reference to curative, palliative and prophylactic treatment, and to the administration of a medicament for use in such treatment.

The term "alkyl" refers to a linear or branched-chain saturated hydrocarbyl substituent (i.e., a substituent obtained from a hydrocarbon by removal of a hydrogen); in one embodiment containing from one to six carbon atoms. Non-limiting examples of such substituents include methyl, ethyl, propyl (including n-propyl and isopropyl), butyl (including n-butyl, isobutyl, sec-butyl and tert-butyl), pentyl, isoamyl, hexyl and the like.

The term "alkoxy" refers to a linear or branched-chain saturated hydrocarbyl substituent attached to an oxygen radical (i.e., a substituent obtained from a hydrocarbon alcohol by removal of the hydrogen from the OH); in one embodiment containing from one to six carbon atoms. Non-limiting examples of such substituents include methoxy, ethoxy, propoxy (including n-propoxy and isopropoxy), butoxy (including n-butoxy, isobutoxy, sec-butoxy and tert-butoxy), pentoxy, hexoxy and the like.

In some instances, the number of carbon atoms in a hydrocarbyl substituent (i.e., alkyl, cycloalkyl, etc.) is indicated by the prefix "$C_x$-$C_y$-" or "$C_{x-y}$", wherein x is the minimum and y is the maximum number of carbon atoms in the substituent. Thus, for example, "$C_1$-$C_6$-alkyl" or "$C_{1-6}$ alkyl" refers to an alkyl substituent containing from 1 to 6 carbon atoms. Illustrating further, $C_3$-$C_6$ cycloalkyl or $C_{3-6}$-cycloalkyl refers to saturated cycloalkyl group containing from 3 to 6 carbon ring atoms.

The term "cycloalkyl" refers to a carbocyclic substituent obtained by removing a hydrogen from a saturated carbocyclic molecule, for example one having three to six carbon atoms. The term "$C_{3-6}$ cycloalkyl" means a radical of a three to six membered ring which includes the groups cyclopropyl, cyclobutyl, cyclopentyl and cyclohexyl. The term "$C_{3-6}$cycloalkoxy" refers to a three to six membered cycloalkyl group attached to an oxygen radical. Examples include cyclopropoxy, cyclobutoxy, cyclopentoxy and cyclohexoxy.

In some instances, the number of atoms in a cyclic substituent containing one or more heteroatoms (i.e., heteroaryl or heterocycloalkyl) is indicated by the prefix "x- to y-membered", wherein x is the minimum and y is the maximum number of atoms forming the cyclic moiety of the substituent. Thus, for example, "4- to 6-membered heterocycloalkyl" refers to a heterocycloalkyl containing from 4 to 6 atoms, including one to three heteroatoms, in the cyclic moiety of the heterocycloalkyl. Likewise the phrase "5- to 6-membered heteroaryl" refers to a heteroaryl containing from 5 to 6 atoms, and "5- to 10-membered heteroaryl" refers to a heteroaryl containing from 5 to 10 atoms, each including one or more heteroatoms, in the cyclic moiety of the heteroaryl. Furthermore the phases "5-membered heteroaryl" and "6-membered heteroaryl" refer to a five membered heteroaromatic ring system and a six membered heteroaromatic ring system, respectively. The heteroatoms present in these ring systems are selected from N, O and S.

The term "hydroxy" or "hydroxyl" refers to —OH. When used in combination with another term(s), the prefix "hydroxy" indicates that the substituent to which the prefix is attached is substituted with one or more hydroxy substituents. Compounds bearing a carbon to which one or more hydroxy substituents include, for example, alcohols, enols and phenol.

The term "halo" or "halogen" refers to fluorine (which may be depicted as —F), chlorine (which may be depicted as —Cl), bromine (which may be depicted as —Br), or iodine (which may be depicted as —I).

The term "heterocycloalkyl" refers to a substituent obtained by removing a hydrogen from a saturated or partially saturated ring structure containing a total of the specified number of atoms, such as 4 to 6 ring atoms, wherein at least one of the ring atoms is a heteroatom (i.e., oxygen, nitrogen, or sulfur), with the remaining ring atoms being independently selected from the group consisting of carbon, oxygen, nitrogen, and sulfur. In a group that has a heterocycloalkyl substituent, the ring atom of the heterocycloalkyl substituent that is bound to the group may be a nitrogen heteroatom, or it may be a ring carbon atom. Similarly, if the heterocycloalkyl substituent is in turn substituted with a group or substituent, the group or substituent may be bound to a nitrogen heteroatom, or it may be bound to a ring carbon atom.

The term "heteroaryl" refers to an aromatic ring structure containing the specified number of ring atoms in which at least one of the ring atoms is a heteroatom (i.e., oxygen, nitrogen, or sulfur), with the remaining ring atoms being independently selected from the group consisting of carbon, oxygen, nitrogen, and sulfur. Examples of heteroaryl substituents include 6-membered heteroaryl substituents such as pyridyl, pyrazyl, pyrimidinyl, and pyridazinyl; and 5-membered heteroaryl substituents such as triazolyl, imidazolyl, furanyl, thiophenyl, pyrazolyl, pyrrolyl, oxazolyl, isoxazolyl, thiazolyl, 1,2,3-, 1,2,4-, 1,2,5-, or 1,3,4-oxadiazolyl and isothiazolyl. The heteroaryl group can also be a bicyclic heteroaromatic group such as indolyl, benzofuranyl, benzothienyl, benzimidazolyl, benzothiazolyl, benzoxazolyl, benzoisoxazolyl, oxazolopyridinyl, imidazopyridinyl, imidazopyrimidinyl and the like. In a group that has a heteroaryl substituent, the ring atom of the heteroaryl substituent that is bound to the group may be one of the heteroatoms, or it may be a ring carbon atom. Similarly, if the heteroaryl substituent is in turn substituted with a group or substituent, the group or substituent may be bound to one of the heteroatoms, or it may be bound to a ring carbon atom. The term "heteroaryl" also includes pyridyl N-oxides and groups containing a pyridine N-oxide ring. In addition, the heteroaryl group may contain an oxo group such as the one present in a pyridone group. Further examples include furyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, pyridin-2 (1H)-onyl, pyridazin-2(1H)-onyl, pyrimidin-2(1H)-onyl, pyrazin-2(1H)-onyl, imidazo[1,2-a]pyridinyl, and pyrazolo [1,5-a]pyridinyl. The heteroaryl can be further substituted as defined herein.

Examples of single-ring heteroaryls and heterocycloalkyls include furanyl, dihydrofuranyl, tetrahydrofuranyl, thiophenyl, dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiaoxadiazolyl, oxathiazolyl, oxadiazolyl (including oxadiazolyl, 1,2,4-oxadiazolyl, 1,2,5-oxadiazolyl, or 1,3,4-oxadiazolyl), pyranyl (including 1,2-pyranyl or 1,4-pyranyl), dihydropyranyl, pyridinyl, piperidinyl, diazinyl (including pyridazinyl, pyrimidinyl, piperazinyl, triazinyl (including s-triazinyl, as-triazinyl and v-triazinyl), oxazinyl (including 2H-1,2-oxazinyl, 6H-1,3-oxazinyl, or 2H-1,4-oxazinyl), isoxazinyl (including o-isoxazinyl or p-isoxazinyl), oxazolidinyl, isoxazolidinyl, oxathiazinyl (including 1,2,5-oxathiazinyl or 1,2,6-oxathiazinyl), oxadiazinyl (including 2H-1,2,4-oxadiazinyl or 2H-1,2,5-oxadiazinyl), morpholinyl.

The term "heteroaryl" can also include, when specified, ring systems having two rings wherein such rings may be fused and wherein one ring is aromatic and the other ring is not fully part of the conjugated aromatic system (i.e., the heteroaromatic ring can be fused to a cycloalkyl or heterocycloalkyl ring). Non-limiting examples of such ring systems include 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c] pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl. It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

If substituents are described as "independently" having more than one variable, each instance of a substituent is selected independent of the other(s) from the list of variables available. Each substituent therefore may be identical to or different from the other substituent(s).

If substituents are described as being "independently selected" from a group, each instance of a substituent is selected independent of the other(s). Each substituent therefore may be identical to or different from the other substituent(s).

As used herein, the term "Formula I" may be hereinafter referred to as a "compound(s) of the invention," "the present invention," and "compound of Formula I." Such terms are also defined to include all forms of the compound of Formula I, including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes. Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components, which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

The compounds of the invention have asymmetric carbon atoms. The carbon-carbon bonds of the compounds of the invention may be depicted herein using a solid line (—) a solid wedge ( ━━━■ ) or a dotted wedge ( ⋯⋯ıııııı ). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of Formula I may exhibit the phenomenon of tautomerism; such tautomers are also regarded as compounds of the invention. For example, the compounds of Formula I may exist in several tautomeric forms, including the 2-amino-dihydrothiazine form, Ia, and the 2-imino-tetrahydrothiazine form, Ib. All such tautomeric forms, and mixtures thereof, are included within the scope of compounds of Formula I. Tautomers exist as mixtures of a tautomeric set in solution. In solid form, usually one tautomer predominates. Even though one tautomer may be described, the present invention includes all tautomers of the compounds of Formula I and salts thereof. Examples of tautomers are described by the compounds of Formula Ia and Ib and, collectively and generically, are referred to as compounds of Formula I.

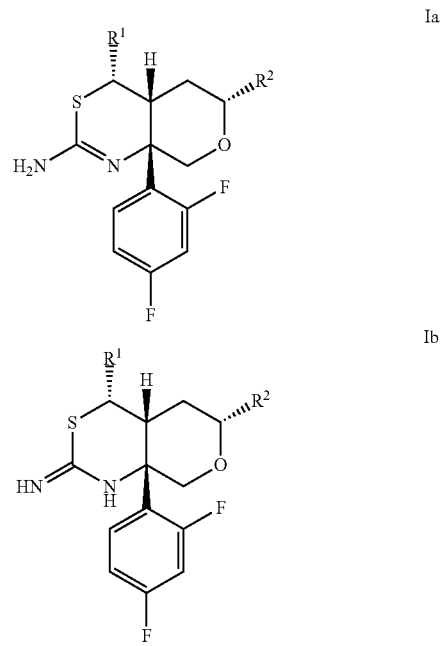

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of Formula I with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention, when possible, include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids.

Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include the lighter alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulfate and hemicalcium salts.

Also within the scope of the present invention are so-called "prodrugs" of the compound of the invention. Thus, certain derivatives of the compound of the invention which may have little or no pharmacological activity themselves can, when administered into or onto the body, be converted into the compound of the invention having the desired activity, for example, by hydrolytic cleavage. Such derivatives are referred to as "prodrugs." Further information on the use of prodrugs may be found in "Pro-drugs as Novel Delivery Systems, Vol. 14, ACS Symposium Series (T. Higuchi and V. Stella) and "Bioreversible Carriers in Drug Design," Pergamon Press, 1987 (ed. E. B. Roche, American Pharmaceutical Association). Prodrugs in accordance with the invention can, for example, be produced by replacing appropriate functionalities present in the compounds of any of Formula I with certain moieties known to those skilled in the art as "pro-moieties" as described, for example, in "Design of Prodrugs" by H. Bundgaard (Elsevier, 1985).

The present invention also includes isotopically labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, sulfur, fluorine and chlorine, such as $^2H$, $^3H$, $^{13}C$, $^{11}C$, $^{14}C$, $^{15}N$, $^{18}O$, $^{17}O$, $^{32}P$, $^{35}S$, $^{18}F$, and $^{36}Cl$, respectively. Compounds of the present invention, prodrugs thereof, and pharmaceutically acceptable salts of said compounds or of said prodrugs that contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of Formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

A second embodiment of the first aspect of the present invention is the compound of the first embodiment of the first aspect wherein $R^2$ is a 5-membered heteroaryl selected from the group consisting of pyrazolyl, oxazolyl, isoxazolyl, triazolyl and oxadiazolyl; each optionally substituted on carbon with one to two $R^3$; and wherein said pyrazolyl and triazolyl are substituted on N with $R^4$; $R^3$ at each occurrence is independently selected from the group consisting of halogen, cyano, $C_{1-6}$alkyl, and $C_{1-6}$ alkoxy; wherein said alkyl is optionally substituted with one to three fluoro; and $R^4$ is hydrogen, methyl or trifluoroethyl; or a tautomer thereof or a pharmaceutically acceptable salt of said compound or tautomer.

A third embodiment of the first aspect of the present invention is the compound of the second embodiment of the first aspect wherein $R^2$ is selected from the group consisting of

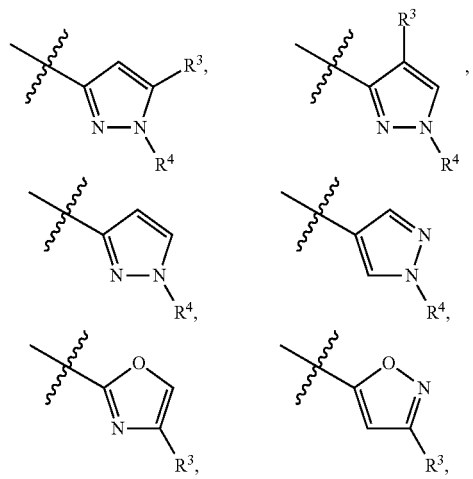

-continued

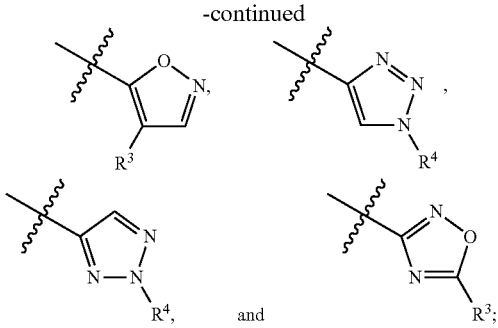

R³ is selected from the group consisting of fluoro, cyano, methyl, fluoromethyl, difluoromethyl, trifluoromethyl, methoxy and ethoxy; and R⁴ is methyl or trifluoroethyl; or a tautomer thereof or a pharmaceutically acceptable salt of said compound or tautomer.

A fourth embodiment of the first aspect of the present invention is the compound of the third embodiment of the first aspect wherein R¹ is hydrogen; or a tautomer thereof or a pharmaceutically acceptable salt of said compound or tautomer.

A fifth embodiment of the first aspect of the present invention is the compound of the third embodiment of the first aspect wherein R¹ is methyl or fluoromethyl; or a tautomer thereof or a pharmaceutically acceptable salt of said compound or tautomer.

A sixth embodiment of the first aspect of the present invention is the compound of the fifth embodiment of the first aspect of the present invention wherein R² is

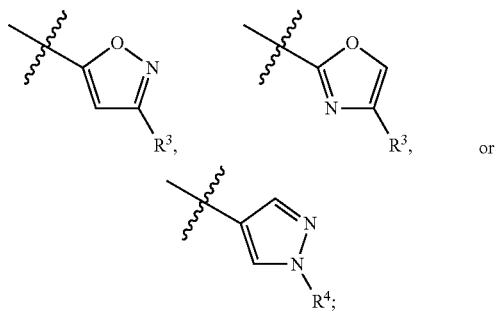

and

R³ is methyl; or a tautomer thereof or a pharmaceutically acceptable salt of said compound or tautomer.

A seventh embodiment of the first aspect of the present invention is the compound of the fourth embodiment of the present invention selected from the group consisting of: (4aR,6R,8aS)-8a-(2,4-Difluorophenyl)-6-(5-fluoro-1-methyl-1H-pyrazol-3-yl)-4,4a,5,6,8,8a-hexahydropyrano[3,4-d][1,3]thiazin-2-amine; (4aR,6R,8aS)-8a-(2,4-Difluorophenyl)-6-[1-(2,2,2-trifluoroethyl)-1H-pyrazol-4-yl]-4,4a,5,6,8,8a-hexahydropyrano[3,4-d][1,3]thiazin-2-amine; (4aR,6R,8aS)-8a-(2,4-Difluorophenyl)-6-(5-methyl-1,2,4-oxadiazol-3-yl)-4,4a,5,6,8,8a-hexahydropyrano[3,4-d][1,3]thiazin-2-amine; (4aR,6R,8aS)-8a-(2,4-Difluorophenyl)-6-(4-fluoro-1-methyl-1H-pyrazol-3-yl)-4,4a,5,6,8,8a-hexahydropyrano[3,4-d][1,3]thiazin-2-amine; (4aR,6R,8aS)-8a-(2,4-Difluorophenyl)-6-(2-methyl-2H-1,2,3-triazol-4-yl)-4,4a,5,6,8,8a-hexahydropyrano[3,4-d][1,3]thiazin-2-amine; (4aR,6R,8aS)-6-[4-(Difluoromethyl)-1,3-oxazol-2-yl]-8a-(2,4-difluorophenyl)-4,4a,5,6,8,8a-hexahydropyrano[3,4-d][1,3]thiazin-2-amine; (4aR,6R,8aS)-8a-(2,4-Difluorophenyl)-6-[1-(²H₃)methyl-1H-pyrazol-4-yl]-4,4a,5,6,8,8a-hexahydropyrano[3,4-d][1,3]thiazin-2-amine; (4aR,6R,8aS)-8a-(2,4-Difluorophenyl)-6-(1-methyl-1H-1,2,3-triazol-4-yl)-4,4a,5,6,8,8a-hexahydropyrano[3,4-d][1,3]thiazin-2-amine; 2-[(4aR,6R,8aS)-2-Amino-8a-(2,4-difluorophenyl)-4,4a,5,6,8,8a-hexahydropyrano[3,4-d][1,3]thiazin-6-yl]-1,3-oxazole-4-carbonitrile; (4aR,6R,8aS)-8a-(2,4-Difluorophenyl)-6-(5-methylpyrazin-2-yl)-4,4a,5,6,8,8a-hexahydropyrano[3,4-d][1,3]thiazin-2-amine; (4aS,6S,8aR)-8a-(2,4-Difluorophenyl)-6-(5-methylpyrazin-2-yl)-4,4a,5,6,8,8a-hexahydropyrano[3,4-d][1,3]thiazin-2-amine; and (4aR,6R,8aS)-8a-(2,4-Difluorophenyl)-6-(5-ethoxy-1-methyl-1H-pyrazol-3-yl)-4,4a,5,6,8,8a-hexahydropyrano[3,4-d][1,3]thiazin-2-amine; or a tautomer thereof or a pharmaceutically acceptable salt of said compound or tautomer.

An eighth embodiment of the first aspect of the present invention is the compound of the fifth embodiment of the first aspect of the present invention selected from the group consisting of: (4R,4aR,6R,8aS)-8a-(2,4-Difluorophenyl)-4-methyl-6-(3-methyl-1,2-oxazol-5-yl)-4,4a,5,6,8,8a-hexahydropyrano[3,4-d][1,3]thiazin-2-amine; (4S,4aR,6R,8aS)-8a-(2,4-Difluorophenyl)-4-(fluoromethyl)-6-(3-methyl-1,2-oxazol-5-yl)-4,4a,5,6,8,8a-hexahydropyrano[3,4-d][1,3]thiazin-2-amine; (4R,4aR,6R,8aS)-8a-(2,4-Difluorophenyl)-4-methyl-6-(1-methyl-1H-pyrazol-4-yl)-4,4a,5,6,8,8a-hexahydropyrano[3,4-d][1,3]thiazin-2-amine; (4S,4aR,6R,8aS)-8a-(2,4-Difluorophenyl)-4-(fluoromethyl)-6-(1-methyl-1H-pyrazol-4-yl)-4,4a,5,6,8,8a-hexahydropyrano[3,4-d][1,3]thiazin-2-amine; or a tautomer thereof or a pharmaceutically acceptable salt of said compound or tautomer.

A ninth embodiment of a first aspect of the present invention is the compound of the first embodiment of the first aspect wherein R² is a 6-membered heteroaryl selected from the group consisting of pyridinyl, pyridonyl, pyrimidinyl and pyrazinyl; each optionally substituted on carbon with one to two R³; and wherein said pyridonyl is substituted on N with R⁴; R³ at each occurrence is independently selected from the group consisting of halogen, cyano, $C_{1-6}$alkyl, and $C_{1-6}$alkoxy; wherein said alkyl is optionally substituted with one to three fluoro; and R⁴ is hydrogen, methyl or trifluoroethyl; or a tautomer thereof or a pharmaceutically acceptable salt of said compound or tautomer.

A tenth embodiment of the first aspect of the present invention is the compound of the ninth embodiment of the first aspect wherein R² is selected from the group consisting of

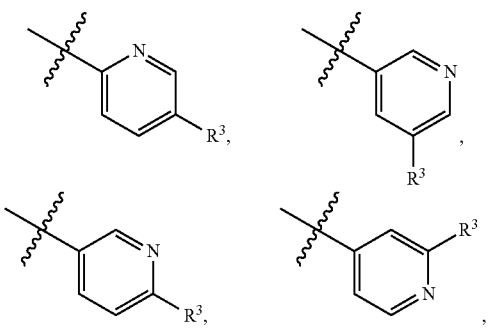

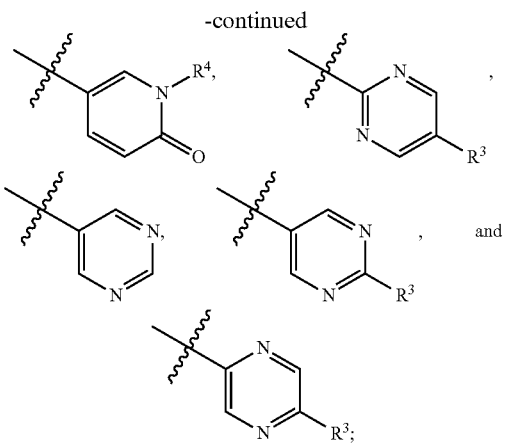

$R^3$ is selected from fluoro, methyl, and methoxy; and $R^4$ is methyl; or a tautomer thereof or pharmaceutically acceptable salt of said compound or tautomer.

An eleventh embodiment of the first aspect of the present invention is the compound of the tenth embodiment of the first aspect wherein $R^1$ is hydrogen; or a tautomer thereof or a pharmaceutically acceptable salt of said compound or tautomer.

A twelfth embodiment of a first aspect of the present invention is the compound of the eleventh embodiment of the first aspect selected from the group consisting of: (4aR,6R,8aS)-8a-(2,4-Difluorophenyl)-6-(5-fluoropyridin-2-yl)-4,4a,5,6,8,8a-hexahydropyrano[3,4-d][1,3]thiazin-2-amine; 5-[(4aR,6R,8aS)-2-Amino-8a-(2,4-difluorophenyl)-4,4a,5,6,8,8a-hexahydropyrano[3,4-d][1,3]thiazin-6-yl]-1-methylpyridin-2(1H)-one; rel-(4aR,6R,8aS)-8a-(2,4-Difluorophenyl)-6-(6-methylpyridin-3-yl)-4,4a,5,6,8,8a-hexahydropyrano[3,4-d][1,3]thiazin-2-amine; (4aR,6R,8aS)-8a-(2,4-Difluorophenyl)-6-(5-methoxypyrimidin-2-yl)-4,4a,5,6,8,8a-hexahydropyrano[3,4-d][1,3]thiazin-2-amine; (4aR,6R,8aS)-8a-(2,4-Difluorophenyl)-6-(2-methylpyrimidin-5-yl)-4,4a,5,6,8,8a-hexahydropyrano[3,4-d][1,3]thiazin-2-amine; (4aR,6R,8aS)-8a-(2,4-Difluorophenyl)-6-(pyrimidin-5-yl)-4,4a,5,6,8,8a-hexahydropyrano[3,4-d][1,3]thiazin-2-amine; (4aR,6R,8aS)-8a-(2,4-Difluorophenyl)-6-(2-methoxypyrimidin-4-yl)-4,4a,5,6,8,8a-hexahydropyrano[3,4-d][1,3]thiazin-2-amine; (4aR,6R,8aS)-8a-(2,4-Difluorophenyl)-6-(5-methoxypyridin-3-yl)-4,4a,5,6,8,8a-hexahydropyrano[3,4-d][1,3]thiazin-2-amine; (4aR,6R,8aS)-8a-(2,4-Difluorophenyl)-6-(2-methylpyridin-4-yl)-4,4a,5,6,8,8a-hexahydropyrano[3,4-d][1,3]thiazin-2-amine; and (4aR,6R,8aS)-8a-(2,4-difluorophenyl)-6-(5-fluoropyridin-3-yl)-4,4a,5,6,8,8a-hexahydropyrano[3,4-d][1,3]thiazin-2-amine or a tautomer thereof or a pharmaceutically acceptable salt of said compound or tautomer.

A thirteenth embodiment of a first aspect of the present invention is the compound of the first embodiment of the first aspect wherein $R^1$ is hydrogen; and $R^2$ is selected from the group consisting of oxazolopyridinyl, imidazopyridinyl and imidazopyrimidinyl; or a tautomer thereof or a pharmaceutically acceptable salt of said compound or tautomer.

A fourteenth embodiment of the first aspect of the present invention is the compound of the thirteenth embodiment of the first aspect wherein $R^2$ is selected from the group consisting of [1,3]oxazolo[4,5-c]pyridinyl, [1,3]oxazolo[5,4-c]pyridinyl, imidazo[1,2-a]pyridinyl and imidazo[1,2-a]pyrimidinyl; or a tautomer thereof or a pharmaceutically acceptable salt of said compound or tautomer.

A fifteenth embodiment of a first aspect of the present invention is the compound of the fourteenth embodiment of the first aspect selected from the group consisting of (4aR,6R,8aS)-8a-(2,4-Difluorophenyl)-6-(imidazo[1,2-a]pyrimidin-2-yl)-4,4a,5,6,8,8a-hexahydropyrano[3,4-d][1,3]thiazin-2-amine; (4aR,6R,8aS)-8a-(2,4-Difluorophenyl)-6-([1,3]oxazolo[4,5-c]pyridin-2-yl)-4,4a,5,6,8,8a-hexahydropyrano[3,4-d][1,3]thiazin-2-amine; (4aR,6R,8aS)-8a-(2,4-Difluorophenyl)-6-([1,3]oxazolo[5,4-c]pyridin-2-yl)-4,4a,5,6,8,8a-hexahydropyrano[3,4-d][1,3]thiazin-2-amine; and (4aR,6R,8aS)-8a-(2,4-Difluorophenyl)-6-(imidazo[1,2-a]pyridin-6-yl)-4,4a,5,6,8,8a-hexahydropyrano[3,4-d][1,3]thiazin-2-amine; or a tautomer thereof or a pharmaceutically acceptable salt of said compound or tautomer.

A first embodiment of a second aspect of the present invention is a pharmaceutical composition comprising a therapeutically effective amount of a compound of any one of the first to fifteenth embodiments of the first aspect of the present invention, or a tautomer thereof or a pharmaceutically acceptable salt of said compound or tautomer, and a pharmaceutically acceptable vehicle, diluent or carrier.

Further embodiments of the present invention include methods of treatment employing the compounds of the present invention.

A first embodiment of a third aspect of the present invention is a method of inhibiting production of amyloid-β protein in a patient; the method comprising administering a therapeutically effective amount of a compound according to any one of the first through fifteenth embodiments of the first aspect of the present invention, or a tautomer thereof or a pharmaceutically acceptable salt of said compound or tautomer to a patient in need of inhibition of production of amyloid-β protein.

A second embodiment of a third aspect of the present invention is a method of inhibiting beta-site amyloid precursor protein cleaving enzyme 1 (BACE1) in a patient, the method comprising administering a therapeutically effective amount of a compound according to any one of the first through fifteenth embodiments of the first aspect of the present invention, or a tautomer thereof or a pharmaceutically acceptable salt of said compound or tautomer to a patient in need of inhibition of beta-site amyloid precursor protein cleaving enzyme 1 (BACE1).

A third embodiment of a third aspect of the present invention is a method for treating a neurodegenerative disease in a patient, the method comprising administering a therapeutically effective amount of a compound according to any one of the first through fifteenth embodiments of the first aspect of the present invention, or a tautomer thereof or a pharmaceutically acceptable salt of said compound or tautomer to a patient in need of treatment thereof.

A fourth embodiment of a third aspect of the present invention is the method of the third embodiment of the third aspect wherein the neurodegenerative disease is Alzheimer's Disease.

A fifth embodiment of a third aspect of the present invention is a method of treating or preventing diabetes in a patient, the method comprising administering a therapeutically effective amount of a compound according to any one of first through fifteenth embodiments of the first aspect of the present invention, or a tautomer thereof or a pharmaceutically acceptable salt of said compound or tautomer to a patient in need of treatment or prevention thereof.

A sixth embodiment of a third aspect of the present invention is the method of the fifth embodiment of the third aspect wherein the diabetes is Type 2 diabetes.

Further embodiments of the present invention include the use of a compound according to any one of first through fifteenth embodiments of the first aspect of the present invention in the preparation of a medicament useful for treating the conditions, diseases and disorders as described herein.

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compound of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of Formula I are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (e.g., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J. Pharm. Sci., 88 (10), 955-958, by Finnin and Morgan (October 1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as cross-linked polyacrylic acid, polyvinyl alcohol, hyaluronic acid, a cellulosic polymer, for example, hydroxypropylmethyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients ($3^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be may be administered simultaneously (either in the same dosage form or in separate dosage forms) or sequentially.

Two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of a BACE inhibitor compound as provided in Formula I and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula I or a pharmaceutically acceptable salt of the compound; (b) a second pharmaceutically active agent; and (c) a pharmaceutically acceptable carrier, vehicle or diluent.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include, without limitation:

(i) anti-obesity agents (including appetite suppressants), include gut-selective MTP inhibitors (e.g., dirlotapide, mitratapide and implitapide, CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonists (e.g., compounds described in U.S. Pat. No. 6,818,658), lipase inhibitors (e.g., Cetilistat), $PYY_{3-36}$ (as used herein "$PYY_{3-36}$" includes analogs, such as peglated $PYY_{3-36}$, e.g., those described in US Publication 2006/0178501), opioid antagonists (e.g., naltrexone), oleoyl-estrone (CAS No. 180003-17-2), obinepitide (TM30338), pramlintide (Symlin®), tesofensine (NS2330), leptin, bromocriptine, orlistat, AOD-9604 (CAS No. 221231-10-3) and sibutramine.

(ii) anti-diabetic agents, such as an acetyl-CoA carboxylase (ACC) inhibitor as described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, a diacylglycerol O-acyltransferase 2 (DGAT-2) inhibitor, a monoacylglycerol O-acyltransferase inhibitor, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPAR γ agonist (e.g., balaglitazone, ciglitazone, darglitazone, englitazone, isaglitazone, pioglitazone and rosiglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, taspoglutide, lixisenatide, dulaglutide, semaglutide, NN-9924, TTP-054, a protein tyrosine phosphatase-1B (PTP-1B) inhibitor (e.g., trodusquemine, hyrtiosal extract, and compounds disclosed by Zhang, S. et al., *Drug Discovery Today*, 12(9/10), 373-381 (2007)), a SIRT-1 inhibitor (e.g., resveratrol, GSK2245840 or GSK184072), a dipeptidyl peptidase IV (DPP-IV) inhibitor (e.g., those in WO2005116014, sitagliptin, vildagliptin, alogliptin, dutogliptin, linagliptin and saxagliptin), an insulin secretagogue, a fatty acid oxidation inhibitor, an A2 antagonist, a c-jun amino-terminal kinase (JNK) inhibitor, a glucokinase activator (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g., GSK1362885), a VPAC2 receptor agonist, an SGLT2 inhibitor, such as those described in E. G. Chao et al., Nature Reviews Drug Discovery 9, 551-559 (July 2010) including dapagliflozin, canagliflozin, BI-10733, tofogliflozin (CSG452), ASP-1941, THR1474, TS-071, ISIS388626 and LX4211 as well as those in WO2010023594, a glucagon receptor modulator such as those described in Demong, D. E. et al., Annual Reports in Medicinal Chemistry 2008, 43, 119-137, a GPR119 modulator, particularly an agonist, such as those described in WO2010140092, WO2010128425, WO2010128414, WO2010106457, Jones, R. M. et al., in Medicinal Chemistry 2009, 44, 149-170 (e.g., MBX-2982, GSK1292263, APD597 and PSN821), an FGF21 derivative or an analog such as those described in Kharitonenkov, A. et al., Current Opinion in Investigational Drugs 2009, 10(4), 359-364, TGR5 (also termed GPBAR1) receptor modulators, particularly agonists, such as those described in Zhong, M., Current Topics in Medicinal Chemistry, 2010, 10(4), 386-396 and INT777, a GPR40 agonist, such as those described in Medina, J. C., Annual Reports in Medicinal Chemistry, 2008, 43, 75-85, including but not limited to TAK-875, a GPR120 modulator, particularly an agonist, a high-affinity nicotinic acid receptor (HM74A) activator, and an SGLT1 inhibitor, such as GSK1614235. A further representative listing of anti-diabetic agents that can be combined with the compounds of the present invention can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g., PKCa, PKCb, PKCg), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g., SSTR1, SSTR2, SSTR3 and SSTR5), inhibitors or modulators of PDHK2 or PDHK4, inhibitors of MAP4K4, modulators of IL1 family including IL1 beta, and modulators of RXRalpha. In addition, suitable anti-diabetic agents include mechanisms listed by Carpino, P. A., Goodwin, B. Expert Opin. Ther. Pat, 2010, 20(12), 1627-51;

(iii) anti-hyperglycemic agents, for example, those described at page 31, line 31 through page 32, line 18 of WO 2011005611;

(iv) lipid lowering agents (for example, those described at page 30, line 20 through page 31, line 30 of WO 2011005611), and anti-hypertensive agents (for example, those described at page 31, line 31 through page 32, line 18 of WO 2011005611);

(v) acetylcholinesterase inhibitors, such as donepezil hydrochloride (ARICEPT®, MEMAC), physostigmine salicylate (ANTILIRIUM®), physostigmine sulfate (ESERINE), ganstigmine, rivastigmine (EXELON®), ladostigil, NP-0361, galantamine hydrobromide (RAZADYNE®, REMINYL®, NIVALIN®), tacrine (COGNEX®), tolserine, memoquin, huperzine A (HUP-A; Neuro-Hitech), phenserine, bisnorcymserine (also known as BNC), and INM-176;

(vi) amyloid-β (or fragments thereof), such as $A\beta_{1-15}$ conjugated to pan HLA DR-binding epitope (PADRE®), ACC-001 (Elan/Wyeth), and Affitope;

(vii) antibodies to amyloid-β (or fragments thereof), such as ponezumab, solanezumab, bapineuzumab (also known as AAB-001), AAB-002 (Wyeth/Elan), Gantenerumab, intravenous Ig (GAMMAGARD®), LY2062430 (humanized m266; Lilly), and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(viii) amyloid-lowering or -inhibiting agents (including those that reduce amyloid production, accumulation and fibrillization) such as eprodisate (KIACTA®), celecoxib, lovastatin, anapsos, colostrinin, pioglitazone, clioquinol (also known as PBT1), PBT2 (Prana Biotechnology), flurbiprofen (ANSAID®, FROBEN®) and its R-enantiomer tarenflurbil (FLURIZAN®), nitroflurbiprofen, fenoprofen (FENOPRON, NALFON®), ibuprofen (ADVIL®, MOTRIN®, NUROFEN®), ibuprofen lysinate, meclofenamic acid, meclofenamate sodium (MECLOMEN®), indomethacin (INDOCIN®), diclofenac sodium (VOLTAREN®), diclofenac potassium, sulindac (CLINORIL®), sulindac sulfide, diflunisal (DOLOBID®), naproxen (NAPROSYN®), naproxen sodium (ANAPROX®, ALEVE®), insulin-degrading enzyme (also known as insulysin), the gingko biloba extract EGb-761 (ROKAN®, TEBONIN®), tramiprosate (CEREBRIL®, ALZHEMED®), neprilysin (also known as neutral endopeptidase (NEP)), scyllo-inositol (also known as scyllitol), atorvastatin (LIPITOR®), simvastatin (ZOCOR®), ibutamoren mesylate, BACE inhibitors such as LY450139 (Lilly), BMS-782450, and GSK-188909; gamma secretase modulators and inhibitors such as ELND-007, BMS-708163 (Avagacestat), and DSP8658 (Dainippon); and RAGE (receptor for advanced glycation end-products) inhibitors, such as TTP488 (Transtech) and TTP4000 (Transtech), and those disclosed in U.S. Pat. No. 7,285,293, including PTI-777;

(ix) alpha-adrenergic receptor agonists, and beta-adrenergic receptor blocking agents (beta blockers); anticholinergics; anticonvulsants; antipsychotics; calcium channel blockers; catechol O-methyltransferase (COMT) inhibitors; central nervous system stimulants; corticosteroids; dopamine receptor agonists and antagonists; dopamine reuptake inhibitors; gamma-aminobutyric acid (GABA) receptor agonists; immunosuppressants; interferons; muscarinic receptor agonists; neuroprotective drugs; nicotinic receptor agonists; norepinephrine (noradrenaline) reuptake inhibitors; quinolines; and trophic factors;

(x) histamine 3 (H3) antagonists, such as PF-3654746 and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600);

(xi) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), methadone, (DOLOPHINE), neramexane, perzinfotel, phencyclidine, tianeptine (STABLON), dizocilpine (also known as MK-801), ibogaine, voacangine, tiletamine, riluzole (RILUTEK), aptiganel (CERESTAT), gavestinel, and remacimide;

(xii) monoamine oxidase (MAO) inhibitors, such as selegiline (EMSAM), selegiline hydrochloride (I-deprenyl, ELDEPRYL, ZELAPAR), dimethylselegiline, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(xiii) phosphodiesterase (PDE) inhibitors, including (a) PDE1 inhibitors (b) PDE2 inhibitors (c) PDE3 inhibitors (d) PDE4 inhibitors (e) PDE5 inhibitors (f) PDE9 inhibitors (e.g., PF-04447943, BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008)), and (g) PDE10 inhibitors such as 2-({4-[1-methyl-4-(pyridin-4-yl)-1H-pyrazol-3-yl]phenoxy}methyl) quinoline (PF-2545920);

(xiv) serotonin (5-hydroxytryptamine) 1A (5-HT$_{1A}$) receptor antagonists, such as spiperone, levo-pindolol, lecozotan;

(xv) serotonin (5-hydroxytryptamine) 2C (5-HT$_{2C}$) receptor agonists, such as vabicaserin, and zicronapine; serotonin (5-hydroxytryptamine) 4 (5-HT$_4$) receptor agonists/antagonists, such as PRX-03140 (Epix) and PF-04995274;

(xvi) serotonin (5-hydroxytryptamine) 3C (5-HT$_{3C}$) receptor antagonists, such as Ondansetron (Zofran);

(xvii) serotonin (5-hydroxytryptamine) 6 (5-HT$_6$) receptor antagonists, such as mianserin (TOLVON, BOLVIDON, NORVAL), methiothepin (also known as metitepine), ritanserin, SB-271046, SB-742457 (GlaxoSmithKline), Lu AE58054 (Lundbeck NS), SAM-760, and PRX-07034 (Epix);

(xviii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine and tesofensine;

(xix) Glycine transporter-1 inhibitors such as paliflutine, ORG-25935, and ORG-26041; and mGluR modulators such as AFQ-059 and amantidine;

(xx) AMPA-type glutamate receptor modulators such as perampanel, mibampator, selurampanel, GSK-729327, and N-{(3S,4S)-4-[4-(5-cyanothiophen-2-yl)phenoxy]tetrahydrofuran-3-yl}propane-2-sulfonamide;

(xxi) P450 inhibitors, such as ritonavir;

(xxii) tau therapy targets, such as davunetide;

and the like.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

General Synthetic Schemes

The compounds of the present invention may be prepared by the methods described below, together with synthetic methods known in the art of organic chemistry, or modifications and transformations that are familiar to those of ordinary skill in the art. The starting materials used herein are commercially available or may be prepared by routine methods known in the art [such as those methods disclosed in standard reference books such as the *Compendium of Organic Synthetic Methods*, Vol. I-XII (published by Wiley-Interscience)]. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of the invention, or tautomers thereof or pharmaceutically acceptable salts of said compounds or tautomers, can be prepared according to the reaction Schemes discussed herein below. Unless otherwise indicated, the substituents in the Schemes are defined as above. Isolation and purification of the products is accomplished by standard procedures, which are known to a chemist of ordinary skill.

One skilled in the art will recognize that in many cases, the compounds in Schemes 1 through 15 will be generated as a mixture of diastereomers and/or enantiomers; these may be separated at various stages of the synthetic schemes using conventional techniques or a combination of such techniques, such as, but not limited to, crystallization, normal-phase chromatography, reversed phase chromatography and chiral chromatography, to afford the single enantiomers of the invention.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. The schemes are representative of methods useful in synthesizing the compounds of the present invention. They are not to constrain the scope of the invention in any way.

Scheme 1 refers to the preparation of compounds of Formula I. Referring to Scheme 1, the compound of Formula I can be prepared from the compound of Formula II through a removal of protecting group $P^1$. $P^1$ in this case refers to groups well known to those skilled in the art for amine protection. For example, $P^1$ may be a benzoyl group (Bz), which can be cleaved via acidic conditions, or through treatment with 1,8-diazabicyclo[5.4.0]undec-7-ene (DBU) in methanol. Alternatively, $P^1$ may be one of many protecting group suitable for amines, including 9-fluorenylmethoxycarbonyl (Fmoc) or tert-butoxycarbonyl (BOC) and can be cleaved under standard conditions known to one skilled in the art.

reaction of enol triflate IV with the corresponding $R^2$-containing boronic acid using standard Suzuki reaction conditions replaces the triflate with $R^2$; subsequent reduction of the resultant enol ether using standard reduction conditions, for instance trimethylsilyl trifluoromethanesulfonate (TMSOTf) and triethylsilane, provides compounds of Formula II. Alternatively, the corresponding $R^2$-containing heteroaryl iodide can be coupled with the compound of Formula IV under palladium-mediated conditions with hexabutyldistannane. Compound II can be converted into a compound of Formula I according to the methods of Scheme 1.

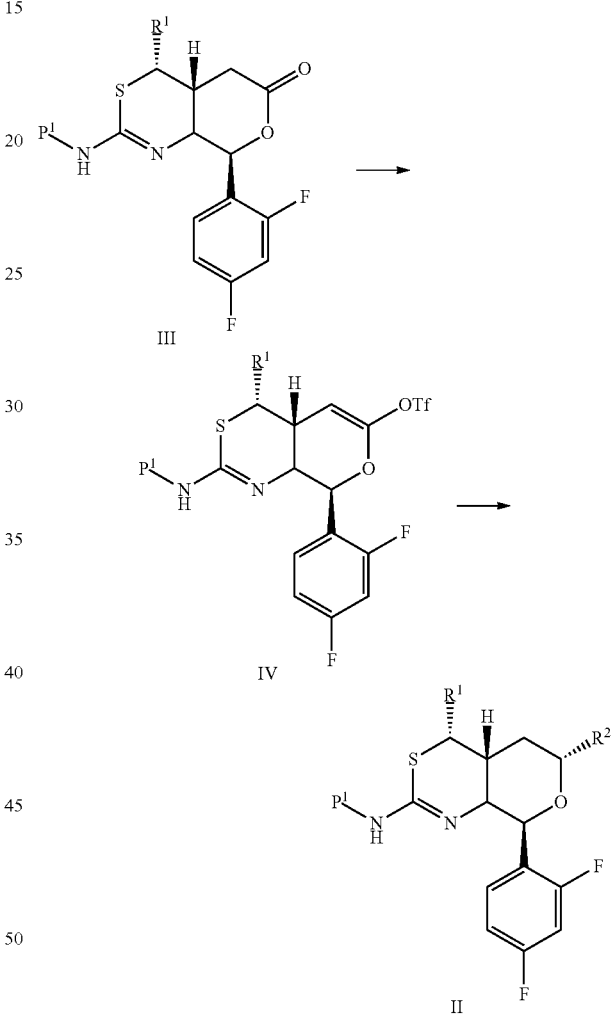

Scheme 2

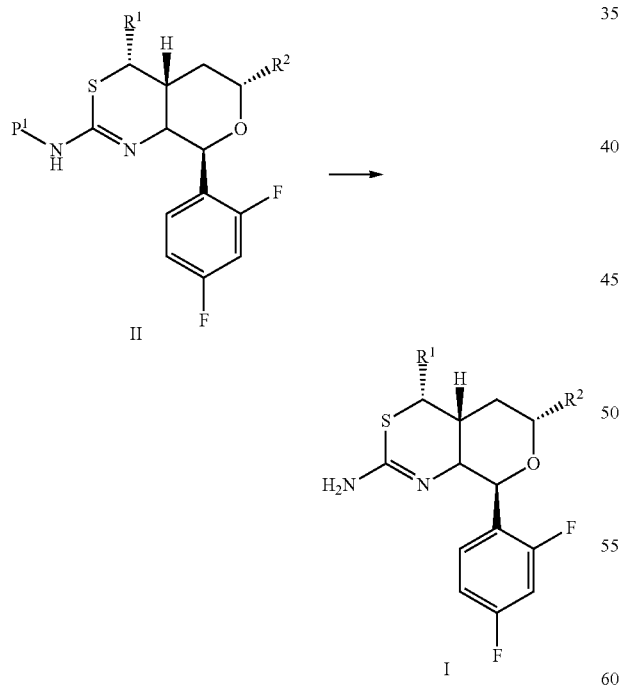

Scheme 1

Scheme 2 refers to the preparation of compounds II wherein $P^1$ is Bz or Fmoc. The treatment of lactones of Formula III with base, for instance potassium bis(trimethylsilyl) amide (KHMDS), and N-(5-chloropyridin-2-yl)-1,1,1-trifluoro-N-[(trifluoromethyl)sulfonyl]-methanesulfonamide (Comins' Reagent) provides compounds of Formula IV. The Scheme 3 refers to the preparation of compounds II wherein $P^1$ is Bz or Fmoc. The oxidation of compounds of Formula V can be accomplished by a number of standard oxidation protocols, for instance using tetrapropylammonium perruthenate (TPAP) and 4-methylmorpholine-N-oxide (NMO) in acetonitrile. Carboxylic acids VI can be converted to compounds of Formula II via a number of methods outlined in the following reference: Practical Synthetic Organic Chemistry: Reactions, Principles, and Techniques. 2011, Chapter 13, Wiley & Sons, Inc., Caron, S., ed., as well as additional methods known to those skilled in the art. Compound II can be converted into a compound of Formula I according to the methods of Scheme 1.

Scheme 3

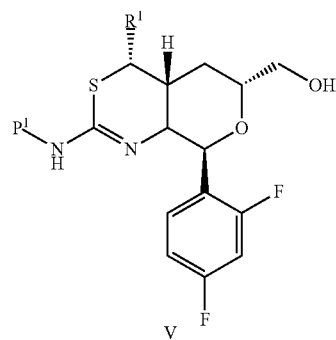

V

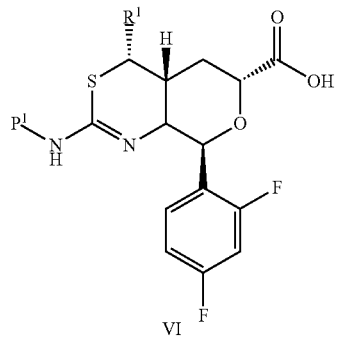

VI

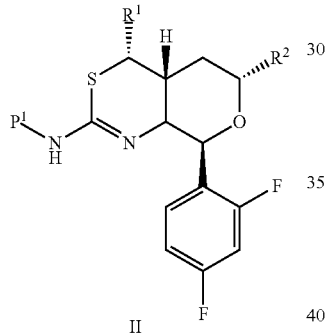

II

Scheme 4 refers to the preparation of compounds II wherein P¹ is Bz or Fmoc. The oxidation of compounds of Formula V can be effected by a number of standard oxidation protocols, for instance using Dess-Martin periodinane or sulfur trioxide-pyridine with DMSO (dimethyl sulfoxide) (Parikh-Doering conditions). Aldehydes VII can be converted to compounds of Formula II via a number of methods outlined in the following reference: Practical Synthetic Organic Chemistry: Reactions, Principles, and Techniques. 2011, Chapter 13, Wiley & Sons, Inc., Caron, S., ed. Compound II can be converted into a compound of Formula I according to the methods of Scheme 1.

Scheme 4

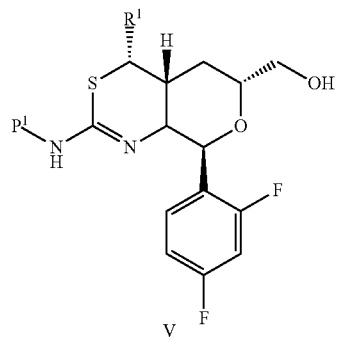

V

-continued

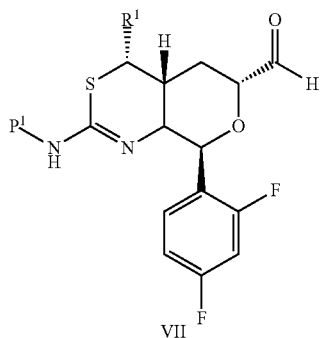

VII

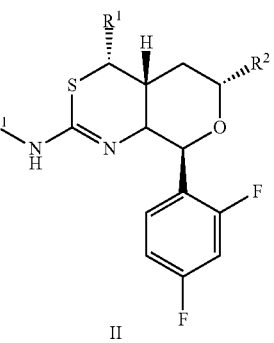

II

Scheme 5 refers to the preparation of compounds II wherein P¹ is Bz or Fmoc. The preparation of compounds of Formula VIII can be effected by activation of the acids VI using a standard peptide coupling reagent, for instance using 2-[2-oxo-1(2H)-pyridyl]-1,1,3,3-tetramethyluronium tetrafluoroborate (TPTU), followed by treatment with an appropriate amine, for instance, a solution of ammonia in 1,4-dioxane. Amides of Formula VIII can be converted to compounds of Formula II via a number of methods outlined in the following reference: Practical Synthetic Organic Chemistry: Reactions, Principles, and Techniques. 2011, Chapter 13, Wiley & Sons, Inc., Caron, S., ed. Compound II can be converted into a compound of Formula I according to the methods of Scheme 1.

Scheme 5

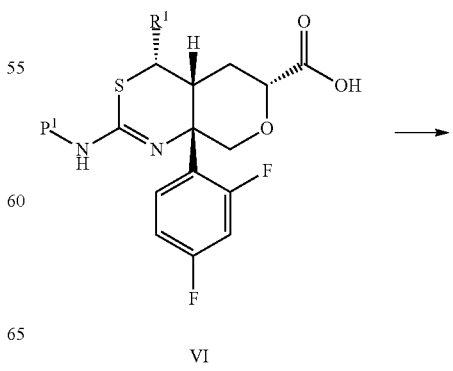

VI

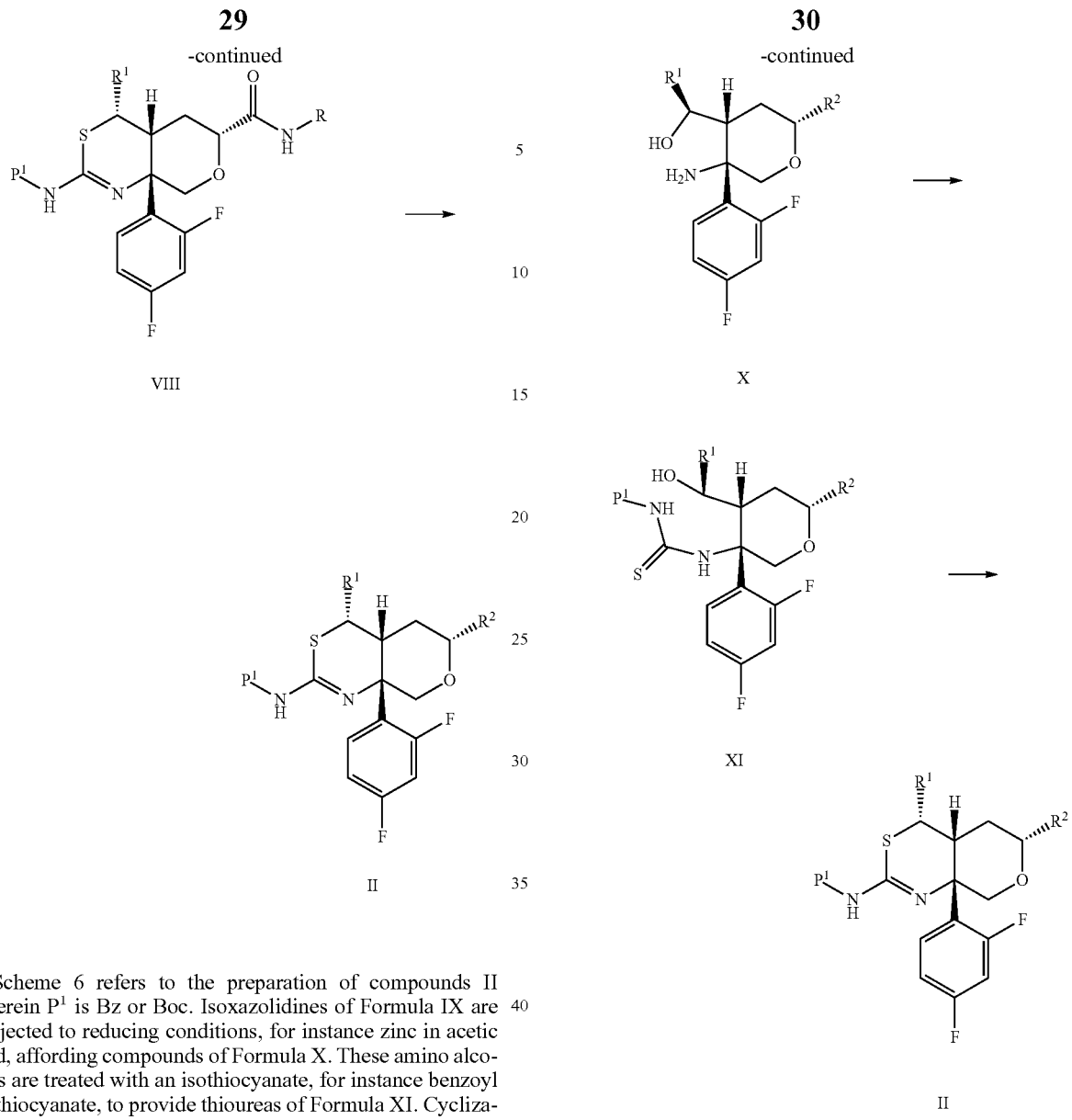

Scheme 6 refers to the preparation of compounds II wherein $P^1$ is Bz or Boc. Isoxazolidines of Formula IX are subjected to reducing conditions, for instance zinc in acetic acid, affording compounds of Formula X. These amino alcohols are treated with an isothiocyanate, for instance benzoyl isothiocyanate, to provide thioureas of Formula XI. Cyclization is induced using strong acid, including for instance sulfuric acid, or alternatively, standard Mitsunobu conditions, to give compounds of Formula II. Compound II can be converted into a compound of Formula I according to the methods of Scheme 1.

Scheme 6

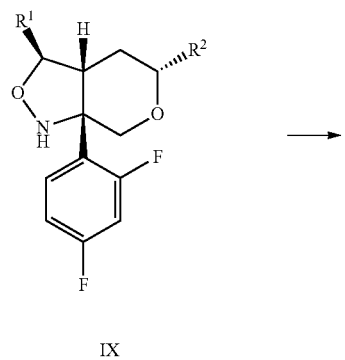

IX

Scheme 7 refers to the preparation of compounds of Formula IX. Homoallylic alcohol XII is alkylated with 2-bromo-1,1-dimethoxyethane under basic conditions, such as treatment with potassium hydride, to provide the corresponding ether XIII. The acetal is cleaved under acidic conditions, aqueous HCl as an example, to give aldehyde XIV. Condensation with a hydroxylamine salt, such as hydroxylamine sulfate, provides a geometric mixture of the corresponding oxime XV. Cycloaddition to form isoxazoline XVI may be carried out by treatment of oxime XV with an oxidizing agent, such as sodium hypochlorite or N-chlorosuccinimide. Reaction of isoxazoline XVI with an appropriate arylmetallic reagent (for instance, an aryllithium such as 2,4-difluorophenyllithium, or the corresponding aryl Grignard reagent) at low temperature, e.g., −78° C., yields compounds of Formula IX. One of ordinary skill in the art will recognize that the stereochemistry of addition of the arylmetallic reagent is determined by the stereochemistry of the adjacent methine center, yielding a racemic mixture of cis-fused diastereomers, which can be converted into compounds of Formula I according to the methods of Schemes 6 and 1.

Scheme 7

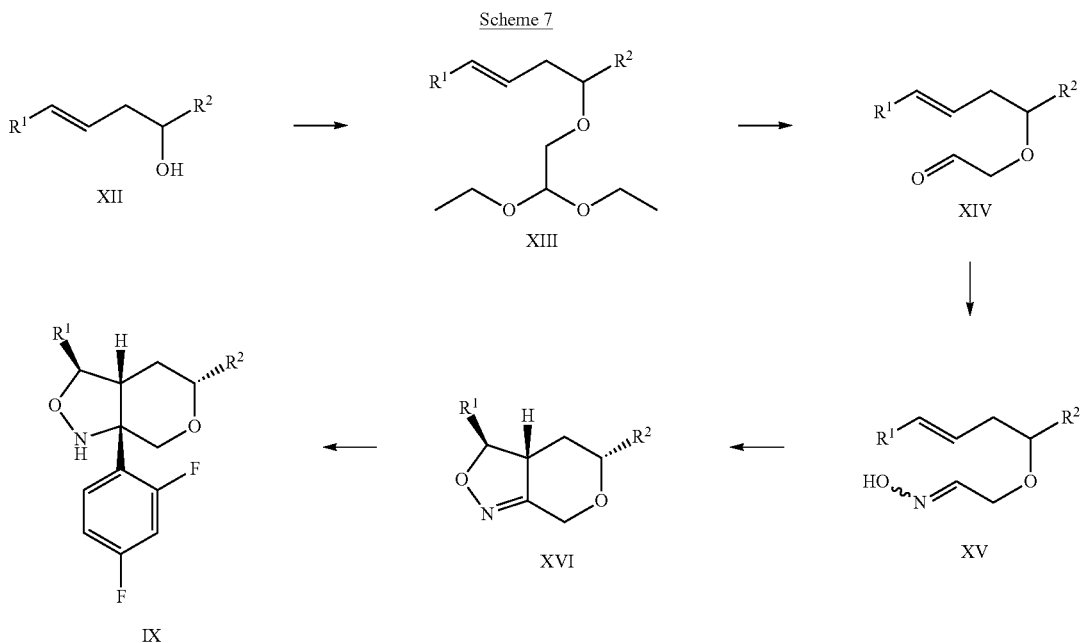

Scheme 8 refers to the preparation of compounds II wherein P¹ is Bz or Fmoc. Compounds of Formula XVII can be prepared by treatment of amides VIII, wherein R=H, with a suitable methylating agent, for instance trimethyloxonium tetrafluoroborate, followed by treatment with an ammonia source, for instance a solution of ammonia in methanol. Amidines XVII can be converted to compounds of Formula II via a number of methods outlined in the following reference: Practical Synthetic Organic Chemistry: Reactions, Principles, and Techniques. 2011, Chapter 13, Wiley & Sons, Inc., Caron, S., ed. Compound II can be converted into a compound of Formula I according to the methods of Scheme 1.

Scheme 8

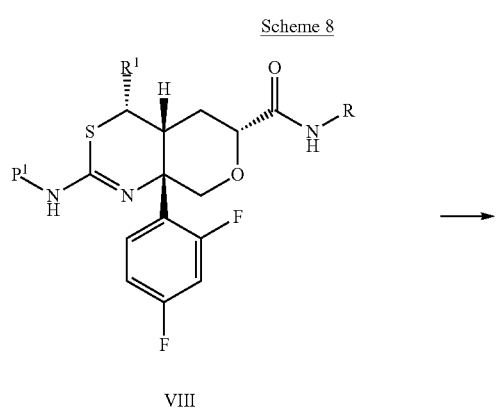

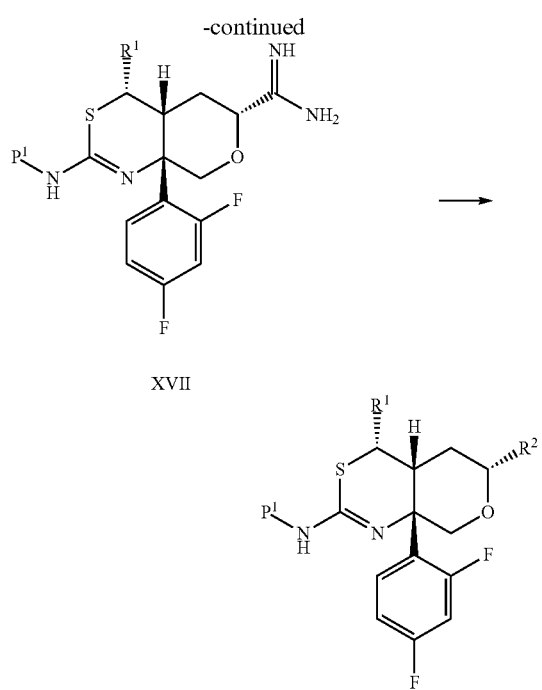

Scheme 9 refers to the preparation of compounds of Formula III wherein P¹ is Bz or Fmoc. Aldehydes of Formula VII are subjected to basic conditions, for instance potassium carbonate in acetonitrile, and trapped using an appropriate anhydride, for instance acetic anhydride, to afford protected enol ethers of Formula XVIII, wherein P² is an acyl group. Oxidative cleavage of the enol ether moiety using standard conditions, including for instance ruthenium chloride and sodium periodate, affords lactones of Formula III. Compound III can be converted into a compound of Formula I according to the methods of Schemes 2, 10 and 1.

Scheme 9

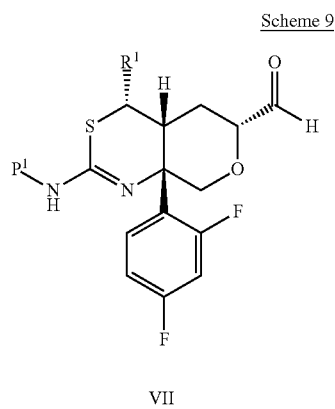

VII

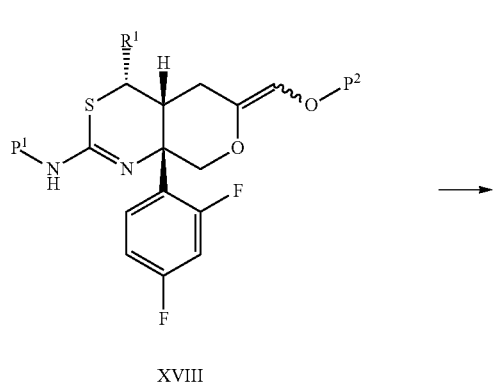

XVIII

Scheme 10

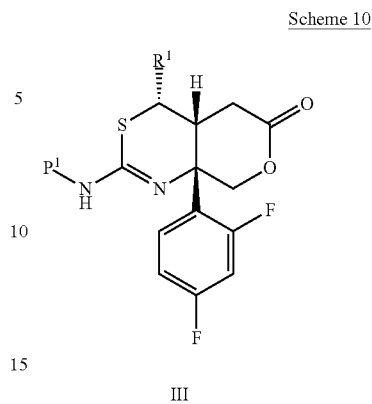

III

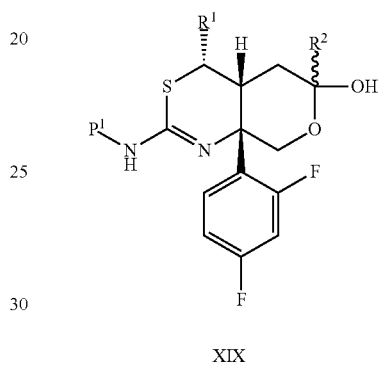

XIX

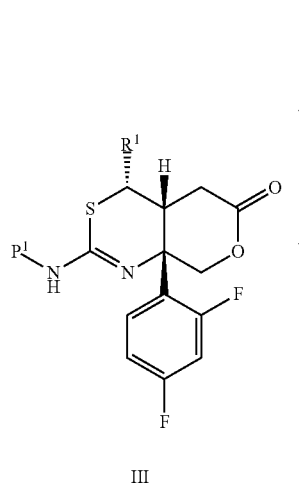

III

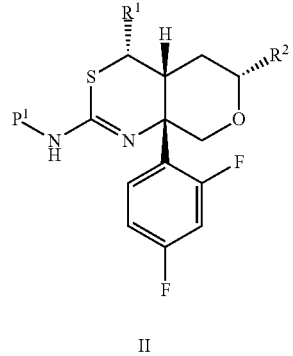

II

Scheme 10 refers to the preparation of compounds II wherein $P^1$ is Bz or Boc. The addition of an organometallic derivative (magnesiate or lithiate) of $R^2$ to compounds of Formula III under standard anionic conditions, for instance in tetrahydrofuran (THF) at −78° C., provides compounds of Formula XIX. Subsequent reduction of the resultant lactol using standard reduction conditions, for instance trimethylsilyl trifluoromethanesulfonate (TMSOTf) and triethylsilane, provides compounds of Formula II. Compound II can be converted into a compound of Formula I according to the methods of Scheme 1.

Scheme 11 refers to the preparation of compounds V wherein $P^1$ is Bz. Isoxazolidines of Formula XX (which may be obtained via the chemistry depicted in Scheme 7, utilizing a benzyloxymethyl group in place of $R^2$) are subjected to reducing conditions, for instance zinc in acetic acid, affording compounds of Formula XXI. The amino alcohols XXI are treated with an isothiocyanate, for instance benzoyl isothiocyanate, to provide thioureas of Formula XXII. Cyclization is induced using strong acid, including for instance sulfuric acid, or alternatively, standard Mitsunobu conditions, to give compounds of Formula XXIII. Cleavage of the benzyl ether under standard conditions, for instance using boron trichloride, provides alcohols of Formula V. Compound V can be converted into a compound of Formula I according to the methods of Schemes 3 or 4, followed by Scheme 1.

Scheme 11 11

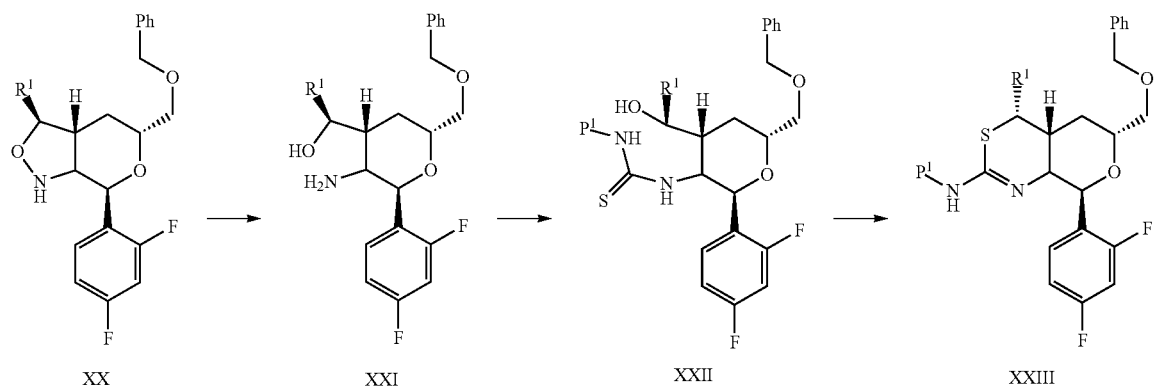

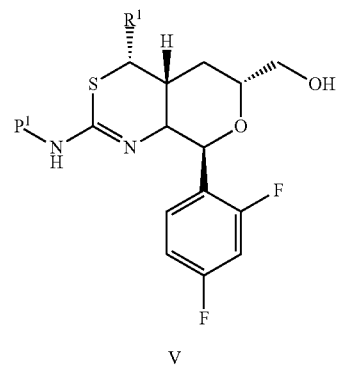

Scheme 12 refers to the preparation of compounds IX wherein $R^1$ is —$CH_2F$. Isoxazolidines of Formula XXIV are subjected to suitable conditions to introduce the fluorine into the $R^1$ group, including, but not limited to, (diethylamino) sulfur trifluoride (DAST) in dichloromethane, affording compounds of Formula XVI. Reaction of isoxazoline XVI with an appropriate arylmetallic reagent (for instance, an aryllithium such as 2,4-difluorophenyllithium, or the corresponding aryl Grignard reagent) at low temperature, e.g., −78° C., yields compounds of Formula IX, which can be converted into compounds of Formula I according to the methods of Schemes 6 and 1.

Scheme 12

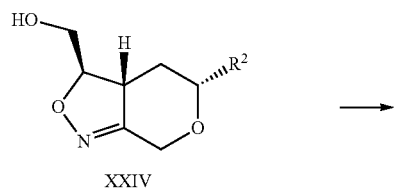

-continued

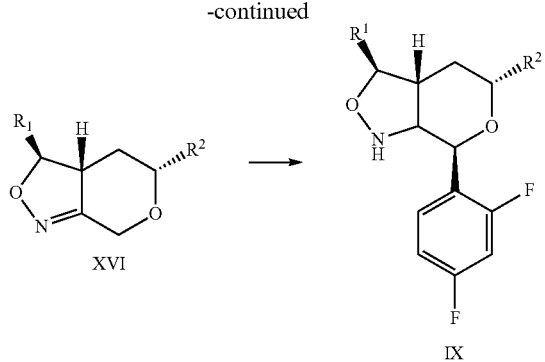

Scheme 13 refers to the preparation of compounds XXIV. Compounds of Formula XXV (formed in analogous fashion to Scheme 7) are subjected to standard ruthenium-catalyzed cross-metathesis conditions, for instance using Grubbs' second-generation metathesis catalyst, in the presence of methyl prop-2-enoate, to afford compounds of Formula XXVI. The acetal is cleaved under acidic conditions, aqueous HCl as an example, to give an aldehyde that is immediately condensed with a hydroxylamine salt, such as hydroxylamine sulfate, providing a geometric mixture of the corresponding oxime XXVII. Cycloaddition to form isoxazoline XXVIII may be carried out by treatment of oxime XXVII with an oxidizing agent, such as sodium hypochlorite or N-chlorosuccinimide. Reduction of the methyl ester of isoxazoline XXVIII can be effected through the use of an appropriate reducing agent, for instance sodium borohydride, to afford a compound of Formula XXIV, which can be converted into a compound of Formula I according to the methods of Schemes 12, 6, and 1.

Scheme 13

Scheme 14 refers to the preparation of chiral homoallyl compounds XII wherein $R^2$ is —$CH_2OBn$. Compounds of Formula XXIX are subjected to treatment with an appropriate alkynyl-metallic reagent, propynyllithium as an example, to afford compounds of Formula XXX. Treatment with an appropriate reducing reagent, lithium aluminum hydride as an example, affords stereochemically defined compounds of Formula XII, which can be converted to compounds of Formula I via Schemes 7, 11, 3, 4, and 1.

Scheme 14

Scheme 15 refers to the preparation of racemic compounds XII. Aldehydes of Formula XXXI are treated with an appropriate allylmetallic reagent (for instance allylmagnesium bromide) to afford alcohols of Formula XII, which can be converted to compounds of Formula I via Schemes 7, 6, and 1.

Scheme 15

Experimental Procedures

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics or DriSolv® products from EMD Chemicals. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin layer chromatography or mass spectrometry, and subjected to work-up when appropriate. Purifications may vary between experiments: in general, solvents and the solvent ratios used for eluents/gradients were chosen to provide appropriate $R_f$s or retention times.

Preparations
Preparation P1
N-[(4aR,6R,8aS)-8a-(2,4-Difluorophenyl)-6-(hydroxymethyl)-4,4a,5,6,8,8a-hexahydropyrano[3,4-d][1,3]thiazin-2-yl]benzamide (P1)
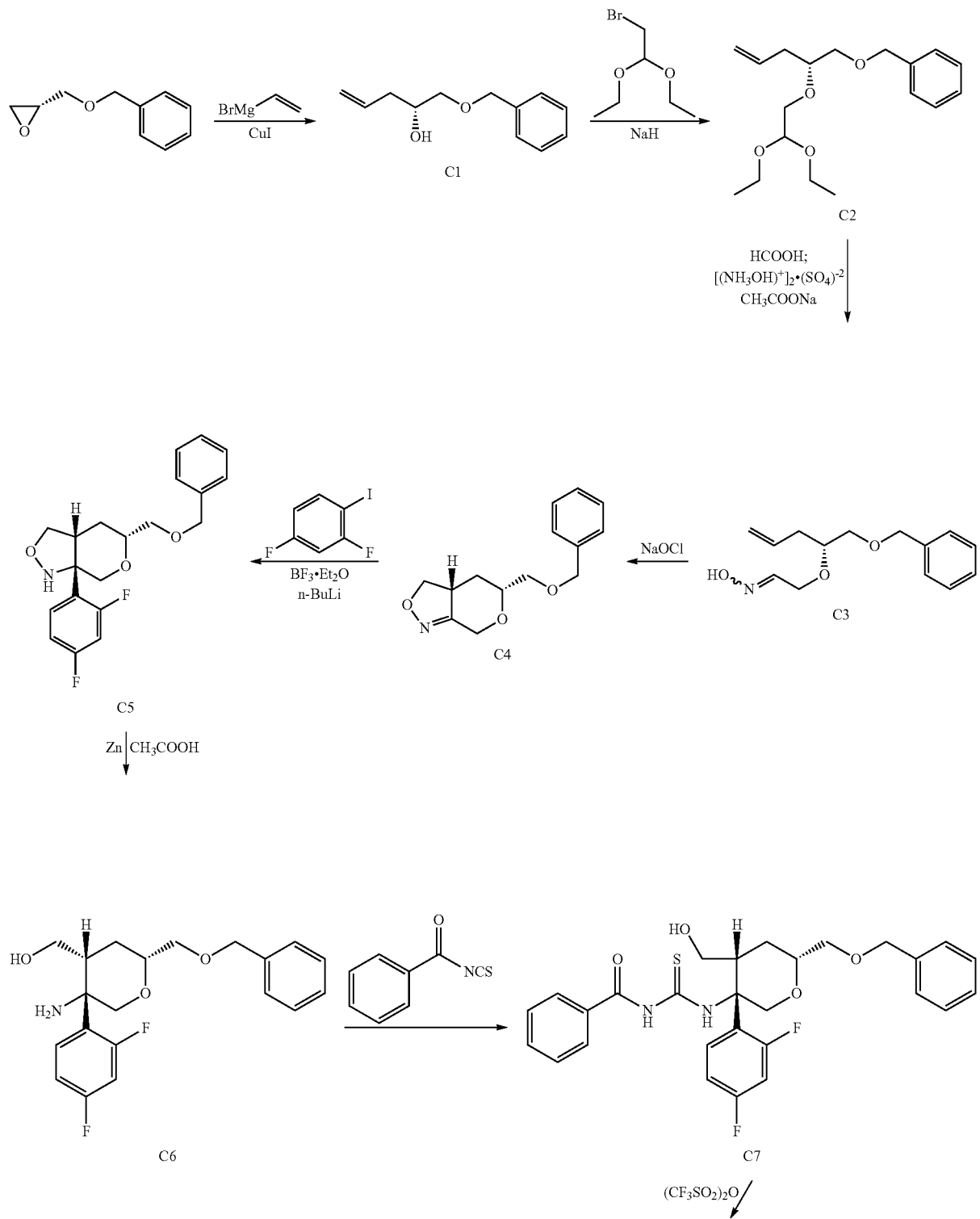

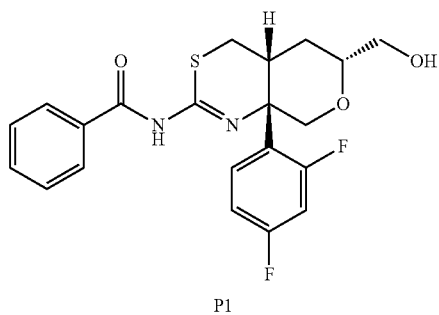

P1

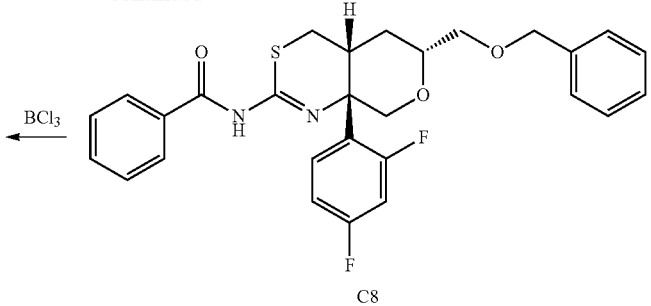

C8

Step 1. Synthesis of (2R)-1-(benzyloxy)pent-4-en-2-ol (C1)

To a solution of (2R)-2-[(benzyloxy)methyl]oxirane (167 g, 1.02 mol) in tetrahydrofuran (2 L) was added copper(I) iodide (11.62 g, 61.02 mmol) at room temperature. The mixture was stirred for 5 minutes, then cooled to −78° C. A solution of vinylmagnesium bromide (1 M in tetrahydrofuran, 1.12 L, 1.12 mol) was added drop-wise over 1 hour while the reaction temperature was maintained below −70° C. Upon completion of the addition, the cooling bath was removed and the reaction mixture was left to stir at room temperature for 1 hour, then quenched by slow addition of aqueous ammonium chloride solution (200 mL). After dilution with aqueous ammonium chloride solution (1.5 L) and ethyl acetate (1.5 L), the aqueous layer was extracted with ethyl acetate (1 L) and the combined organic layers were washed with aqueous ammonium chloride solution (1.5 L), dried over magnesium sulfate, filtered, and concentrated in vacuo. Three batches of this reaction were carried out and combined to give the product as an orange oil. Yield: 600 g, 3.1 mol, quantitative. $^1$H NMR (400 MHz, CDCl$_3$) δ 7.28-7.40 (m, 5H), 5.78-5.90 (m, 1H), 5.08-5.17 (m, 2H), 4.57 (s, 2H), 3.86-3.94 (m, 1H), 3.53 (dd, J=9.6, 3.3 Hz, 1H), 3.39 (dd, J=9.6, 7.4 Hz, 1H), 2.26-2.34 (m, 3H).

Step 2. Synthesis of ({[(2R)-2-(2,2-diethoxyethoxy)pent-4-en-1-yl]oxy}methyl)benzene (C2)

This reaction was carried out in two identical experiments. To a 0° C. suspension of sodium hydride (60% in mineral oil, 125 g, 3.12 mol) in tetrahydrofuran (1 L) was added a solution of C1 (200 g, 1.04 mol) in tetrahydrofuran (500 mL). The reaction was stirred for 30 minutes at room temperature, whereupon 2-bromo-1,1-diethoxyethane (528 g, 2.68 mol) was added, and the reaction mixture was heated at reflux for 18 hours. The mixture was carefully quenched with water (2×300 mL) and the combined experiments were concentrated in vacuo. The aqueous residue was partitioned between ethyl acetate (5 L) and water (5 L). The organic layer was washed with saturated aqueous sodium chloride solution (5 L), dried, and concentrated. Purification via silica gel chromatography (Eluent: 20:1 petroleum ether/ethyl acetate) provided the product as a yellow oil. Yield: 300 g, 0.97 mol, 47%. $^1$H NMR (400 MHz, CDCl$_3$) δ 7.26-7.37 (m, 5H), 5.78-5.90 (m, 1H), 5.01-5.13 (m, 2H), 4.61 (t, J=5.3 Hz, 1H), 4.55 (s, 2H), 3.48-3.74 (m, 9H), 2.30-2.36 (m, 2H), 1.22 (t, J=7.1 Hz, 3H), 1.21 (t, J=7.0 Hz, 3H).

Step 3. Synthesis of 2-{[(2R)-1-(benzyloxy)pent-4-en-2-yl]oxy}-N-hydroxyethanimine (C3)

A solution of C2 (234 g, 0.759 mol) in formic acid (400 mL) and water (100 mL) was stirred at room temperature for 2 hours. As LCMS analysis revealed a small amount of remaining starting material, formic acid (50 mL) was added and the reaction mixture was stirred for a further 30 minutes. The reaction mixture was diluted with ethanol (1 L) and water (400 mL). Hydroxylamine sulfate (435 g, 2.65 mol) and sodium acetate (217 g, 2.64 mol) were added and the reaction was stirred at room temperature for 18 hours. The reaction mixture was then filtered and concentrated in vacuo. The residue was partitioned between ethyl acetate (500 mL) and water (1 L), and the aqueous layer was extracted with ethyl acetate (3×500 mL). The combined organic layers were washed with saturated aqueous sodium chloride solution (2×500 mL), dried over magnesium sulfate, filtered, and concentrated under reduced pressure to provide the product as an orange oil. By $^1$H NMR, this material consisted of a roughly 1:1 mixture of oxime isomers. Yield: 234 g, which was taken directly to the following step. LCMS m/z 250.1 [M+H]$^+$. $^1$H NMR (400 MHz, CDCl$_3$), characteristic peaks: δ [7.52 (t, J=5.5 Hz) and 6.96 (t, J=3.6 Hz), total 1H], 7.28-7.39 (m, 5H), 5.74-5.87 (m, 1H), 5.04-5.14 (m, 2H), 4.55 and 4.56 (2 s, total 2H), {4.45-4.55 (m) and [4.27 (dd, half of ABX pattern, J=13.2, 5.4 Hz) and 4.21 (dd, half of ABX pattern, J=13.2, 5.6 Hz)], total 2H}, 2.30-2.37 (m, 2H).

Step 4. Synthesis of (3aR,5R)-5[(benzyloxy)methyl]-3,3a,4,5-tetrahydro-7H-pyrano[3,4-c][1,2]oxazole (C4)

An aqueous solution of sodium hypochlorite (14.5% solution, 600 mL) was added drop-wise to a 0° C. solution of C3 (224 g from the previous step, ≤0.726 mol) in dichloromethane (1 L), while the internal temperature was maintained below 15° C. After completion of the addition, the reaction mixture was left to stir at 0° C. for 1.5 hours, then diluted with water (1 L) and dichloromethane (500 mL). The aqueous layer was extracted with dichloromethane (2×500 mL), and the combined organic layers were washed with saturated aqueous sodium chloride solution (500 mL), water (500 mL) and again with saturated aqueous sodium chloride solution (500 mL). They were subsequently dried over magnesium sulfate, filtered, and concentrated in vacuo. Silica gel chromatography (Gradient: 0% to 25% ethyl acetate in heptane) afforded the product as a colorless oil. The indicated relative stereochemistry of compound C4 was assigned based on nuclear Overhauser enhancement (NOE) studies, which revealed an interaction between the methine protons on carbons 3a and 5. Yield: 85.3 g, 345 mmol, 45% over 2 steps. LCMS m/z 248.1 [M+H]$^+$. $^1$H NMR (400 MHz, CDCl$_3$) δ 7.27-7.40 (m, 5H), 4.77 (d, J=13.5 Hz, 1H), 4.54-4.65 (m, 3H), 4.22 (dd, J=13.5, 1 Hz, 1H), 3.79 (dd, J=11.7, 8.0 Hz, 1H), 3.69-3.76 (m, 1H), 3.57 (dd, half of ABX pattern, J=10.1, 5.9 Hz, 1H), 3.49 (dd, half of ABX pattern, J=10.1, 4.3 Hz, 1H), 3.39-3.5 (m, 1H), 2.20 (ddd, J=12.9, 6.5, 1.6 Hz, 1H), 1.51-1.62 (m, 1H).

Step 5. Synthesis of (3aR,5R,7a5)-5-[(benzyloxy)methyl]-7a-(2,4-difluorophenyl)hexahydro-1H-pyrano[3,4-c][1,2]oxazole (C5)

Boron trifluoride diethyl etherate (60.1 mL, 474 mmol) was added to a solution of C4 (50.0 g, 202 mmol) in a 1:1 mixture of toluene and diisopropyl ether (2 L) at an internal temperature of −76° C. The reaction was stirred at this temperature for 30 minutes, then treated with 2,4-difluoro-1-iodobenzene (27.1 mL, 226 mmol). While the reaction temperature was maintained at −76 to −71° C., n-butyllithium (2.5 M in hexanes, 85.7 mL, 214 mmol) was slowly added. The reaction mixture was stirred at −76° C. for 1.5 hours, then quenched with saturated aqueous ammonium chloride solution (1 L) and partitioned between water (1 L) and ethyl acetate (750 mL). After the mixture warmed to room temperature, the aqueous layer was extracted with ethyl acetate (3×250 mL), and the combined organic layers were washed with saturated aqueous sodium chloride solution (550 mL), dried over sodium sulfate, filtered, and concentrated in vacuo. Silica gel chromatography (Gradient: 0% to 70% ethyl acetate in heptane) gave the product as a yellow oil. Yield: 48.14 g, 133.2 mmol, 66%. $^1$H NMR (400 MHz, CDCl$_3$) δ 7.94 (ddd, J=9, 9, 7 Hz, 1H), 7.28-7.40 (m, 5H), 6.87-6.93 (m, 1H), 6.80 (ddd, J=12.0, 8.6, 2.4 Hz, 1H), 4.60 (AB quartet, $J_{AB}$=12.1 Hz, $\Delta v_{AB}$=21.4 Hz, 2H), 4.14 (br dd, J=12.8, 1.3 Hz, 1H), 3.82-3.90 (m, 2H), 3.72 (d, J=7.2 Hz, 1H), 3.54-3.60 (m, 2H), 3.50 (dd, half of ABX pattern, J=10.3, 4.1 Hz, 1H), 3.04-3.13 (m, 1H), 1.86 (ddd, J=14.0, 7.0, 2.0 Hz, 1H), 1.49-1.61 (m, 1H).

Step 6. Synthesis of [(2R,4R,5S)-5-amino-2-[(benzyloxy)methyl]-5-(2,4-difluorophenyl)tetrahydro-2H-pyran-4-yl]methanol (C6)

Compound C5 (48.1 g, 133 mmol) was dissolved in acetic acid (444 mL) and treated with zinc powder (113 g, 1.73 mol). The reaction mixture, which had warmed to 40° C., was allowed to cool to room temperature and stir for 16 hours. Insoluble material was removed via filtration through a pad of diatomaceous earth, and the pad was washed with ethyl acetate (3×500 mL). The combined filtrates were neutralized with saturated aqueous sodium bicarbonate solution (2.5 L), and the aqueous layer was extracted with ethyl acetate (3×500 mL). The combined organic layers were washed with saturated aqueous sodium chloride solution (1 L), dried over sodium sulfate, filtered, and concentrated in vacuo to provide the product as a thick yellow oil, which was used in the following reaction without additional purification. Yield: 48.7 g, assumed quantitative. $^1$H NMR (400 MHz, CDCl$_3$), characteristic peaks: δ 7.62-7.80 (br m, 1H), 7.28-7.39 (m, 5H), 6.94-7.06 (m, 1H), 6.83 (ddd, J=12.7, 8.5, 2.6 Hz, 1H), 4.61 (AB quartet, upfield doublet is broadened, $J_{AB}$=12.2 Hz, $\Delta v_{AB}$=30.5 Hz, 2H), 4.22 (dd, J=11.6, 2.2 Hz, 1H), 3.83-3.92 (br m, 1H), 3.62-3.73 (br m, 1H), 3.56 (dd, J=10.2, 3.5 Hz, 1H), 3.34-3.41 (m, 1H), 2.26-2.43 (br m, 1H), 2.00-2.17 (br m, 1H), 1.65 (ddd, J=14.1, 4.5, 2.5 Hz, 1H).

Step 7. Synthesis of N-{[(3S,4R,6R)-6-[(benzyloxy)methyl]-3-(2,4-difluorophenyl)-4-(hydroxymethyl)tetrahydro-2H-pyran-3-yl]carbamothioyl}benzamide (C7)

Benzoyl isothiocyanate (17.8 mL, 132 mmol) was added to a solution of C6 (48.7 g, 133 mmol) in dichloromethane (1.34 L), and the reaction mixture was allowed to stir at room temperature for 18 hours. Removal of solvent in vacuo afforded the product as a white solid, which was used without additional purification. Yield: 72.2 g, assumed quantitative. LCMS m/z 527.2 [M+H]$^+$. $^1$H NMR (400 MHz, CD$_3$OD), characteristic peaks: δ 7.89-7.93 (m, 2H), 7.62-7.67 (m, 1H), 7.50-7.56 (m, 2H), 7.42-7.54 (br m, 1H), 7.31-7.36 (m, 2H), 7.17-7.28 (m, 3H), 6.86-6.98 (m, 2H), 4.57 (AB quartet, $J_{AB}$=11.9 Hz, $\Delta v_{AB}$=11.8 Hz, 2H), 3.84-3.91 (m, 1H), 3.64 (br dd, half of ABX pattern, J=10.6, 6.0 Hz, 1H), 3.58 (dd, half of ABX pattern, J=10.6, 3.8 Hz, 1H), 3.44-3.54 (br m, 1H), 2.32-2.59 (br m, 1H), 1.82-2.06 (m, 2H).

Step 8. Synthesis of N-[(4aR,6R,8aS)-6-[(benzyloxy)methyl]-8a-(2,4-difluorophenyl)-4,4a,5,6,8,8a-hexahydropyrano[3,4-d][1,3]thiazin-2-yl]benzamide (C8)

Pyridine (11.0 mL, 137 mmol) was added to a solution of C7 (19.00 g, 36.08 mmol) in dichloromethane (150 mL), and the resulting solution was cooled to −50 to −60° C. Trifluoromethanesulfonic anhydride (12.1 mL, 71.9 mmol) in dichloromethane (50 mL) was added drop-wise, and the reaction mixture was gradually warmed to −5° C. over 3 hours. Water was added, and the aqueous layer was extracted with dichloromethane. The combined organic layers were washed with saturated aqueous sodium chloride solution, dried over magnesium sulfate, filtered, and concentrated in vacuo. Purification via silica gel chromatography (Gradient: 20% to 40% ethyl acetate in heptane) provided the product as a yellow foam. Yield: 15.51 g, 30.50 mmol, 85%. LCMS m/z 509.2 [M+H]$^+$. $^1$H NMR (400 MHz, CDCl$_3$) δ 8.23 (br d, J=7 Hz, 2H), 7.37-7.57 (br m, 4H), 7.24-7.36 (m, 5H), 6.85-6.97 (m, 2H), 4.58 (AB quartet, upfield signals are slightly broadened, $J_{AB}$=11.9 Hz, $\Delta v_{AB}$=23.5 Hz, 2H), 4.17 (br d, J=12 Hz, 1H), 3.90-3.97 (m, 1H), 3.83 (br d, J=12 Hz, 1H), 3.64 (dd, half of ABX pattern, J=10.1, 6.4 Hz, 1H), 3.50 (dd, half of ABX pattern, J=10.2, 4.4 Hz, 1H), 3.11-3.21 (br m, 1H), 3.02 (dd, J=12.9, 4.1 Hz, 1H), 2.64 (br d, J=13 Hz, 1H), 1.92-2.05 (br m, 1H), 1.71 (br d, J=13 Hz, 1H).

Step 9. Synthesis of N-[(4aR,6R,8aS)-8a-(2,4-difluorophenyl)-6-(hydroxymethyl)-4,4a,5,6,8,8a-hexahydropyrano[3,4-d][1,3]thiazin-2-yl]benzamide (P1)

Boron trichloride (1 M solution in heptane, 89.7 mL, 89.7 mmol) was added to a 0° C. solution of C8 (15.20 g, 29.89 mmol) in dichloromethane (150 mL). After 15 minutes, the reaction mixture was allowed to warm to room temperature and stirred for 4 hours. Methanol (50 mL) was then added, first drop-wise {Caution: violent reaction} and then at a steady rate, while the interior of the flask was flushed with nitrogen gas. The mixture was heated at reflux for 30 minutes, cooled to room temperature and concentrated in vacuo. The residue was again dissolved in methanol, stirred, and concentrated in vacuo. The resulting material was taken up in dichloromethane and washed sequentially with 1 M aqueous sodium hydroxide solution, water, and saturated aqueous sodium chloride solution. The organic layer was dried over magnesium sulfate, filtered, and concentrated under reduced pressure. Chromatographic purification on silica gel (Gradient: 0% to 3% methanol in ethyl acetate) provided the product as a yellow foam. Yield: 11.97 g, 28.60 mmol, 96%. LCMS m/z 419.2 [M+H]$^+$. $^1$H NMR (400 MHz, CD$_3$OD) δ 8.13 (d, J=7.4 Hz, 2H), 7.50-7.56 (m, 1H), 7.41-7.49 (m, 3H), 7.02-7.11 (m, 2H), 4.13 (dd, J=11.9, 1.8 Hz, 1H), 3.90 (d, J=12.1 Hz, 1H), 3.72-3.80 (m, 1H), 3.59 (d, J=5.1 Hz, 2H), 3.14-3.24 (br m, 1H), 2.96 (dd, half of ABX pattern, J=13.1, 4.1 Hz, 1H), 2.75 (dd, half of ABX pattern, J=13.1, 2.7 Hz, 1H), 1.80-1.92 (m, 1H), 1.70 (ddd, J=13.4, 4.2, 2.4 Hz, 1H).

Preparation P2

(4a R,6R,8aS)-2-(Benzoylamino)-8a-(2,4-difluorophenyl)-4,4a,5,6,8,8a-hexahydropyrano[3,4-d][1,3]thiazine-6-carboxylic acid (P2)

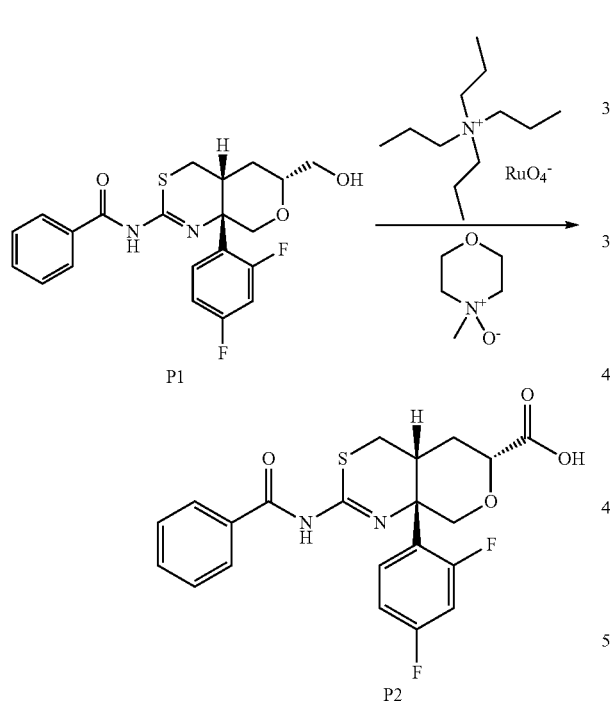

Tetrapropylammonium perruthenate (1.09 g, 3.10 mmol) was added to a mixture of P1 (13.0 g, 31.1 mmol) and 4-methylmorpholine N-oxide monohydrate (25.2 g, 186 mmol) in acetonitrile (207 mL), and the reaction mixture was stirred for 90 minutes at room temperature. After addition of 2-propanol (100 mL), it was stirred for an additional 2 hours and then concentrated in vacuo. The residue was partitioned between ethyl acetate and 0.5 M aqueous sodium hydroxide solution. The organic layer was extracted twice with 0.5 M aqueous sodium hydroxide solution, and the combined aqueous layers were acidified to a pH of approximately 1 with 2 M aqueous hydrochloric acid, then extracted three times with ethyl acetate. The combined ethyl acetate layers were dried over sodium sulfate, filtered, and concentrated under reduced pressure; the residue was dissolved in dichloromethane, washed with water and with saturated aqueous sodium chloride solution, dried over sodium sulfate, filtered, and concentrated in vacuo. Purification via chromatography on silica gel (Gradient: 0% to 20% methanol in dichloromethane) provided the product as a reddish solid. Yield: 12.36 g, 28.58 mmol, 92%. LCMS m/z 433.2 [M+H]$^+$. $^1$H NMR (400 MHz, CD$_3$OD) δ 8.09-8.13 (m, 2H), 7.52-7.57 (m, 1H), 7.43-7.51 (m, 3H), 7.03-7.11 (m, 2H), 4.35 (dd, J=11.2, 3.4 Hz, 1H), 4.19 (dd, J=12.0, 1.4 Hz, 1H), 3.97 (d, J=12.1 Hz, 1H), 3.20-3.27 (m, 1H), 2.96 (dd, half of ABX pattern, J=13.1, 4.0 Hz, 1H), 2.78 (dd, half of ABX pattern, J=13.2, 2.8 Hz, 1H), 2.03-2.15 (m, 2H).

Preparation P3

N-[(4aR,6R,8aS)-8a-(2,4-Difluorophenyl)-6-formyl-4,4a,5,6,8,8a-hexahydropyrano[3,4-d][1,3]thiazin-2-yl]benzamide (P3)

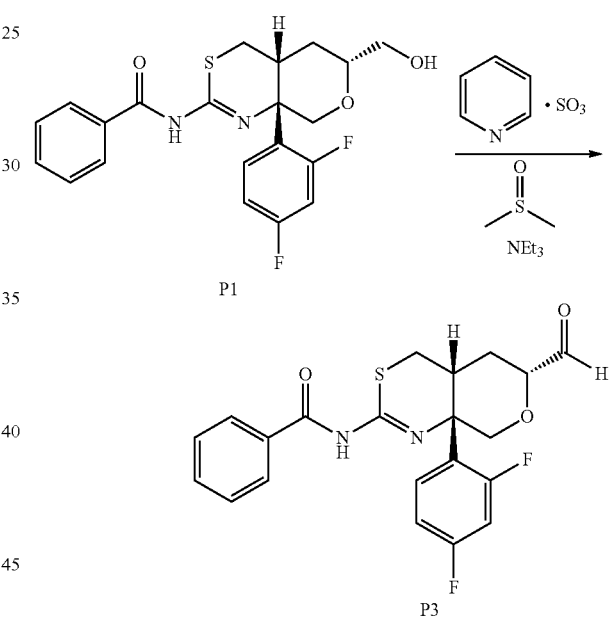

Triethylamine (16.7 mL, 120 mmol) was added in one rapid portion to a solution of P1 (4.18 g, 10.0 mmol) in dichloromethane (200 mL) that was immersed in a room temperature water bath. After 5 minutes, anhydrous dimethyl sulfoxide (9.94 mL, 140 mmol) was rapidly added, followed immediately by solid sulfur trioxide pyridine complex (98%, 13.0 g, 80.0 mmol) in a single portion. The resulting solution was stirred at ambient temperature for 6.5 hours, then diluted with a 1:1 mixture of water and saturated aqueous sodium chloride solution (200 mL) and stirred for 10 minutes. The aqueous layer was extracted with dichloromethane (2×200 mL), and the combined organic layers were washed with water (100 mL), washed with saturated aqueous sodium chloride solution (100 mL), dried over sodium sulfate, filtered, and concentrated in vacuo. Purification via silica gel chromatography (Gradient: 0% to 100% ethyl acetate in heptane) gave the product as a white solid. Yield: 2.81 g, 6.75 mmol, 67%. LCMS m/z 414.9 [M−H$^+$]. $^1$H NMR (400 MHz, CDCl$_3$)

47
δ 9.71 (s, 1H), 8.20 (br d, J=7 Hz, 2H), 7.50-7.56 (m, 1H), 7.36-7.49 (m, 3H), 6.86-6.99 (m, 2H), 4.23 (br d, J=12.1 Hz, 1H), 4.12 (dd, J=12.1, 2.9 Hz, 1H), 3.94 (d, J=12.5 Hz, 1H), 3.13-3.22 (m, 1H), 3.04 (dd, J=13.1, 4.1 Hz, 1H), 2.69 (dd, J=13.1, 2.9 Hz, 1H), 2.02-2.14 (m, 1H), 1.92-1.99 (m, 1H).
48
Preparation P4
N-[(4R,4aR,6R,8aS)-8a-(2,4-Difluorophenyl)-6-(hydroxymethyl)-4-methyl-4,4a,5,6,8,8a-hexahydropyrano[3,4-d][1,3]thiazin-2-yl]benzamide (P4)
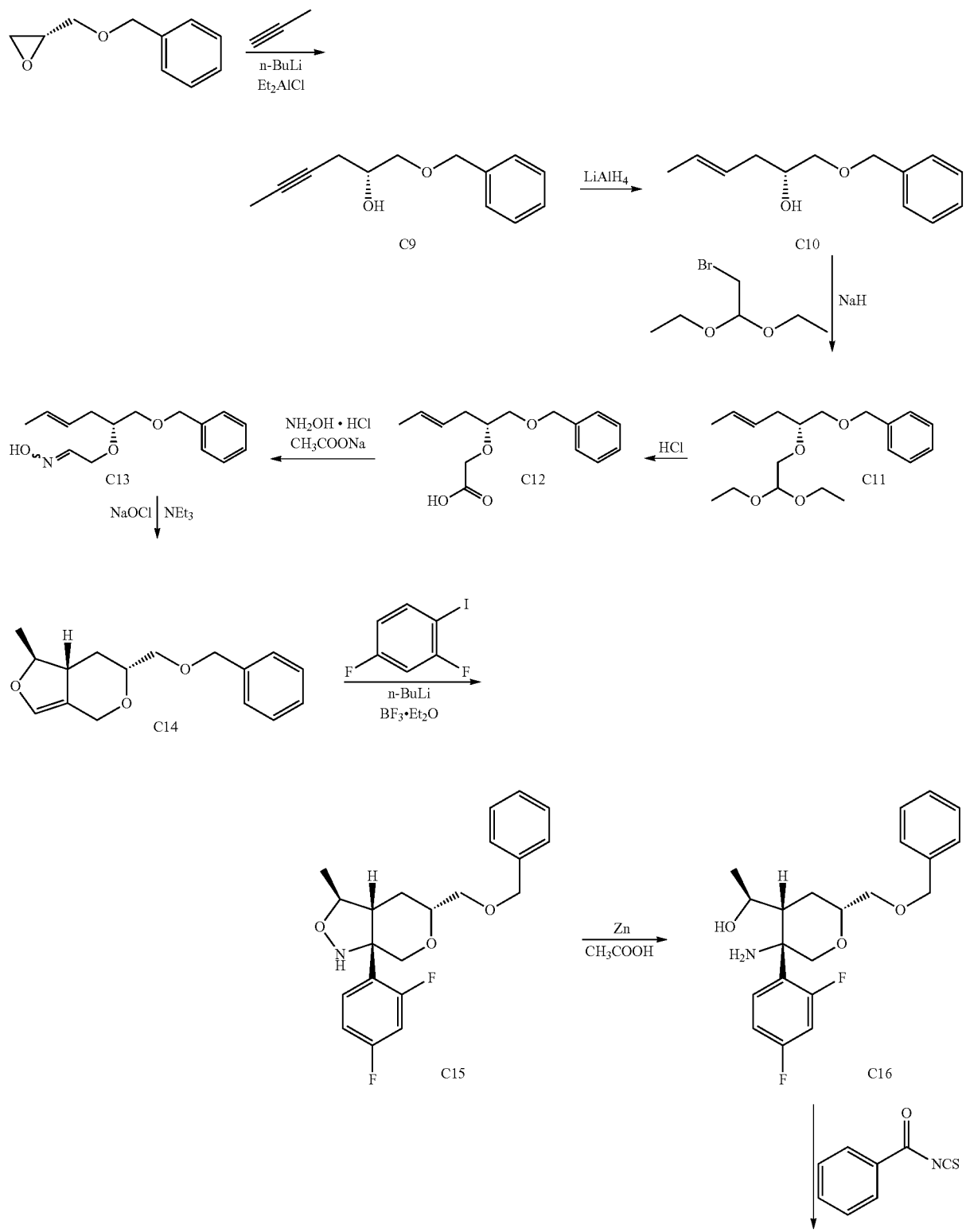

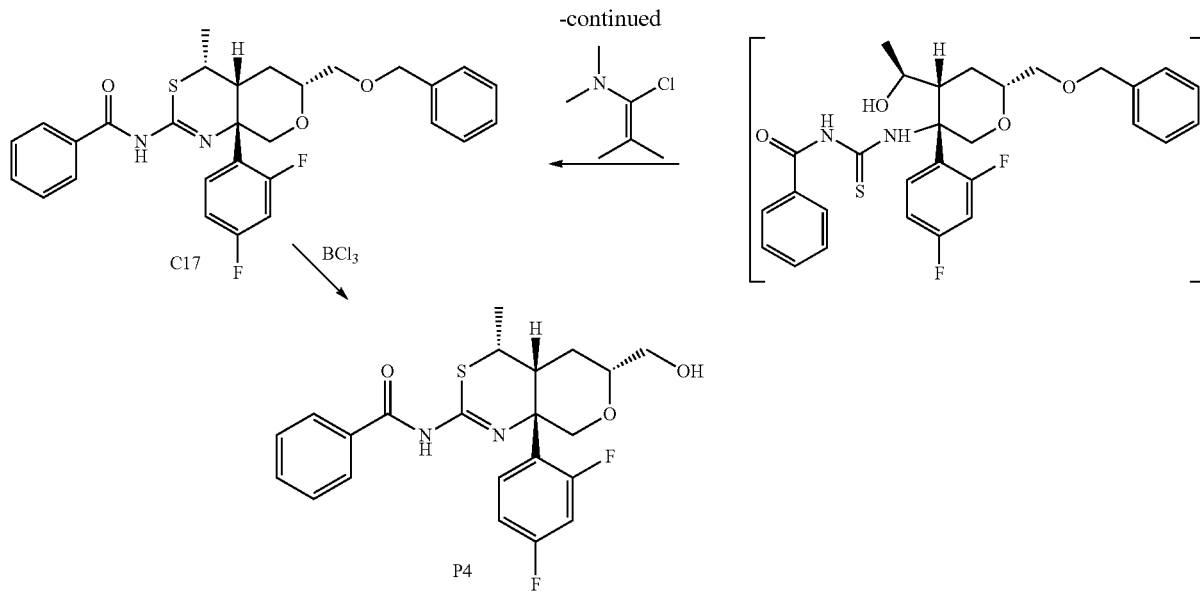

Step 1. Synthesis of (2R)-1-(benzyloxy)hex-4-yn-2-ol (C9)

Prop-1-yne was bubbled through a solution of n-butyllithium (2.5 M in hexanes, 1.06 L, 2.65 mol) in toluene (5 L) at 0° C. for 1.5 hours, until a thin suspension was obtained. Diethylaluminum chloride (1 M in hexanes, 2.44 L, 2.44 mol) was added, and the reaction mixture was stirred at 0° C. for 2 hours, whereupon (2R)-2-[(benzyloxy)methyl]oxirane (200 g, 1.22 mol) was added. After 10 minutes, the reaction was quenched with water (100 mL) and then with aqueous hydrochloric acid (2 M, 2 L). The mixture was extracted with ethyl acetate (2 L), and the combined organic layers were dried over sodium sulfate, concentrated, and purified by chromatography on silica gel (Gradient: 2% to 17% ethyl acetate in petroleum ether) to afford the product as a pale brown oil. Yield: 250 g, 1.22 mol, 100%. $^1$H NMR (400 MHz, CDCl$_3$) δ 7.28-7.41 (m, 5H), 4.58 (s, 2H), 3.89-3.97 (s, 1H), 3.60 (dd, half of ABX pattern, J=9.5, 3.9 Hz, 1H), 3.50 (dd, half of ABX pattern, J=9.5, 6.7 Hz, 1H), 2.50 (br s, 1H), 2.38-2.43 (m, 2H), 1.79 (t, J=2.6 Hz, 3H).

Step 2. Synthesis of (2R,4E)-1-(benzyloxy)hex-4-en-2-ol (C10)

Lithium aluminum hydride (93 g, 2.4 mol) was gradually added portion-wise to a 10-20° C. solution of C9 (167 g, 0.818 mol) in 1,2-dimethoxyethane (2.2 L), and the reaction was heated at 100° C. for 16 hours. The reaction mixture was allowed to cool to room temperature, and was then quenched with ice followed by aqueous hydrochloric acid (2 M, 2 L) at 10-20° C. The resulting mixture was extracted with ethyl acetate (2 L), and the combined organic layers were dried over sodium sulfate and concentrated, affording the product as a pale brown oil. This material was used for the next step without further purification. Yield: 160 g, 0.78 mol, 95%. $^1$H NMR (400 MHz, CDCl$_3$) δ 7.27-7.41 (m, 5H), 5.49-5.60 (m, 1H), 5.39-5.49 (m, 1H), 4.56 (s, 2H), 3.80-3.88 (m, 1H), 3.51 (dd, half of ABX pattern, J=9.5, 3.4 Hz, 1H), 3.39 (dd, half of ABX pattern, J=9.3, 1.9 Hz, 1H), 2.4 (br s, 1H), 2.16-2.24 (m, 2H), 1.66-1.70 (m, 3H).

Step 3. Synthesis of ({[(2R,4E)-2-(2,2-diethoxyethoxyl)hex-4-en-1-yl]oxy}methyl)benzene (C11)

To a 0° C. suspension of sodium hydride (60% in mineral oil, 93 g, 2.3 mol) in tetrahydrofuran (1.6 L) was slowly added C10 (160 g, 0.78 mol), and the reaction mixture was stirred at 0° C. for 1 hour. 2-Bromo-1,1-diethoxyethane (460 g, 2.33 mol) was added to the cold mixture, which was then heated at reflux for 16 hours. The reaction was carefully quenched by addition of water (1 L) and the mixture was extracted with ethyl acetate (2 L). The combined organic layers were dried over sodium sulfate and concentrated to provide the product as a brown oil, which was used for the next step without purification. $^1$H NMR (400 MHz, CDCl$_3$), characteristic peaks: δ 7.24-7.38 (m, 5H), 5.37-5.54 (m, 2H), 4.54 (s, 2H), 2.19-2.30 (m, 2H), 1.64 (br d, J=5 Hz, 3H).

Step 4. Synthesis of {[(2R,4E)-1-(benzyloxy)hex-4-en-2-yl]oxy}acetaldehyde (C12)

To a solution of crude C11 (from the previous step, 0.78 mol) in tetrahydrofuran (1.5 L) was added aqueous hydrochloric acid (2 M, 850 mL, 1.7 mol) at 25° C., and the reaction mixture was stirred at 60° C. for 1 hour. After it had cooled to room temperature, it was saturated with solid sodium chloride and extracted with ethyl acetate (2 L). The combined organic layers were washed with saturated aqueous sodium chloride solution (3×1 L), dried over sodium sulfate and concentrated to afford the product as a pale brown oil, which was used for the next step without further purification. $^1$H NMR (400 MHz, CDCl$_3$), characteristic peaks: δ 9.72 (br s, <1H), 7.27-7.40 (m, 5H), 5.4-5.57 (m, 2H), 1.66 (br d, J=5 Hz, 3H).

Step 5. Synthesis of 2-{[(2R,4E)-1-(benzyloxy)hex-4-en-2-yl]oxy}-N-hydroxyethanimine (C13)

To a solution of crude C12 (from the previous step, 0.78 mol) in a mixture of ethanol and water (2:1, 2.1 L) was added sodium acetate (472 g, 5.75 mol) followed by hydroxylamine hydrochloride (238 g, 3.42 mol). The reaction mixture was stirred at 60° C. for 16 hours, then concentrated to remove ethanol and extracted with dichloromethane (2 L). The combined organic layers were washed sequentially with saturated aqueous sodium carbonate solution (2×1 L) and saturated aqueous sodium chloride solution (1 L), dried over sodium sulfate, and concentrated. Silica gel chromatography (Gradient: 2% to 17% ethyl acetate in petroleum ether) provided the product as a pale yellow oil. Yield: 105 g, 0.399 mol, 51% over three steps.

Step 6. Synthesis of (3S,3aR,5R)-5-[(benzyloxy)methyl]-3-methyl-3,3a,4,5-tetrahydro-7H-pyrano[3,4-c][1,2]oxazole (C14)

Aqueous sodium hypochlorite (6.15%, 1 L) was slowly added to a mixture of C13 (100 g, 0.38 mol) and triethylamine (2.9 g, 28.6 mmol) in dichloromethane (2 L). The reaction mixture was stirred at 25° C. for 1 hour, then washed with water (5×2 L), dried over sodium sulfate and concentrated. Silica gel chromatography (Gradient: 2% to 17% ethyl acetate in petroleum ether) afforded the product as a white solid. Yield: 58 g, 0.22 mol, 58%.

Additional purification could be carried out via recrystallization. To a solution of C14 (174 g) at reflux in tert-butyl methyl ether (135 mL) was added heptane (430 mL), until a thin cloudy mixture was obtained. This was allowed to slowly cool to 25° C. and then kept motionless for 16 hours. The resulting precipitate was collected via filtration and washed with heptane (100 mL) to provide a white solid (142 g); this was recrystallized again in the same manner to afford the product as a white solid. Yield:

102 g, 59%. LCMS m/z 262.2 [M+H]$^+$. $^1$H NMR (400 MHz, CDCl$_3$) δ 7.26-7.39 (m, 5H), 4.70 (d, J=13.7 Hz, 1H), 4.58 (AB quartet, J$_{AB}$=12.1 Hz, Δv$_{AB}$=13.2 Hz, 2H), 4.14-4.25 (m, 2H), 3.63-3.71 (m, 1H), 3.56 (dd, half of ABX pattern, J=10.2, 5.9 Hz, 1H), 3.48 (dd, half of ABX pattern, J=10.1, 4.3 Hz, 1H), 2.93 (ddd, J=11.3, 11.2, 6.7 Hz, 1H), 2.12 (ddd, J=12.8, 6.6, 1.2 Hz, 1H), 1.46 (d, J=6.2 Hz, 3H), 1.45-1.57 (m, 1H).

Step 7. Synthesis of (3S,3aR,5R,7aS)-5-[(benzyloxy)methyl]-7a-(2,4-difluorophenyl)-3-methylhexahydro-1H-pyrano[3,4-c][1,2]oxazole (C15)

A solution of 2,4-difluoro-1-iodobenzene (30 mL, 250 mmol) in a 10:1 mixture of toluene and tetrahydrofuran (191 mL) was cooled to −70° C. and treated drop-wise with n-butyllithium (2.5 M in hexanes, 90 mL, 220 mmol) over 30 minutes. After the reaction mixture had stirred at −70° C. for an additional 30 minutes, boron trifluoride diethyl etherate (28 mL, 230 mmol) and a solution of C14 (30 g, 110 mmol) in a 10:1 mixture of toluene and tetrahydrofuran (574 mL) were simultaneously added drop-wise over 30 minutes. At this point, the reaction was quenched via addition of aqueous ammonium chloride solution. The aqueous layer was extracted three times with ethyl acetate, and the combined organic layers were washed with water and with saturated aqueous sodium chloride solution. The organic layer was dried over sodium sulfate, filtered, and concentrated in vacuo; purification via silica gel chromatography (Gradient: 0% to 100% ethyl acetate in heptane) afforded the product as a dark yellow oil. Yield: 39.4 g, 105 mmol, 95%. LCMS m/z 376.3 [M+H]$^+$. $^1$H NMR (400 MHz, CDCl$_3$) δ 7.98 (ddd, J=9.2, 9.0, 6.8 Hz, 1H), 7.29-7.40 (m, 5H), 6.90 (dddd, J=8.9, 7.9, 2.5, 1.0 Hz, 1H), 6.80 (ddd, J=11.9, 8.6, 2.5 Hz, 1H), 4.60 (AB quartet, J$_{AB}$=12.1 Hz, Δv$_{AB}$=19.9 Hz, 2H), 4.03 (qd, J=6.4, 2.5 Hz, 1H), 3.81-3.88 (m, 2H), 3.56 (dd, half of ABX pattern, J=10.2, 6.2 Hz, 1H), 3.49 (dd, half of ABX pattern, J=10.2, 4.1 Hz, 1H), 2.81-2.87 (m, 1H), 2.04 (ddd, J=14.2, 7.5, 2.9 Hz, 1H), 1.49-1.60 (m, 1H), 0.79 (d, J=6.4 Hz, 3H).

Step 8. Synthesis of (1S)-1-[(2R,4R,5S)-5-amino-2-[(benzyloxy)methyl]-5-(2,4-difluorophenyl)tetrahydro-2H-pyran-4-yl]ethanol (C16)

To a mixture of C15 (39.4 g, 105 mmol) in acetic acid (379 mL) was added zinc dust (89.2 g, 1.36 mol), and the reaction mixture was stirred at room temperature for 18 hours. The zinc was removed via filtration through diatomaceous earth, and the filtrate was concentrated in vacuo and partitioned between ethyl acetate and aqueous 1 M sodium hydroxide solution. The aqueous layer was extracted twice with ethyl acetate, and the combined organic layers were washed with saturated aqueous sodium chloride solution, dried over sodium sulfate, filtered, and concentrated under reduced pressure. Chromatography on silica gel (Gradient: 0% to 100% ethyl acetate in heptane) provided the product as a colorless oil. Yield: 32.6 g, 86.4 mmol, 82%. LCMS m/z 378.3 [M+H]$^+$. $^1$H NMR (400 MHz, CDCl$_3$) δ 7.67 (ddd, J=9, 9, 6.5 Hz, 1H), 7.28-7.39 (m, 5H), 6.89-6.97 (m, 1H), 6.81 (ddd, J=12.6, 8.6, 2.6 Hz, 1H), 4.61 (AB quartet, J$_{AB}$=12.2 Hz, Δv$_{AB}$=22.2 Hz, 2H), 4.06 (dd, J=11.5, 2.4 Hz, 1H), 3.76-3.84 (m, 1H), 3.66-3.74 (m, 1H), 3.60 (br dd, half of ABX pattern, J=10.2, 6.3 Hz, 1H), 3.53 (dd, half of ABX pattern, J=10.2, 3.8 Hz, 1H), 3.32 (br d, J=11 Hz, 1H), 2.52 (ddd, J=12.6, 4.5, 4.5 Hz, 1H), 1.70-1.83 (m, 1H), 1.61 (ddd, J=13.9, 4.7, 2.6 Hz, 1H), 0.87 (d, J=6.6 Hz, 3H).

Step 9. Synthesis of N-[(4R,4aR,6R,8aS)-6-[(benzyloxy)methyl]-8a-(2,4-difluorophenyl)-4-methyl-4,4a,5,6,8,8a-hexahydropyrano[3,4-d][1,3]thiazin-2-yl]benzamide (C17)

Benzoyl isothiocyanate (98%, 13.1 mL, 95.5 mmol) was added drop-wise to a solution of C16 (36.4 g, 96.4 mmol) in dichloromethane (964 mL), and the reaction mixture was allowed to stir at room temperature for 18 hours. LCMS indicated formation of the acyl thiourea intermediate: LCMS m/z 541.2 [M+H]$^+$. 1-Chloro-N,N,2-trimethylprop-1-en-1-amine (Ghosez's reagent, 96%, 33.2 mL, 241 mmol) was added drop-wise, and the reaction mixture was stirred at room temperature for 30 minutes. It was then diluted with aqueous sodium bicarbonate solution and extracted three times with dichloromethane. The combined organic layers were washed with water and with saturated aqueous sodium chloride solution, dried over sodium sulfate, filtered, and concentrated in vacuo. Silica gel chromatography (Gradient: 20% to 40% ethyl acetate in heptane) provided the product as a white foam. Yield: 40.0 g, 76.5 mmol, 79%. LCMS m/z 523.2 [M+H]$^+$. $^1$H NMR (400 MHz, CDCl$_3$), characteristic peaks: δ 6.84-6.96 (m, 2H), 4.58 (AB quartet, J$_{AB}$=12.0 Hz, Δv$_{AB}$=24.7 Hz, 2H), 4.15-4.21 (m, 1H), 3.86-3.94 (m, 1H), 3.84 (d, J=12 Hz, 1H), 3.63 (dd, half of ABX pattern, J=10.1, 6.3 Hz, 1H), 3.50 (dd, half of ABX pattern, J=10.2, 4.4 Hz, 1H), 3.22-3.33 (br m, 1H), 2.87-2.98 (br m, 1H), 1.25 (d, J=7.0 Hz, 3H).

Step 10. Synthesis of N-[(4R,4aR,6R,8a5)-8a-(2,4-difluorophenyl)-6-(hydroxymethyl)-4-methyl-4,4a,5,6,8,8a-hexahydropyrano[3,4-d][1,3]thiazin-2-yl]benzamide (P4)

Compound C17 was converted to the product according to the method described for synthesis of P1 in Preparation P1. In this case, rather than chromatographic purification, the crude product was triturated with dichloromethane and heptane to afford the product as a white solid. Yield: 14.3 g, 33.1 mmol, 92%. LCMS m/z 433.3 [M+H]+. ¹H NMR (400 MHz, CD₃OD) δ 8.12 (br d, J=7 Hz, 2H), 7.51-7.57 (m, 1H), 7.40-7.49 (m, 3H), 7.02-7.11 (m, 2H), 4.15 (br d, J=12 Hz, 1H), 3.91 (d, J=12.0 Hz, 1H), 3.71-3.78 (m, 1H), 3.60 (d, J=5.2 Hz, 2H), 3.19-3.28 (br m, 1H), 2.97-3.05 (br m, 1H), 1.74-1.82 (m, 1H), 1.50-1.62 (m, 1H), 1.26 (d, J=7.0 Hz, 3H).

Preparation P5 (4R,4aR,6R,8aS)-2-(Benzoylamino)-8a-(2,4-difluorophenyl)-4-methyl-4,4a,5,6,8,8a-hexahydropyrano[3,4-d][1,3]thiazine-6-carboxylic acid (P5)

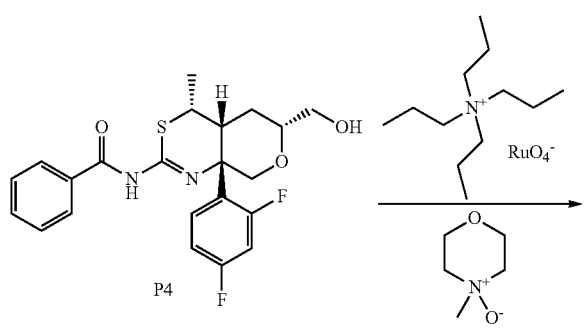

Tetrapropylammonium perruthenate (2.50 g, 7.11 mmol) was added in four equal portions to a mixture of P4 (32.4 g, 75.0 mmol) and 4-methylmorpholine N-oxide monohydrate (50.0 g, 370 mmol) in acetonitrile (200 mL). An exotherm occurred; the reaction flask was cooled in an ice-methanol slurry as needed and stirred for 2 hours. 2-Propanol (125 mL) was added, and stirring was continued for 1 hour at room temperature. After removal of solvent in vacuo, the residue was partitioned between dichloromethane (700 mL) and aqueous hydrochloric acid (1 M, 500 mL). The aqueous layer was extracted with dichloromethane (2×300 mL), and the combined organic layers were extracted with aqueous sodium hydroxide solution (0.25 M, 3×600 mL). The combined aqueous layers were adjusted to pH 1-2 with 5 M aqueous hydrochloric acid, and then extracted with dichloromethane (3×650 mL). The combined organic layers were dried over sodium sulfate, filtered, and concentrated under reduced pressure; purification via silica gel chromatography [Gradient: 0% to 100% (89:10:1 dichloromethane/methanol/acetic acid) in dichloromethane] provided material that was then co-concentrated with toluene (3×50 mL). The resulting solid was partitioned between dichloromethane (200 mL) and aqueous sodium hydroxide solution (0.25 M, 600 mL). The organic layer was extracted with additional aqueous sodium hydroxide solution (0.25 M, 100 mL), and the combined aqueous layers were adjusted to pH 1-2 with 5 M aqueous hydrochloric acid. The aqueous layer was extracted with dichloromethane (3×500 mL), and the combined organic layers were dried over sodium sulfate, filtered, and concentrated in vacuo to afford the product as an off-white granular solid. Yield: 30.6 g, 68.5 mmol, 91%. LCMS m/z 447.1 [M+H]+. ¹H NMR (400 MHz, DMSO-d₆) δ 8.10-8.15 (m, 2H), 7.55-7.61 (m, 1H), 7.47-7.53 (m, 2H), 7.32-7.44 (m, 2H), 7.22 (ddd, J=8.5, 8.5, 2.5 Hz, 1H), 4.28 (dd, J=11.8, 2.4 Hz, 1H), 4.01 (br AB quartet, J$_{AB}$=12 Hz, Δν$_{AB}$=12 Hz, 2H), 3.06-3.16 (m, 1H), 2.95-3.04 (m, 1H), 1.99-2.07 (m, 1H), 1.53-1.66 (m, 1H), 1.21 (d, J=6.9 Hz, 3H).

Preparation P6

N-[(4S,4aR,6R,8aS)-8a-(2,4-Difluorophenyl)-4-(fluoromethyl)-6-(hydroxymethyl)-4,4a,5,6,8,8a-hexahydropyrano[3,4-d][1,3]thiazin-2-yl]benzamide (P6)

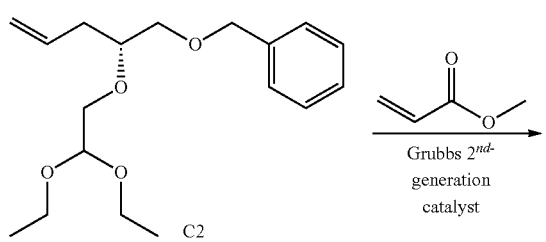

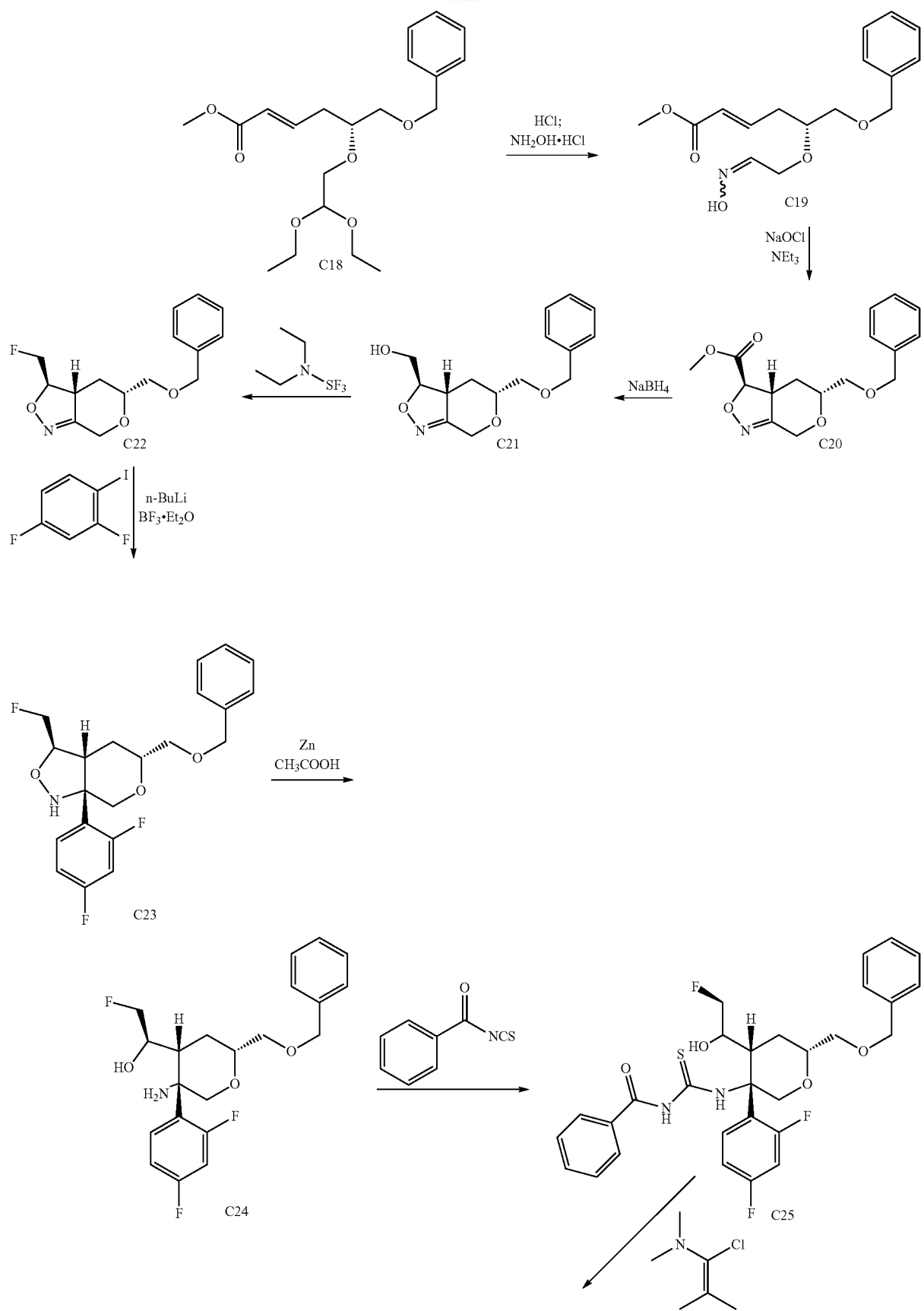

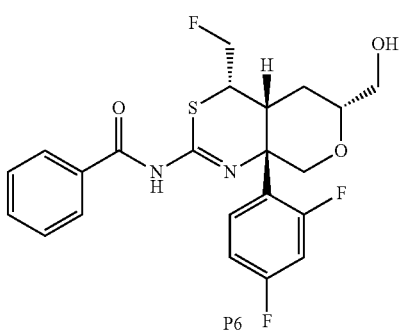

P6

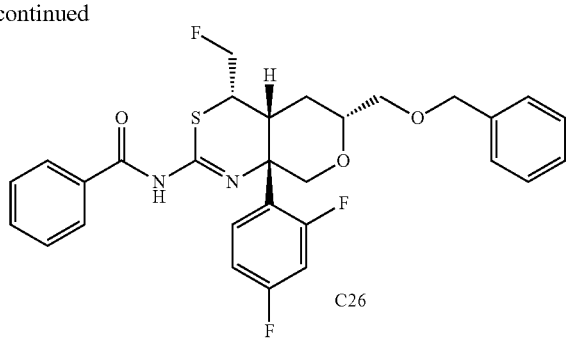

C26

Step 1. Synthesis of methyl (2E,5R)-6-(benzyloxy)-5-(2,2-diethoxyethoxyl)hex-2-enoate (C18)

This reaction was carried out in 10 batches. To a solution of C2 (10 g, 32 mmol) in dichloromethane (400 mL) was added [1,3-bis-(2,4,6-trimethylphenyl)-2-imidazolidinylidene]dichloro(phenylmethylene)(tricyclohexylphosphine)ruthenium (Grubbs $2^{nd}$-generation catalyst, 1.38 g, 1.62 mmol) and methyl prop-2-enoate (69.7 g, 0.81 mol), and the reaction mixture was stirred at room temperature for 18 hours. Solvent was removed in vacuo, and the residue was purified via silica gel chromatography (Eluent: 3:1 petroleum ether/ethyl acetate) to provide the product as a yellow oil. Combined yield: 70 g, 0.19 mol, 59%. $^1$H NMR (400 MHz, CDCl$_3$) δ 7.27-7.38 (m, 5H), 6.94-7.04 (m, 1H), 5.89 (br d, J=15.6 Hz, 1H), 4.58 (dd, J=5.3, 5.0 Hz, 1H), 4.54 (s, 2H), 3.73 (s, 3H), 3.44-3.7 (m, 9H), 2.41-2.55 (m, 2H), 1.21 (t, J=7.0 Hz, 3H), 1.20 (t, J=7.0 Hz, 3H).

Step 2. Synthesis of methyl (2E,5R)-6-(benzyloxy)-5-{[2-(hydroxyimino)ethyl]oxy}hex-2-enoate (C19)

This reaction was carried out in 13 batches. Aqueous hydrochloric acid (1 M, 27 mL, 27 mmol) was added to a solution of C18 (10 g, 27 mmol) in tetrahydrofuran (20 mL), and the reaction mixture was stirred at room temperature for 15 minutes. Hydroxylamine hydrochloride (3.8 g, 55 mmol) was added, and stirring was continued for 18 hours. After concentration in vacuo, the aqueous residues from the various batches were combined and extracted with ethyl acetate (3×500 mL), and the combined organic layers were dried over sodium sulfate and concentrated, providing the product as a yellow oil. This material was used in the next step without further purification. Combined yield: 110 g, assumed quantitative.

Step 3. Synthesis of methyl (3R,3a R,5R)-5-[(benzyloxy)methyl]-3,3a,4,5-tetrahydro-7H-pyrano[3,4-c][1,2]oxazole-3-carboxylate (C20)

To a solution of C19 (110 g from the previous step, 0.35 mol) in dichloromethane (500 mL) was added triethylamine (2.7 g, 27 mmol). Aqueous sodium hypochlorite (6%, 1.5 L, 1.2 mol) was then added at a rate such that the internal reaction temperature remained between 20° C. and 25° C. The reaction mixture was stirred at 20-25° C. for 20 minutes, whereupon it was partitioned between water (500 mL) and dichloromethane (500 mL). The organic layer was dried over sodium sulfate and concentrated; silica gel chromatography (Eluent: 3:1 petroleum ether/ethyl acetate) afforded the product as a yellow oil. Yield: 65 g, 0.21 mol, 60% over 2 steps. $^1$H NMR (400 MHz, CDCl$_3$), characteristic peaks: δ 7.28-7.40 (m, 5H), 4.75 (d, J=13.3 Hz, 1H), 4.56-4.63 (m, 3H), 4.22 (dd, J=13.4, 1.0 Hz, 1H), 3.83 (s, 3H), 3.58 (dd, half of ABX pattern, J=10.2, 5.6 Hz, 1H), 3.50 (dd, half of ABX pattern, J=10.2, 4.4 Hz, 1H), 2.30 (br dd, J=13, 6.5 Hz, 1H), 1.64-1.75 (m, 1H).

Step 4. Synthesis of {(3R,3aR,5R)-5-[(benzyloxy)methyl]-3,3a,4,5-tetrahydro-7H-pyrano[3,4-c][1,2]oxazol-3-yl}methanol (C21)

This reaction was carried out in 5 batches. A solution of C20 (13 g, 42 mmol) in ethanol (90 mL) and tetrahydrofuran (180 mL) was cooled to 0° C. Sodium borohydride (2.4 g, 63 mmol) was added, and the reaction mixture was stirred at room temperature for 20 minutes. The reaction mixture was quenched with saturated aqueous ammonium chloride solution (100 mL) and concentrated in vacuo. The aqueous residue was extracted with ethyl acetate (3×300 mL), and the combined organic layers were dried over sodium sulfate, filtered and concentrated. Chromatography on silica gel (Eluent: 3:1 petroleum ether/ethyl acetate) provided the product as a yellow oil. Combined yield: 50 g, 180 mmol, 86%. $^1$H NMR (400 MHz, CDCl$_3$) δ 7.27-7.39 (m, 5H), 4.71 (d, J=13.4 Hz, 1H), 4.58 (AB quartet, $J_{AB}$=12.2 Hz, $\Delta v_{AB}$=11.8 Hz, 2H), 4.24-4.29 (m, 1H), 4.21 (dd, J=13.4, 1.1 Hz, 1H), 3.96-4.03 (m, 1H), 3.68-3.77 (m, 2H), 3.57 (dd, half of ABX pattern, J=10.2, 5.8 Hz, 1H), 3.49 (dd, half of ABX pattern, J=10.1, 4.3 Hz, 1H), 3.38-3.47 (m, 1H), 2.15 (ddd, J=12.9, 6.7, 1.5 Hz, 1H), 1.83-1.89 (m, 1H), 1.6-1.67 (m, 1H).

Step 5. Synthesis of (3R,3aR,5R)-5-[(benzyloxy)methyl]-3-(fluoromethyl)-3,3a,4,5-tetrahydro-7H-pyrano[3,4-c][1,2]oxazole (C22)

This reaction was carried out in 10 batches. To a −70° C. solution of C21 (5.0 g, 18 mmol) in dichloromethane (150 mL) was added (diethylamino)sulfur trifluoride (11.6 g, 72.0 mmol); the reaction mixture was stirred at −70° C. for 2 hours, then warmed to room temperature and stirred for 1 hour. The reaction was quenched by addition of saturated aqueous sodium bicarbonate solution (500 mL), and the aqueous layer was extracted with dichloromethane (2×300 mL). The combined organic layers were dried over sodium sulfate, filtered and concentrated. Silica gel chromatography (Eluent: 5:1 petroleum ether/ethyl acetate) provided the product as a yellow oil. Combined yield: 12.6 g, 45.1 mmol, 25%. LCMS m/z 280.1 [M+H]$^+$. $^1$H NMR (400 MHz, CDCl$_3$) δ 7.28-7.41 (m, 5H), 4.51-4.76 (m, 5H), 4.30-4.42 (m, 1H), 4.22 (dd, J=13.4, 1.1 Hz, 1H), 3.69-3.77 (m, 1H), 3.58 (dd, half of ABX pattern, J=10.0, 5.8 Hz, 1H), 3.50 (dd, half of ABX pattern, J=10.2, 4.4 Hz, 1H), 3.32-3.42 (m, 1H), 2.19 (br dd, J=13, 7 Hz, 1H), 1.60-1.71 (m, 1H).

Step 6. Synthesis of (3R,3a R,5R,7a5)-5-[(benzyloxy)methyl]-7a-(2,4-difluorophenyl)-3-(fluoromethyl)hexahydro-1H-pyrano[3,4-c][1,2]oxazole (C23)

Boron trifluoride diethyl etherate (12.7 mL, 103 mmol) was added to a −78° C. solution of 2,4-difluoro-1-iodobenzene (12.6 mL, 105 mmol) in a 10:1 mixture of toluene and tetrahydrofuran (250 mL). n-Butyllithium (2.5 M in hexanes, 40 mL, 100 mmol) was added drop-wise, and the reaction mixture was stirred at −78° C. for 15 minutes. A solution of C22 (14 g, 50 mmol) in minimal 10:1 toluene/tetrahydrofuran was added, and stirring was continued at −78° C. for 15 minutes. At this point, the reaction mixture was poured into aqueous ammonium chloride solution; the aqueous layer was extracted three times with ethyl acetate, and the combined organic layers were washed with water, washed with saturated aqueous sodium chloride solution, dried over sodium sulfate, filtered and concentrated in vacuo. Chromatography on silica gel (Gradient: 0% to 30% ethyl acetate in heptane) afforded the product as an oil. Yield: 18 g, 46 mmol, 92%. LCMS m/z 394.2 [M+H]$^+$. $^1$H NMR (400 MHz, CDCl$_3$) δ 7.94 (ddd, J=9.1, 9.0, 6.7 Hz, 1H), 7.29-7.41 (m, 5H), 6.88-6.94 (m, 1H), 6.82 (ddd, J=11.9, 8.6, 2.5 Hz, 1H), 6.42 (br s, 1H), 4.61 (AB quartet, J$_{AB}$=12.2 Hz, Δν$_{AB}$=13.7 Hz, 2H), 4.11-4.20 (m, 1H), 4.01 (dd, half of ABX pattern, J=12.9, 2.0 Hz, 1H), [3.81-3.91, 3.73-3.80 and 3.63-3.68 (multiplets, total 4H)], 3.58 (dd, half of ABX pattern, J=10.2, 6.0 Hz, 1H), 3.51 (dd, half of ABX pattern, J=10.2, 4.2 Hz, 1H), 3.09-3.17 (m, 1H), 2.07 (ddd, J=14.1, 7.5, 2.2 Hz, 1H), 1.57-1.69 (m, 1H).

Step 7. Synthesis of (1R)-1-[(2R,4R,5S)-5-amino-2-[(benzyloxy)methyl]-5-(2,4-difluorophenyl)tetrahydro-2H-pyran-4-yl]-2-fluoroethanol (C24)

Compound C23 was converted to the product according to the method described for synthesis of C16 in Preparation P4. In this case, no chromatographic purification was carried out. Yield: 15.6 g, 39.4 mmol, 86%. LCMS m/z 396.2 [M+H]$^+$. $^1$H NMR (400 MHz, CD$_3$OD) δ 7.73 (ddd, J=9.1, 9.0, 6.5 Hz, 1H), 7.26-7.40 (m, 5H), 6.96-7.02 (m, 1H), 6.92 (ddd, J=12.8, 8.9, 2.6 Hz, 1H), 4.59 (s, 2H), [4.11-4.15 and 3.99-4.06 (multiplets, total 2H)], 3.90 (ddd, J=48.2, 9.5, 7.0 Hz, 1H), 3.64-3.79 (m, 2H), 3.63 (dd, half of ABX pattern, J=10.4, 5.7 Hz, 1H), 3.58 (dd, half of ABX pattern, J=10.4, 3.9 Hz, 1H), 3.39 (d, J=11.3 Hz, 1H), 2.73 (ddd, J=12.8, 4.4, 4.3 Hz, 1H), 1.79-1.91 (m, 1H), 1.64 (ddd, J=13.7, 4.2, 2.6 Hz, 1H).

Step 8. Synthesis of N-({(3S,4R,6R)-6-[(benzyloxy)methyl]-3-(2,4-difluorophenyl)-4-[(1R)-2-fluoro-1-hydroxyethyl]tetrahydro-2H-pyran-3-yl}carbamothioyl)benzamide (C25)

Compound C24 was converted to the product according to the method described for synthesis of C7 in Preparation P1. In this case, silica gel chromatography (Gradient: 0% to 100% ethyl acetate in heptane) provided the product as a solid. Yield: 18.7 g, 33.5 mmol, 85%.

Step 9. Synthesis of N-[(4S,4aR,6R,8aS)-6-[(benzyloxy)methyl]-8a-(2,4-difluorophenyl)-4-(fluoromethyl)-4,4a,5,6,8,8a-hexahydropyrano[3,4-d][1,3]thiazin-2-yl]benzamide (C26)

To a solution of C25 (7.50 g, 13.4 mmol) in dichloromethane (180 mL) was added 1-chloro-N,N,2-trimethylprop-1-en-1-amine (8.83 mL, 20.1 mmol), and the reaction mixture was stirred at ambient temperature for 2 hours. It was then partitioned between dichloromethane and water; the aqueous layer was extracted with dichloromethane, and the combined organic layers were washed with saturated aqueous sodium chloride solution, dried over magnesium sulfate, filtered and concentrated in vacuo. Silica gel chromatography (Gradient: 0% to 60% ethyl acetate in heptane) afforded the product as a solid. By $^1$H NMR analysis, some reagent-derived material was still present. Corrected yield: 3.86 g, 7.14 mmol, 53%. LCMS m/z 541.3 [M+H]$^+$. $^1$H NMR (400 MHz, CDCl$_3$), product peaks only, characteristic peaks: δ 8.20 (br d, J=7 Hz, 2H), 7.51-7.57 (m, 1H), 7.43-7.49 (m, 2H), 7.34-7.42 (m, 1H), 7.23-7.34 (m, 5H), 6.86-6.98 (m, 2H), 4.57 (AB quartet, J$_{AB}$=11.9 Hz, Δν$_{AB}$=18.1 Hz, 2H), [4.45-4.66 and 4.33-4.39 (multiplets, total 2H)], 4.19 (br d, J=12 Hz, 1H), 3.82-3.94 (m, 2H), 3.63 (dd, half of ABX pattern, J=10.2, 6.2 Hz, 1H), 3.5-3.57 (m, 1H), 3.49 (dd, half of ABX pattern, J=10.2, 4.4 Hz, 1H), 3.21-3.29 (m, 1H).

Step 10. Synthesis of N-[(4S,4aR,6R,8a5)-8a-(2,4-difluorophenyl)-4-(fluoromethyl)-6-(hydroxymethyl)-4,4a,5,6,8,8a-hexahydropyrano[3,4-d][1,3]thiazin-2-yl]benzamide (P6)

A solution of C26 (13.8 g, 25.5 mmol) in dichloromethane (130 mL) was cooled to 0° C. Boron trichloride (1 M solution in toluene, 76.6 mL, 76.6 mmol) was added in a rapid drop-wise manner, at a rate such that the temperature of the reaction mixture remained at <5° C. throughout the addition. After 10 minutes at 0° C., the reaction mixture was allowed to warm to room temperature and stir for 30 minutes before being carefully quenched via drop-wise addition of methanol (20 mL). The resulting solution was heated at reflux for 30 minutes, cooled to room temperature and concentrated in vacuo. The residue was dissolved in methanol (460 mL) and concentrated under reduced pressure; the resulting material was dissolved in dichloromethane and washed twice with 1 M aqueous sodium hydroxide solution and once with saturated aqueous sodium chloride solution, then dried over sodium sulfate and filtered. The organic layer was concentrated in vacuo to approximately 30% of its original volume, and treated with heptane until a precipitate formed; this was collected via filtration to afford the product as a solid. Yield: 8.5 g, 19 mmol, 74%. LCMS m/z 451.3 [M+H]$^+$. $^1$H NMR (400 MHz, CD$_3$OD) δ 8.06-8.18 (m, 2H), 7.51-7.59 (m, 1H), 7.42-7.51 (m, 3H), 7.02-7.14 (m, 2H), 4.68 (ddd, J=46.6, 9.7, 6.5 Hz, 1H), 4.51 (ddd, J=46.6, 9.7, 7.0 Hz, 1H), 4.16 (br d, J=12 Hz, 1H), 3.93 (d, J=11.9 Hz, 1H), 3.69-3.78 (m, 1H), 3.59 (d, J=5.2 Hz, 2H), 3.40-3.51 (br m, 1H), 3.23-3.3 (br m, 1H, assumed; partially obscured by solvent peak), 1.59-1.74 (m, 2H).

Preparation P7

(4S,4a R,6R,8aS)-2-(Benzoylamino)-8a-(2,4-difluorophenyl)-4-(fluoromethyl)-4,4a,5,6,8,8a-hexahydropyrano[3,4-d][1,3]thiazine-6-carboxylic acid (P7)

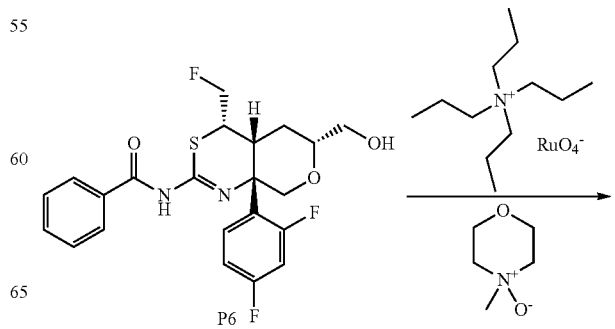

-continued

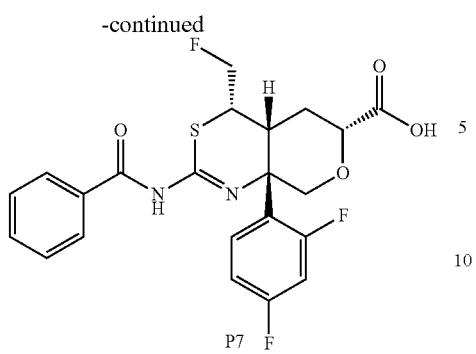

P7

Compound P6 was converted to the product according to the method described for synthesis of P5 in Example P5. The product was obtained as a solid. Yield: 9.9 g, 21 mmol, 74%. LCMS m/z 465.2 [M+H]$^+$. $^1$H NMR (400 MHz, CDCl$_3$), obtained from a similar reaction carried out on small scale (110 mg P6, 80% yield): δ 9.09 (v br s, 2H), 8.07-8.12 (m, 2H), 7.52-7.58 (m, 1H), 7.46 (br dd, J=8, 7 Hz, 2H), 7.32 (ddd, J=8.9, 8.9, 6.2 Hz, 1H), 6.85-6.98 (m, 2H), 4.35-4.66 (m, 2H), 4.08-4.20 (m, 2H), 4.03 (d, half of AB quartet, J=12.2 Hz, 1H), 3.43-3.52 (m, 1H), 3.22 (ddd, J=12.0, 3.9, 3.8 Hz, 1H), 2.06-2.14 (m, 1H), 1.84-1.97 (m, 1H).

Preparation P8

N-[(4S,4aR,6R,8aS)-8a-(2,4-Difluorophenyl)-4-(fluoromethyl)-6-formyl-4,4a,5,6,8,8a-hexahydropyrano[3,4-d][1,3]thiazin-2-yl]benzamide (P8)

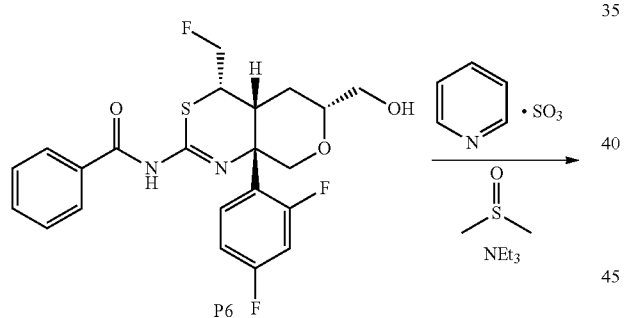

-continued

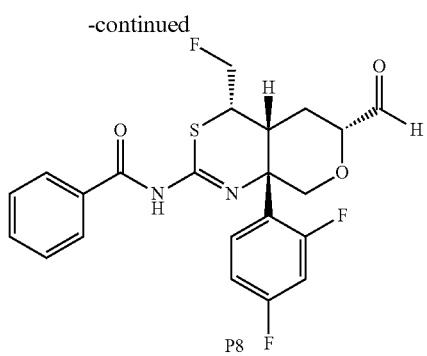

P8

Triethylamine (0.817 mL, 5.86 mmol) was added rapidly to a solution of P6 (660 mg, 1.46 mmol) in dichloromethane (29 mL). After 5 minutes, anhydrous dimethyl sulfoxide (468 μL, 6.59 mmol) was rapidly added, followed immediately by solid sulfur trioxide pyridine complex (98%, 654 mg, 4.03 mmol) in a single portion. The resulting solution was stirred at ambient temperature for 3.5 hours, then diluted with a 1:1 mixture of water and saturated aqueous sodium chloride solution and stirred for 10 minutes. The aqueous layer was extracted twice with dichloromethane, and the combined organic layers were washed with water until the pH of the aqueous wash was pH 6-7. The organic layer was then washed twice with 0.2 M aqueous hydrochloric acid and once with saturated aqueous sodium chloride solution, dried over sodium sulfate, filtered, and concentrated in vacuo. Purification via silica gel chromatography (Gradient: 0% to 75% ethyl acetate in heptane) provided the product as a solid. Yield: 0.54 g, 1.2 mmol, 82%. LCMS m/z 449.1 [M+H]$^+$. $^1$H NMR (400 MHz, CDCl$_3$) δ 9.69 (s, 1H), 8.14 (br d, J=7 Hz, 2H), 7.50-7.57 (m, 1H), 7.46 (br dd, J=8, 7 Hz, 2H), 7.36 (ddd, J=9.0, 8.8, 6.2 Hz, 1H), 6.86-6.98 (m, 2H), 4.35-4.67 (m, 2H), 4.23 (br d, J=12 Hz, 1H), 4.06-4.12 (m, 1H), 3.97 (d, J=12.1 Hz, 1H), 3.46-3.56 (m, 1H), 3.25 (ddd, J=12.0, 4.0, 3.9 Hz, 1H), 1.97 (ddd, J=13.5, 3.5, 3.5 Hz, 1H), 1.74-1.86 (m, 1H).

EXAMPLES

Example 1

(4aR,6R,8aS)-8a-(2,4-Difluorophenyl)-6-(5-fluoro-1-methyl-1H-pyrazol-3-yl)-4,4a,5,6,8,8a-hexahydropyrano[3,4-d][1,3]thiazin-2-amine (1)

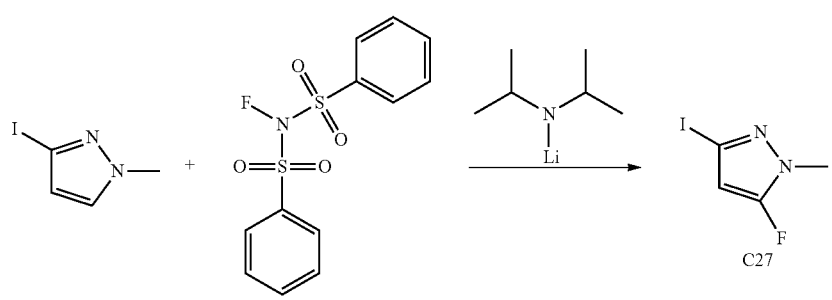

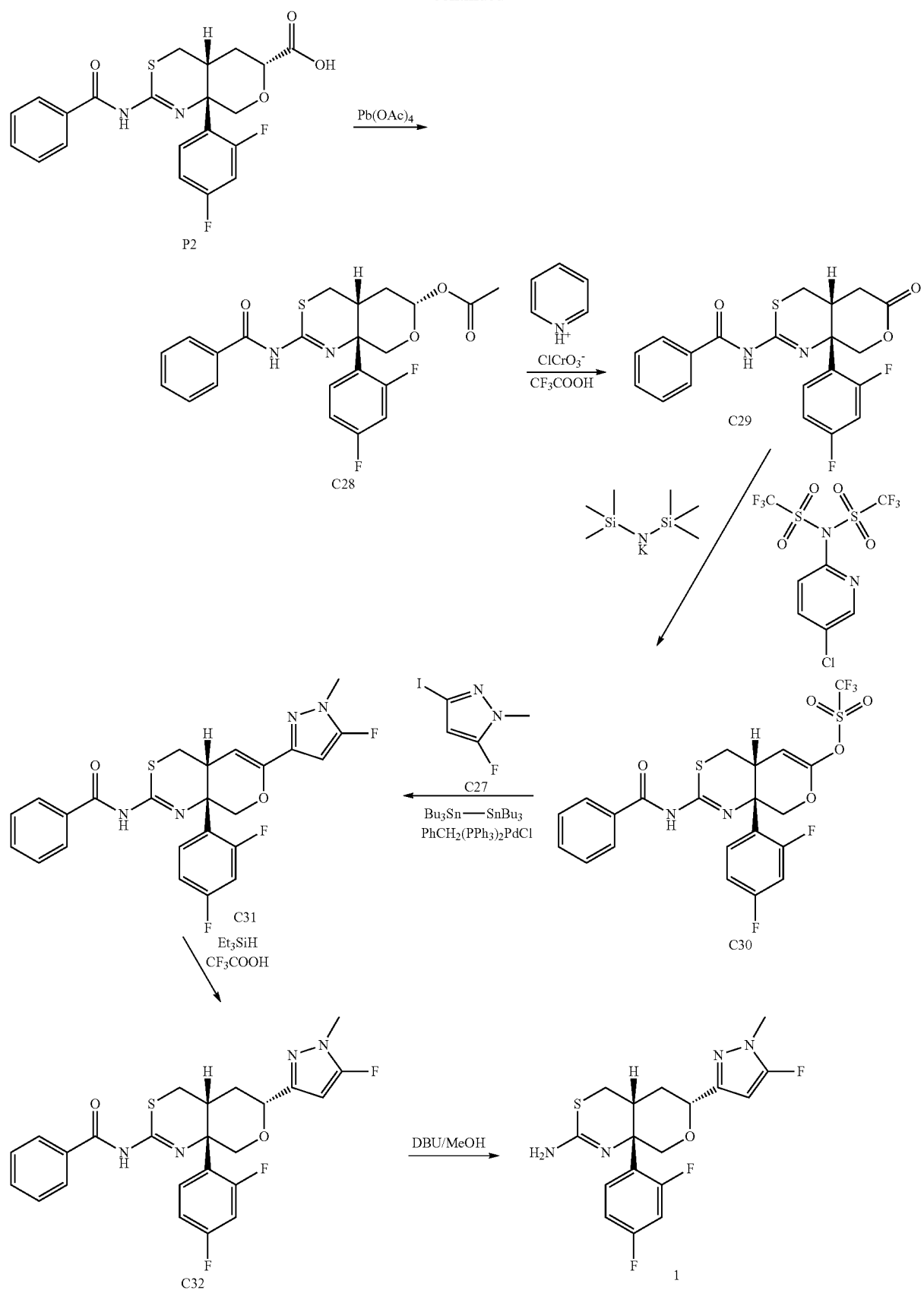

Step 1. Synthesis of 5-fluoro-3-iodo-1-methyl-1H-pyrazole (C27)

Lithium diisopropylamide (2.0 M in heptane/tetrahydrofuran/ethylbenzene, 3.30 mL, 6.60 mmol) was added drop-wise to a −75° C. solution of 3-iodo-1-methyl-1H-pyrazole (97%, 1.29 g, 6.02 mmol) in tetrahydrofuran (25 mL). After 5 minutes, N-fluoro-N-(phenylsulfonyl)benzenesulfonamide (97%, 2.60 g, 8.00 mmol) was added to the cold solution in one portion. The reaction mixture was allowed to warm to 0° C. over 30 minutes, and was then quenched with saturated aqueous ammonium chloride solution (25 mL) and extracted with ethyl acetate (3×30 mL). The combined organic layers were washed with saturated aqueous sodium chloride solution (15 mL), dried over sodium sulfate, filtered, and concentrated in vacuo. Purification via silica gel chromatography (Gradient: 0% to 50% ethyl acetate in heptane) afforded the product as a pale yellow oil. Yield: 435 mg, 1.92 mmol, 32%. GCMS m/z 226 [M+]. $^1$H NMR (400 MHz, CDCl$_3$) δ 5.93 (d, J=6.0 Hz, 1H), 3.74 (d, J=1.2 Hz, 3H).

Step 2. Synthesis of (4a R,6S,8aS)-2-(benzoylamino)-8a-(2,4-difluorophenyl)-4,4a,5,6,8,8a-hexahydropyrano[3,4-d][1,3]thiazin-6-yl acetate (C28)

To a solution of P2 (3.0 g, 6.9 mmol) in tetrahydrofuran (80 mL) and acetic acid (15 mL) was added lead(IV) acetate (19.3 g, 43.5 mmol). After stirring at room temperature for 18 hours, the reaction mixture was diluted with ethyl acetate and filtered through diatomaceous earth. The filtrate was concentrated in vacuo and the residue was purified via chromatography on silica gel (Gradient: 0% to 100% ethyl acetate in heptane), affording the product as a white solid. Yield: 1.38 g, 3.09 mmol, 45%. LCMS m/z 445.1 [M−H+]. $^1$H NMR (400 MHz, CDCl$_3$) δ 8.21 (br d, J=7 Hz, 2H), 7.50-7.56 (m, 1H), 7.36-7.49 (m, 3H), 6.87-6.98 (m, 2H), 6.31 (br d, J=3 Hz, 1H), 4.55 (d, J=12.2 Hz, 1H), 3.59 (br d, J=12 Hz, 1H), 3.44-3.52 (m, 1H), 3.05 (dd, J=13.0, 4.2 Hz, 1H), 2.63 (dd, J=13.0, 2.8 Hz, 1H), 2.38-2.48 (m, 1H), 2.19 (s, 3H), 1.80 (br dd, J=14, 4 Hz, 1H).

Step 3. Synthesis of N-[(4aR,8aS)-8a-(2,4-difluorophenyl)-6-oxo-4,4a,5,6,8,8a-hexahydropyrano[3,4-d][1,3]thiazin-2-yl]benzamide (C29)

The reaction was carried out in two batches. To a solution of C28 (2.5 g, 5.6 mmol/1.66 g, 3.72 mmol) in acetonitrile (25 mL/15 mL) was added trifluoroacetic acid (6 mL/4 mL) at room temperature, followed by pyridinium chlorochromate (6.02 g, 28 mmol/3.98 g, 18.5 mmol) in one portion. The resulting reaction mixtures were stirred at room temperature for 3.5 hours, then combined and poured slowly into saturated aqueous sodium bicarbonate solution (350 mL). The aqueous layer was extracted with ethyl acetate (2×400 mL), and the combined organic layers were washed with saturated aqueous sodium bicarbonate solution (100 mL) and saturated aqueous sodium chloride solution (100 mL), dried over sodium sulfate, filtered, and concentrated in vacuo. Purification via silica gel chromatography (Gradient: 0% to 50% ethyl acetate in petroleum ether) afforded the product as a white foam containing residual dichloromethane. Corrected yield: 2.51 g, 6.24 mmol, 67%. LCMS m/z 403.0 [M+H]+. $^1$H NMR (400 MHz, CDCl$_3$) δ 8.03 (br d, J=7 Hz, 2H), 7.56-7.62 (m, 1H), 7.47-7.54 (m, 2H), 7.31-7.39 (m, 1H), 6.88-6.99 (m, 2H), 4.90 (d, J=11.5 Hz, 1H), 4.29 (d, J=11.7 Hz, 1H), 3.39-3.48 (m, 1H), 2.94-3.05 (m, 2H), 2.84 (dd, half of ABX pattern, J=18.5, 7.6 Hz, 1H), 2.68 (dd, J=13.2, 3.1 Hz, 1H).

Step 4. Synthesis of (4aR,8aS)-2-(benzoylamino)-8a-(2,4-difluorophenyl)-4,4a,8,8a-tetrahydropyrano[3,4-d][1,3]thiazin-6-yl trifluoromethanesulfonate (C30)

A mixture of C29 [2.51 g, 6.24 mmol; this material had been azeotroped with toluene (2×10 mL)] and N-(5-chloropyridin-2-yl)-1,1,1-trifluoro-N-[(trifluoromethyl)sulfonyl]methane-sulfonamide (Comins' reagent, 96%, 10.2 g, 24.9 mmol) in tetrahydrofuran (100 mL) was cooled to −78° C. Potassium bis(trimethylsilyl)amide (0.5 M solution in toluene, 62.4 mL, 31.2 mmol) was added drop-wise over 20 minutes, and the reaction mixture was stirred at −78° C. for 1.1 hours; after addition of aqueous sodium bicarbonate solution (50 mL), it was allowed to warm to room temperature and extracted with ethyl acetate (2×75 mL). The combined organic layers were dried over sodium sulfate, filtered, and concentrated in vacuo. Silica gel chromatography (Gradient: 0% to 60% ethyl acetate in heptane) afforded the product as a pale yellow solid. Yield: 2.43 g, 4.55 mmol, 73%. $^1$H NMR (400 MHz, CDCl$_3$) δ 7.99 (br d, J=8 Hz, 2H), 7.55-7.60 (m, 1H), 7.49 (br dd, J=8, 7 Hz, 2H), 7.39 (ddd, J=9, 9, 6.4 Hz, 1H), 6.94-7.00 (m, 1H), 6.90 (ddd, J=12.4, 8.4, 2.6 Hz, 1H), 4.82 (d, J=10.7 Hz, 1H), 4.77 (d, J=2.0 Hz, 1H), 4.17 (d, J=10.7 Hz, 1H), 3.63-3.69 (m, 1H), 2.97 (dd, J=13.3, 3.1 Hz, 1H), 2.68 (dd, J=13.3, 4.3 Hz, 1H).

Step 5. Synthesis of N-[(4aR,8a5)-8a-(2,4-difluorophenyl)-6-(5-fluoro-1-methyl-1H-pyrazol-3-yl)-4,4a,8,8a-tetrahydropyrano[3,4-d][1,3]thiazin-2-yl]benzamide (C31)

Compound C27 (73.0 mg, 0.323 mmol), C30 (121 mg, 0.226 mmol) and hexabutyldistannane (130 μL, 0.257 mmol) were combined in N,N-dimethylformamide (0.8 mL) in a vial containing a micro stir bar. The vial was vacuum purged and back-filled with nitrogen three times. Benzyl(chloro)bis(triphenylphosphine)palladium(II) (10 mg, 26 μmol) was added, and the purging/back-filling process was carried out twice. The reaction mixture was then stirred at 120° C. for 15 minutes. After cooling to room temperature, the reaction mixture was diluted with ethyl acetate (15 mL) and filtered through a nylon disc. The filtrate was washed with water (2×7 mL), dried over sodium sulfate, filtered, and concentrated in vacuo. Purification via silica gel chromatography (Gradient: 0% to 100% ethyl acetate in heptane) provided the product as an amber solid. Yield: 43 mg, 89 μmol, 39%. LCMS m/z 485.3 [M+H]+. $^1$H NMR (400 MHz, CDCl$_3$) δ 8.11 (br d, J=8 Hz, 2H), 7.47-7.55 (m, 2H), 7.39-7.45 (m, 2H), 6.93-6.99 (m, 1H), 6.89 (ddd, J=12.3, 8.4, 2.6 Hz, 1H), 5.88 (d, J=5.8 Hz, 1H), 5.34 (d, J=2.4 Hz, 1H), 4.75 (br d, J=11.2 Hz, 1H), 4.18 (d, J=11.4 Hz, 1H), 3.72 (d, J=1.2 Hz, 3H), 3.66-3.71 (m, 1H), 3.06 (dd, J=13.2, 3.3 Hz, 1H), 2.78 (dd, J=13.2, 4.7 Hz, 1H).

Step 6. Synthesis of N-[(4aR,6R,8a5)-8a-(2,4-difluorophenyl)-6-(5-fluoro-1-methyl-1H-pyrazol-3-yl)-4,4a,5,6,8,8a-hexahydropyrano[3,4-d][1,3]thiazin-2-yl]benzamide (C32)

Triethylsilane (0.10 mL, 0.63 mmol) and trifluoroacetic acid (25 μL, 0.32 mmol) were added to a 0° C. solution of C31 (32 mg, 66 μmol) in dichloromethane (1.2 mL), and the reaction was allowed to warm to room temperature and stir for 1 hour. Additional triethylsilane and trifluoroacetic acid were periodically added while monitoring the progress of the reaction by LCMS. After addition of a total of 66 equivalents of triethylsilane and 38 equivalents of trifluoroacetic acid, the reaction mixture was allowed to stir at room temperature for 15 hours, then concentrated under a stream of nitrogen and partitioned between dichloromethane (15 mL) and saturated aqueous sodium carbonate solution (10 mL). The aqueous layer was extracted with dichloromethane (2×5 mL) and the combined organic layers were washed with saturated aqueous sodium chloride solution (10 mL), dried over sodium sulfate, filtered, and concentrated in vacuo. Silica gel chromatography (Gradient: 0% to 100% ethyl acetate in heptane) provided the product as an off-white solid. The indicated stereochemistry was supported by NOE studies showing an interaction between the protons at carbons 4a and 6. Yield: 24 mg, 49 μmol, 74%. LCMS m/z 487.2 [M+H]+. $^1$H NMR (400 MHz, CDCl$_3$) δ 8.22 (br d, J=7 Hz, 2H), 7.49-7.55 (m, 1H), 7.39-7.48 (m, 3H), 6.86-6.98 (m, 2H), 5.80 (d, J=5.7 Hz, 1H), 4.69 (dd, J=11.6, 2.4 Hz, 1H), 4.30 (dd, J=12.2, 1.7 Hz, 1H), 3.91 (br d, J=12 Hz, 1H), 3.70 (d, J=1.2 Hz, 3H), 3.22-3.30 (m, 1H), 3.05 (dd, J=12.9, 4.1 Hz, 1H), 2.69 (dd, J=12.9, 2.8 Hz, 1H), 2.27-2.39 (m, 1H), 1.95-2.03 (m, 1H).

Step 7. Synthesis of (4aR,6R,8aS)-8a-(2,4-difluorophenyl)-6-(5-fluoro-1-methyl-1H-pyrazol-3-yl)-4,4a,5,6,8,8a-hexahydropyrano[3,4-d][1,3]thiazin-2-amine (1)

1,8-Diazabicyclo[5.4.0]undec-7-ene (DBU, 4.0 μL, 27 μmol) was added to a solution of C32 (17 mg, 35 μmol) in methanol (0.75 mL), and the reaction mixture was heated at 50° C. for 18 hours. Solvent was removed in vacuo, and the residue was partitioned between saturated aqueous sodium bicarbonate solution (2 mL) and ethyl acetate (5 mL). The aqueous layer was extracted with ethyl acetate (2×5 mL) and the combined organic layers were dried over sodium sulfate, filtered, and concentrated under reduced pressure to afford the crude product as an off-white solid (12 mg). This was combined with the crude product (5 mg) from a similar reaction carried out on C32 (6.3 mg, 13 μmol) and subjected to purification via silica gel chromatography (Gradient: 0% to 17.5% methanol in dichloromethane) to afford the product as a white solid. Yield: 11.7 mg, 30.0 μmol, 62%. LCMS m/z 383.2 [M+H]+. $^1$H NMR (400 MHz, CDCl$_3$) δ 7.40 (ddd, J=9.0, 9.0, 6.6 Hz, 1H), 6.85-6.91 (m, 1H), 6.81 (ddd, J=12.4, 8.5, 2.6 Hz, 1H), 5.81 (d, J=5.7 Hz, 1H), 4.64 (dd, J=11.7, 2.4 Hz, 1H), 4.21 (dd, J=11.2, 2.3 Hz, 1H), 3.94 (d, J=11.4 Hz, 1H), 3.72 (d, J=1.2 Hz, 3H), 2.97-3.07 (m, 2H), 2.62-2.68 (m, 1H), 2.13-2.24 (m, 1H), 1.78-1.85 (m, 1H).

Example 2

(4a R,6R,8aS)-8a-(2,4-Difluorophenyl)-6-(5-fluoropyridin-2-yl)-4,4a,5,6,8,8a-hexahydropyrano[3,4-d][1,3]thiazin-2-amine (2)

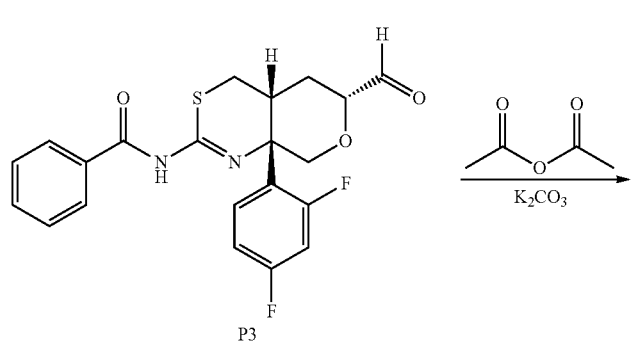

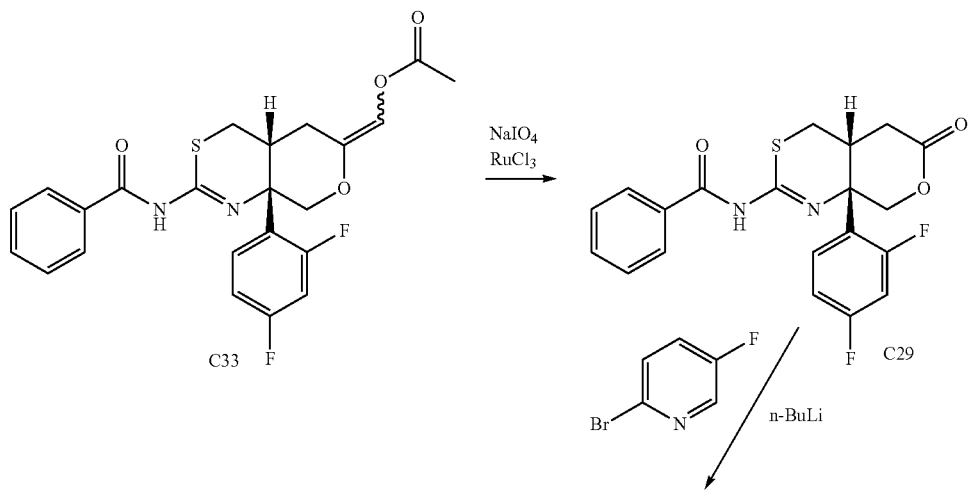

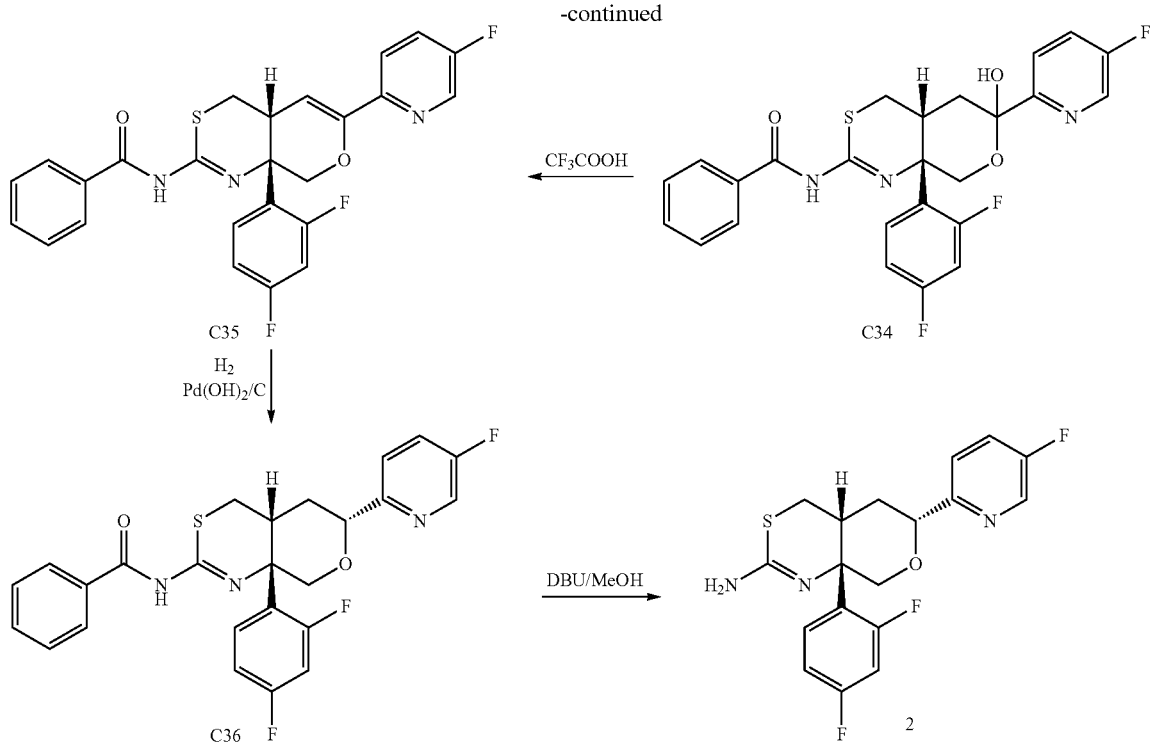

Step 1. Synthesis of [(4aR,8aS)-2-(benzoylamino)-8a-(2,4-difluorophenyl)-4a,5,8,8a-tetrahydropyrano[3,4-d][1,3]thiazin-6(4H)-ylidene]methyl acetate (C33)

Acetic anhydride (1.5 mL, 16 mmol) was added to a slurry of P3 (661 mg, 1.59 mmol) and potassium carbonate (1.34 g, 9.70 mmol) in acetonitrile (16 mL). After the flask had been flushed with nitrogen, the reaction mixture was heated at reflux for 2.5 hours, then allowed to cool to room temperature and stir for 18 hours. The slurry was diluted with ethyl acetate and filtered; the solids were washed with ethyl acetate, and the combined filtrates were concentrated in vacuo. Purification using silica gel chromatography (Gradient: 0% to 100% ethyl acetate in heptane) afforded the product as a white solid, which was assigned via $^1$H NMR as a roughly 4:1 mixture of geometric isomers. Yield: 437 mg, 0.953 mmol, 60%. LCMS m/z 459.1 [M+H]$^+$. $^1$H NMR (400 MHz, CDCl$_3$), peaks from major isomer only: δ8.09-8.32 (br s, 2H), 7.50-7.56 (m, 1H), 7.39-7.45 (m, 3H), 6.85-6.99 (m, 2H), 6.75 (d, J=1.9 Hz, 1H), 4.31 (dd, J=11.7, 1.2 Hz, 1H), 4.02 (d, J=11.8 Hz, 1H), 3.13-3.26 (m, 1H), 2.97-3.07 (m, 1H), 2.70-2.87 (m, 2H), 2.19 (s, 3H), 2.17-2.25 (m, 1H).

Step 2. Synthesis of N-[(4aR,8aS)-8a-(2,4-difluorophenyl)-6-oxo-4,4a,5,6,8,8a-hexahydropyrano[3,4-d][1,3]thiazin-2-yl]benzamide (C29)

A solution of C33 (430 mg, 0.938 mmol), ruthenium(III) chloride (5.8 mg, 28 μmol) and sodium periodate (98.5%, 407 mg, 1.87 mmol) in acetonitrile (0.5 mL) and a 1:1 mixture of 1,2-dichloroethane and water (5 mL) was stirred for 3 hours at room temperature, then allowed to stand for 18 hours without stirring. After dilution with saturated aqueous sodium thiosulfate solution (25 mL), the mixture was extracted with ethyl acetate (3×50 mL), and the combined organic layers were dried over sodium sulfate, filtered, and concentrated in vacuo. Silica gel chromatography (Gradient: 0% to 80% ethyl acetate in heptane) provided the product as a white solid. Yield: 237 mg, 0.589 mmol, 63%. LCMS m/z 403.1 [M+H]$^+$. $^1$H NMR (400 MHz, CDCl$_3$) δ 7.99 (br d, J=8 Hz, 2H), 7.49-7.54 (m, 1H), 7.43 (br dd, J=8, 7 Hz, 2H), 7.32 (ddd, J=9.0, 9.0, 6.3 Hz, 1H), 6.81-6.93 (m, 2H), 4.85 (d, J=11.7 Hz, 1H), 4.24 (d, J=11.5 Hz, 1H), 3.35-3.44 (m, 1H), 2.87-2.97 (m, 2H), 2.80 (dd, half of ABX pattern, J=18.7, 7.5 Hz, 1H), 2.63 (dd, J=13.1, 3.1 Hz, 1H).

Step 3. Synthesis of N-[(4aR,8a5)-8a-(2,4-difluorophenyl)-6-(5-fluoropyridin-2-yl)-6-hydroxy-4,4a,5,6,8,8a-hexahydropyrano[3,4-d][1,3]thiazin-2-yl]benzamide (C34)

A solution of 2-bromo-5-fluoropyridine (355 mg, 2.02 mmol) in toluene (10 mL) was cooled to −78° C. n-Butyllithium (2.5 M solution in hexanes, 790 μL, 1.98 mmol) was added drop-wise over 5 minutes, and stirring was continued at −78° C. for 50 minutes. After addition of a solution of C29 (162 mg, 403 μmol) in toluene (1 mL), the reaction mixture was stirred for an additional 1.5 hours at −78° C., whereupon it was quenched with saturated aqueous sodium bicarbonate solution (20 mL) and allowed to warm to room temperature. Ethyl acetate (20 mL) was added, and the aqueous layer was extracted with additional ethyl acetate (2×30 mL). The combined organic layers were dried over sodium sulfate, filtered, and concentrated in vacuo; purification via silica gel chromatography (Gradient: 0% to 90% ethyl acetate in heptane) afforded the product as an off-white solid. By $^1$H NMR analysis, this was tentatively assigned as a mixture of epimers at the hydroxyl group. Yield: 120 mg, 240 μmol, 60%. LCMS m/z 500.2 [M+H]$^+$. $^1$H NMR (400 MHz, CDCl$_3$), characteristic peaks of major epimer: δ 8.38 (d, J=2.7 Hz, 1H), 8.28 (br d, J=7.5 Hz, 2H), 7.61 (dd, J=8.7, 4.4 Hz, 1H), 7.52-7.57 (m, 1H), 4.89 (d, J=12.3 Hz, 1H), 3.76-3.84 (m, 1H), 3.68 (d, J=12.2 Hz, 1H), 3.12 (dd, J=12.9, 4.1 Hz, 1H), 2.67 (dd, J=13.0, 2.8 Hz, 1H), 2.43-2.52 (m, 1H), 1.88 (dd, J=13.4, 4.2 Hz, 1H); characteristic peaks of minor epimer: δ8.32 (d, J=2.7 Hz, 1H), 7.67 (dd, J=9, 4 Hz, 1H), 4.94 (dd, J=9.5, 2 Hz, 1H), 4.64 (d, J=9 Hz, 1H), 2.89-2.96 (m, 1H), 2.71-2.77 (m, 1H), 2.21-2.28 (m, 1H).

Step 4. Synthesis of N-[(4aR,8aS)-8a-(2,4-difluorophenyl)-6-(5-fluoropyridin-2-yl)-4,4a,8,8a-tetrahydropyrano[3,4-d][1,3]thiazin-2-yl]benzamide (C35)

A mixture of C34 (56.7 mg, 114 μmol), trifluoroacetic acid (1.0 mL) and 1,2-dichloroethane (1.0 mL) was stirred at 42° C. for 5.5 hours, and then at 38° C. for 18 hours. After removal of solvents in vacuo, the residue was partitioned between aqueous sodium bicarbonate solution (4 mL) and ethyl acetate (5 mL). The aqueous layer was extracted with additional ethyl acetate (3×5 mL) and the combined organic layers were dried over sodium sulfate, filtered, and concentrated under reduced pressure. Chromatography on silica gel (Gradient: 0% to 90% ethyl acetate in heptane) provided the product as a white solid. Yield: 42 mg, 87 μmol, 76%. NMR (400 MHz, CD$_3$OD), characteristic peaks: δ 8.38 (br d, J=2.9 Hz, 1H), 8.00 (br d, J=7 Hz, 2H), 7.70 (dd, J=9.0, 4.4 Hz, 1H), 7.47-7.63 (m, 3H), 7.41 (br dd, J=7.7, 7.3 Hz, 2H), 7.03-7.11 (m, 2H), 5.98 (d, J=2.4 Hz, 1H), 4.78 (d, J=11.0 Hz, 1H), 4.33 (d, J=11.0 Hz, 1H), 3.06 (dd, half of ABX pattern, J=13.2, 3.3 Hz, 1H), 2.95 (dd, half of ABX pattern, J=13.3, 4.6 Hz, 1H).

Step 5. Synthesis of N-[(4aR,6R,8aS)-8a-(2,4-difluorophenyl)-6-(5-fluoropyridin-2-yl)-4,4a,5,6,8,8a-hexahydropyrano[3,4-d][1,3]thiazin-2-yl]benzamide (C36)

A mixture of C35 (43 mg, 90 μmol) and palladium hydroxide (20% on carbon, wet, 50 mg) in methanol (10 mL) was shaken vigorously at 40° C. under hydrogen (45 psi) for 18 hours. The reaction mixture was filtered through diatomaceous earth, and the filtrate was concentrated in vacuo. Silica gel chromatography (Gradient: 0% to 100% ethyl acetate in heptane) afforded the product as a white solid. Starting material C35 was also isolated, as a white solid (16 mg). Yield, corrected for recovered starting material: 6.5 mg, 13 μmol, 23%. LCMS m/z 484.2 [M+H]$^+$. $^1$H NMR (400 MHz, CD$_3$OD), characteristic peaks: δ 8.39-8.41 (m, 1H), 8.13 (br d, J=7 Hz, 2H), 7.45 (br dd, J=8, 7 Hz, 2H), 7.05-7.15 (m, 2H), 4.35 (dd, J=11.9, 1.7 Hz, 1H), 4.08 (d, J=11.9 Hz, 1H), 3.01 (dd, half of ABX pattern, J=13.2, 4.1 Hz, 1H), 2.81 (dd, half of ABX pattern, J=13.2, 2.9 Hz, 1H), 2.12-2.20 (m, 1H), 1.98-2.10 (m, 1H).

Step 6. Synthesis of (4aR,6R,8aS)-8a-(2,4-difluorophenyl)-6-(5-fluoropyridin-2-yl)-4,4a,5,6,8,8a-hexahydropyrano[3,4-d][1,3]thiazin-2-amine (2)

A mixture of C36 (16 mg, 33 μmol) and 1,8-diazabicyclo[5.4.0]undec-7-ene (5.0 μL, 33 μmol) in methanol (2 mL) was heated at 63° C. for 18 hours. After removal of solvent in vacuo, silica gel chromatography (Gradient: 0% to 15% methanol in dichloromethane) provided the product as a white solid. Yield: 8.7 mg, 23 μmol, 70%. LCMS m/z 380.1 [M+H]$^+$. $^1$H NMR (400 MHz, CD$_3$OD) δ 8.38-8.40 (m, 1H), 7.61-7.65 (m, 2H), 7.40 (ddd, J=9.6, 8.8, 6.6 Hz, 1H), 6.96-7.05 (m, 2H), 4.76 (dd, J=11.4, 2.8 Hz, 1H), 4.29 (dd, J=11.2, 2.0 Hz, 1H), 3.89 (d, J=11.2 Hz, 1H), 3.08-3.16 (m, 1H), 2.94 (dd, J=12.6, 4.2 Hz, 1H), 2.72-2.77 (m, 1H), 1.97-2.04 (m, 1H), 1.86-1.97 (m, 1H).

Example 3

5-[(4aR,6R,8aS)-2-Amino-8a-(2,4-difluorophenyl)-4,4a,5,6,8,8a-hexahydropyrano[3,4-d][1,3]thiazin-6-yl]-1-methylpyridin-2(1H)-one (3)

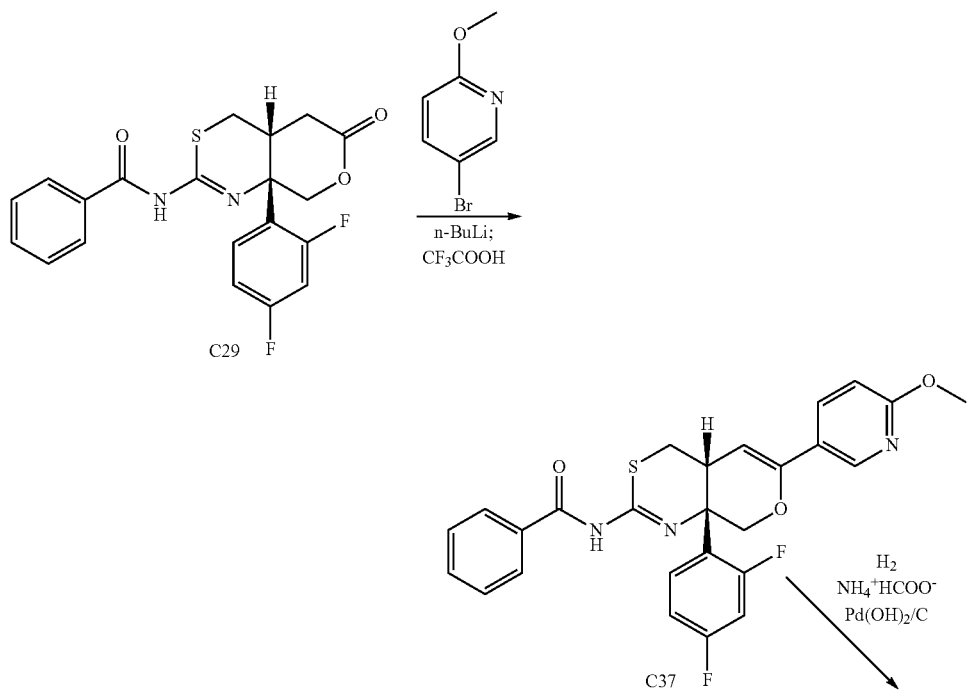

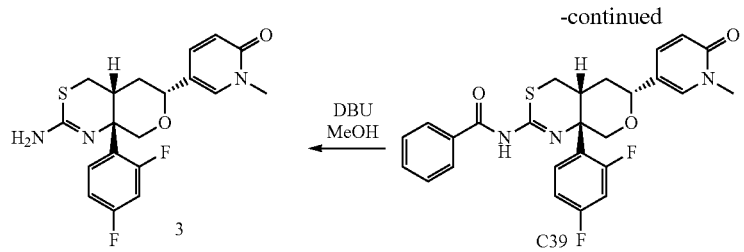
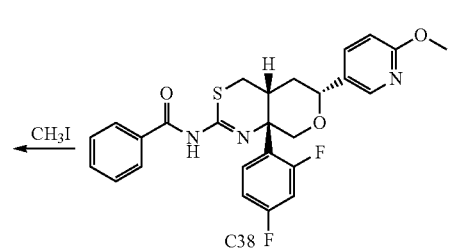

Step 1. Synthesis of N-[(4aR,8aS)-8a-(2,4-difluorophenyl)-6-(6-methoxypyridin-3-yl)-4,4a,8,8a-tetrahydropyrano[3,4-d][1,3]thiazin-2-yl]benzamide (C37)

The product was synthesized from C29 using the method described for preparation of C35 in Example 2, except that 5-bromo-2-methoxypyridine was used instead of 2-bromo-5-fluoropyridine, and the first step was carried out in tetrahydrofuran instead of toluene. The product was obtained as a white solid. LCMS m/z 494.2 [M+H]+. 1H NMR (400 MHz, CDCl3) δ 8.40 (dd, J=2.5, 0.6 Hz, 1H), 8.08-8.13 (m, 2H), 7.75 (dd, J=8.7, 2.5 Hz, 1H), 7.46-7.54 (m, 2H), 7.38-7.43 (m, 2H), 6.94-7.00 (m, 1H), 6.91 (ddd, J=12.3, 8.4, 2.5 Hz, 1H), 6.69 (dd, J=8.7, 0.8 Hz, 1H), 5.16 (d, J=2.4 Hz, 1H), 4.78 (br d, J=11.2 Hz, 1H), 4.20 (d, J=11.2 Hz, 1H), 3.93 (s, 3H), 3.69-3.74 (br m, 1H), 3.08 (d, J=13.2, 3.2 Hz, 1H), 2.79 (dd, J=13.2, 4.6 Hz, 1H).

Step 2. Synthesis of N-[(4aR,6R,8aS)-8a-(2,4-difluorophenyl)-6-(6-methoxypyridin-3-yl)-4,4a,5,6,8,8a-hexahydropyrano[3,4-d][1,3]thiazin-2-yl]benzamide (C38)

Ammonium formate (97%, 32 mg, 0.49 mmol) was added to a mixture of C37 (116 mg, 0.235 mmol) and palladium hydroxide (20% on carbon, wet, 200 mg) in methanol (10 mL), and the reaction mixture was vigorously shaken at 40° C. under hydrogen (45 psi) for 24 hours. Additional palladium hydroxide (50 mg) was added, and hydrogenation was continued at 40° C. for an additional 24 hours. The reaction mixture was filtered through diatomaceous earth, and the filter pad was washed sequentially with methanol, dichloromethane and ethyl acetate; the combined filtrates were concentrated in vacuo. Purification via chromatography on silica gel (Gradient: 0% to 100% ethyl acetate in hexanes) provided the product. Starting material C37 (17 mg) was also isolated. Yield, corrected for recovered starting material: 30 mg, 60 µmol, 30%. LCMS m/z 496.3 [M+H]+.

Step 3. Synthesis of N-[(4aR,6R,8aS)-8a-(2,4-difluorophenyl)-6-(1-methyl-6-oxo-1,6-dihydropyridin-3-yl)-4,4a,5,6,8,8a-hexahydropyrano[3,4-d][1,3]thiazin-2-yl]benzamide (C39)

Iodomethane (0.05 mL, 0.8 mmol) was added to a solution of C38 (35.2 mg, 71.0 µmol) in acetonitrile (0.8 mL), and the reaction mixture was heated at 45° C. for 30 hours. Solvent was removed in vacuo, and the crude product was used directly in the following reaction. Yield: 35 mg, assumed quantitative. 1H NMR (400 MHz, CDCl3), characteristic peaks: δ 8.23 (br d, J=8 Hz, 2H), 6.87-6.99 (m, 2H), 4.51 (br d, J=11 Hz, 1H), 4.26 (br d, J=12 Hz, 1H), 3.05 (dd, J=13.0, 4.0 Hz, 1H), 2.71 (dd, J=13.1, 2.6 Hz, 1H), 1.87-1.94 (m, 1H).

Step 4. Synthesis of 5-[(4aR,6R,8aS)-2-amino-8a-(2,4-difluorophenyl)-4,4a,5,6,8,8a-hexahydropyrano[3,4-d][1,3]thiazin-6-yl]-1-methylpyridin-2(1H)-one (3)

1,8-Diazabicyclo[5.4.0]undec-7-ene (7.0 µL, 50 µmol) was added to a solution of C39 (from the previous step, 35 mg, 71 µmol) in methanol (1 mL), and the reaction mixture was stirred at 60° C. for 18 hours. Purification via reversed phase high-performance liquid chromatography (Column: Waters XBridge C18, 5 µm; Mobile phase A: 0.03% ammonium hydroxide in water (v/v); Mobile phase B: 0.03% ammonium hydroxide in acetonitrile (v/v); Gradient: 20% to 50% B) afforded the product as a solid. Yield: 7.0 mg, 18 µmol, 25% over two steps. LCMS m/z 392.1 [M+H]+. 1H NMR (600 MHz, DMSO-d6) δ 7.61 (d, J=2.2 Hz, 1H), 7.34-7.40 (m, 2H), 7.18-7.24 (m, 1H), 7.11 (ddd, J=8.5, 8.4, 2.5 Hz, 1H), 6.39 (d, J=9.2 Hz, 1H), 6.12 (br s, 2H), 4.41 (br d, J=11 Hz, 1H), 4.03 (dd, J=10.7, 2 Hz, 1H), 3.65 (d, J=10.5 Hz, 1H), 3.42 (s, 3H), 2.80-2.85 (m, 1H), 2.76 (dd, half of ABX pattern, J=12.5, 4.0 Hz, 1H), 2.68 (dd, half of ABX pattern, J=12.7, 2.8 Hz, 1H), 1.80-1.89 (m, 1H), 1.68-1.74 (m, 1H).

Example 4

(4aR,6R,8aS)-8a-(2,4-Difluorophenyl)-6-(imidazo[1,2-a]pyrimidin-2-yl)-4,4a,5,6,8,8a-hexahydropyrano[3,4-d][1,3]thiazin-2-amine, hydrochloride salt (4)

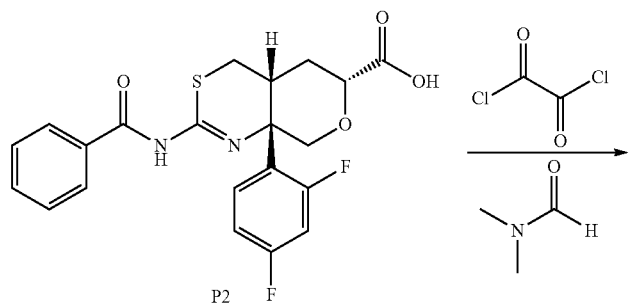

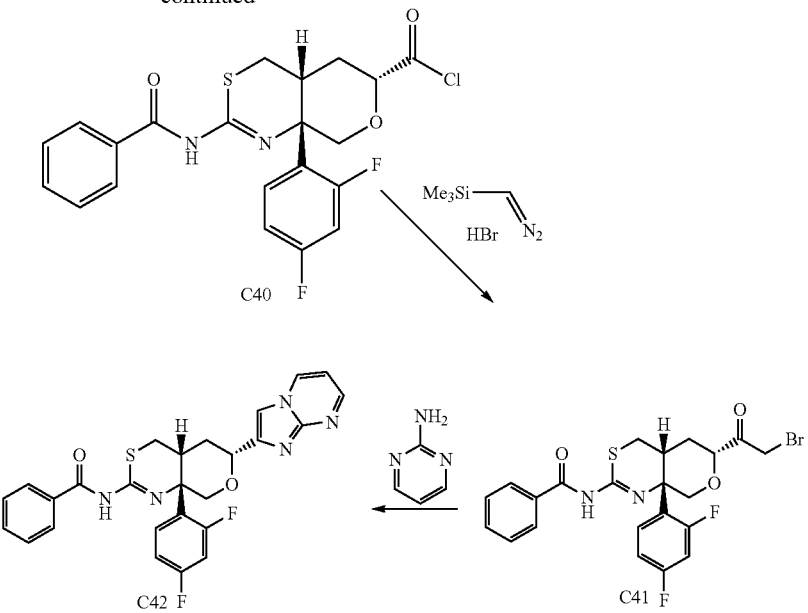

Step 1. Synthesis of (4aR,6R,8aS)-2-(benzoylamino)-8a-(2,4-difluorophenyl)-4,4a,5,6,8,8a-hexahydropyrano[3,4-d][1,3]thiazine-6-carbonyl chloride (C40)

To a solution of P2 (580 mg, 1.34 mmol) in dichloromethane (7 mL) was added oxalyl chloride (0.253 mL, 2.95 mmol) drop-wise, followed by N,N-dimethylformamide (16 µL, 0.21 mmol). The reaction mixture was stirred for 30 minutes, then concentrated in vacuo. This material was used directly in the following step. Yield: 600 mg, 1.33 mmol, 99%. LCMS m/z 447.1 ([M+H]$^+$ for corresponding methyl ester, due to reaction of acid chloride with methanol in the LCMS eluent). $^1$H NMR (400 MHz, CDCl$_3$) δ 8.39-8.43 (m, 2H), 7.66-7.71 (m, 1H), 7.50-7.62 (m, 3H), 7.04-7.10 (m, 1H), 6.95 (ddd, J=12.7, 8.0, 2.5 Hz, 1H), 4.51 (dd, J=11.8, 2.5 Hz, 1H), 4.46 (d, J=12.9 Hz, 1H), 4.18 (dd, J=12.8, 1.3 Hz, 1H), 3.36-3.44 (m, 1H), 3.09 (dd, J=13.6, 3.7 Hz, 1H), 2.85 (dd, J=13.7, 3.2 Hz, 1H), 2.36 (ddd, J=13.7, 4.5, 2.5 Hz, 1H), 2.10-2.21 (m, 1H).

Step 2. Synthesis of N-[(4aR,6R,8aS)-6-(bromoacetyl)-8a-(2,4-difluorophenyl)-4,4a,5,6,8,8a-hexahydropyrano[3,4-d][1,3]thiazin-2-yl]benzamide (C41)

Compound C40 (from the preceding step, 600 mg, 1.33 mmol) was dissolved in a 1:1 mixture of tetrahydrofuran and acetonitrile (7 mL) and added to a 0° C. solution of (diazomethyl)(trimethyl)silane (2 M in 1:1 tetrahydrofuran/acetonitrile, 2.33 mL, 4.66 mmol). After 2.5 hours, aqueous hydrobromic acid (48%, 1.51 mL, 13.3 mmol) was added drop-wise. The reaction mixture was stirred for 10 minutes, then quenched via addition of saturated aqueous sodium bicarbonate solution. The aqueous layer was extracted three times with ethyl acetate, and the combined organic layers were washed with saturated aqueous sodium chloride solution, dried over sodium sulfate, filtered, and concentrated in vacuo. Chromatography on silica gel (Gradient: 0% to 40% ethyl acetate in heptane) afforded the product as a solid. Yield: 330 mg, 0.648 mmol, 49%. LCMS m/z 509.0, 511.0 [M+H]$^+$. $^1$H NMR (400 MHz, CDCl$_3$), characteristic peaks: δ 8.19 (br d, J=7 Hz, 2H), 7.48-7.54 (m, 1H), 7.34-7.47 (m, 3H), 6.85-6.97 (m, 2H), 4.26 (AB quartet, J$_{AB}$=14.1 Hz, Δν$_{AB}$=44.1 Hz, 2H), 3.11-3.19 (m, 1H), 3.00 (dd, J=13.1, 3.9 Hz, 1H), 2.68 (dd, J=13.0, 2.8 Hz, 1H), 2.04-2.17 (m, 2H).

Step 3. Synthesis of N-[(4aR,6R,8aS)-8a-(2,4-difluorophenyl)-6-(imidazo[1,2-a]pyrimidin-2-yl)-4,4a,5,6,8,8a-hexahydropyrano[3,4-d][1,3]thiazin-2-yl]benzamide (C42)

To a solution of C41 (35 mg, 69 µmol) in ethanol (0.69 mL) was added 2-aminopyrimidine (26.2 mg, 0.276 mmol) and the reaction was stirred at 100° C. for 3 hours, then concentrated in vacuo. This material was used directly in the following step. Yield: 34 mg, 67 µmol, 97%. LCMS m/z 506.2 [M+H]$^+$.

Step 4. Synthesis of (4aR,6R,8aS)-8a-(2,4-difluorophenyl)-6-(imidazo[1,2-a]pyrimidin-2-yl)-4,4a,5,6,8,8a-hexahydropyrano[3,4-d][1,3]thiazin-2-amine, hydrochloride salt (4)

A solution of C42 (34 mg, 67 µmol) and 1,8-diazabicyclo[5.4.0]undec-7-ene (13.3 µL, 84.0 µmol) in methanol (1.34 mL) was heated at 70° C. for 18 hours, then concentrated in vacuo. Chromatography on silica gel (Gradient: 0% to 15% methanol in dichloromethane) provided the free base of the product, which was then dissolved in dichloromethane and treated with excess hydrogen chloride (1 M in diethyl ether) to provide the product. Yield: 25.6 mg, 58.3 µmol, 87%. LCMS m/z 402.2 [M+H]$^+$. $^1$H NMR (400 MHz, CDCl$_3$), characteristic peaks for free base: δ 8.98 (dd, J=6.6, 1.2 Hz, 1H), 8.53 (dd, J=3.9, 1.6 Hz, 1H), 7.99 (s, 1H), 7.40-7.46 (m, 1H), 6.89-7.00 (m, 3H), 5.04 (d, J=11.7 Hz, 1H), 4.24-4.31 (m, 2H), 2.94-3.20 (m, 2H), 2.37 (q, J=12.2 Hz, 1H).

Example 5

(4a R,6R,8aS)-8a-(2,4-Difluorophenyl)-6-[1-(2,2,2-trifluoroethyl)-1H-pyrazol-4-yl]-4,4a,5,6,8,8a-hexahydropyrano[3,4-d][1,3]thiazin-2-amine (5)

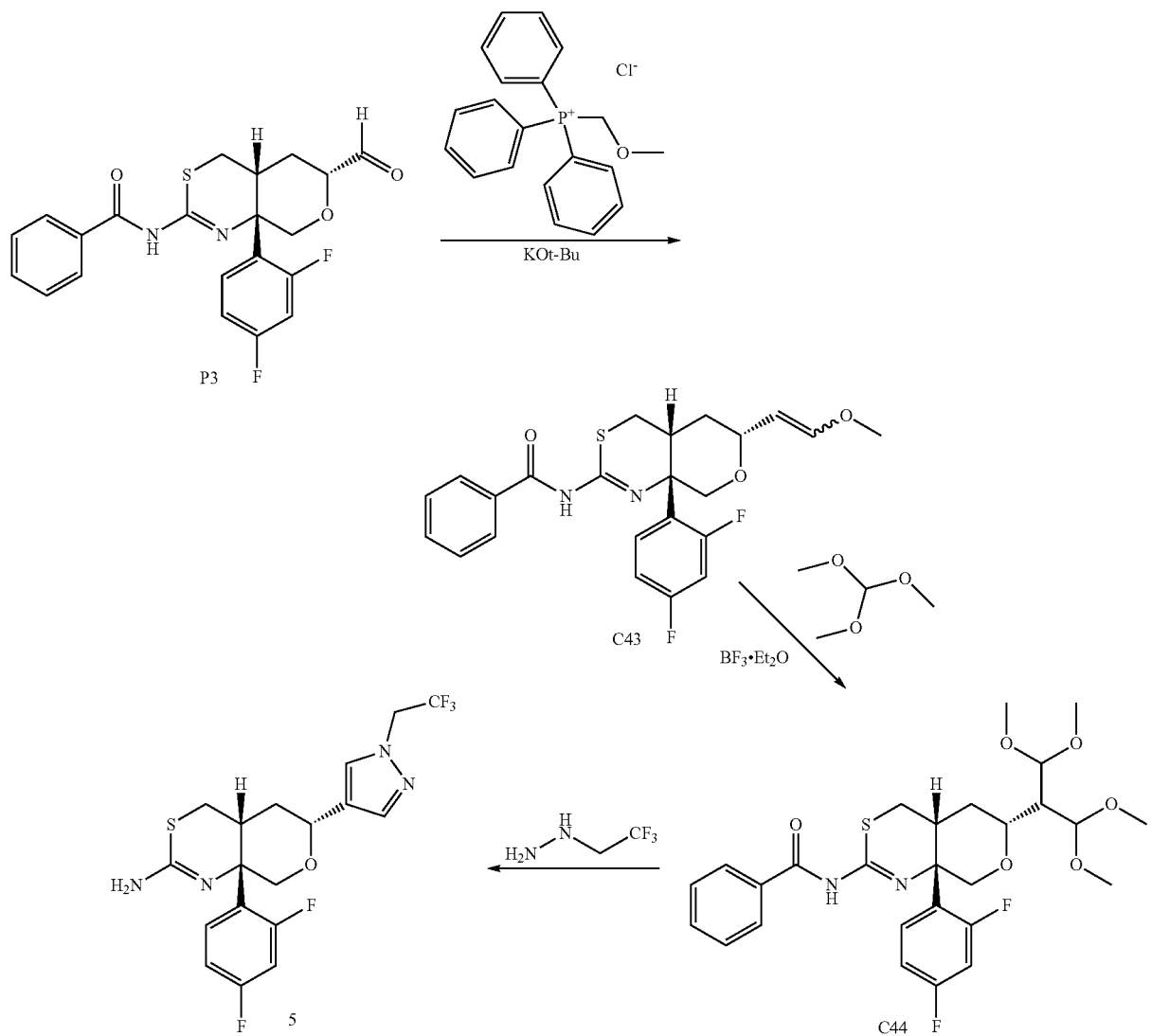

Step 1. Synthesis of N-{(4aR,6R,8aS)-8a-(2,4-difluorophenyl)-6-(2-methoxyethenyl)-4,4a,5,6,8,8a-hexahydropyrano[3,4-d][1,3]thiazin-2-yl}benzamide (C43)

A suspension of (methoxymethyl)(triphenyl)phosphonium chloride (4.73 g, 13.8 mmol) in tetrahydrofuran (65 mL) was cooled in an ice bath. Potassium tert-butoxide (1.0 M solution in tetrahydrofuran, 12.0 mL, 12.0 mmol) was added slowly, at a rate that kept the internal reaction temperature below 5° C. The resulting solution was stirred for 5 minutes at an internal temperature of 2-5° C., allowed to warm to room temperature over 15 minutes, and subsequently cooled in an ice bath. A solution of P3 (1.57 g, 3.77 mmol) in tetrahydrofuran (10 mL) was added over 2 minutes, while keeping the internal temperature under 6° C. The reaction mixture was stirred for 15 minutes under ice cooling, allowed to warm to room temperature over 20 minutes, and then cooled to an internal temperature of 12° C., whereupon it was quenched via addition of saturated aqueous sodium bicarbonate solution (75 mL). The resulting mixture was extracted with ethyl acetate (3×100 mL), and the combined organic layers were dried over sodium sulfate, filtered, and concentrated in vacuo. Chromatography on silica gel (Gradient: 0% to 80% ethyl acetate in heptane) afforded the product as a white solid. By $^1$H NMR analysis, this material consisted of a roughly equimolar mixture of E- and Z-isomers at the enol ether. Yield: 1.33 g, 2.99 mmol, 79%. LCMS m/z 445.2 [M+H]$^+$. $^1$H NMR (400 MHz, CDCl$_3$) δ 8.24 (br d, J=8 Hz, 2H), 7.48-7.55 (m, 1H), 7.37-7.48 (m, 3H), 6.84-6.97 (m, 2H), [6.69 (d, J=12.8 Hz) and 5.99 (dd, J=6.2, 0.7 Hz), total 1H], [4.86 (dd, J=12.7, 8.1 Hz) and 4.55 (dd, half of ABX pattern, J=8.0, 6.3

Hz), total 1H], [4.60-4.68 (m) and 4.06-4.14 (m), total 1H], 4.16-4.23 (m, 1H), 3.76-3.84 (m, 1H), 3.55 and 3.66 (2 s, total 3H), 3.14-3.23 (m, 1H), 2.97-3.05 (m, 1H), 2.60-2.67 (m, 1H), 1.97-2.19 (m, 1H), 1.66-1.75 (m, 1H).

Step 2. Synthesis of N-[(4aR,6R,8aS)-8a-(2,4-difluorophenyl)-6-(1,1,3,3-tetramethoxypropan-2-yl)-4,4a,5,6,8,8a-hexahydropyrano[3,4-d][1,3]thiazin-2-yl]benzamide (C44)

Trimethyl orthoformate (167 µL, 1.52 mmol) was added to an ice-cooled solution of C43 (331 mg, 0.745 mmol) in dichloromethane (1.5 mL). Boron trifluoride diethyl etherate (95.0 µL, 0.756 mmol) was then added drop-wise, while keeping the internal temperature below 3.5° C. After 1.5 hours under ice cooling, the reaction mixture was partitioned between dichloromethane (15 mL) and saturated aqueous sodium bicarbonate solution (10 mL). The aqueous layer was extracted with dichloromethane (15 mL) and the combined organic layers were dried over sodium sulfate, filtered, and concentrated in vacuo to provide the product as an off-white, foam-like solid. Yield: 381 mg, 0.692 mmol, 93%. LCMS m/z 551.2 [M+H]$^+$. $^1$H NMR (400 MHz, CDCl$_3$), characteristic peaks: δ 4.56 (d, J=5.0 Hz, 1H), 4.52 (d, J=3.7 Hz, 1H), 4.14 (br d, J=12 Hz, 1H), 4.03-4.09 (m, 1H), 3.79 (d, J=12.3 Hz, 1H), 3.44 (s, 3H), 3.41 (s, 3H), 3.40 (s, 3H), 3.36 (s, 3H), 2.95-3.01 (m, 1H), 2.62-2.69 (m, 1H), 2.22-2.33 (m, 1H), 2.12-2.17 (m, 1H), 1.74-1.80 (m, 1H).

Step 3. Synthesis of (4aR,6R,8aS)-8a-(2,4-difluorophenyl)-6-[1-(2,2,2-trifluoroethyl)-1H-pyrazol-4-yl]-4,4a,5,6,8,8a-hexahydropyrano[3,4-d][1,3]thiazin-2-amine (5)

(2,2,2-Trifluoroethyl)hydrazine (70% in water, 25.0 µL, 0.20 mmol) was added to a mixture of C44 (60 mg, 0.11 mmol) in methanol (200 µL) and water (100 µL). Concentrated sulfuric acid (13 µL, 0.24 mmol) was then added, followed by additional methanol (200 µL); the reaction mixture was then heated to 60° C. for 18 hours, during which time the initial gel became a solution. The reaction mixture was partitioned between water (5 mL) and dichloromethane (2 mL), and the aqueous layer was adjusted to a pH of 8-9 by drop-wise addition of 1 M aqueous sodium hydroxide solution. The aqueous layer was extracted with ethyl acetate (2×10 mL), and the combined organic layers were dried over sodium sulfate, filtered, and concentrated under reduced pressure. Silica gel chromatography (Gradient: 0% to 15% methanol in dichloromethane) afforded the product as a white solid. Yield: 13.7 mg, 31.7 µmol, 29%. LCMS m/z 433.2 [M+H]$^+$. $^1$H NMR (400 MHz, CDCl$_3$) δ 7.59 (s, 1H), 7.55 (s, 1H), 7.38 (ddd, J=9.0, 8.8, 6.9 Hz, 1H), 6.86-6.92 (m, 1H), 6.82 (ddd, J=12.5, 8.5, 2.4 Hz, 1H), 4.63-4.73 (m, 3H), 4.23 (dd, J=11.1, 2.0 Hz, 1H), 3.87 (d, J=11.1 Hz, 1H), 2.98-3.06 (m, 2H), 2.61-2.68 (m, 1H), 2.06-2.18 (m, 1H), 1.76-1.83 (m, 1H).

Example 6

(4a R,6R,8aS)-8a-(2,4-Difluorophenyl)-6-(5-methyl-1,2,4-oxadiazol-3-yl)-4,4a,5,6,8,8a-hexahydropyrano[3,4-d][1,3]thiazin-2-amine (6)

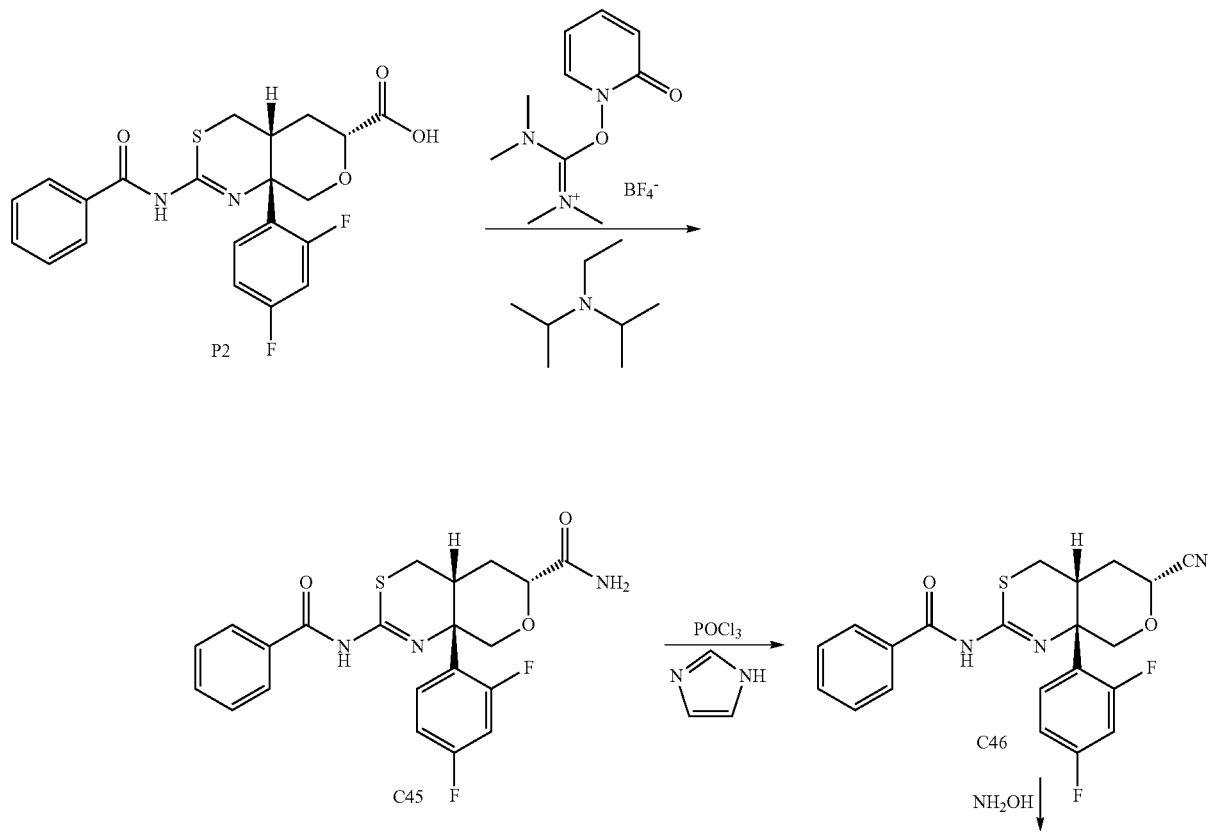

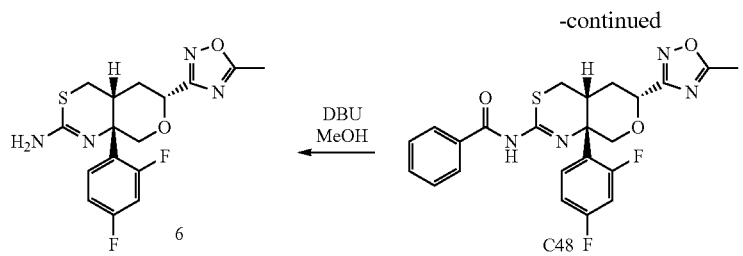
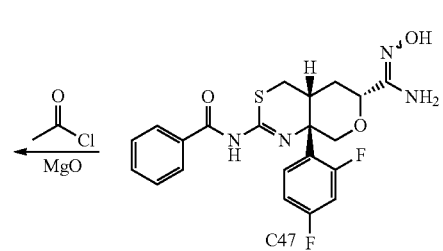

Step 1. Synthesis of (4aR,6R,8aS)-2-(benzoylamino)-8a-(2,4-difluorophenyl)-4,4a,5,6,8,8a-hexahydropyrano[3,4-d][1,3]thiazine-6-carboxamide (C45)

A mixture of P2 [3.0 g, 6.94 mmol], N,N-diisopropylethylamine (1.79 g, 13.9 mmol) and 2-[2-oxo-1(2H)-pyridyl]-1,1,3,3-tetramethyluronium tetrafluoroborate (TPTU, 2.16 g, 27.3 mmol) in N,N-dimethylformamide (20 mL) was stirred at room temperature for 25 minutes. A solution of ammonia in 1,4-dioxane (0.5 M, 55.5 mL, 27.7 mmol) was added, and stirring was continued for 18 hours, at which time the reaction mixture was diluted with saturated aqueous sodium bicarbonate solution (30 mL) and water (30 mL), and extracted with diethyl ether (3×50 mL). The combined organic layers were dried over sodium sulfate, filtered, and concentrated in vacuo. The resulting oil was purified via silica gel chromatography (Gradient: 0% to 100% ethyl acetate in heptane) to afford the product as a white solid. Yield: 2.14 g, 4.93 mmol, 71%. LCMS m/z 432.2 [M+H]$^+$. $^1$H NMR (400 MHz, CD$_3$OD) δ 8.12 (br d, J=7 Hz, 2H), 7.43-7.57 (m, 4H), 7.03-7.13 (m, 2H), 4.21 (dd, J=12.0, 1.5 Hz, 1H), 4.20 (dd, J=11.9, 2.7 Hz, 1H), 4.00 (d, J=11.9 Hz, 1H), 3.19-3.28 (br m, 1H), 2.97 (dd, half of ABX pattern, J=13.0, 4.0 Hz, 1H), 2.80 (dd, half of ABX pattern, J=13.2, 2.8 Hz, 1H), 2.09-2.16 (m, 1H), 1.88-2.00 (m, 1H).

Step 2. Synthesis of N-[(4aR,6R,8aS)-6-cyano-8a-(2,4-difluorophenyl)-4,4a,5,6,8,8a-hexahydropyrano[3,4-d][1,3]thiazin-2-yl]benzamide (C46)

A mixture of C45 (2.1 g, 4.9 mmol), imidazole (682 mg, 9.92 mmol) and phosphorus oxychloride (768 mg, 4.94 mmol) in pyridine (25 mL) was heated at 80° C. for 3 hours, at which time the reaction mixture was diluted with water (10 mL). The reaction mixture was extracted with dichloromethane, and the combined organic layers were dried over magnesium sulfate, filtered, and concentrated in vacuo. The resulting foam was purified via silica gel chromatography (Gradient: 0% to 100% ethyl acetate in heptane) to afford the product as a white solid. Yield: 1.56 g, 3.78 mmol, 77%. LCMS m/z 414.2 [M+H]$^+$. $^1$H NMR (400 MHz, CDCl$_3$) δ 8.10-8.20 (m, 2H), 7.53-7.59 (m, 1H), 7.45-7.52 (m, 2H), 7.31-7.40 (m, 1H), 6.92-6.98 (m, 1H), 6.89 (ddd, J=12.6, 8.3, 2.6 Hz, 1H), 4.56 (dd, J=12.1, 2.6 Hz, 1H), 4.13 (dd, J=12.2, 1.5 Hz, 1H), 3.88 (d, J=12.3 Hz, 1H), 3.06-3.14 (br m, 1H), 3.00 (dd, J=13.2, 3.9 Hz, 1H), 2.67 (dd, J=13.1, 2.9 Hz, 1H), 2.46-2.59 (m, 1H), 1.98-2.06 (m, 1H).

Step 3. Synthesis of N-[(4aR,6R,8aS)-8a-(2,4-difluorophenyl)-6-(N'-hydroxycarbamimidoyl)-4,4a,5,6,8,8a-hexahydropyrano[3,4-d][1,3]thiazin-2-yl]benzamide (C47)

A mixture of C46 (1.27 g, 3.07 mmol) and hydroxylamine (233 mg, 3.53 mmol) in ethanol (15 mL) was heated at reflux for 6 hours. After concentration in vacuo, the solid was azeotroped with dichloromethane (3×25 mL) to afford the product as a white solid (1.68 g), which was used in the next step without further purification. By $^1$H NMR analysis, this was a roughly 2:1 mixture, assumed to be the E/Z isomers at the oxime. LCMS m/z 447.2 [M+H]$^+$. $^1$H NMR (400 MHz, CDCl$_3$), characteristic peaks for major isomer: δ 6.89 (ddd, J=12.3, 8.3, 2.6 Hz, 1H), 4.24 (dd, J=11.7, 2.5 Hz, 1H), 4.20 (dd, J=12.1, 1.6 Hz, 1H), 1.87 (ddd, J=13.8, 4.1, 2.7 Hz, 1H); characteristic peaks for minor isomer: δ 6.81 (ddd, J=12.4, 8.5, 2.6 Hz, 1H), 4.17 (dd, J=11.5, 2.7 Hz, 1H), 4.09 (dd, J=11.3, 2.1 Hz, 1H), 1.64-1.70 (m, 1H).

Step 4. Synthesis of N-[(4aR,6R,8aS)-8a-(2,4-difluorophenyl)-6-(5-methyl-1,2,4-oxadiazol-3-yl)-4,4a,5,6,8,8a-hexahydropyrano[3,4-d][1,3]thiazin-2-yl]benzamide (C48)

A mixture of C47 (337 mg, 0.755 mmol), acetyl chloride (151 mg, 1.89 mmol), and magnesium oxide (152 mg, 3.78 mmol) in benzene (4 mL) was heated at 150° C. for 30 minutes in a microwave reactor. The crude reaction mixture was combined with those from two additional experiments starting with C47 (2×500 mg, 2.2 mmol), diluted with water (10 mL) and extracted with ethyl acetate; the combined organic layers were dried over magnesium sulfate, filtered, and concentrated in vacuo. Two purifications via silica gel chromatography (Gradient #1: 0% to 100% ethyl acetate in heptane; Gradient #2: 0% to 75% ethyl acetate in heptane) afforded the product as a white solid. Yield: 187 mg, 0.397 mmol, 13%. LCMS m/z 471.1 [M+H]$^+$. $^1$H NMR (400 MHz, CDCl$_3$) δ 8.11-8.25 (br m, 2H), 7.49-7.55 (m, 1H), 7.38-7.48 (m, 3H), 6.87-6.98 (m, 2H), 4.92 (dd, J=11.8, 2.4 Hz, 1H), 4.34 (dd, J=12.3, 1.6 Hz, 1H), 3.98 (d, J=12.2 Hz, 1H), 3.22-3.33 (br m, 1H), 3.06 (dd, J=13, 4 Hz, 1H), 2.70 (dd, J=13, 2.5 Hz, 1H), 2.60 (s, 3H), 2.49-2.6 (br m, 1H), 2.07-2.15 (m, 1H).

Step 5. Synthesis of (4a R,6R,8aS)-8a-(2,4-difluorophenyl)-6-(5-methyl-1,2,4-oxadiazol-3-yl)-4,4a,5,6,8,8a-hexahydropyrano[3,4-d][1,3]thiazin-2-amine (6)

Compound C48 was converted to the product using the method described for synthesis of the free base of 4 in Example 4. The product was obtained as a white solid. Yield: 102 mg, 0.278 mmol, 73%. LCMS m/z 367.2 [M+H]$^+$. $^1$H NMR (400 MHz, CD$_3$OD) δ 7.38 (ddd, J=9.4, 9.0, 6.6 Hz, 1H), 6.96-7.04 (m, 2H), 4.87 (dd, J=12.0, 2.4 Hz, 1H, assumed; partially obscured by water peak), 4.27 (dd, J=11.2, 2.0 Hz, 1H), 3.82 (d, J=11.2 Hz, 1H), 3.05-3.12 (m, 1H), 2.93 (dd, J=12.6, 4.1 Hz, 1H), 2.76 (dd, J=12.7, 2.9 Hz, 1H), 2.60 (s, 3H), 2.26-2.37 (m, 1H), 1.90 (ddd, J=13.3, 4.0, 2.5 Hz, 1H).

Example 7 rel-(4aR,6R,8aS)-8a-(2,4-Difluorophenyl)-6-(6-methylpyridin-3-yl)-4,4a,5,6,8,8a-hexahydropyrano[3,4-d][1,3]thiazin-2-amine, hydrochloride salt (7)

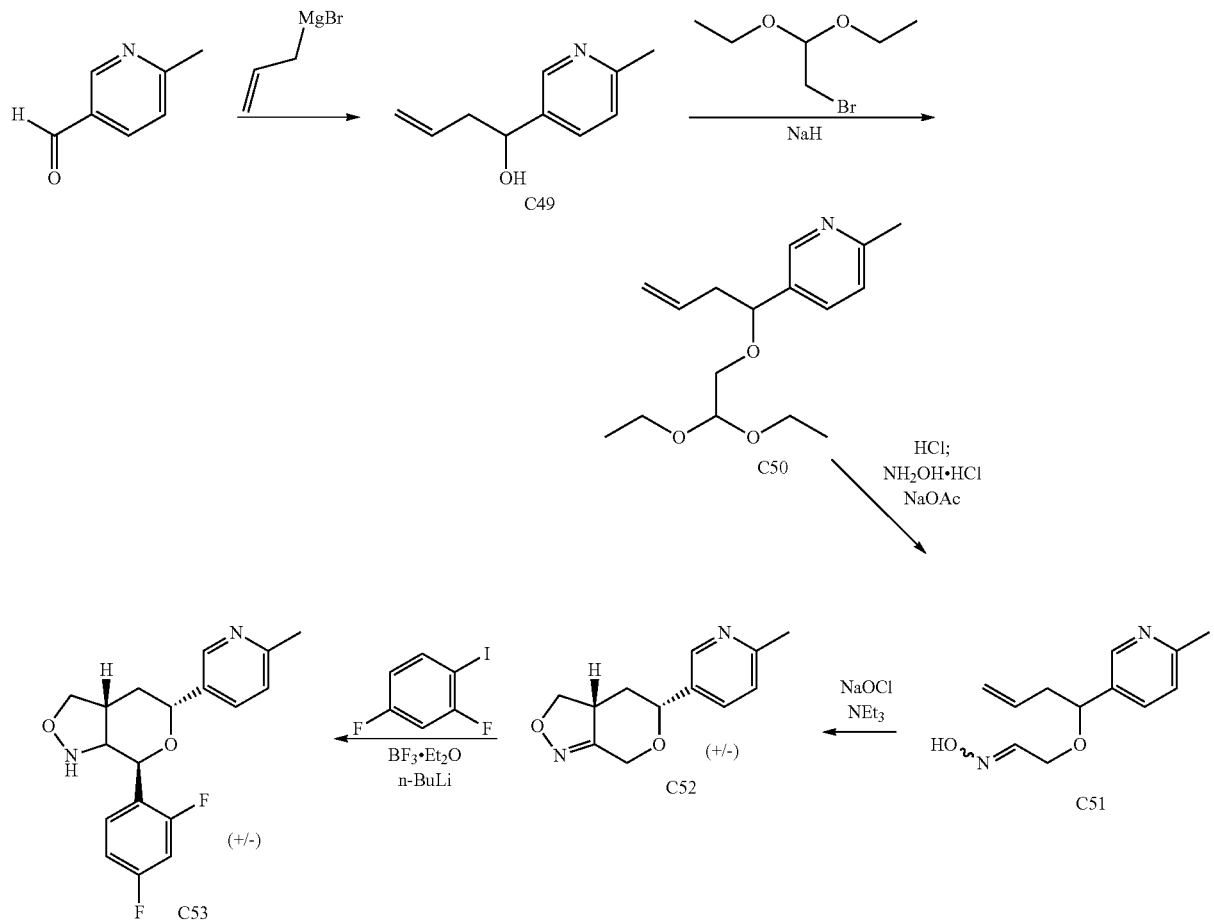

Step 1. Synthesis of 1-(6-methylpyridin-3-yl)but-3-en-1-ol (C49)

To a mixture of 6-methylpyridine-3-carbaldehyde (20 g, 0.16 mol) in tetrahydrofuran (400 mL) was added allylmagnesium bromide (246 mL, 0.246 mol) drop-wise at −40° C. The mixture was stirred at −20° C. for 10 minutes and a second aliquot of allylmagnesium bromide (82 mL, 82 mmol) was added drop-wise at −20° C. When thin layer chromatography (Eluent: 3:1 petroleum ether/ethyl acetate) indicated the reaction was complete, the reaction was quenched with saturated aqueous ammonium chloride solution (20 mL) at 0° C. The resulting mixture was partitioned between ethyl acetate (200 mL) and water (100 mL), and the aqueous phase was extracted with ethyl acetate (2×200 mL). The combined organic layers were washed with saturated aqueous sodium chloride solution (100 mL), dried, filtered, and concentrated in vacuo to afford the product as a yellow oil. Yield 25 g, 0.15 mol, 94%. $^1$H NMR (400 MHz, CDCl$_3$) δ 8.42-8.48 (m, 1H), 7.61 (dd, J=8.0, 2.3 Hz, 1H), 7.15 (d, J=8.2 Hz, 1H), 5.74-5.86 (m, 1H), 5.12-5.22 (m, 2H), 4.77 (dd, J=7.5, 5.5 Hz, 1H), 2.55 (s, 3H), 2.46-2.58 (m, 2H).

Step 2. Synthesis of 5-[1-(2,2-diethoxyethoxy)but-3-en-1-yl]-2-methylpyridine (C50)

To a 0° C. suspension of sodium hydride (60% in mineral oil, 18.4 g, 0.46 mol) in tetrahydrofuran (400 mL) was added a solution of C49 (25 g, 0.15 mol) in tetrahydrofuran (100 mL) drop-wise; after the reaction mixture had stirred at 0° C. for 30 minutes, 2-bromo-1,1-diethoxyethane (90.6 g, 0.46 mol) was added drop-wise. The reaction mixture was stirred at 80° C. for 18 hours, then carefully quenched with water (200 mL) and extracted with dichloromethane (2×500 mL). The combined organic layers were washed with saturated aqueous sodium chloride solution (2×300 mL), dried, and concentrated in vacua Silica gel chromatography (Gradient: 0% to 75% ethyl acetate in heptane) provided the product as a yellow oil. Yield: 30 g, 0.11 mol, 73%. $^1$H NMR (400 MHz, CDCl$_3$) δ 8.40 (d, J=2.1 Hz, 1H), 7.54 (dd, J=7.9, 2.3 Hz, 1H), 7.14 (d, J=8.0 Hz, 1H), 5.69-5.81 (m, 1H), 5.03-5.07 (m, 1H), 5.00-5.02 (m, 1H), 4.60 (dd, J=5.4, 5.1 Hz, 1H), 4.36 (dd, J=6.8, 6.6 Hz, 1H), 3.45-3.74 (m, 4H), 3.31-3.40 (m, 2H), 2.57-2.66 (m, 1H), 2.55 (s, 3H), 2.36-2.44 (m, 1H), 1.22 (t, J=7.1 Hz, 3H), 1.18 (t, J=7.0 Hz, 3H).

Step 3. Synthesis of N-hydroxy-2-{[1-(6-methylpyridin-3-yl)but-3-en-1-yl]oxy}ethanimine (C51)

To a solution of C50 (30 g, 0.11 mol) in tetrahydrofuran (300 mL) was added aqueous hydrochloric acid (1 M, 100 mL), and the reaction mixture was stirred at 70° C. for 1 hour. After removal of tetrahydrofuran in vacuo, the volume of the aqueous residue was brought to 150 mL by addition of water, and the pH was adjusted to 6-7 with solid sodium acetate. Additional sodium acetate (12.4 g, 0.15 mol) was added, followed by hydroxylamine hydrochloride (10.5 g, 0.151 mol) and ethanol (150 mL). The reaction mixture was stirred for 10 minutes and then partitioned between ethyl acetate (300 mL) and water (100 mL). The organic layer was washed with saturated aqueous sodium chloride solution (2×300 mL), concentrated in vacuo, and purified via silica gel chromatography (Gradient: 40% to 100% ethyl acetate in petroleum ether); subsequent recrystallization from petroleum ether provided the product as a white solid, presumed to be a mixture of oxime isomers. Yield 22.5 g, 0.102 mol, 93%. $^1$H NMR (400 MHz, CDCl$_3$) δ 8.38-8.41 (m, 1H), 7.59-7.64 (m, 1H), 7.45-7.50 (m, 1H), 7.20 (br d, J=7.9 Hz, 1H), 5.66-5.78 (m, 1H), 5.00-5.09 (m, 2H), 4.38-4.45 (m, 1H), 4.00-4.08 (m, 1H), 3.84-3.92 (m, 1H), 2.57-2.66 (m, 1H), 2.57 (s, 3H), 2.38-2.46 (m, 1H).

Step 4. Synthesis of rel-(3aR,5R)-5-(6-methylpyridin-3-yl)-3,3a,4,5-tetrahydro-7H-pyrano[3,4-c][1,2]oxazole (C52)

To a mixture of C51 (10 g, 45 mmol) and triethylamine (0.47 mL, 3.4 mmol) in dichloromethane (200 mL) was added 6% aqueous sodium hypochlorite solution (56 mL, 44 mmol) drop-wise at 10-20° C. The reaction mixture was then washed with saturated aqueous sodium chloride solution (2×200 mL), dried, and concentrated in vacua Silica gel chromatography (Gradient: 45% to 100% ethyl acetate in petroleum ether) afforded the product as a yellow solid. This material was combined with two additional batches of product (2×5 g, 46 mmol) and crystallized from petroleum ether to give the product as a pale yellow solid. Combined yield: 10.1 g, 46.3 mmol, 51%. LCMS m/z 219.1 [M+H]$^+$. $^1$H NMR (400 MHz, CDCl$_3$) δ 8.47 (d, J=2.3 Hz, 1H), 7.60 (dd, J=8.0, 2.4 Hz, 1H), 7.17 (d, J=8.0 Hz, 1H), 4.89 (d, J=13.4 Hz, 1H), 4.67 (dd, J=10.2, 8.1 Hz, 1H), 4.57 (br dd, J=11.4, 1.9 Hz, 1H), 4.38 (dd, J=13.5, 1.2 Hz, 1H), 3.86 (dd, J=11.5, 8.0 Hz, 1H), 3.60-3.71 (m, 1H), 2.56 (s, 3H), 2.40 (ddd, J=13.2, 6.3, 1.6 Hz, 1H), 1.82 (ddd, J=13.0, 11.4, 11.4 Hz, 1H).

Step 5. Synthesis of rel-(3aR,5R,7aS)-7a-(2,4-difluorophenyl)-5-(6-methylpyridin-3-yl)hexahydro-1H-pyrano[3,4-c][1,2]oxazole (C53)

Compound C52 was converted to the product using the method employed for synthesis of C5 in Preparation P1. The product was obtained as a solid. Yield 0.2 g, 0.6 mmol, 9%. LCMS m/z 333.2 [M+H]$^+$. $^1$H NMR (400 MHz, CDCl$_3$) δ 8.51 (d, J=2 Hz, 1H), 7.99 (ddd, J=9, 9, 7 Hz, 1H), 7.65 (dd, J=8, 2 Hz, 1H), 7.19 (d, J=8.0 Hz, 1H), 6.90-6.96 (m, 1H), 6.86 (ddd, J=12.0, 8.6, 2.4 Hz, 1H), 4.68 (br d, J=11.7 Hz, 1H), 4.30 (br d, J=12.7 Hz, 1H), 3.99 (d, J=12.8 Hz, 1H), 3.76 (d, J=7.3 Hz, 1H), 3.61 (dd, J=7.2, 5.0 Hz, 1H), 3.22-3.30 (m, 1H), 2.57 (s, 3H), 2.12 (br ddd, J=14, 7, 1 Hz, 1H), 1.74-1.86 (m, 1H).

Step 6. Synthesis of rel-[(2R,4R,5S)-5-amino-5-(2,4-difluorophenyl)-2-(6-methylpyridin-3-yl)tetrahydro-2H-pyran-4-yl]methanol (C54)

A mixture of acetic acid (2 mL) and C53 (200 mg, 0.60 mmol)) was treated with zinc powder (512 mg, 7.83 mmol). The resulting mixture was allowed to cool to room temperature and was stirred for 5 hours. The reaction was filtered through a nylon disc, concentrated in vacuo, and used in the next step without further purification. Yield: 160 mg, 0.48 mmol, 80%.

Step 7. Synthesis of rel-N-{[(S,4R,6R)-3-(2,4-difluorophenyl)-4-(hydroxymethyl)-6-(6-methylpyridin-3-yl)tetrahydro-2H-pyran-3-yl]carbamothioyl}benzamide (C55)

A mixture of C54 (160 mg, 0.48 mmol) in dichloromethane (2.4 mL) was treated drop-wise with benzoyl isothiocyanate (32 μL, 0.24 mmol), and the reaction mixture was stirred at room temperature for 18 hours. The reaction mixture was concentrated in vacuo; silica gel chromatography (Gradient: 0% to 60% ethyl acetate in heptane) provided the product as an oil. Yield 100 mg, 0.20 mmol, 83%. LCMS m/z 498.2 [M+H]$^+$.

Step 8. Synthesis of rel-N-[(4aR,6R,8aS)-8a-(2,4-difluorophenyl)-6-(6-methylpyridin-3-yl)-4,4a,5,6,8,8a-hexahydropyrano[3,4-d][1,3]thiazin-2-yl]benzamide (C56)

To a solution of triphenylphosphine (47 mg, 0.18 mmol) in tetrahydrofuran (1.2 mL) was added diethyl azodicarboxylate (28.2 μL, 0.18 mmol) and the mixture was stirred for 30 minutes. The reaction was cooled to 0° C. and a solution of C55 (30 mg, 60 μmol) in minimal tetrahydrofuran was added drop-wise. The reaction mixture was stirred for 1 hour at 0° C. and at room temperature for 18 hours, then was filtered and concentrated in vacuo; silica gel chromatography (Gradient: 0% to 100% ethyl acetate in heptane) afforded the product as an oil. Yield 9 mg, 0.02 mmol, 30%. LCMS m/z 480.2 [M+H]$^+$. $^1$H NMR (400 MHz, CDCl$_3$) δ 8.48 (br d, J=2 Hz, 1H), 8.24 (br d, J=7.6 Hz, 2H), 7.67 (br dd, J=8, 2 Hz, 1H), 7.50-7.56 (m, 1H), 7.41-7.49 (m, 3H), 7.15 (d, J=8.0 Hz, 1H), 6.88-7.00 (m, 2H), 4.75 (br d, J=11 Hz, 1H), 4.33 (br d, J=12 Hz, 1H), 3.96 (d, J=12.4 Hz, 1H), 3.29-3.38 (m, 1H), 3.07 (dd, J=13.0, 4.1 Hz, 1H), 2.69 (dd, J=13.0, 2.7 Hz, 1H), 2.55 (s, 3H), 2.17-2.29 (m, 1H), 1.87-1.97 (m, 1H).

Step 9. Synthesis of rel-(4aR,6R,8aS)-8a-(2,4-difluorophenyl)-6-(6-methylpyridin-3-yl)-4,4a,5,6,8,8a-hexahydropyrano[3,4-d][1,3]thiazin-2-amine, hydrochloride salt (7)

A solution of C56 (9 mg, 0.02 mmol) in methanol (0.38 mL) was treated with 1,8-diazabicyclo[5.4.0]undec-7-ene (3.8 mg, 24 μmol); the reaction vial was then sealed and heated to 70° C. for 18 hours. The reaction mixture was concentrated in vacuo and purified via silica gel chromatography (Gradient: 0% to 15% methanol in dichloromethane) to afford the free base of the product as a white solid. Yield 1.8 mg, 4.8 μmol, 24%. LCMS m/z 376.3 [M+H]$^+$. $^1$H NMR (400 MHz, CDCl$_3$) δ 8.51 (br d, J=2 Hz, 1H), 7.70 (dd, J=8.0, 2.3 Hz, 1H), 7.41 (ddd, J=9.2, 8.9, 6.7 Hz, 1H), 7.16 (d, J=8.0 Hz, 1H), 6.89-6.96 (m, 1H), 6.85 (ddd, J=12.5, 8.5, 2.5 Hz, 1H), 4.70 (br d, J=12 Hz, 1H), 4.24 (dd, J=11.6, 1.8 Hz, 1H), 4.01 (d, J=11.3 Hz, 1H), 3.11-3.18 (m, 1H), 3.04 (dd, J=12.4, 4.0 Hz, 1H), 2.67 (dd, J=12.5, 2.7 Hz, 1H), 2.56 (s, 3H), 2.01-2.13 (m, 1H), 1.74-1.81 (m, 1H). The free base of 7 was converted to the product by dissolution in dichloromethane and treatment with a 1 M solution of hydrogen chloride in diethyl ether. Removal of solvent in vacuo provided the product as a solid.

Example 8

(4a R,6R,8aS)-8a-(2,4-Difluorophenyl)-6-(4-fluoro-1-methyl-1H-pyrazol-3-yl)-4,4a,5,6,8,8a-hexahydro-pyrano[3,4-d][1,3]thiazin-2-amine, hydrochloride salt (8)

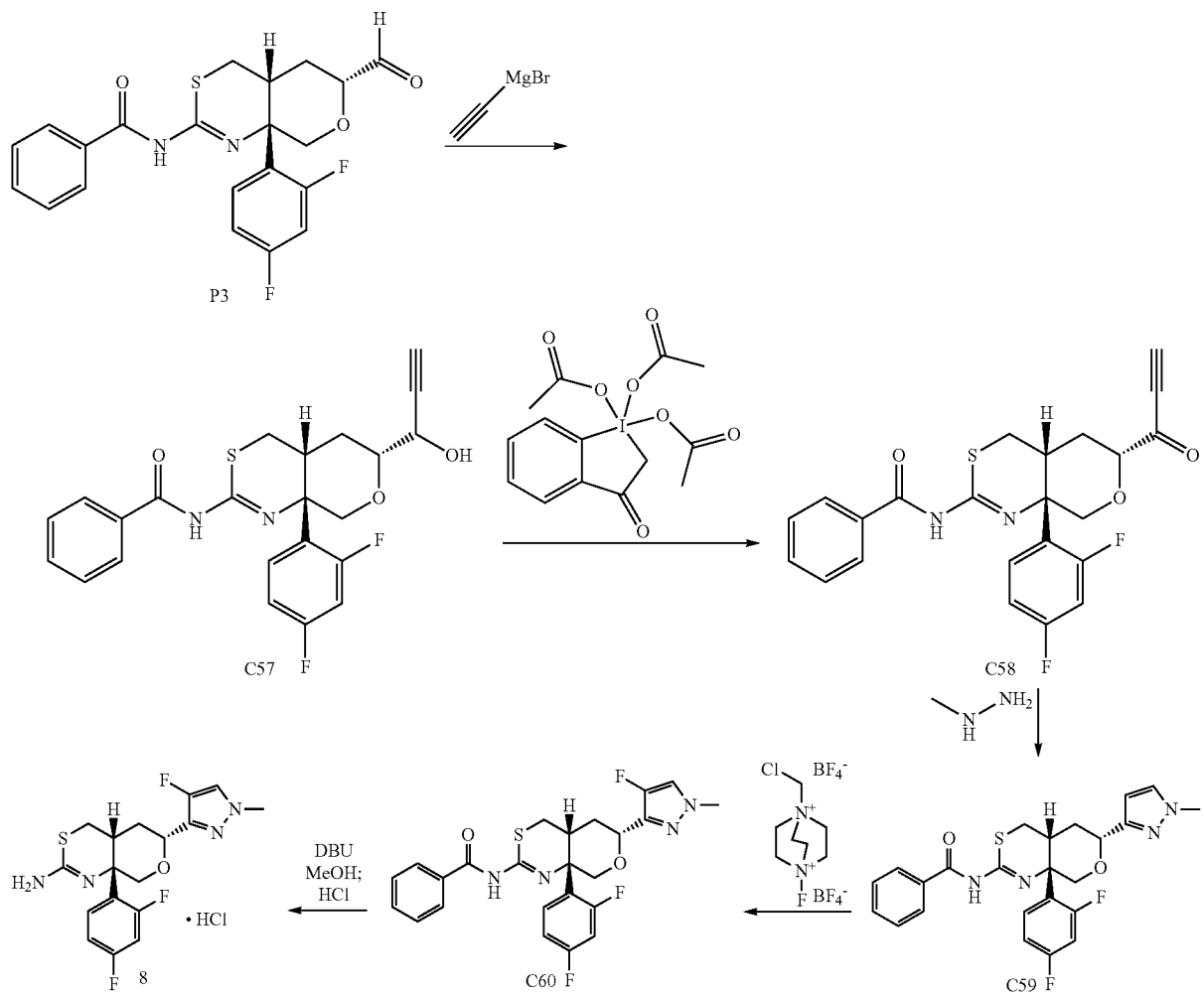

Step 1. Synthesis of N-[(4aR,6R,8aS)-8a-(2,4-difluorophenyl)-6-(1-hydroxyprop-2-yn-1-yl)-4,4a,5,6,8,8a-hexahydropyrano[3,4-d][1,3]thiazin-2-yl]benzamide (C57)

A solution of ethynylmagnesium bromide in tetrahydrofuran (0.5 M, 17.3 mL, 8.64 mmol) was cooled to 15° C. A solution of P3 (800 mg, 1.92 mmol) in tetrahydrofuran (5 mL) was then added drop-wise over 15 minutes, during which time the internal reaction temperature rose to 23° C. The reaction mixture was stirred at room temperature for an additional 60 minutes, then cooled to 0° C., quenched with saturated aqueous ammonium chloride solution (15 mL) and extracted three times with ethyl acetate. The combined organic layers were dried over sodium sulfate, filtered, and concentrated in vacuo to afford the crude product as an amber foam (750 mg, <88%), which was taken directly to the following step. LCMS m/z 443.2 [M+H]$^+$.

Step 2. Synthesis of N-[(4aR,6R,8aS)-8a-(2,4-difluorophenyl)-6-(prop-2-ynoyl)-4,4a,5,6,8,8a-hexahydropyrano[3,4-d][1,3]thiazin-2-yl]benzamide (C58)

Dess-Martin periodinane[1,1,1-tris(acetyloxy)-1,1-dihydro-1,2-benziodoxol-3-(1H)-one] (791 mg, 1.86 mmol) was added to a 0° C. solution of C57 (material from the previous step, 750 mg, <1.7 mmol) in dichloromethane (34 mL). The reaction mixture was allowed to warm to room temperature and then stirred for 1.5 hours. Dichloromethane was added, followed by saturated aqueous sodium thiosulfate solution and saturated aqueous sodium bicarbonate solution, and the mixture was stirred for 30 minutes. The organic layer was washed with saturated aqueous sodium bicarbonate solution and with saturated aqueous sodium chloride solution, dried over sodium sulfate, filtered, and concentrated in vacua Silica gel chromatography (Gradient: 0% to 65% ethyl acetate in heptane) afforded the product as an off-white solid. Yield: 470 mg, 1.07 mmol, 63% over two steps. LCMS m/z 441.2

[M+H]⁺. ¹H NMR (400 MHz, CDCl₃) δ 8.18 (br d, J=7.6 Hz, 2H), 7.50-7.57 (m, 1H), 7.36-7.49 (m, 3H), 6.86-6.99 (m, 2H), 4.28 (dd, J=11.5, 3.1 Hz, 1H), 4.22 (dd, J=12.2, 1.5 Hz, 1H), 3.97 (d, J=12.1 Hz, 1H), 3.42 (s, 1H), 3.15-3.25 (m, 1H), 3.04 (dd, J=13.0, 4.0 Hz, 1H), 2.69 (dd, J=13.1, 2.7 Hz, 1H), 2.07-2.25 (m, 2H).

Step 3. Synthesis of N-[(4aR,6R,8a5)-8a-(2,4-difluorophenyl)-6-(1-methyl-1H-pyrazol-3-yl)-4,4a,5,6,8, 8a-hexahydropyrano[3,4-d][1,3]thiazin-2-yl]benzamide (C59)

A slurry of C58 (470 mg, 1.07 mmol) and methylhydrazine (56.2 μL, 1.07 mmol) in 2-propanol (21 mL) was stirred at room temperature for 3 hours, then concentrated and purified via silica gel chromatography (Gradient: 0% to 50% ethyl acetate in heptane) to afford the product as an off-white foam. Yield: 280 mg, 0.599 mmol, 56%. LCMS m/z 469.2 [M+H]⁺. ¹H NMR (400 MHz, CDCl₃): δ 8.22 (br d, J=7.4 Hz, 2H), 7.40-7.55 (m, 4H), 7.29 (d, J=2.2 Hz, 1H), 6.86-6.97 (m, 2H), 6.29 (d, J=2.2 Hz, 1H), 4.83 (dd, J=11.6, 2.3 Hz, 1H), 4.33 (dd, J=12.2, 1.5 Hz, 1H), 3.9-3.96 (m, 1H), 3.87 (s, 3H), 3.24-3.33 (m, 1H), 3.06 (dd, J=12.9, 4.1 Hz, 1H), 2.69 (dd, J=12.9, 2.7 Hz, 1H), 2.34-2.47 (m, 1H), 1.99-2.07 (m, 1H).

Step 4. Synthesis of N-[(4aR,6R,8a5)-8a-(2,4-difluorophenyl)-6-(4-fluoro-1-methyl-1H-pyrazol-3-yl)-4, 4a,5,6,8,8a-hexahydropyrano[3,4-d][1,3]thiazin-2-yl]benzamide (C60)

To C59 (90 mg, 0.19 mmol) dissolved in 2-propanol (1.9 mL) was added 1-chloromethyl-4-fluoro-1,4-diazoniabicyclo[2.2.2]octane bis(tetrafluoroborate) (136 mg, 0.384 mmol) and the reaction was degassed with nitrogen for 1 minute. The reaction mixture was heated at 80° C. for 6 hours, then concentrated in vacuo. Silica gel chromatography (Gradient: 0% to 100% ethyl acetate in heptane) afforded the product as a solid. Yield: 13 mg, 27 μmol, 14%. LCMS m/z 487.2 [M+H]⁺. ¹H NMR (400 MHz, CDCl₃) δ 8.23 (br d, J=7.4 Hz, 1H), 7.85 (d, J=7.8 Hz, 1H), 7.44-7.58 (m, 4H), 7.22 (d, J=5.1 Hz, 1H), 6.89-6.99 (m, 2H), 4.89 (dd, J=11.9, 2.1 Hz, 1H), 4.35 (d, J=12.1 Hz, 1H), 3.91-3.96 (m, 1H), 3.81 (s, 3H), 3.26-3.32 (m, 1H), 3.08 (dd, J=12.9, 3.9 Hz, 1H), 2.65-2.74 (m, 2H), 1.97-2.02 (m, 1H).

Step 5. Synthesis of (4aR,6R,8a5)-8a-(2,4-difluorophenyl)-6-(4-fluoro-1-methyl-1H-pyrazol-3-yl)-4, 4a,5,6,8,8a-hexahydropyrano[3,4-d][1,3]thiazin-2-amine, hydrochloride salt (8)

Compound C60 was converted to the product using the method employed for synthesis of 7 in Example 7. Yield: 3.6 mg, 8.6 μmol, 32%. LCMS m/z 383.1 [M+H]⁺. ¹H NMR (400 MHz, CDCl₃) for free base: δ 7.46 (td, J=9, 6.7 Hz, 1H), 7.2 (d, J=4.9 Hz, 1H), 6.76-6.87 (m, 2H), 4.82 (dd, J=11.8, 2.2 Hz, 1H), 4.25 (dd, J=11, 2.3 Hz, 1H), 3.95 (d, J=11.2 Hz, 1H), 3.85 (s, 3H), 2.96-3.03 (m, 2H), 2.62-2.66 (m, 1H), 2.36-2.46 (m, 1H), 1.72 (dt, J=13.2, 3 Hz, 1H)

Example 9

(4R,4aR,6R,8aS)-8a-(2,4-Difluorophenyl)-4-methyl-6-(3-methyl-1,2-oxazol-5-yl)-4,4a,5,6,8,8a-hexahydropyrano[3,4-d][1,3]thiazin-2-amine (9)

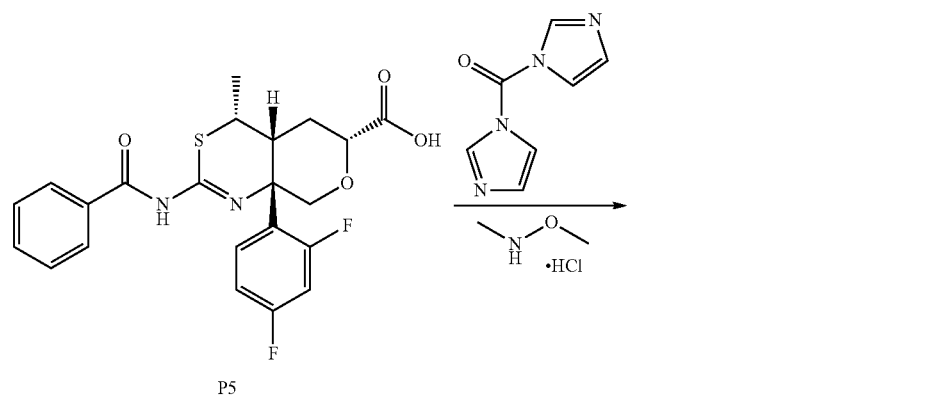

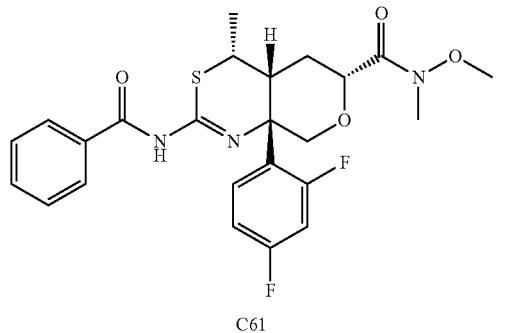

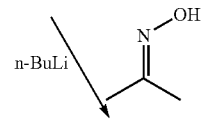

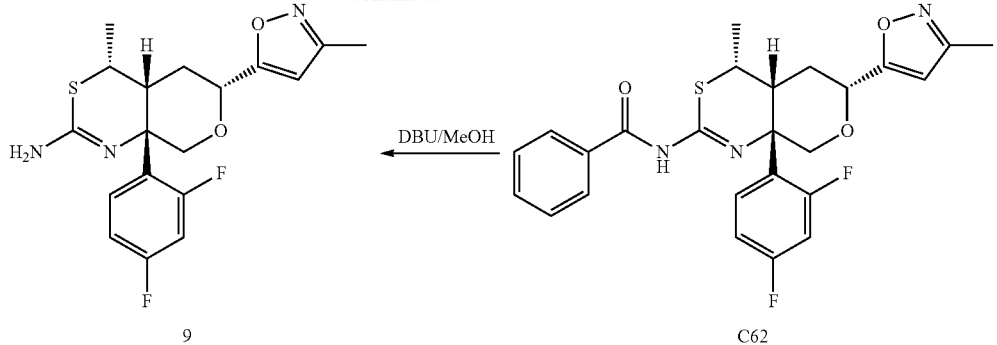

Step 1. Synthesis of (4R,4aR,6R,8aS)-2-(benzoylamino)-8a-(2,4-difluorophenyl)-N-methoxy-N,4-dimethyl-4,4a,5,6,8,8a-hexahydropyrano[3,4-d][1,3]thiazine-6-carboxamide (C61)

To a solution of P5 (893 mg, 2.00 mmol) in 1,2-dichloroethane (5 mL) was added 1,1'-carbonyldiimidazole (389 mg, 2.40 mmol), and the reaction mixture was stirred at room temperature for 2 hours. N,O-Dimethylhydroxylamine hydrochloride (273 mg, 2.80 mmol) was added, and stirring was continued for 2 hours, whereupon the reaction mixture was partitioned between water (60 mL) and dichloromethane (50 mL). The organic layer was washed sequentially with aqueous hydrochloric acid (0.5 M, 20 mL), saturated aqueous sodium bicarbonate solution (20 mL) and saturated aqueous sodium chloride solution (20 mL), dried over sodium sulfate, filtered, and concentrated in vacuo. The residue was azeotroped with dichloromethane (3×10 mL) to afford the product as an off-white solid. Yield: 953 mg, 1.95 mmol, 98%. LCMS m/z 490.3 [M+H]+. 1H NMR (400 MHz, CDCl3) δ 8.18 (v br d, J=7 Hz, 2H), 7.49-7.55 (m, 1H), 7.36-7.48 (m, 3H), 6.90-6.97 (m, 1H), 6.89 (ddd, J=12.3, 8.3, 2.5 Hz, 1H), 4.53 (br d, J=11.5 Hz, 1H), 4.22 (br d, J=12 Hz, 1H), 3.92 (br d, J=12 Hz, 1H), 3.76 (s, 3H), 3.18-3.31 (m, 4H), 2.90-2.99 (m, 1H), 2.06-2.20 (m, 1H), 1.88 (br d, J=13 Hz, 1H), 1.27 (d, J=6.9 Hz, 3H).

Step 2. Synthesis of N-[(4R,4aR,6R,8aS)-8a-(2,4-difluorophenyl)-4-methyl-6-(3-methyl-1,2-oxazol-5-yl)-4,4a,5,6,8,8a-hexahydropyrano[3,4-d][1,3]thiazin-2-yl]benzamide (C62)

A solution of N-hydroxypropan-2-imine (272 mg, 3.72 mmol) in tetrahydrofuran (10 mL) was cooled in an ice bath. n-Butyllithium (2.5 M solution in hexanes, 3.00 mL, 7.50 mmol) was added to the cold solution over 8 minutes. The cooling bath was removed, and the reaction mixture was allowed to warm to room temperature, whereupon it was cooled in an ice bath and treated with a solution of C61 (617 mg, 1.26 mmol) in tetrahydrofuran (5 mL) over 15 minutes. Stirring was continued under ice cooling for 2 minutes, at which time concentrated sulfuric acid (1.01 mL, 18.9 mmol) was slowly added. The reaction mixture was stirred at room temperature for 1.5 hours, then cooled in an ice bath and quenched via addition of 15% aqueous sodium hydroxide solution until the pH of the aqueous phase reached 9-10. The mixture was partitioned between water (60 mL) and ethyl acetate (50 mL) and the aqueous layer was extracted with ethyl acetate (2×50 mL). The combined organic layers were dried over sodium sulfate, filtered, and concentrated in vacuo. Chromatography on silica gel (Gradient: 0% to 80% ethyl acetate in heptane) provided the product as a white solid. Yield: 491 mg, 1.02 mmol, 81%. LCMS m/z 484.2 [M+H]+. 1H NMR (400 MHz, CDCl3) δ 8.19 (br d, J=7 Hz, 2H), 7.50-7.56 (m, 1H), 7.36-7.49 (m, 3H), 6.87-6.98 (m, 2H), 6.14 (s, 1H), 4.86 (br dd, J=11.8, 2.4 Hz, 1H), 4.31 (dd, J=12.2, 1.5 Hz, 1H), 3.94 (d, J=12.2 Hz, 1H), 3.26-3.34 (m, 1H), 3.00-3.08 (m, 1H), 2.28 (s, 3H), 2.12-2.20 (m, 1H), 1.94-2.05 (m, 1H), 1.30 (d, J=7.0 Hz, 3H).

Step 3. Synthesis of (4R,4aR,6R,8aS)-8a-(2,4-difluorophenyl)-4-methyl-6-(3-methyl-1,2-oxazol-5-yl)-4,4a,5,6,8,8a-hexahydropyrano[3,4-d][1,3]thiazin-2-amine (9)

1,8-Diazabicyclo[5.4.0]undec-7-ene (47.5 µL, 0.318 mmol) was added to a solution of C62 (154 mg, 0.318 mmol) in methanol (3 mL), and the reaction mixture was heated at 60° C. for 18 hours. Solvent was removed in vacuo, and the residue was partitioned between ethyl acetate and aqueous sodium bicarbonate solution. The aqueous layer was extracted twice with ethyl acetate, and the combined organic layers were washed with saturated aqueous sodium chloride solution, dried over sodium sulfate, filtered, and concentrated under reduced pressure. Silica gel chromatography (Gradient: 0% to 15% methanol in dichloromethane) afforded the product as a white solid. Yield: 103 mg, 0.271 mmol, 85%. LCMS m/z 380.2 [M+H]+. 1H NMR (400 MHz, DMSO-d6) δ 7.33 (ddd, J=9.0, 9.0, 7.0 Hz, 1H), 7.23 (ddd, J=12.6, 9.1, 2.6 Hz, 1H), 7.08-7.14 (m, 1H), 6.30 (s, 1H), 6.22 (br s, 2H), 4.80 (dd, J=11.7, 2.1 Hz, 1H), 4.09 (dd, J=10.6, 2.1 Hz, 1H), 3.69 (d, J=10.8 Hz, 1H), 2.96 (qd, J=6.9, 3.3 Hz, 1H), 2.71 (ddd, J=11.9, 4, 3 Hz, 1H), 2.22 (s, 3H), 1.81-1.88 (m, 1H), 1.62-1.73 (m, 1H), 1.10 (d, J=6.9 Hz, 3H).

Example 10
(4aR,6R,8aS)-8a-(2,4-Difluorophenyl)-6-([1,3]ox-azolo[4,5-c]pyridin-2-yl)-4,4a,5,6,8,8a-hexahydro-pyrano[3,4-d][1,3]thiazin-2-amine (10)
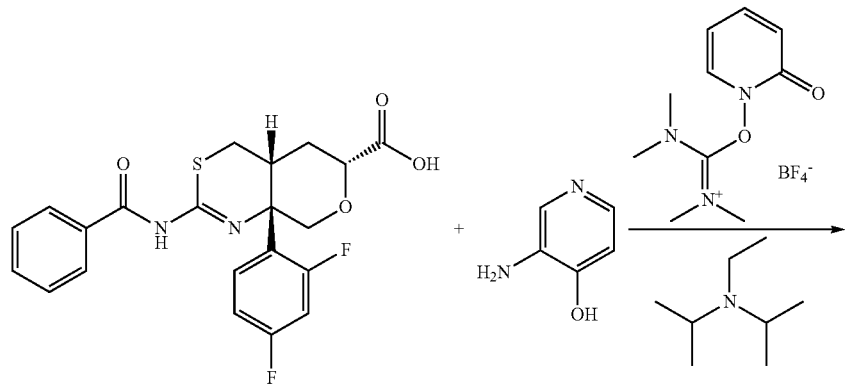
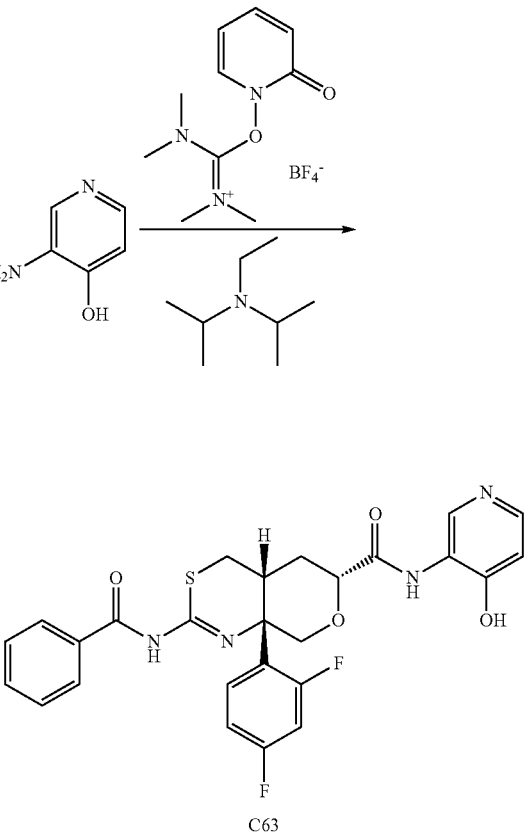
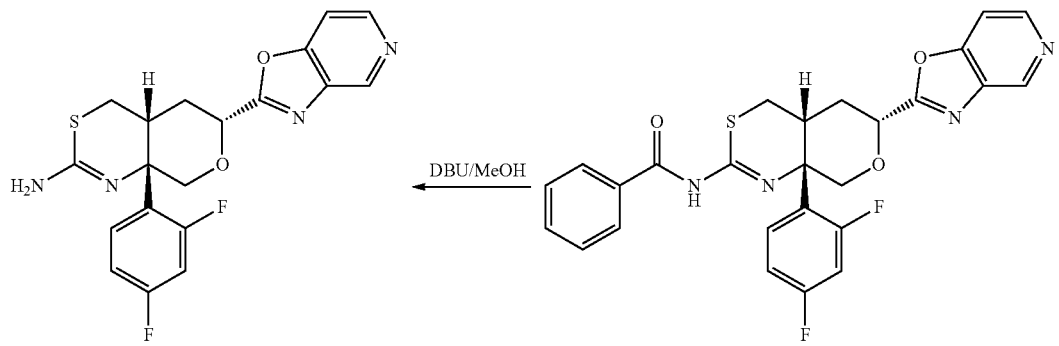

Step 1. Synthesis of (4aR,6R,8aS)-2-(benzoylamino)-8a-(2,4-difluorophenyl)-N-(4-hydroxypyridin-3-yl)-4,4a,5,6,8,8a-hexahydropyrano[3,4-d][1,3]thiazine-6-carboxamide (C63)

To a mixture of P2 (135 mg, 0.312 mmol) in N,N-dimethylformamide (5 mL) was added N,N-diisopropylethylamine (120 mg, 0.94 mmol) and 2-[2-oxo-1(2H)-pyridyl]-1,1,3,3-tetramethyluronium tetrafluoroborate (TPTU) (102 mg, 0.343 mmol) and the reaction mixture was stirred for 45 minutes. 3-Amino-4-hydroxypyridine (137 mg, 1.25 mmol) was added, and the reaction mixture was stirred for 18 hours. The reaction was diluted with aqueous sodium bicarbonate solution (10 mL) and water (10 mL), and then extracted with ethyl acetate (3×20 mL). The combined organic layers were concentrated in vacuo and purified via silica gel chromatography (Gradient: 0% to 15% methanol in dichloromethane) to afford the product as a white solid. Yield 145 mg, 0.276 mmol, 88%. LCMS m/z 525.3 [M+H]$^+$. $^1$H NMR (400 MHz, CD$_3$OD) δ 8.90 (d, J=1.7 Hz, 1H), 8.09 (br d, J=7 Hz, 2H), 7.69 (dd, J=7.1, 1.6 Hz, 1H), 7.41-7.55 (m, 4H), 7.04-7.12 (m, 2H), 6.49 (d, J=7.0 Hz, 1H), 4.42 (dd, J=11.9, 2.7 Hz, 1H), 4.29 (dd, J=11.9, 1.3 Hz, 1H), 4.12 (d, J=12.1 Hz, 1H), 3.22-3.3 (m, 1H), 2.96 (dd, half of ABX pattern, J=13.2, 4.1 Hz, 1H), 2.80 (dd, half of ABX pattern, J=13.2, 2.9 Hz, 1H), 2.20-2.27 (m, 1H), 1.96-2.07 (m, 1H).

Step 2. Synthesis of N-[(4aR,6R,8aS)-8a-(2,4-difluorophenyl)-6-([1,3]oxazolo[4,5-c]pyridin-2-yl)-4,4a,5,6,8,8a-hexahydropyrano[3,4-d][1,3]thiazin-2-yl]benzamide (C64)

A mixture of triphenylphosphine (278 mg, 1.06 mmol) and di-tert-butyl azodicarboxylate
(183 mg, 0.795 mmol) in dichloromethane (7 mL) was stirred for 7 minutes. A solution of C63 (139 mg, 0.265 mmol) in dichloromethane (2 mL) was added, and the reaction mixture was stirred for 18 hours. After concentration in vacuo, the residue was purified via silica gel chromatography (Gradient: 50% to 100% ethyl acetate in heptane) to afford a white solid (126 mg) containing the product contaminated with triphenylphosphine oxide. This material was used in the next step without further purification. LCMS m/z 507.2 [M+H]$^+$. $^1$H NMR (400 MHz, CDCl$_3$), characteristic product peaks: δ 9.00 (s, 1H), 8.55 (d, J=5.8 Hz, 1H), 8.06-8.16 (br m, 2H), 7.77 (d, J=5.5 Hz, 1H), 7.05-7.15 (m, 2H), 5.22 (br d, J=12 Hz, 1H), 4.40 (d, J=12.1 Hz, 1H), 3.02 (dd, half of ABX pattern, J=13.4, 4.0 Hz, 1H), 2.86 (br dd, half of ABX pattern, J=13, 2 Hz, 1H), 2.49-2.61 (m, 1H), 2.22-2.30 (m, 1H).

Step 3. Synthesis of (4aR,6R,8aS)-8a-(2,4-difluorophenyl)-6-([1,3]oxazolo[4,5-c]pyridin-2-yl)-4,4a,5,6,8,8a-hexahydropyrano[3,4-d][1,3]thiazin-2-amine (10)

To a mixture of C64 (from the previous step, 120 mg, <0.24 mmol) in methanol (7.5 mL) was added 1,8-diazabicyclo[5.4.0]undec-7-ene (38 mg, 0.24 mmol). The reaction mixture was heated to 68° C. for 18 hours and then concentrated in vacuo. Silica gel chromatography (Gradient: 0% to 10% methanol in dichloromethane) provided the product as a white solid. Yield 4.5 mg, 11 μmol, 4% over two steps. $^1$H NMR (400 MHz, CD$_3$OD) δ 9.00 (d, J=0.9 Hz, 1H), 8.56 (d, J=5.7 Hz, 1H), 7.76 (dd, J=5.7, 1.0 Hz, 1H), 7.39 (ddd, J=9.5, 8.8, 6.5 Hz, 1H), 6.97-7.05 (m, 2H), 5.13 (dd, J=11.9, 2.6 Hz, 1H), 4.35 (dd, J=11.4, 1.8 Hz, 1H), 3.91 (d, J=11.4 Hz, 1H), 3.15-3.23 (m, 1H), 2.99 (dd, half of ABX pattern, J=12.6, 4.1 Hz, 1H), 2.84 (dd, half of ABX pattern, J=12.7, 2.8 Hz, 1H), 2.42-2.53 (m, 1H), 2.12 (ddd, J=13.4, 3.9, 2.8 Hz, 1H).

Example 11

(4aR,6R,8aS)-8a-(2,4-Difluorophenyl)-6-(5-methoxypyrimidin-2-yl)-4,4a,5,6,8,8a-hexahydropyrano[3,4-d][1,3]thiazin-2-amine, trifluoroacetate salt (11)

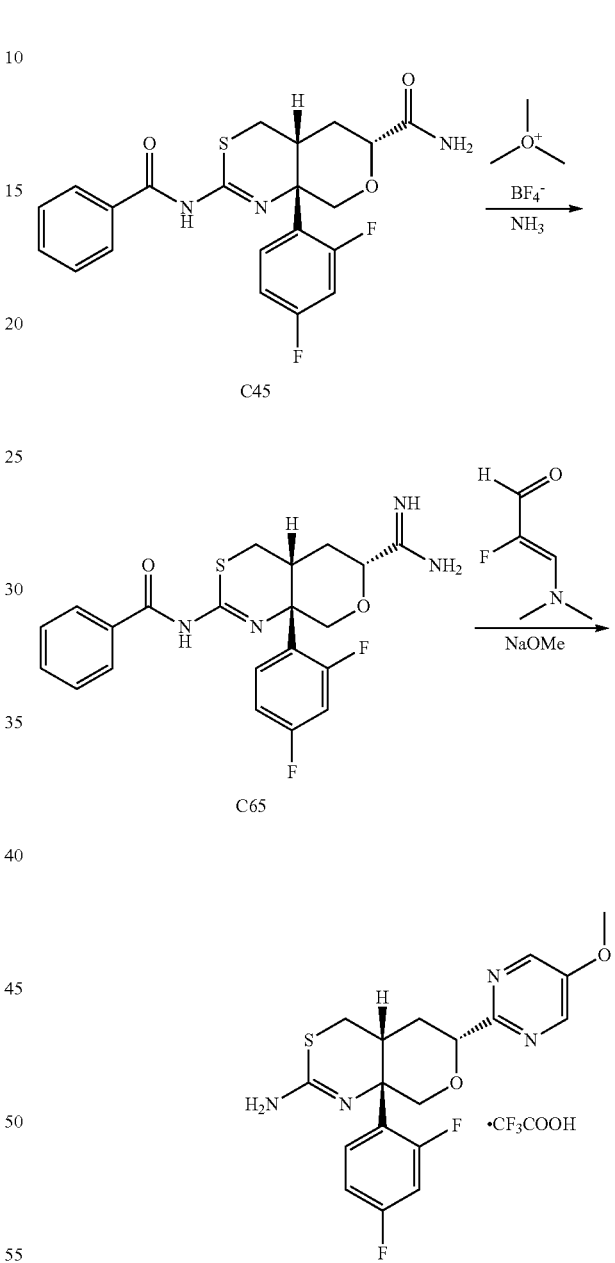

Step 1. Synthesis of N-[(4aR,6R,8aS)-6-carbamimidoyl-8a-(2,4-difluorophenyl)-4,4a,5,6,8,8a-hexahydropyrano[3,4-d][1,3]thiazin-2-yl]benzamide (C65)

To a suspension of C45 (1.82 g, 4.22 mmol) in dichloromethane (26 mL) was added trimethyloxonium tetrafluoroborate (1.40 g, 9.28 mmol) at room temperature. The reaction mixture was stirred at room temperature for 4 hours and then concentrated in vacuo. Diethyl ether (20 mL) was added, swirled and then decanted off; the residue was transferred into a sealable tube with methanol (3.3 mL). A solution of ammonia in methanol (7.0 M, 31 mL) was added and the reaction mixture was stirred at room temperature for 18 hours, then concentrated under reduced pressure. The residue was diluted with ethyl acetate and washed with saturated aqueous sodium bicarbonate solution. The aqueous layer was extracted twice with ethyl acetate, and the combined organic extracts were washed with saturated aqueous sodium chloride solution, dried over sodium sulfate, filtered, and concentrated in vacuo. Chromatography on silica gel (Gradient: 0% to 20% methanol in dichloromethane) afforded the product as a white solid. Yield: 958 mg, 2.21 mmol, 52%. LCMS m/z 431.2 [M+H]$^+$. $^1$H NMR (400 MHz, CDCl$_3$), characteristic peaks: δ 8.15-8.18 (m, 2H), 7.41-7.55 (m, 4H), 6.68-6.95 (m, 2H), 4.73 (dd, J=11.9, 2.1 Hz, 1H), 4.20 (d, J=11.5 Hz, 1H), 3.82 (d, J=12.3 Hz, 1H), 2.93-3.00 (m, 1H), 3.27-3.36 (m, 1H), 2.76-2.81 (m, 1H), 2.33-2.44 (m, 1H), 1.99-2.08 (m, 1H).

Step 2. Synthesis of (4aR,6R,8aS)-8a-(2,4-difluorophenyl)-6-(5-methoxypyrimidin-2-yl)-4,4a,5,6,8,8a-hexahydropyrano[3,4-d][1,3]thiazin-2-amine, trifluoroacetate salt (11)

To a solution of (2Z)-3-(dimethylamino)-2-fluoroprop-2-enal (87 mg, 0.72 mmol) in methanol (0.3 mL) was added C65 (89 mg, 0.21 mmol). The reaction mixture was stirred at 65° C. for 5 minutes, whereupon a solution of sodium methoxide in methanol (0.5 M, 0.828 mL, 0.414 mmol) was added. The reaction mixture was stirred at 65° C. for 18 hours and then cooled to room temperature, diluted with water (20 mL) and extracted with ethyl acetate (3×30 mL). The combined organic layers were washed with saturated aqueous sodium chloride solution (20 mL), dried over sodium sulfate, filtered, and concentrated in vacuo. Chromatography on silica gel (Gradient: 0% to 10% methanol in dichloromethane) afforded the free base of the product as a yellow solid. Yield: 9.8 mg, 20 μmol, 9%. $^1$H NMR (400 MHz, CDCl$_3$) δ 8.44 (s, J=8.4 Hz, 2H), 7.43-7.53 (m, 1H), 6.81-7.01 (m, 2H), 4.90 (dd, J=11.6, 2.2 Hz, 1H), 4.31 (dd, J=11.3, 2.2 Hz, 1H), 4.09-4.11 (m, 1H), 3.93 (s, 3H), 3.11-3.15 (m, 1H), 2.98-3.05 (m, 1H), 2.69 (dd, J=12.2, 2.6 Hz, 1H), 2.22-2.32 (m, 1H), 1.93-1.97 (m, 1H). Further purification via reversed phase HPLC (Column: Waters Sunfire C18, 5 μm; Mobile phase A: 0.05% trifluoroacetic acid in water (v/v); Mobile phase B: 0.05% trifluoroacetic acid in acetonitrile (v/v); Gradient: 5.0% to 50% B) afforded the product. Yield: 6.0 mg, 12 μmol, 6%. LCMS m/z 393.3 [M+H]$^+$.

Example 12

(4aR,6R,8aS)-8a-(2,4-Difluorophenyl)-6-(2-methyl-2H-1,2,3-triazol-4-yl)-4,4a,5,6,8,8a-hexahydropyrano[3,4-d][1,3]thiazin-2-amine, hydrochloride salt (12)

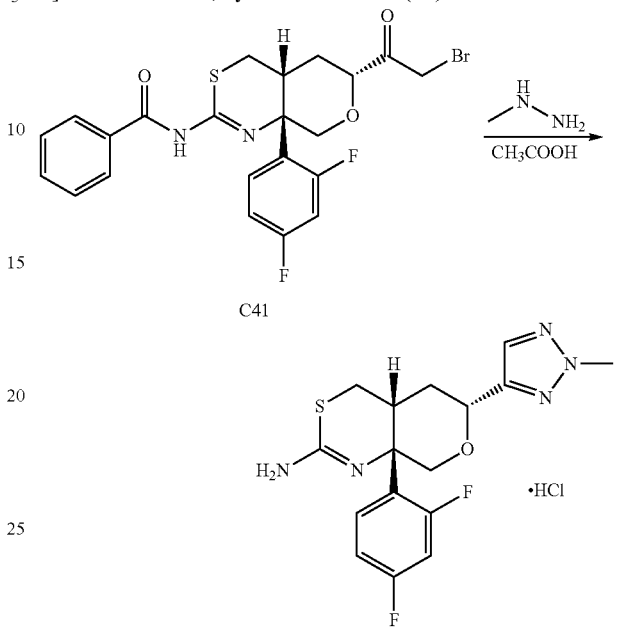

Using the method described by B. Xu and Y. Hu, *J. Chem. Research (S)* 2003, 96-97, methylhydrazine (19.8 mg, 0.43 mmol) was added slowly to a solution of C41 (44 mg, 86 μmol) in acetic acid (0.17 mL). The reaction mixture was heated to 130° C. for 3 hours, then cooled to room temperature and quenched with 1 N aqueous sodium hydroxide solution. The mixture was extracted three times with dichloromethane, and the combined organic layers were dried over sodium sulfate, filtered, and concentrated in vacuo. Purification via silica gel chromatography (Gradient: 0% to 10% methanol in dichloromethane) afforded the free base of 12. This material was dissolved in dichloromethane and treated with 1 M hydrogen chloride in dichloromethane; concentration in vacuo provided the product as a solid. Yield: 4.5 mg, 12 μmol, 14%. LCMS m/z 366.3 [M+H]$^+$. $^1$H NMR (400 MHz, CDCl$_3$) δ 7.60 (s, 1H), 7.43-7.32 (m, 1H), 6.93-6.78 (m, 2H), 4.88-4.82 (m, 1H), 4.26 (dd, J=11.2, 2.2 Hz, 1H), 4.18 (s, 3H), 3.92 (d, J=11.4 Hz, 1H), 2.95-3.09 (m, 2H), 2.61-2.72 (m, 1H), 2.16-2.30 (m, 1H), 1.84-1.94 (m, 1H).

Example 13

(4S,4aR,6R,8aS)-8a-(2,4-Difluorophenyl)-4-(fluoromethyl)-6-(3-methyl-1,2-oxazol-5-yl)-4,4a,5,6,8,8a-hexahydropyrano[3,4-d][1,3]thiazin-2-amine (13)

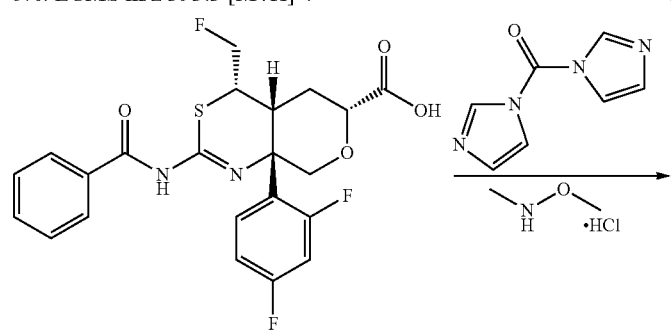

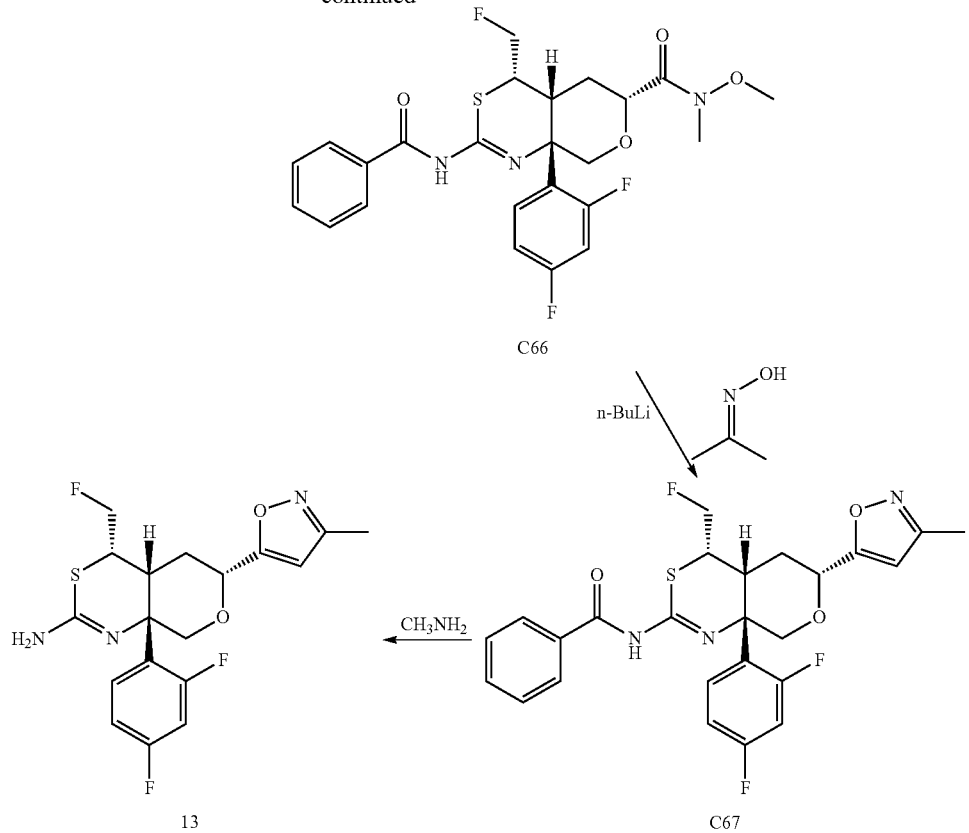

Step 1. Synthesis of (4S,4aR,6R,8aS)-2-(benzoylamino)-8a-(2,4-difluorophenyl)-4-(fluoromethyl)-N-methoxy-N-methyl-4,4a,5,6,8,8a-hexahydropyrano[3,4-d][1,3]thiazine-6-carboxamide (C66)

1,1'-Carbonyldiimidazole (4.40 g, 27.1 mmol) was added to a solution of P7 (9.7 g, 21 mmol) in 1,2-dichloroethane (70 mL), and the reaction mixture was stirred at room temperature for 1.5 hours. N,O-Dimethylhydroxylamine hydrochloride (3.06 g, 31.4 mmol) was then added, and stirring was continued for 18 hours. The reaction mixture was partitioned between water and dichloromethane, and the organic layer was washed sequentially with 0.5 M aqueous hydrochloric acid, saturated aqueous sodium bicarbonate solution, and saturated aqueous sodium chloride solution, then dried over sodium sulfate, filtered, and concentrated in vacuo. The residue was azeotroped with dichloromethane (3×100 mL) to afford the product as a solid. Yield: 7.6 g, 15 mmol, 71%. LCMS m/z 508.2 [M+H]$^+$.

Step 2. Synthesis of N-[(4S,4aR,6R,8aS)-8a-(2,4-difluorophenyl)-4-(fluoromethyl)-6-(3-methyl-1,2-oxazol-5-yl)-4,4a,5,6,8,8a-hexahydropyrano[3,4-d][1,3]thiazin-2-yl]benzamide (C67)

A solution of N-hydroxypropan-2-imine (3.28 g, 44.9 mmol) in tetrahydrofuran (150 mL) was cooled to an internal temperature of −9° C. n-Butyllithium (2.5 M solution in hexanes, 35.9 mL, 89.8 mmol) was slowly added to the cold solution. The cooling bath was removed, and the reaction mixture was allowed to warm to room temperature, whereupon it was cooled to −8° C. and treated drop-wise over less than 20 minutes with a solution of C66 (7.6 g, 15 mmol) in a minimum volume of tetrahydrofuran, at a rate such that the internal reaction temperature never exceeded −5° C. Stirring was continued at −5° C. for 2 minutes, then at 0° C. for 10 minutes, at which time concentrated sulfuric acid (12.0 mL, 225 mmol) was slowly added. The reaction mixture was stirred at room temperature for 1 hour, then cooled to −5° C. and slowly quenched via addition of 15% aqueous sodium hydroxide solution until the pH of the aqueous phase reached 9-10. The mixture was partitioned between water and ethyl acetate, and the aqueous layer was extracted with ethyl acetate. The combined organic layers were dried over sodium sulfate, filtered, and concentrated in vacuo. Chromatography on silica gel (Gradient: 0% to 20% ethyl acetate in heptane) provided the product as a solid. Yield: 5.65 g, 11.3 mmol, 75%. $^1$H NMR (400 MHz, CDCl$_3$) δ 8.17 (br s, 2H), 7.43-7.59 (m, 3H), 7.33-7.43 (m, 1H), 6.89-7.00 (m, 2H), 6.14 (s, 1H), 4.87 (dd, J=10.7, 3.5 Hz, 1H), 4.61 (ddd, J=46.9, 9.6, 7.9 Hz, 1H), 4.46 (ddd, J=46.1, 9.7, 6.2 Hz, 1H), 4.33 (dd, J=12.1, 1.3 Hz, 1H), 3.96 (d, J=12.1 Hz, 1H), 3.50-3.62 (br m, 1H), 3.32-3.43 (br m, 1H), 2.28 (s, 3H), 2.0-2.16 (m, 2H).

Step 3. Synthesis of (4S,4aR,6R,8aS)-8a-(2,4-difluorophenyl)-4-(fluoromethyl)-6-(3-methyl-1,2-oxazol-5-yl)-4,4a,5,6,8,8a-hexahydropyrano[3,4-d][1,3]thiazin-2-amine (13)

Methylamine (33% solution in absolute ethanol, 23.8 mL, 200 mmol) was added to a solution of C67 (1.00 g, 1.99 mmol) in ethanol (40 mL), and the reaction mixture was allowed to stir for 2 hours. After concentration under reduced pressure, the residue was purified via silica gel chromatography (Gradient: 0% to 60% ethyl acetate in heptane) to afford the product. Yield: 0.71 g, 1.8 mmol, 90%. LCMS m/z 398.0 [M+H]+. 1H NMR (400 MHz, CDCl3) δ 7.36 (ddd, J=9.0, 8.8, 6.6 Hz, 1H), 6.81-6.92 (m, 2H), 6.14 (s, 1H), 4.78-4.84 (m, 1H), 4.56 (ddd, J=46.8, 9.5, 7.3 Hz, 1H), 4.37 (ddd, J=46.3, 9.5, 6.7 Hz, 1H), 4.24 (dd, J=11.2, 2.0 Hz, 1H), 3.93 (d, J=11.3 Hz, 1H), 3.47-3.57 (m, 1H), 3.10-3.17 (m, 1H), 2.30 (s, 3H), 1.88-2.00 (m, 2H). A sample of 13 was dissolved in acetonitrile and concentrated in vacuo; the resulting solid was crystalline, as determined by X-ray powder diffraction.

Example 14

(4aR,6R,8aS)-6-[4-(Difluoromethyl)-1,3-oxazol-2-yl]-8a-(2,4-difluorophenyl)-4,4a,5,6,8,8a-hexahydropyrano[3,4-d][1,3]thiazin-2-amine (14)

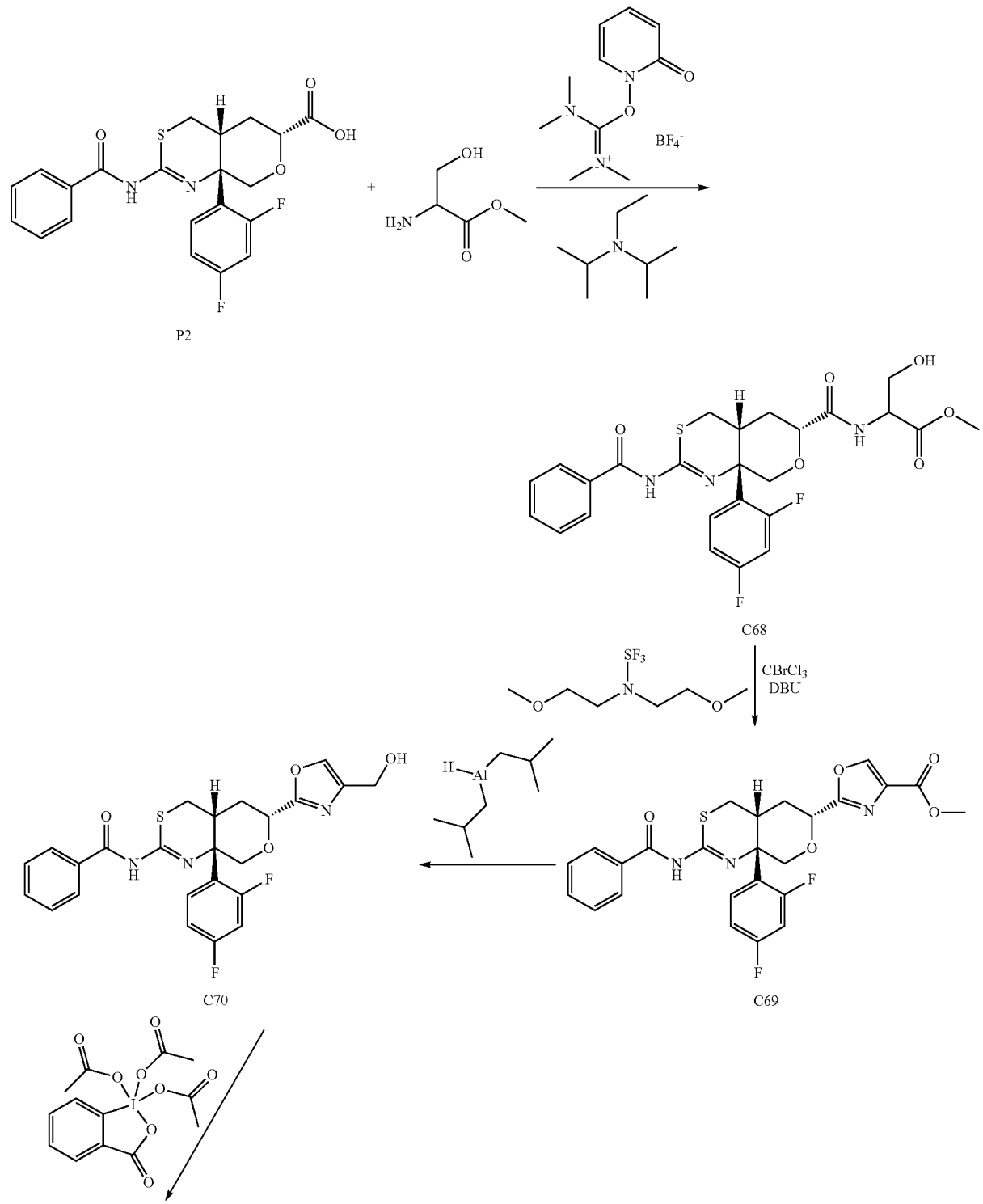

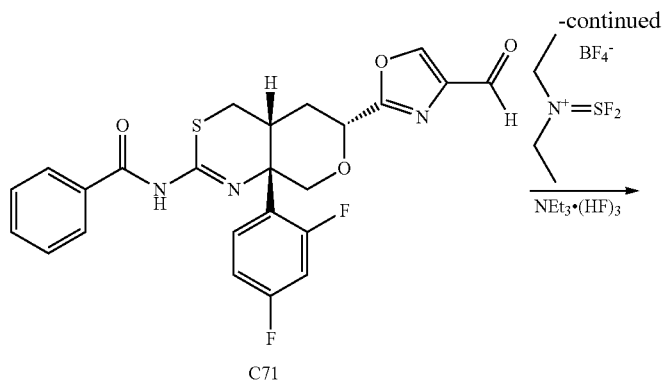
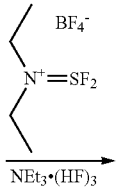
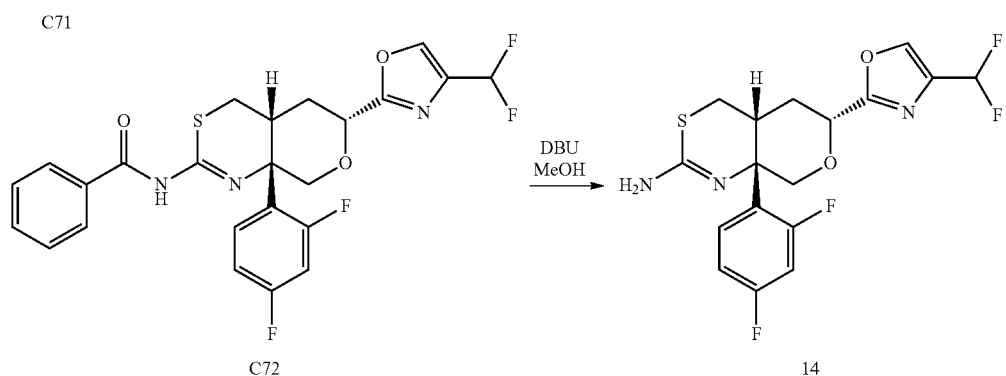

Step 1. Synthesis of methyl N-{[(4aR,6R,8aS)-2-(benzoylamino)-8a-(2,4-difluorophenyl)-4,4a,5,6,8,8a-hexahydropyrano[3,4-d][1,3]thiazin-6-yl]carbonyl}serinate (C68)

To a solution of P2 (812 mg, 1.88 mmol) in N,N-dimethylformamide (10 mL) was added N,N-diisopropylethylamine (1 mL) and 2-[2-oxo-1(2H)-pyridyl]-1,1,3,3-tetramethyluronium tetrafluoroborate (TPTU) (614 mg, 2.07 mmol). The mixture was stirred at room temperature for 35 minutes and further N,N-diisopropylethylamine (960 µL) and methyl 2-amino-3-hydroxypropanoate hydrochloride (1020 mg, 6.57 mmol) were added. The mixture was stirred at room temperature for 18 hours, diluted with saturated aqueous sodium bicarbonate solution (30 mL) and water (30 mL), and extracted with tert-butyl methyl ether (3×60 mL). The combined organic extracts were dried over sodium sulfate, filtered, and concentrated in vacuo. Chromatography on silica gel (Gradient: 30% to 100% ethyl acetate in heptane) afforded the product as a white solid. By $^1$H NMR, this was judged to be a mixture of diastereomers. Yield: 840 mg, 1.57 mmol, 84%. LCMS m/z 534.2 [M+H]$^+$. $^1$H NMR (400 MHz, CD$_3$OD) δ 8.11 (br d, J=6 Hz, 2H), 7.44-7.57 (m, 4H), 7.04-7.23 (m, 4H), 4.54 (t, J=3.8 Hz, 1H), 4.23-4.31 (m, 2H), 4.05 (dd, J=11.9, 3.9 Hz, 1H), 3.92-3.95 (m, 1H), 3.82 (ddd, J=11.5, 8.3, 3.6 Hz, 1H), 3.75 and 3.68 (2 s, total 3H), 3.23-3.25 (m, 1H), 2.97 (dd, J=13.3, 4.1 Hz, 1H), 2.78-2.82 (m, 1H), 2.11-2.16 (m, 1H), 1.98-2.04 (m, 1H).

Step 2. Synthesis of methyl 2-[(4aR,6R,8aS)-2-(benzoylamino)-8a-(2,4-difluorophenyl)-4,4a,5,6,8,8a-hexahydropyrano[3,4-d][1,3]thiazin-6-yl]-1,3-oxazole-4-carboxylate (C69)

2-Methoxy-N-(2-methoxyethyl)-N-(trifluoro-λ$^4$-sulfanyl)ethanamine (Deoxo-Fluor®, 373 µL, 2.02 mmol) was added to a solution of C68 (830 mg, 1.56 mmol) in dichloromethane (40 mL) at −20° C. The reaction mixture was stirred for 50 minutes at −20° C., prior to drop-wise addition of bromotrichloromethane (568 µL, 5.76 mmol) and 1,8-diazabicyclo[5.4.0]undec-7-ene (906 µL, 5.76 mmol). The reaction mixture was allowed to warm to 0° C. and stirred at 0° C. for 18 hours, then diluted with saturated aqueous sodium bicarbonate solution (50 mL) and dichloromethane (50 mL). The aqueous phase was extracted with dichloromethane (2×50 mL), and the combined organic layers were dried over sodium sulfate, filtered, and concentrated in vacuo. Chromatography on silica gel (Gradient: 0% to 100% ethyl acetate in heptane) afforded the product as a white solid. Yield: 95 mg, 0.18 mmol, 12%. LCMS m/z 514.1 [M+H]$^+$. $^1$H NMR (400 MHz, CD$_3$OD), characteristic peaks: δ 8.55 (s, 1H), 8.11 (br d, J=6.5 Hz, 2H), 7.43-7.55 (m, 4H), 7.04-7.13 (m, 2H), 5.00 (dd, J=11.9, 2.5 Hz, 1H), 4.32 (dd, J=12, 1.5 Hz, 1H), 4.01 (d, J=11.9 Hz, 1H), 3.86 (s, 3H), 2.99 (dd, J=13.2, 4.0 Hz, 1H), 2.82 (dd, J=13.2, 2.8 Hz, 1H), 2.42-2.51 (m, 1H), 2.07-2.14 (m, 1H).

Step 3. Synthesis of N-{(4aR,6R,8aS)-8a-(2,4-difluorophenyl)-6-[4-(hydroxymethyl)-1,3-oxazol-2-yl]-4,4a,5,6,8,8a-hexahydropyrano[3,4-d][1,3]thiazin-2-yl}benzamide (C70)

To a solution of C69 (59 mg, 0.12 mmol) in dichloromethane (5 mL) at −78° C. was added a solution of diisobutylaluminum hydride in toluene (1.5 M, 269 µL, 0.403 mmol) drop-wise over 3 minutes. The reaction mixture was stirred at −78° C. for 45 minutes, then diluted with saturated aqueous potassium sodium tartrate solution (10 mL) and allowed to warm to room temperature. The mixture was extracted with ethyl acetate (3×15 mL), and the combined organic layers were dried over sodium sulfate, filtered, and concentrated in vacuo. Chromatography on silica gel (Gradient: 0% to 100% ethyl acetate in heptane) afforded the product as a white solid. Yield: 32 mg, 66 µmol, 55%. LCMS m/z 486.2 [M+H]$^+$. $^1$H NMR (400 MHz, CD$_3$OD), characteristic peaks: δ 8.11 (br d, J=7 Hz, 2H), 7.79 (t, J=1.0 Hz, 1H), 7.43-7.55 (m, 4H), 7.04-7.12 (m, 2H), 4.93 (dd, J=11.9, 2.3 Hz, 1H), 4.49 (d, J=1.0 Hz, 2H), 4.30 (dd, J=11.9, 1.6 Hz, 1H), 3.99 (d, J=11.9 Hz, 1H), 2.98 (dd, J=13.1, 4.1 Hz, 1H), 2.8 (dd, J=13.3, 2.9 Hz, 1H), 2.40-2.50 (m, 1H), 2.03-2.10 (m, 1H).

Step 5. Synthesis of N-[(4aR,6R,8aS)-8a-(2,4-difluorophenyl)-6-(4-formyl-1,3-oxazol-2-yl)-4,4a,5,6,8,8a-hexahydropyrano[3,4-d][1,3]thiazin-2-yl]benzamide (C71)

To a solution of C70 (30 mg, 62 μmol) in dichloromethane (2 mL), was added Dess-Martin periodinane[1,1,1-tris(acetyloxy)-1,1-dihydro-1,2-benziodoxol-3-(1H)-one] (39.4 mg, 93 μmol). The mixture was stirred at room temperature for 1 hour, then was diluted with a mixture of saturated aqueous sodium bicarbonate solution and saturated aqueous sodium thiosulfate solution (1:1, 7.5 mL). After stirring for 5 minutes, the mixture was extracted with ethyl acetate (3×10 mL). The combined organic extracts were dried over sodium sulfate, filtered, and concentrated in vacuo. Chromatography on silica gel (Gradient: 0% to 100% ethyl acetate in heptane) afforded the product as a white solid. Yield: 26.5 mg, 54.8 μmol, 88%. LCMS m/z 484.2 [M+H]$^+$. $^1$H NMR (400 MHz, CDCl$_3$) δ 9.94 (s, 1H), 8.27 (s, 1H), 8.17-8.20 (m, 2H), 7.39-7.55 (m, 4H), 6.90-6.98 (m, 2H), 4.95 (dd, J=11.9, 2.5 Hz, 1H), 4.35 (dd, J=12.3, 1.6 Hz, 1H), 3.97 (d, J=12.4 Hz, 1H), 3.25-3.28 (m, 1H), 3.07 (dd, J=13.1, 3.9 Hz, 1H), 2.72 (dd, J=13.1, 2.9 Hz, 1H), 2.56-2.68 (m, 1H), 2.15-2.19 (m, 1H).

Step 6. Synthesis of N-[(4aR,6R,8aS)-6-[4-(difluoromethyl)-1,3-oxazol-2-yl]-8a-(2,4-difluorophenyl)-4,4a,5,6,8,8a-hexahydropyrano[3,4-d][1,3]thiazin-2-yl]benzamide (C72)

To a solution of C71 (30 mg, 62 μmol) in dichloromethane was added triethylamine trihydrofluoride (35 μL, 0.217 mmol) and N-(difluoro-λ$^4$-sulfanylidene)-N-ethylethanaminium tetrafluoroborate (XtalFluor-E®) (29 mg, 0.124 mmol). The reaction mixture was stirred at room temperature for 3 hours. To the mixture was added further triethylamine trihydrofluoride (35 μL, 0.217 mmol) and XtalFluor-E® (29 mg, 0.124 mmol), and stirring was continued for 18 hours. The mixture was quenched with saturated aqueous sodium bicarbonate solution (10 mL) and stirred for 10 minutes, and the resulting mixture was extracted with dichloromethane (2×15 mL). The combined organic extracts were dried over sodium sulfate, filtered, and concentrated in vacuo. Chromatography on silica gel (Gradient: 0% to 90% ethyl acetate in heptane) afforded the product as a white solid. Yield: 8.6 mg, 17 μmol, 27%. LCMS m/z 506.2 [M+H]$^+$. $^1$H NMR (400 MHz, CD$_3$OD), characteristic peaks: δ 8.23 (td, J=2.6, 0.5 Hz, 1H), 8.11 (br d, J=7 Hz, 2H), 7.44-7.56 (m, 4H), 7.04-7.13 (m, 2H), 6.77 (td, J=54.3, 0.5 Hz, 1H), 5.00 (dd, J=11.9, 2.4 Hz, 1H), 4.33 (dd, J=11.9, 1.5 Hz, 1H), 4.01 (d, J=12.0 Hz, 1H), 2.99 (dd, J=13.2, 4.1 Hz, 1H), 2.82 (dd, J=13.2, 2.8 Hz, 1H), 2.41-2.50 (m, 1H), 2.08-2.12 (m, 1H).

Step 7. Synthesis of (4aR,6R,8aS)-6-[4-(difluoromethyl)-1,3-oxazol-2-yl]-8a-(2,4-difluorophenyl)-4,4a,5,6,8,8a-hexahydropyrano[3,4-d][1,3]thiazin-2-amine (14)

Compound C72 was converted to the product using the method employed for synthesis of 2 in Example 2. The product was isolated as a white solid. Yield: 6.5 mg, 16 μmol, 89%. LCMS m/z 402.2 [M+H]$^+$. $^1$H NMR (400 MHz, CDCl$_3$) δ 8.21 (t, J=2.3 Hz, 1H), 7.32-7.43 (m, 1H), 7.00-7.05 (m, 2H), 6.77 (td, J=54.6, 0.8 Hz, 1H), 4.93 (dd, J=11.7, 2.5 Hz, 1H), 4.28 (dd, J=11.6, 1.7 Hz, 1H), 3.90 (d, J=11.7 Hz, 1H), 3.16-3.22 (m, 1H), 2.99 (dd, J=12.7, 4.1 Hz, 1H), 2.85 (dd, J=12.7, 2.9 Hz, 1H), 2.33-2.43 (m, 1H), 1.98-2.03 (m, 1H).

Example 15

(4aR,6R,8aS)-8a-(2,4-Difluorophenyl)-6-[1-($^2$H$_3$)methyl-1H-pyrazol-4-yl]-4,4a,5,6,8,8a-hexahydropyrano[3,4-d][1,3]thiazin-2-amine (15)

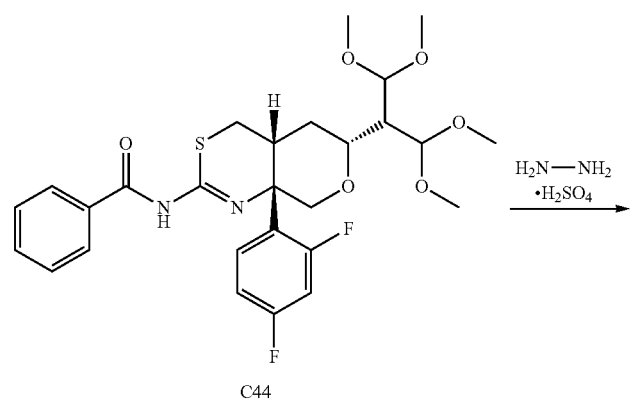

C44

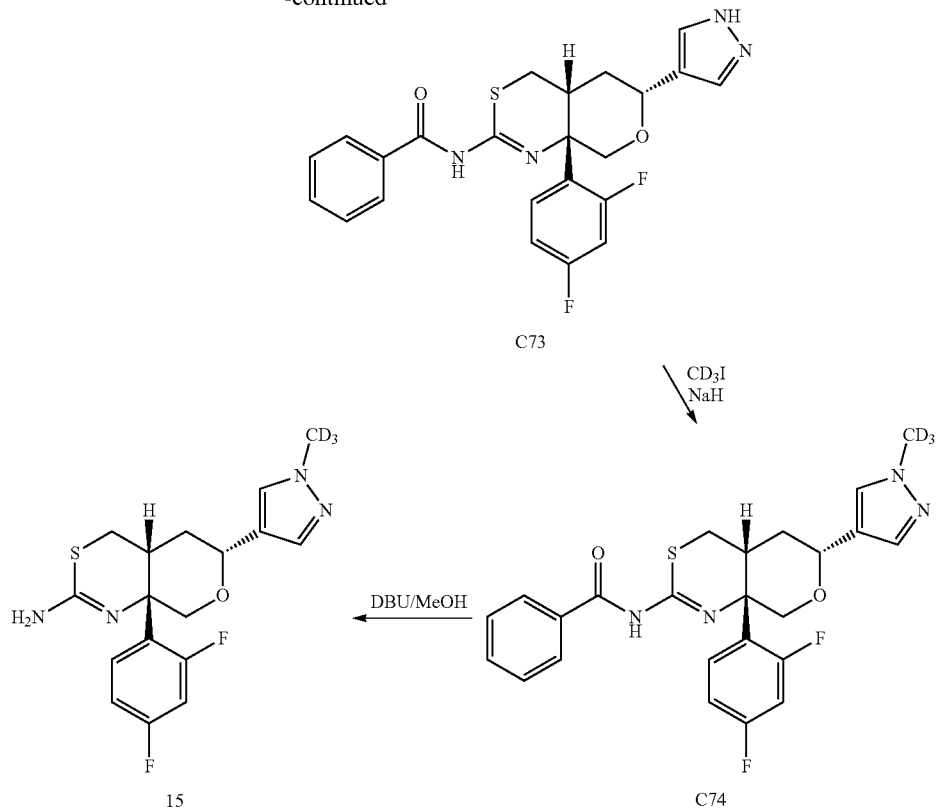

Step 1. Synthesis of N-[(4aR,6R,8aS)-8a-(2,4-difluorophenyl)-6-(1H-pyrazol-4-yl)-4,4a,5,6,8,8a-hexahydropyrano[3,4-d][1,3]thiazin-2-yl]benzamide (C73)

To C44 (620 mg, 1.13 mmol) dissolved in an ethanol/water mixture (3:1, 4 mL) was added hydrazine sulfate (150 mg, 1.15 mmol) and the mixture was heated at 60° C. for 16 hours. Aqueous saturated sodium carbonate solution was added until a pH of 9 was obtained, followed by addition of methanol (1 mL) and extraction with ethyl acetate (3×25 mL). The combined organic layers were washed with saturated aqueous sodium chloride solution, dried over sodium sulfate, filtered, and concentrated in vacuo. Purification via silica gel chromatography (Gradient: 0% to 17.5% methanol in dichloromethane) provided the product as a tan solid. Yield: 47 mg, 0.10 mmol, 9%. LCMS m/z 455.2 [M+H]+. 1H NMR (400 MHz, CDCl3) δ 8.20-8.22 (m, 2H), 7.39-7.53 (m, 6H), 6.86-6.96 (m, 2H), 4.77 (dd, J=11.6, 2.1 Hz, 1H), 4.3 (dd, J=12.1, 1.8 Hz, 1H), 3.89 (d, J=12.1 Hz, 1H), 3.22-3.28 (m, 1H), 3.04 (dd, J=12.8, 4.2 Hz, 1H), 2.67 (dd, J=12.9, 2.7 Hz, 1H), 2.21-2.31 (m, 1H), 1.91-1.96 (m, 1H).

Step 2. Synthesis of N-{(4aR,6R,8aS)-8a-(2,4-difluorophenyl)-6-[1-(2H3)methyl-1H-pyrazol-4-yl]-4,4a,5,6,8,8a-hexahydropyrano[3,4-d][1,3]thiazin-2-yl}benzamide (C74)

To C73 (32 mg, 70 μmol) in tetrahydrofuran (0.30 mL) was added sodium hydride (60% in mineral oil, 9.00 mg, 0.224 mmol) followed by stirring at room temperature for 10 minutes. Iodo(2H3)methane (11.7 mg, 81 μmol) in tetrahydrofuran (0.40 mL) was added, and the reaction mixture was stirred at room temperature for 30 minutes, then at 32° C. for 45 minutes. Aqueous hydrochloric acid (1 M, 5 drops) and water (2 mL) were added, followed by extraction with ethyl acetate (2×5 mL). The combined organic layers were dried over magnesium sulfate, filtered, and concentrated in vacuo. Silica gel chromatography (Gradient: 10% to 100% ethyl acetate in heptane) provided the product as a white solid. Yield: 22 mg, 47 μmol, 67%. LCMS m/z 472.2 [M+H]+. 1H NMR (400 MHz, CDCl3) δ 8.20-8.23 (m, 2H), 7.39-7.53 (m, 6H), 6.87-6.96 (m, 2H), 4.72 (dd, J=11.5, 2.2 Hz, 1H), 4.29 (dd, J=12.3, 1.4 Hz, 1H), 3.86 (d, J=12.3 Hz, 1H), 3.22-3.28 (m, 1H), 3.04 (dd, J=12.8, 4.0 Hz, 1H), 2.67 (dd, J=12.9, 2.7 Hz, 1H), 2.24-2.23 (m, 1H), 1.90-1.95 (m, 1H).

Step 3. Synthesis of (4aR,6R,8aS)-8a-(2,4-difluorophenyl)-6-[1-(2H3)methyl-1H-pyrazol-4-yl]-4,4a,5,6,8,8a-hexahydropyrano[3,4-d][1,3]thiazin-2-amine (15)

A solution of C74 (20 mg, 42 μmol) and 1,8-diazabicyclo[5.4.0]undec-7-ene (4.0 μL, 27.0 μmol) in methanol (0.50 mL) was heated at 55° C. for 16 hours, then concentrated in vacuo. Water was added (2 mL) and the mixture was extracted with ethyl acetate (2×5 mL). The combined organic layers were dried over magnesium sulfate, filtered, and concentrated in vacuo. Silica gel chromatography (Gradient: 0% to 17.5% methanol in dichloromethane) afforded the product as a white solid. Yield: 12.3 mg, 33.6 μmol, 80%. LCMS m/z 368.2 [M+H]+. 1H NMR (400 MHz, CD3OD) δ 7.58 (s, 1H), 7.45 (s, 1H), 7.33-7.39 (m, 1H), 6.94-7.01 (m, 2H), 4.68 (dd, J=11.5, 2.3 Hz, 1H), 4.23 (dd, J=11.2, 2.2 Hz, 1H), 3.74 (d, J=11.3 Hz, 1H), 3.00-3.05 (m, 1H), 2.9 (dd, J=12.5, 4.3 Hz, 1H), 2.71 (dd, J=12.5, 2.7 Hz, 1H), 2.02-2.12 (m, 1H), 1.78-1.83 (m, 1H).

Example 16

(4R,4aR,6R,8aS)-8a-(2,4-Difluorophenyl)-4-methyl-6-(1-methyl-1H-pyrazol-4-yl)-4,4a,5,6,8,8a-hexahydropyrano[3,4-d][1,3]thiazin-2-amine (16)

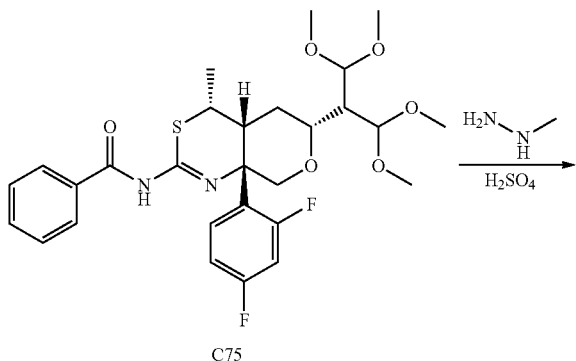

C75

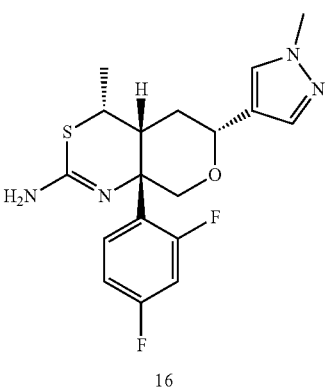

16

N-[(4R,4aR,6R,8aS)-8a-(2,4-Difluorophenyl)-4-methyl-6-(1,1,3,3-tetramethoxypropan-2-yl)-4,4a,5,6,8,8a-hexahydropyrano[3,4-d][1,3]thiazin-2-yl]benzamide (C75) [prepared from P4 via a method similar to that used for the conversion of P1 to C44 in Preparation P3 and Example 5] (297 mg, 0.526 mmol) was combined with ethanol (1.75 mL) and methyl hydrazine (36.4 mg, 0.789 mmol) followed by addition of water (0.6 mL). Concentrated sulfuric acid (55 µL, 1.0 mmol) was slowly added and the reaction mixture was heated at 70° C. for 18 hours. Saturated aqueous sodium bicarbonate solution was added, and the aqueous layer was extracted three times with ethyl acetate; the combined organic layers were extracted three times with 0.2 M aqueous hydrochloric acid, and the combined aqueous layers were washed with ethyl acetate. The pH was adjusted to 9-10 by addition of 1 M aqueous sodium hydroxide solution, and the mixture was extracted three times with ethyl acetate. The combined organic layers were dried over sodium sulfate, filtered, and concentrated under reduced pressure. Silica gel chromatography (Gradient: 0% to 15% methanol in dichloromethane) provided the product as an off-white solid. Yield: 109 mg, 0.287 mmol, 55%. LCMS m/z 379.2 [M+H]$^+$. $^1$H NMR (400 MHz, CD$_3$OD) δ 7.48 (s, 1H), 7.36 (s, 1H), 7.22-7.28 (m, 1H), 6.85-6.92 (m, 2H), 4.57 (dd, J=11.3, 2.3 Hz, 1H), 4.16 (dd, J=11.1, 2.1 Hz, 1H), 3.76 (s, 3H), 3.69 (d, J=11.3, 1H), 3.01-3.06 (m, 1H), 2.78 (dt, J=11.9, 3.8 Hz, 1H), 1.75-1.80 (m, 1H), 1.59-1.68 (m, 1H), 1.10 (d, J=7 Hz, 3H).

Example 17

(4a R,6R,8aS)-8a-(2,4-Difluorophenyl)-6-(2-methylpyrimidin-5-yl)-4,4a,5,6,8,8a-hexahydropyrano[3,4-d][1,3]thiazin-2-amine (17)

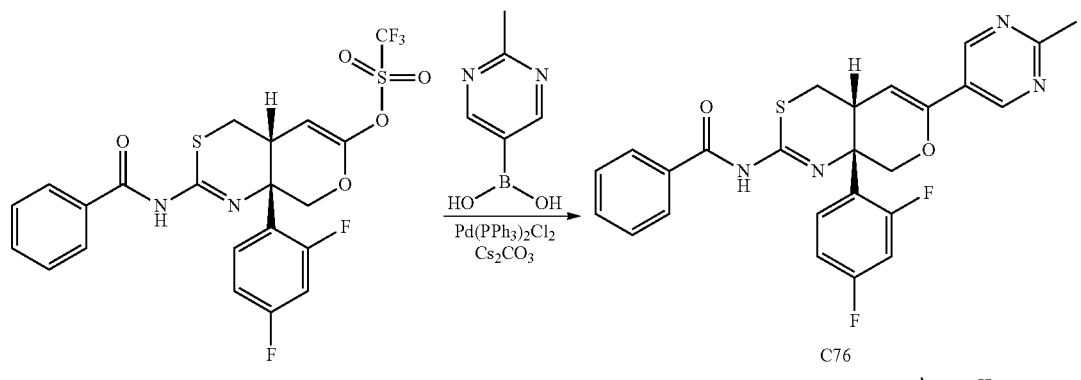

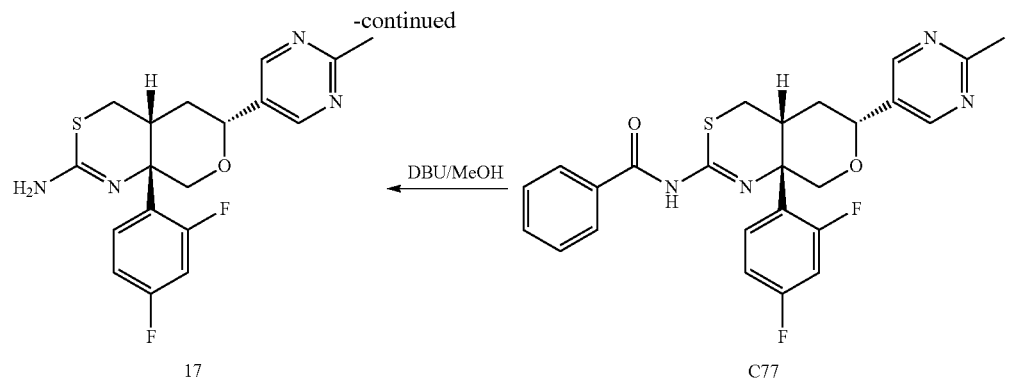

Step 1. Synthesis of N-[(4aR,8aS)-8a-(2,4-difluorophenyl)-6-(2-methylpyrimidin-5-yl)-4,4a,8,8a-tetrahydropyrano[3,4-d][1,3]thiazin-2-yl]benzamide (C76)

A mixture of C30 (60 mg, 0.11 mmol), 2-methylpyrimidine-5-boronic acid (30.9 mg, 0.224 mmol), bis(triphenylphosphine)palladium(II) dichloride (4.3 mg, 6.0 μmol) and tetrahydrofuran (5 mL) was sparged with argon for 5 minutes, followed by addition of aqueous cesium carbonate solution (2 M, 280 μL). The reaction mixture was stirred at 65° C. for 18 hours and then concentrated in vacuo; the residue was diluted with water (15 mL) and extracted with ethyl acetate (3×20 mL). The organic layers were combined, dried over sodium sulfate, filtered, and concentrated in vacuo. Silica gel chromatography (Gradient: 30% to 100% ethyl acetate in heptane) afforded the product as a white solid. Yield: 44 mg, 92 μmol, 84%. $^1$H NMR (400 MHz, CD$_3$OD) δ 8.88 (d, J=1.4 Hz, 2H), 8.00 (br d, J=6.7 Hz, 2H), 7.56-7.62 (m, 1H), 7.50-7.53 (m, 1H), 7.40-7.44 (m, 2H), 7.07-7.12 (m, 2H), 5.66 (br s, 1H), 4.79 (d, J=11 Hz, 1H), 4.34 (br d, J=10.8 Hz, 1H), 3.73 (br s, 1H), 2.93-3.05 (m, 2H), 2.67 (s, 3H)

Step 2. Synthesis of N-[(4aR,6R,8aS)-8a-(2,4-difluorophenyl)-6-(2-methylpyrimidin-5-yl)-4,4a,5,6,8,8a-hexahydropyrano[3,4-d][1,3]thiazin-2-yl]benzamide (C77)

Compound C76 was converted to the product using the method employed for synthesis of C36 in Example 2. The product was obtained as a white solid. Yield: 17.4 mg, 36 μmol, 40%. LCMS m/z 481.2 [M+H]$^+$. $^1$H NMR (400 MHz, CD$_3$OD) δ 8.74 (s, 2H), 8.12 (br d, J=7.4 Hz, 2H), 7.44-7.56 (m, 4H), 7.05-7.13 (m, 2H), 4.88-4.92 (m, 1H), 4.34 (d, J=12.7 Hz, 1H), 4.07 (d, J=11.9 Hz, 1H), 3.37 (br s, 1H), 2.99 (dd, J=13.1, 4.1 Hz, 1H), 2.8 (dd, J=13.1, 2.7 Hz, 1H), 2.67 (s, 3H), 2.05-2.08 (m, 2H).

Step 3. Synthesis of (4aR,6R,8aS)-8a-(2,4-difluorophenyl)-6-(2-methylpyrimidin-5-yl)-4,4a,5,6,8,8a-hexahydropyrano[3,4-d][1,3]thiazin-2-amine (17)

Compound C77 was converted to the product using the method employed for synthesis of 2 in Example 2. The product was isolated as a white solid. Yield: 8.7 mg, 23 μmol, 66%. LCMS m/z 378.2 [M+H]$^+$. $^1$H NMR (400 MHz, CD$_3$OD) δ 8.72 (s, 2H), 7.36-7.42 (m, 1H), 6.97-7.04 (m, 2H), 4.80-4.83 (m, 1H), 4.28 (dd, J=11.2, 2 Hz, 1H), 3.87 (d, J=11.3 Hz, 1H), 3.14 (m, 1H), 2.94 (dd, J=12.5, 4.1 Hz, 1H), 2.75 (dd, J=12.5, 2.7 Hz, 1H), 2.68 (s, 3H), 1.87-1.98 (m, 2H).

Example 18

(4aR,6R,8aS)-8a-(2,4-Difluorophenyl)-6-(1-methyl-1H-1,2,3-triazol-4-yl)-4,4a,5,6,8,8a-hexahydropyrano[3,4-d][1,3]thiazin-2-amine (18)

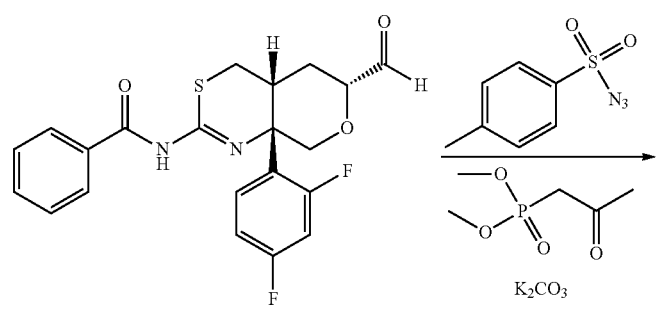

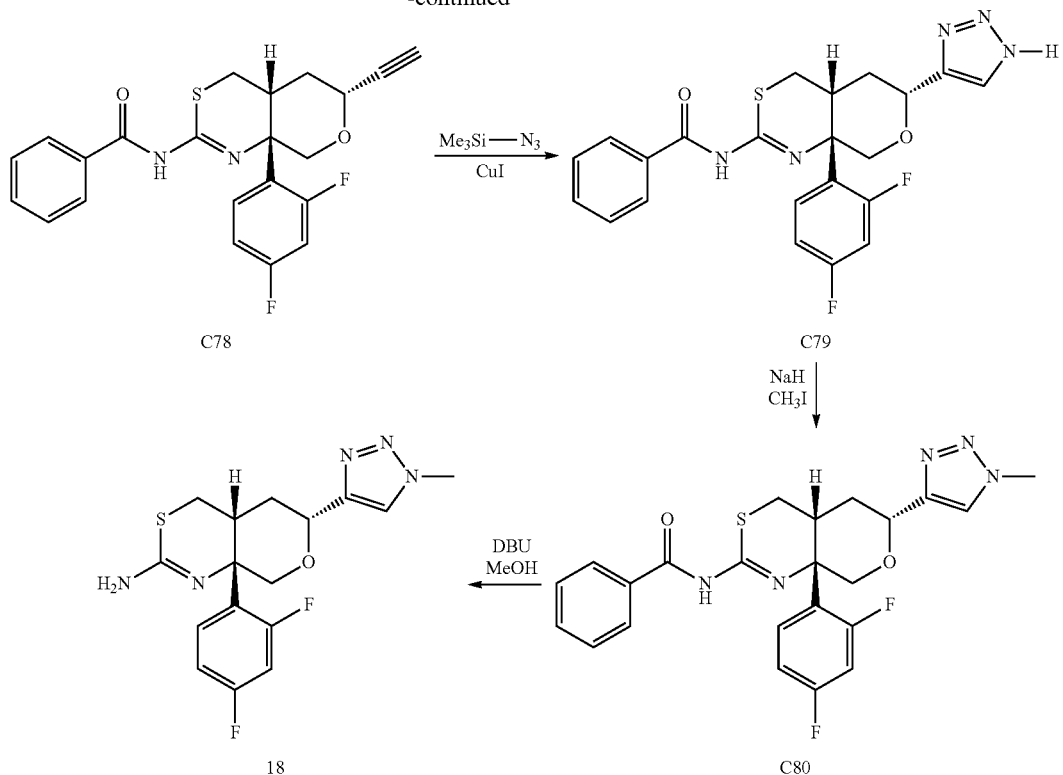

Step 1. Synthesis of N-[(4aR,6R,8aS)-8a-(2,4-difluorophenyl)-6-ethynyl-4,4a,5,6,8,8a-hexahydropyrano[3,4-d][1,3]thiazin-2-yl]benzamide (C78)

Using the method described by Roth, G. J., Liepold, B., Mueller, S. G., and Bestmann, H. J., *Synthesis* 2004, 59-62, dimethyl (2-oxopropyl)phosphonate (229 mg, 1.38 mmol) was slowly added to a suspension of potassium carbonate (477 mg, 3.45 mmol) and 4-methylbenzenesulfonyl azide (13% solution, 2.09 g, 1.38 mmol) in acetonitrile (18 mL) and the reaction mixture was stirred for 2 hours. To this mixture was added a solution of P3 (479 mg, 1.15 mmol) in methanol (4 mL) and the reaction mixture was stirred for an additional 17 hours. Solvents were then removed in vacuo, and the residue was partitioned between ethyl acetate (50 mL) and water (30 mL). The organic layer was washed sequentially with water (20 mL) and saturated aqueous sodium chloride solution (120 mL), dried over sodium sulfate, filtered, and concentrated in vacuo. Purification via silica gel chromatography (Gradient: 0% to 50% ethyl acetate in heptane) afforded the product as an off-white solid. Yield: 332 mg, 1.15 mmol, 70%. LCMS m/z 413.0 [M+H]$^+$. $^1$H NMR (400 MHz, CDCl$_3$) δ 8.20 (d, J=7.6 Hz, 2H), 7.56-7.30 (m, 4H), 6.99-6.82 (m, 2H), 4.44 (d, J=11.4 Hz, 1H), 4.14 (d, J=12.3 Hz, 1H), 3.83 (d, J=11.9 Hz, 1H), 3.17-2.96 (m, 2H), 2.69-2.61 (m, 1H), 2.45-2.33 (m, 1H), 1.97-1.87 (m, 1H), 1.32-1.22 (m, 1H).

Step 2. Synthesis of N-[(4aR,6R,8aS)-8a-(2,4-difluorophenyl)-6-(1H-1,2,3-triazol-4-yl)-4,4a,5,6,8,8a-hexahydropyrano[3,4-d][1,3]thiazin-2-yl]benzamide (C79)

{Caution: Thermal azide reactions are inherently dangerous—utilize appropriate shielding!} To a stirring mixture of C78 (325 mg, 0.788 mmol) and copper(I) iodide (10 mg, 0.05 mmol) in N,N-dimethylformamide (1.2 mL) and methanol (0.30 mL) in a reaction vial was added trimethylsilyl azide (174 mg, 1.51 mmol). The vial was sealed tightly with a septum cap, placed behind a blast shield, and heated to 100° C. with stirring for 1 hour, then cooled to 80° C. and stirred for an additional 3.5 hours. The reaction mixture was subsequently cooled to room temperature, diluted with ethyl acetate (30 mL), washed with aqueous ammonium hydroxide solution (30%, 8 mL), dried over sodium sulfate, filtered, and concentrated in vacuo. Silica gel chromatography (Gradient: 20% to 100% ethyl acetate in heptane) afforded the product as a sticky tan solid. Yield: 86 mg, 0.79 mmol, 24%. LCMS m/z 456.2 [M+H]$^+$.

Step 3. Synthesis of N-[(4aR,6R,8aS)-8a-(2,4-difluorophenyl)-6-(1-methyl-1H-1,2,3-triazol-4-yl)-4,4a,5,6,8,8a-hexahydropyrano[3,4-d][1,3]thiazin-2-yl]benzamide (C80)

To a stirring solution of C79 (82 mg, 0.18 mmol) in tetrahydrofuran (1 mL) at room temperature was added sodium hydride (60% in mineral oil, 22.5 mg, 0.562 mmol) in one portion. The reaction mixture was stirred at room temperature for 10 minutes, at which point a solution of methyl iodide (28.1 mg, 0.29 mmol) in tetrahydrofuran (200 μL) was added drop-wise. The reaction mixture was stirred for 30 minutes, warmed to 32° C. (heating block temperature) and stirred for 18 hours. The reaction mixture was then cooled to room temperature and quenched with aqueous hydrochloric acid (1 M, 10 drops) followed by water (4 mL). The product was extracted with ethyl acetate (2×10 mL), dried over magnesium sulfate, filtered, and concentrated in vacuo. Silica gel chromatography (Gradient: 10% to 100% ethyl acetate in heptane) afforded the product as a white solid. Yield: 41 mg, 87 μmol, 48%. LCMS m/z 470.2 [M+H]$^+$. $^1$H NMR (400 MHz, CDCl$_3$) δ 8.22 (d, J=7.1 Hz, 2H), 7.55 (s, 1H), 7.51 (t, J=7.3 Hz, 1H), 7.46-7.39 (m, 3H), 6.97-6.88 (m, 2H), 4.99 (dd, J=11.0, 3.4 Hz, 1H), 4.33 (d, J=11.2 Hz, 1H), 4.06 (s, 3H), 3.90 (d, J=12.4 Hz, 1H), 3.34-3.28 (m, 1H), 3.06 (dd, J=12.9, 4.2 Hz, 1H), 2.71 (dd, J=12.9, 2.9 Hz, 1H), 2.31-2.17 (m, 2H).

Step 4. Synthesis of (4aR,6R,8aS)-8a-(2,4-difluorophenyl)-6-(1-methyl-1H-1,2,3-triazol-4-yl)-4,4a,5,6,8,8a-hexahydropyrano[3,4-d][1,3]thiazin-2-amine (18)

To a suspension of C80 (36 mg, 77 μmol) in methanol (0.8 mL) was added 1,8-diazabicyclo[5.4.0]undec-7-ene (8.1 mg, 53 μmol). The reaction mixture was warmed to 55° C. and stirred for 14 hours, then cooled to room temperature, concentrated in vacuo (backfilling with nitrogen), and partitioned between ethyl acetate (5 mL) and water (2 mL). The aqueous layer was extracted with ethyl acetate (5 mL), and the combined organic layers were dried over magnesium sulfate, filtered, and concentrated in vacuo. Purification via silica gel chromatography (Gradient: 0% to 17.5% methanol in dichloromethane) afforded the product as a white solid. Yield: 21 mg, 57 μmol, 74%. LCMS m/z 366.2 [M+H]$^+$. $^1$H NMR (400 MHz, CDCl$_3$) δ 7.59 (s, 1H), 7.37 (td, J=9.2, 6.8 Hz, 1H), 6.92-6.80 (m, 2H), 5.31 (s, 1H), 4.92 (dd, J=10.7, 3.5 Hz, 1H), 4.27 (dd, J=11.2, 2.2 Hz, 1H), 4.08 (s, 3H), 3.91 (d, J=11.2 Hz, 1H), 3.13-3.05 (m, 1H), 3.02 (dd, J=12.3, 4.3 Hz, 1H), 2.69 (dd, J=12.3, 2.7 Hz, 1H), 2.20-1.99 (m, 2H).

Example 19

2-[(4aR,6R,8aS)-2-Amino-8a-(2,4-difluorophenyl)-4,4a,5,6,8,8a-hexahydropyrano[3,4-d][1,3]thiazin-6-yl]-1,3-oxazole-4-carbonitrile (19)

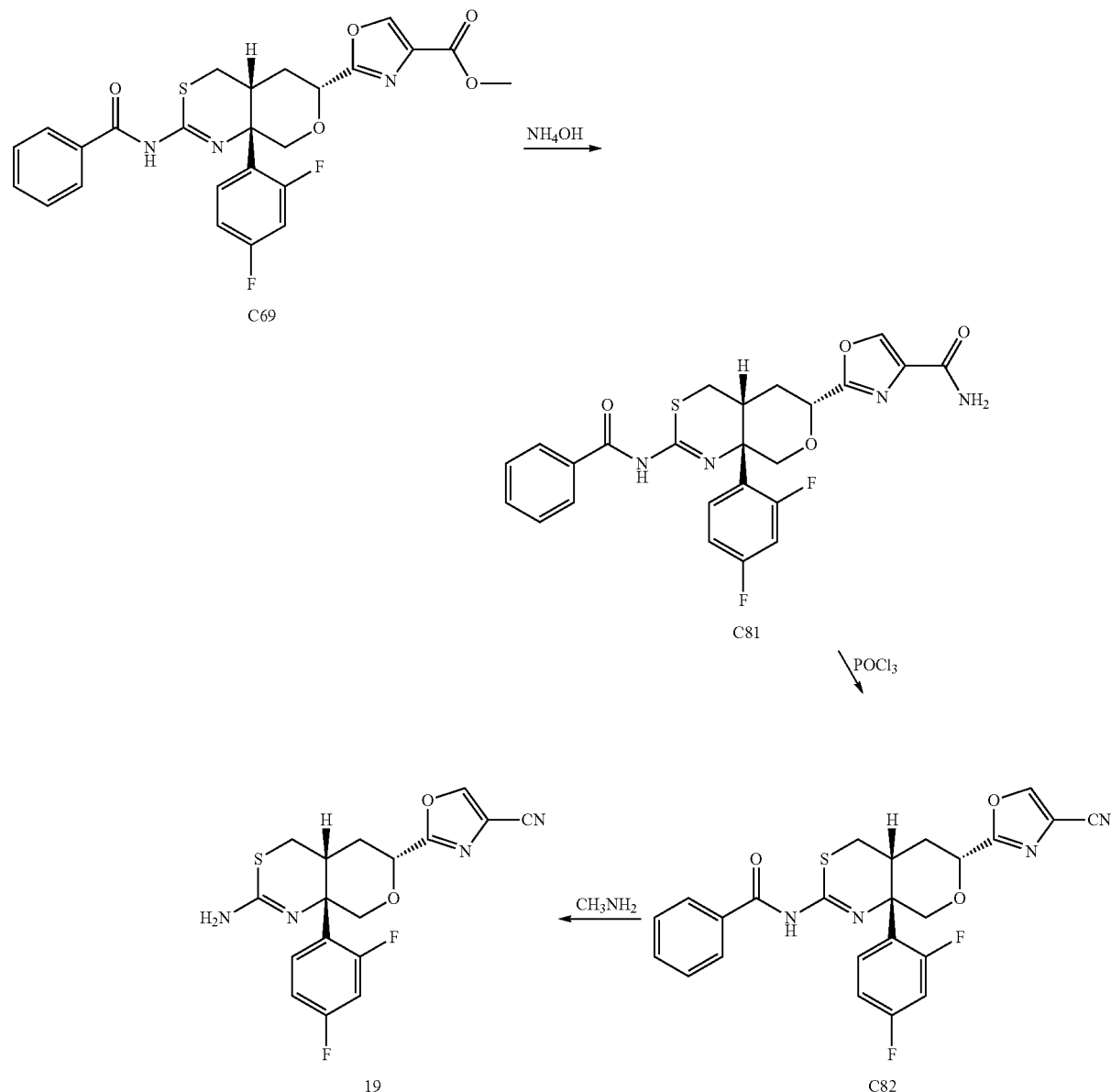

Step 1. Synthesis of 2-[(4aR,6R,8aS)-2-(benzoylamino)-8a-(2,4-difluorophenyl)-4,4a,5,6,8,8a-hexahydropyrano[3,4-d][1,3]thiazin-6-yl]-1,3-oxazole-4-carboxamide (C81)

Aqueous ammonium hydroxide solution (28-32%, 2 mL) was added to a solution of C69 (84 mg, 0.16 mmol) in methanol (0.5 mL). The milky suspension was stirred at room temperature. After 2 hours, additional methanol (2 mL) and ammonium hydroxide solution (2 mL) were added, providing a solution; this was diluted with saturated aqueous sodium bicarbonate solution (20 mL) and extracted with ethyl acetate (2×30 mL). The combined organic extracts were dried over sodium sulfate, filtered, and concentrated in vacuo. Chromatography on silica gel (Gradient: 0% to 100% ethyl acetate in heptane) afforded the product as a white solid. Yield: 55.9 mg, 0.112 mmol, 70%. LCMS m/z 499.2 [M+H]$^+$. $^1$H NMR (400 MHz, CD$_3$OD), characteristic peaks: δ 8.38 (s, 1H), 8.11 (br d, J=7 Hz, 2H), 7.43-7.56 (m, 4H), 7.04-7.12 (m, 2H), 4.99 (dd, J=11.7, 2.0 Hz, 1H), 4.33 (br d, J=12.1 Hz, 1H), 4.00-4.03 (m, 1H), 2.99 (dd, J=13.3, 4.3 Hz, 1H), 2.82 (dd, J=13.3, 2.7 Hz, 1H), 2.45-2.54 (m, 1H), 2.08-2.16 (m, 1H).

Step 2. Synthesis of N-[(4aR,6R,8aS)-6-(4-cyano-1,3-oxazol-2-yl)-8a-(2,4-difluorophenyl)-4,4a,5,6,8,8a-hexahydropyrano[3,4-d][1,3]thiazin-2-yl]benzamide (C82)

N,N-Dimethylformamide (0.5 mL) was cooled to 0° C. and treated in a drop-wise manner with phosphorus oxychloride (17 μL, 0.18 mmol). The mixture was stirred at 0° C. for a further 15 minutes prior to drop-wise addition of a solution of C81 (30 mg, 60 μmol) in N,N-dimethylformamide (0.5 mL). The reaction mixture was stirred at 0° C. for 1.2 hours, then diluted with saturated aqueous sodium chloride solution (10 mL) and extracted with dichloromethane (3×10 mL). The combined organic layers were dried over sodium sulfate, filtered, and concentrated in vacuo. Chromatography on silica gel (Gradient: 0% to 100% ethyl acetate in heptane) afforded the product as a white solid. Yield: 24.8 mg, 51.6 μmol, 86%. LCMS m/z 481.2 [M+H]$^+$. $^1$H NMR (400 MHz, CD$_3$OD), characteristic peaks: δ 8.69 (s, 1H), 8.10 (br d, J=7 Hz, 2H), 7.44-7.56 (m, 4H), 7.04-7.12 (m, 2H), 5.02 (dd, J=11.8, 2.4 Hz, 1H), 4.32 (dd, J=12.0, 1.5 Hz, 1H), 4.02 (d, J=12.0 Hz, 1H), 2.99 (dd, J=13.3, 4.1 Hz, 1H), 2.82 (dd, J=13.2, 2.8 Hz, 1H), 2.37-2.47 (m, 1H), 2.07-2.14 (m, 1H).

Step 3. Synthesis of 2-[(4aR,6R,8aS)-2-amino-8a-(2,4-difluorophenyl)-4,4a,5,6,8,8a-hexahydropyrano[3,4-d][1,3]thiazin-6-yl]-1,3-oxazole-4-carbonitrile (19)

To a solution of C82 (19.3 mg, 40.2 μmol) in ethanol (1.0 mL), in a sealable reaction vial, was added a solution of methylamine in ethanol (8 M, 0.6 mL, 5.0 mmol). The reaction mixture was stirred at room temperature for 2.5 hours and then concentrated in vacuo. Chromatography on silica gel (Gradient: 0% to 15% methanol in dichloromethane) afforded the product as a white solid. Yield: 10.8 mg, 28.7 μmol, 71%. LCMS m/z 377.1 [M+H]$^+$. $^1$H NMR (400 MHz, CDCl$_3$) δ 8.70 (s, 1H), 7.37 (td, J=9.2, 6.6 Hz, 1H), 6.97-7.03 (m, 2H), 4.93 (dd, J=11.9, 2.5 Hz, 1H), 4.27 (dd, J=11.1, 1.8 Hz, 1H), 3.80 (d, J=11.3 Hz, 1H), 3.05-3.09 (m, 1H), 2.93 (dd, J=12.5, 3.9 Hz, 1H), 2.77 (dd, J=12.7, 2.9 Hz, 1H), 2.34-2.37 (m, 1H), 1.92-1.97 (m, 1H).

Example 20

(4aR,6R,8aS)-8a-(2,4-Difluorophenyl)-6-(5-methylpyrazin-2-yl)-4,4a,5,6,8,8a-hexahydropyrano[3,4-d][1,3]thiazin-2-a mine (20)

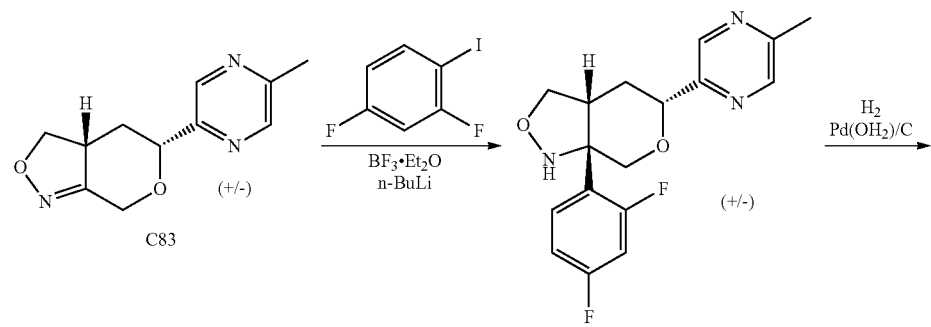

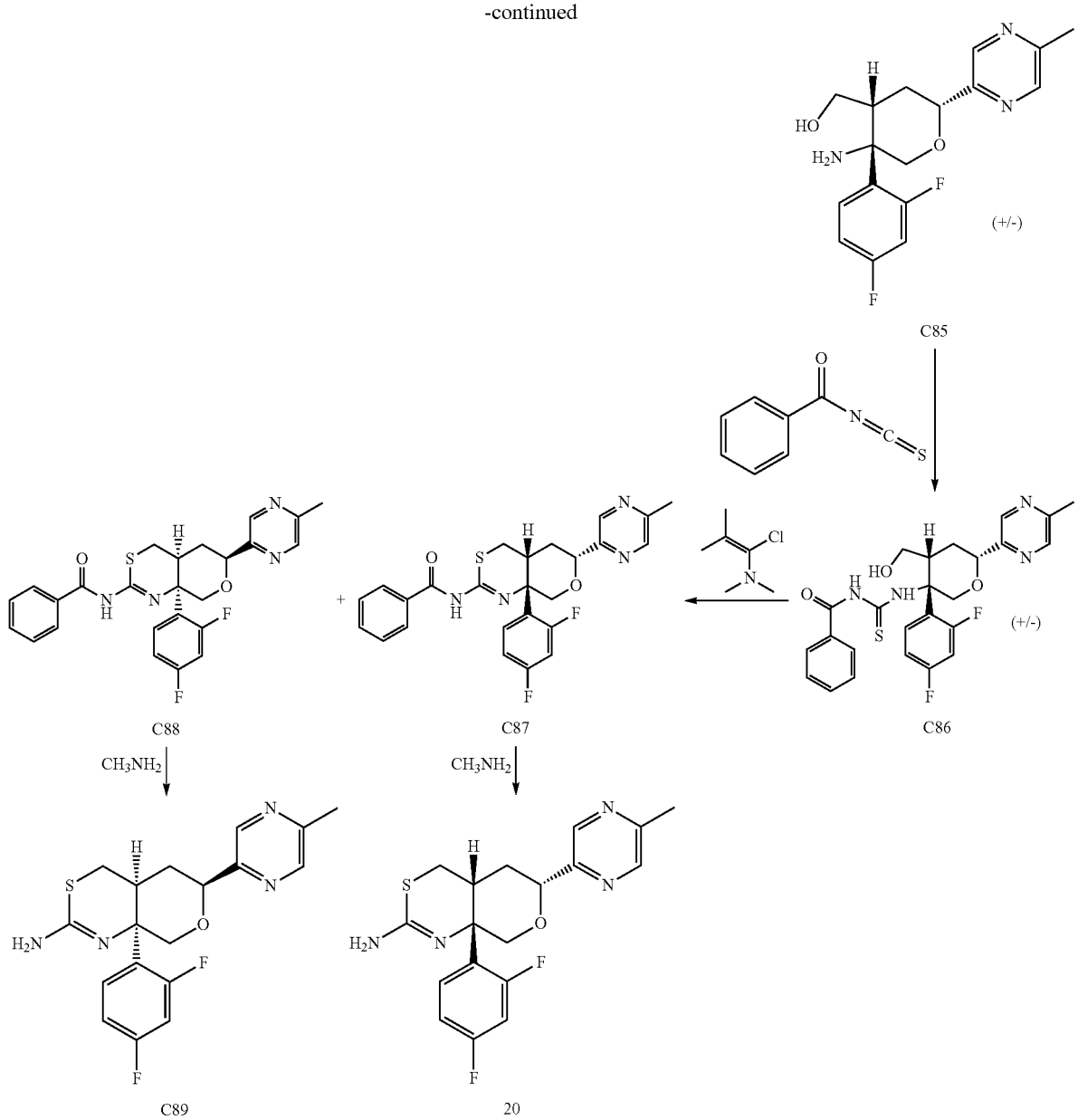

Step 1. Synthesis of rel-(3aR,5R,7aS)-7a-(2,4-difluorophenyl)-5-(5-methylpyrazin-2-yl)hexahydro-1H-pyrano[3,4-c][1,2]oxazole (C84)

rel-(3aR,5R)-5-(5-Methylpyrazin-2-yl)-3,3a,4,5-tetrahydro-7H-pyrano[3,4-c][1,2]oxazole (C83, prepared from 5-methylpyrazine-2-carbaldehyde using the general procedures described for synthesis of C52 in Example 7) was converted to the product using the method employed for synthesis of C53 in Example 7. The product was obtained as an off-white/yellow solid. Yield: 130 mg, 0.390 mmol, 20%. LCMS m/z 334.3 [M+H]+. 1H NMR (400 MHz, CD3OD) δ 8.65 (s, 1H), 8.50 (s, 1H), 7.94 (td, J=9.2, 6.9 Hz, 1H), 7.04-6.95 (m, 2H), 4.81 (d, J=10.8 Hz, 1H), 4.32 (dd, J=12.7, 1.8 Hz, 1H), 3.99 (d, J=12.9 Hz, 1H), 3.74 (d, J=7.2 Hz, 1H), 3.55 (dd, J=7.2, 5.1 Hz, 1H), 3.32-3.26 (m, 1H; partially obscured by solvent peak), 2.56 (s, 3H), 2.25 (ddd, J=14.1, 6.8, 2.3 Hz, 1H), 1.85 (dtd, J=13.8, 11.8, 1.7 Hz, 1H).

Step 2. Synthesis of rel-[(2R,4R,5S)-5-amino-5-(2,4-difluorophenyl)-2-(5-methylpyrazin-2-yl)tetrahydro-2H-pyran-4-yl]methanol (C85)

To a 200 mL Parr bottle was added C84 (352 mg, 1.06 mmol), methanol (20 mL), and 20% palladium hydroxide on carbon (350 mg). The bottle was capped and evacuated and then placed under 42 psi hydrogen. The reaction mixture was shaken vigorously for 5.75 hours, then filtered through diatomaceous earth and concentrated in vacuo. Silica gel chromatography [Gradient: 0% to 40% (84:15:1 dichloromethane/methanol/concentrated ammonium hydroxide) in dichloromethane] provided the product as a white solid. Yield: 154 mg, 0.461 mmol, 43% yield. LCMS m/z 336.4 [M+H]+. 1H NMR (400 MHz, CDCl3) δ 8.68 (s, 1H), 8.42 (s, 1H), 7.79-7.62 (m, 1H), 7.05-6.92 (m, 1H), 6.90-6.79 (m, 1H), 4.78 (d, J=11.4 Hz, 1H), 4.40 (d, J=11.5 Hz, 1H), 3.60 (d, J=11.5 Hz, 2H), 3.42 (dd, J=11.3, 2.3 Hz, 1H), 2.59 (s, 3H), 2.49 (d, J=12.7 Hz, 1H), 2.36-2.22 (m, 1H), 2.18-2.10 (m, 1H).

Step 3. Synthesis of rel-N-{[(3S,4R,6R)-3-(2,4-difluorophenyl)-4-(hydroxymethyl)-6-(5-methylpyrazin-2-yl)tetrahydro-2H-pyran-3-yl]carbamothioyl}benzamide (C86)

Compound C85 was converted to the product using the method described for synthesis of C55 in Example 7. The product was isolated as a white solid. Yield: 200 mg, 0.40 mmol, 88%. LCMS m/z 499.3 [M+H]$^+$. $^1$H NMR (400 MHz, CDCl$_3$) δ 12.14-11.73 (br s, 1H), 8.91 (s, 1H), 8.37 (s, 1H), 7.93-7.86 (m, 2H), 7.80-7.59 (m, 2H), 7.56-7.49 (m, 2H), 6.97-6.89 (m, 1H), 6.87-6.75 (m, 1H), 4.78 (d, J=9.4 Hz, 1H), 3.87-3.66 (m, 3H), 3.12-2.84 (m, 1H), 2.59 (s, 3H), 2.23 (d, J=11.9 Hz, 1H), 2.01-1.53 (m, 1H).

Step 4. Synthesis of N-((4aR,6R,8a5)-8a-(2,4-difluorophenyl)-6-(5-methylpyrazin-2-yl)-4,4a,5,6,8,8a-hexahydropyrano[3,4-d][1,3]thiazin-2-yl)benzamide (C87)

To a solution of C86 (198 mg, 0.397 mmol) in dichloromethane (10 mL) was added 1-chloro-N,N,2-trimethylprop-1-en-1-amine (Ghosez's reagent) (158 μL, 1.19 mmol) in a drop-wise manner. The mixture was stirred at ambient temperature for 20 minutes, then diluted with saturated aqueous sodium bicarbonate solution (10 mL) and extracted with dichloromethane (3×15 mL). The combined organic layers were dried over sodium sulfate, filtered, and concentrated in vacuo. Silica gel chromatography (Gradient: 0% to 100% ethyl acetate in heptane) provided the racemic product as a white solid. Yield: 164 mg, 0.341 mmol, 86%. LCMS m/z 481.3 [M+H]$^+$. $^1$H NMR (400 MHz, CDCl$_3$) δ 8.69 (s, 1H), 8.35 (s, 1H), 8.26-8.10 (m, 2H), 7.58-7.36 (m, 4H), 7.04-6.74 (m, 2H), 4.97-4.78 (m, 1H), 4.36 (dd, J=12.3, 1.2 Hz, 1H), 4.00 (d, J=12.1 Hz, 1H), 3.41-3.25 (m, 1H), 3.11-3.01 (m, 1H), 2.70 (dd, J=12.9, 2.5 Hz, 1H), 2.55 (s, 3H), 2.25-2.17 (m, 2H). This was combined with material from a similar reaction carried out on C86 (96 mg, 0.19 mmol), and subjected to chiral separation via supercritical fluid chromatography (Column: Chiral Technologies, Chiralcel OJ-H, 5 μm; Eluent: 3:1 carbon dioxide/methanol). The first-eluting peak provided C87 as an off-white solid. Yield: 106 mg, 0.220 mmol, 41% from the SFC. The indicated absolute stereochemistry was assigned to C87 on the basis of the biological activity of derived final product 20 (below), which was substantially improved over that of final product C89 [(4aS,6S,8aR)-8a-(2,4-difluorophenyl)-6-(5-methylpyrazin-2-yl)-4,4a,5,6,8,8a-hexahydropyrano[3,4-d][1,3]thiazin-2-amine, obtained from second-eluting enantiomer C88 using the method described in step 5 below]. See Table 2.

Step 5. Synthesis of (4aR,6R,8aS)-8a-(2,4-difluorophenyl)-6-(5-methylpyrazin-2-yl)-4,4a,5,6,8,8a-hexahydropyrano[3,4-d][1,3]thiazin-2-amine (20)

Compound C87 was converted to the product according to the method described for synthesis of 19 in Example 19. The product was obtained as a solid. Yield: 45.2 mg, 0.120 mmol, 54%. LCMS m/z 377.2 [M+H]$^+$. 1H NMR (400 MHz, CD$_3$OD) δ 8.63 (s, 1H), 8.47 (s, 1H), 7.46-7.32 (m, 1H), 7.08-6.92 (m, 2H), 4.84-4.79 (m, 1H; partially obscured by water peak), 4.30 (dd, J=11.2, 1.9 Hz, 1H), 3.89 (d, J=11.2 Hz), 3.17-3.05 (m, 1H), 2.93 (dd, J=12.6, 4.2 Hz, 1H), 2.74 (dd, J=12.5, 2.7 Hz, 1H), 2.55 (s, 3H), 2.06-1.91 (m, 2H).

Example 21

(4aR,6R,8aS)-8a-(2,4-Difluorophenyl)-6-(5-ethoxy-1-methyl-1H-pyrazol-3-yl)-4,4a,5,6,8,8a-hexahydropyrano[3,4-d][1,3]thiazin-2-amine, trifluoroacetate salt (21)

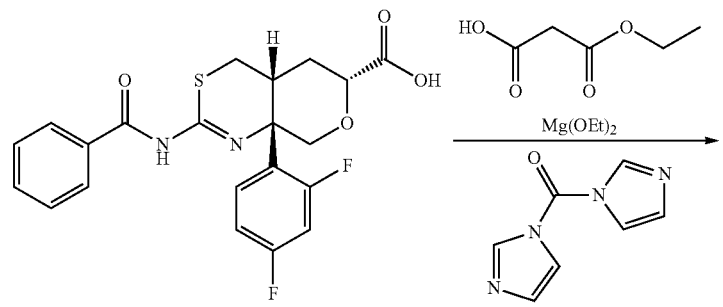

P2

-continued

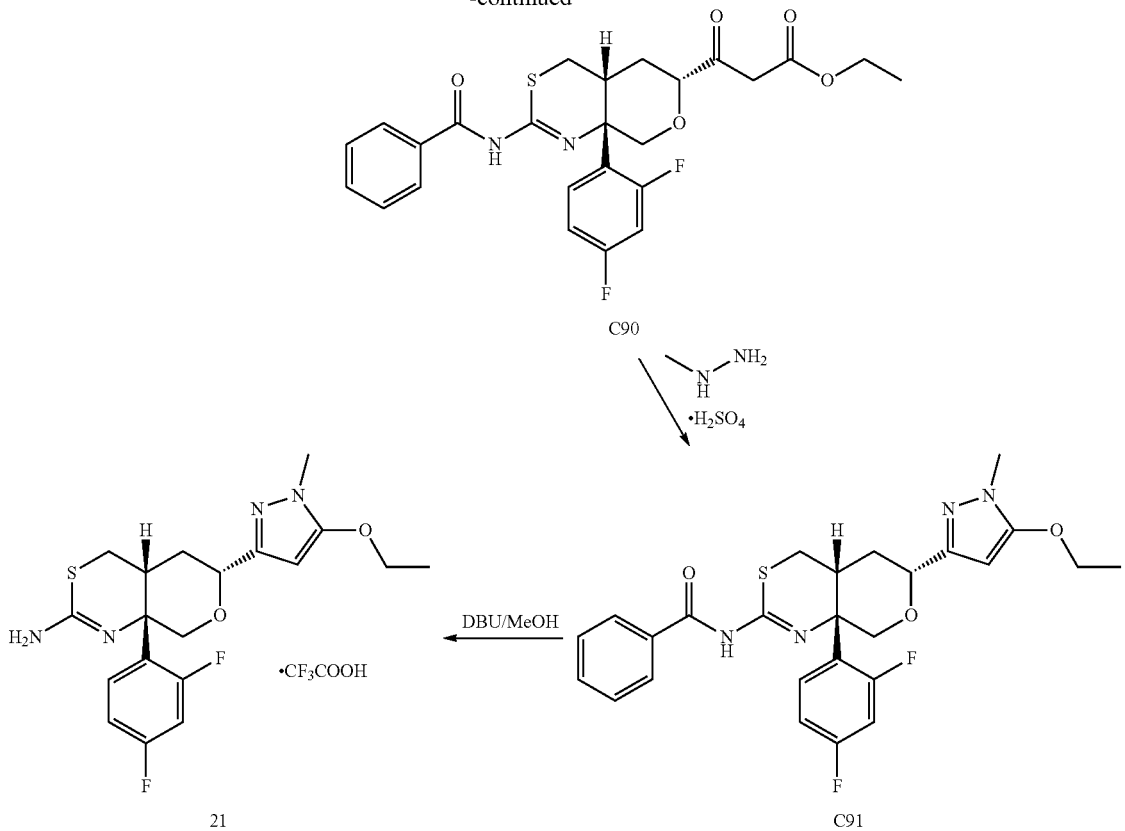

Step 1. Synthesis of ethyl 3-[(4aR,6R,8a5)-2-(benzoylamino)-8a-(2,4-difluorophenyl)-4,4a,5,6,8,8a-hexahydropyrano[3,4-d][1,3]thiazin-6-yl]-3-oxopropanoate (C90)

To a solution of monoethyl malonate (182 mg, 1.38 mmol) in tetrahydrofuran (2.5 mL) was added magnesium ethoxide (79 mg, 0.69 mmol). The reaction mixture was stirred for 1 hour at room temperature, then concentrated in vacuo. In a separate reaction vessel, a solution of P2 (284 mg, 0.657 mmol) in tetrahydrofuran (5 mL) was treated with 1,1'-carbonyldiimidazole (117 mg, 0.723 mmol) and stirred for 6 hours at room temperature, at which time the magnesium ethyl malonate generated in the first reaction flask was added, and the resulting mixture was stirred at room temperature for 18 hours. The mixture was then concentrated in vacuo, and partitioned between aqueous hydrochloric acid (0.25 M, 20 mL) and ethyl acetate (20 mL). The aqueous layer was extracted with ethyl acetate (10 mL), and the combined organic layers were washed with saturated aqueous sodium bicarbonate solution, dried over sodium sulfate, filtered, and concentrated in vacuo. Purification via silica gel chromatography (Gradient: 30% to 100% ethyl acetate in heptane) afforded the product as a pale amber solid. Yield: 163 mg, 0.324 mmol, 49%. LCMS m/z 503.2 [M+H]$^+$. $^1$H NMR (400 MHz, CDCl$_3$) δ 8.21 (d, J=7.2 Hz, 2H), 7.52 (t, J=7.0 Hz, 1H), 7.44 (t, J=7.4 Hz, 2H), 7.41-7.35 (m, 1H), 7.00-6.84 (m, 2H), 4.26-4.01 (m, 4H), 3.89 (d, J=11.9 Hz, 1H), 3.69 (d, J=16.6 Hz, 1H), 3.59 (d, J=16.4 Hz, 1H), 3.20-3.11 (m, 1H), 3.02 (dd, J=12.9, 4.1 Hz, 1H), 2.68 (dd, J=13.1, 2.2 Hz, 1H), 2, 18-2.02 (m, 2H), 1.21 (t, J=7.2 Hz, 3H).

Step 2. Synthesis of N-[(4aR,6R,8aS)-8a-(2,4-difluorophenyl)-6-(5-ethoxy-1-methyl-1H-pyrazol-3-yl)-4,4a,5,6,8,8a-hexahydropyrano[3,4-d][1,3]thiazin-2-yl]benzamide (C91)

To a solution of C90 (50.3 mg, 100 μmol) in ethanol (0.75 mL) was added methylhydrazine sulfate (14.4 mg, 100 μmol). The reaction mixture was warmed to 60° C. and stirred for 1 hour before being concentrated in vacuo (backfilled with nitrogen). The residue was partitioned between saturated aqueous sodium bicarbonate solution (3 mL) and ethyl acetate (5 mL). The aqueous layer was extracted with ethyl acetate (2×5 mL), and the combined organic layers were dried over sodium sulfate, filtered, and concentrated in vacuo. Purification via silica gel chromatography (Gradient: 0% to 100% ethyl acetate in heptane) afforded the product as a sticky amber solid. Yield: 35 mg, 68 μmol, 68%. LCMS m/z 513.2 [M+H]$^+$. $^1$H NMR (400 MHz, CD$_3$OD) δ 8.15 (d, J=7.0 Hz, 2H), 7.58-7.44 (m, 4H), 7.15-7.05 (m, 2H), 5.70 (s, 1H), 4.67 (d, J=11.3 Hz, 1H), 4.29 (d, J=12.1 Hz, 1H), 4.12 (q, J=7.0 Hz, 2H), 3.98 (d, J=12.1 Hz, 1H), 3.58 (s, 3H), 3.00 (dd, J=13.3, 3.9 Hz, 1H), 2.81 (dd, J=13.3, 2.7 Hz, 1H), 2.33-2.22 (m, 1H), 1.97 (d, J=12.1 Hz, 1H), 1.39 (t, J=7.0 Hz, 3H).

Step 3. Synthesis of (4aR,6R,8aS)-8a-(2,4-difluorophenyl)-6-(5-ethoxy-1-methyl-1H-pyrazol-3-yl)-4,4a,5,6,8,8a-hexahydropyrano[3,4-d][1,3]thiazin-2-amine, trifluoroacetate salt (21)

To a solution of C91 (13 mg, 25 μmol) in methanol (0.5 mL) was added 1,8-diazabicyclo[5.4.0]undec-7-ene (3.1 mg, 20 μmol), and the resulting solution was warmed to 60° C. and stirred for 18 hours. The reaction mixture was then concentrated in vacuo (backfilled with nitrogen) and partitioned between saturated aqueous sodium bicarbonate solution (2 mL) and ethyl acetate (5 mL). The aqueous layer was extracted with ethyl acetate (2×2 mL), and the combined organic layers were washed with saturated aqueous sodium chloride solution, dried over sodium sulfate, filtered, and concentrated in vacuo. Purification was carried out via reversed phase HPLC (Column: Waters Atlantis dC18, 5 μm; Mobile phase A: 0.05% trifluoroacetic acid in water (v/v); Mobile phase B: 0.05% trifluoroacetic acid in acetonitrile (v/v); Gradient: 5% to 95% B). Yield: 7.6 mg, 14 μmol, 58%. LCMS m/z 409.3 [M+H]$^+$. $^1$H NMR (600 MHz, DMSO-d$_6$) δ 7.40 (ddd, J=13, 9, 2 Hz, 1H), 7.31-7.37 (m, 1H), 7.25 (ddd, J=9, 8, 2 Hz, 1H), 5.65 (s, 1H), 4.62 (dd, J=11, 3 Hz, 1H), 4.11 (q, J=7 Hz, 2H), 4.05 (d, J=12.3 Hz, 1H), 3.93 (d, J=12.3 Hz, 1H), 3.52 (s, 3H), 3.25-3.30 (m, 1H), 3.08 (dd, J=13.1, 2.2 Hz, 1H), 2.93 (dd, J=13.2, 3.5 Hz, 1H), 1.90-2.01 (m, 2H), 1.33 (t, J=7.0 Hz, 3H).

Example 22

(4S,4aR,6R,8aS)-8a-(2,4-Difluorophenyl)-4-(fluoromethyl)-6-(1-methyl-1H-pyrazol-4-yl)-4,4a,5,6,8,8a-hexahydropyrano[3,4-d][1,3]thiazin-2-amine, hydrochloride salt (22)

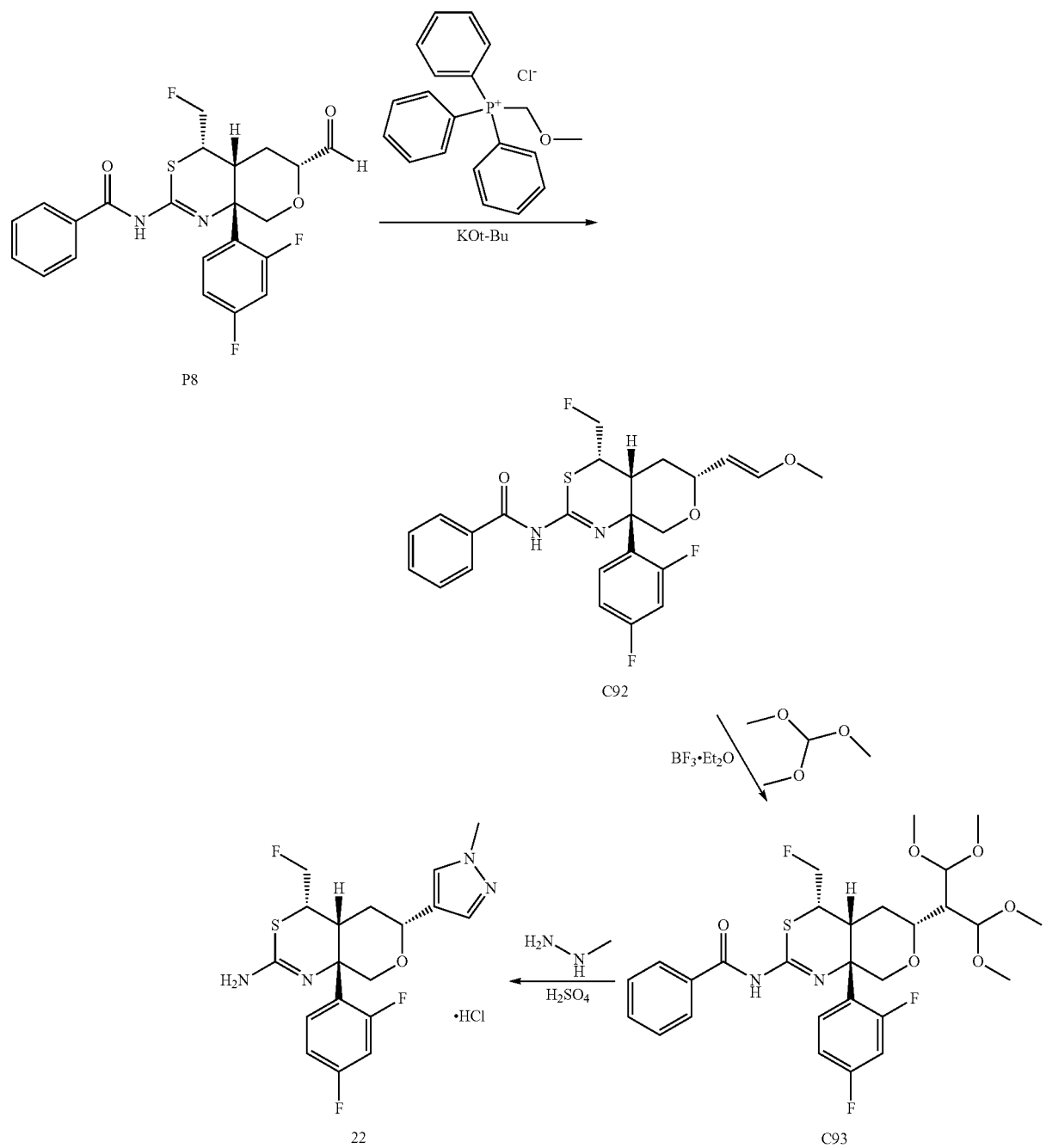

Step 1. Synthesis of N-[(4S,4aR,6R,8aS)-8a-(2,4-difluorophenyl)-4-(fluoromethyl)-6-(2-methoxyethenyl)-4,4a,5,6,8,8a-hexahydropyrano[3,4-d][1,3]thiazin-2-yl]benzamide (C92)

To a stirring suspension of (methoxymethyl)triphenylphosphonium chloride (1.47 g, 4.29 mmol) in tetrahydrofuran (20 mL) cooled to 2° C. was added potassium tert-butoxide (1 M in tetrahydrofuran, 3.68 mL, 3.68 mmol) drop-wise. The reaction mixture was allowed to warm to room temperature over 30 minutes and was then cooled back down to 3° C., at which point a solution of P8 (540 mg, 1.20 mmol) in tetrahydrofuran (6 mL) was added over 2 minutes, while ensuring that the internal temperature remained below 6° C. The reaction mixture was allowed to stir at 3-6° C. for 20 minutes, was warmed to room temperature over 30 minutes, and was then cooled back down to 14° C., at which point saturated aqueous sodium bicarbonate solution was added. The mixture was extracted three times with ethyl acetate, and the combined organic layers were dried over sodium sulfate, filtered, and concentrated under reduced pressure. Silica gel chromatography (Gradient: 0% to 75% ethyl acetate in heptane) provided the product. Yield: 200 mg, 0.418 mmol, 35%. LCMS m/z 379.2 [M+H]$^+$.

Step 2. Synthesis of N-[(4S,4aR,6R,8a5)-8a-(2,4-difluorophenyl)-4-(fluoromethyl)-6-(1,1,3,3-tetramethoxypropan-2-yl)-4,4a,5,6,8,8a-hexahydropyrano[3,4-d][1,3]thiazin-2-yl]benzamide (C93)

To a solution of C92 (200 mg, 0.40 mmol) in dichloromethane (4.2 mL) cooled to 0° C. was added trimethyl orthoformate (0.940 mL, 0.861 mmol) followed by drop-wise addition of boron trifluoride diethyl etherate (58.4 µL, 0.462 mmol). The reaction was stirred at 0° C. for 1.5 hours, then partitioned between dichloromethane and saturated aqueous sodium bicarbonate solution. The aqueous layer was extracted with dichloromethane, and the combined organic layers were washed with saturated aqueous sodium chloride solution, dried over sodium sulfate, filtered, and concentrated in vacuo. This material (300 mg) was carried into the subsequent step without further purification.

Step 3. Synthesis of (4S,4aR,6R,8aS)-8a-(2,4-difluorophenyl)-4-(fluoromethyl)-6-(1-methyl-1H-pyrazol-4-yl)-4,4a,5,6,8,8a-hexahydropyrano[3,4-d][1,3]thiazin-2-amine, hydrochloride salt (22)

To a solution of C93 (material from the previous step, 300 mg, ≤0.40 mmol) in ethanol (3 mL) was added methylhydrazine (34.0 mg, 0.736 mmol) and water (1.3 mL). Concentrated sulfuric acid (51 µL, 0.96 mmol) was added drop-wise, and the reaction mixture was heated at 60° C. for 16 hours. The reaction was partitioned between ethyl acetate and saturated aqueous sodium bicarbonate solution, and the aqueous layer was extracted three times with ethyl acetate. The combined organic layers were dried over sodium sulfate, filtered, and concentrated in vacuo. Purification via chromatography on silica gel (Gradient: 0% to 4% methanol in dichloromethane) provided the free base of the product. This material was dissolved in dichloromethane and treated with excess hydrogen chloride (1 M in diethyl ether) to afford the product as a solid. Yield: 44.0 mg, 0.102 mmol, 26% over 2 steps. LCMS m/z 397.1 [M+H]$^+$. $^1$H NMR (400 MHz, CD$_3$OD) of free base: δ 7.27-7.40 (m, 3H), 6.73-6.81 (m, 2H), 4.40-4.59 (m, 2H), 4.20-4.35 (m, 1H), 4.15 (dd, J=11.1, 2.1 Hz, 1H), 3.78-3.81 (m, 4H), 3.39-3.40 (m, 1H), 3.03 (dt, J=11.8, 3.9 Hz, 1H), 1.75-1.85 (m, 1H), 1.65 (dt, J=12.9, 3.1 Hz, 1H).

METHODS

Method A

Synthesis of (4a R,6R,8aS)-8a-(2,4-difluorophenyl)-6-heteroaryl-4,4a,5,6,8,8a-hexahydropyrano[3,4-d][1,3]thiazin-2-amines

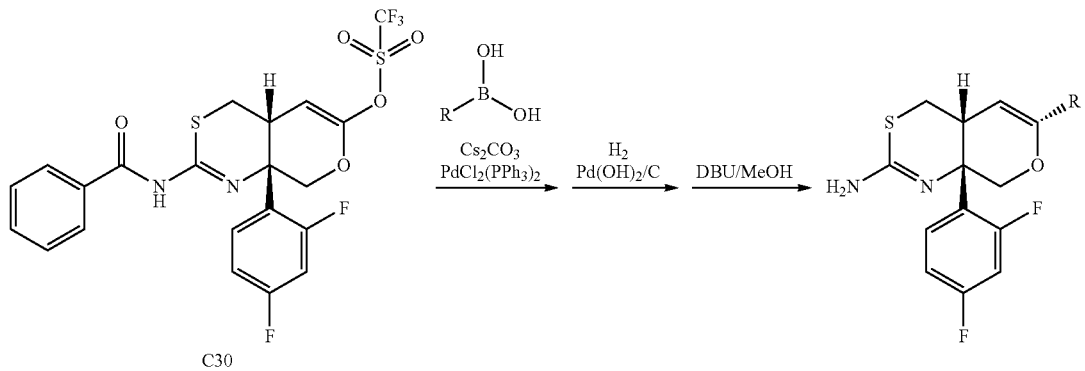

To the requisite heteroaryl boronic acids (0.15 mmol, 2.0 equiv) in 2-dram vials was added a solution of C30 (40 mg, 75 µmol, 1.0 equiv) in tetrahydrofuran (1 mL). An aqueous solution of cesium carbonate (2 M, 0.19 mL, 0.375 mmol, 5.0 equiv) and dichlorobis(triphenylphosphine)palladium(II) (~3 mg, 4 µmol, 0.05 equiv) were added to each vial. The reactions were de-gassed and shaken at 65° C. for 17 hours. The reaction mixtures were each partitioned between water (1.5 mL) and ethyl acetate (2.4 mL), and the organic layer was separated. The extraction was repeated twice and the organics from each individual reaction were combined and passed through solid phase extraction cartridges containing sodium sulfate (6 mL cartridge, approximately 1 g bed weight). The filtrates were concentrated in vacuo. The crude residues (~0.1 mmol, 1 equiv) were dissolved in methanol (4 mL) and 20% palladium hydroxide on carbon (50 mg, 0.31 mmol, 4.1 equiv) was added. The reaction mixtures were stirred at 50°

C. under 45 psi hydrogen for 16 hours. The reaction mixtures were each filtered through diatomaceous earth and the filtrates were concentrated in vacuo. The crude residues (~75 µmol) were dissolved in methanol (0.5 mL) and 1,8-diazabicyclo[5.4.0]undec-7-ene (15 µL, 0.1 mmol, 1 equiv) was added. The reaction vials were shaken at 65° C. for 16 hours and then concentrated in vacuo. Purification was carried out via reversed phase HPLC (Column: Waters XBridge C18, 5 µm; Mobile phase A: 0.03% ammonium hydroxide in water (v/v); Mobile phase B: 0.03% ammonium hydroxide in acetonitrile (v/v); Gradient: 20% to 60% B, or 5% to 100% B). See Table 1 for characterization data.

TABLE 1

Physical Data and Method of Preparation for Examples 23-29

| Example Number | Structure | Method of Preparation | $^1$H NMR (400 MHz, CD$_3$OD), δ (ppm); Mass spectrum, observed ion m/z [M + H]$^+$ or HPLC retention time$^1$ (minutes); Mass spectrum m/z [M + H]$^+$ (unless otherwise indicated) |
|---|---|---|---|
| 23 | 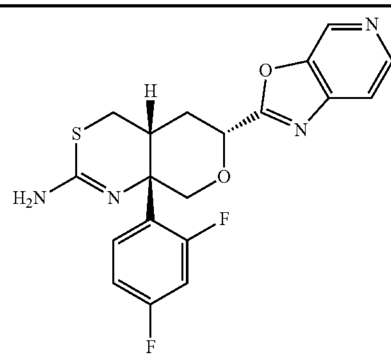 | Example 10$^2$ | 8.96 (d, J = 1.0 Hz, 1H), 8.53 (d, J = 5.5 Hz, 1H), 7.80 (dd, J = 5.4, 1.0 Hz, 1H), 7.34-7.42 (m, 1H), 6.92-7.01 (m, 2H), 5.13 (dd, J = 11.9, 2.6 Hz, 1H), 4.34 (dd, J = 11.2, 1.8 Hz, 1H), 3.89 (d, J = 11.2 Hz, 1H), 3.10-3.17 (m, 1H), 2.97 (dd, J = 12.5, 4.1 Hz, 1H), 2.78 (dd, J = 12.6, 2.8 Hz, 1H), 2.41-2.52 (m, 1H), 2.07-2.14 (m, 1H); 403.2 |
| 24 | 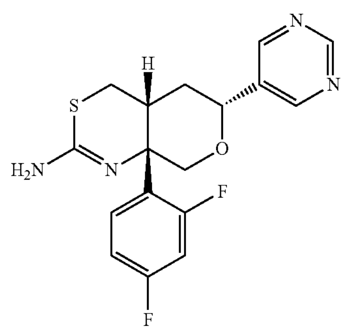 [SMILES: NC1=N[C@@]2(c3ccc(F)cc3F)CO[C@@H](c3cncnc3)C[C@H]2CS1] | Example 17 | 9.08 (s, 1H), 8.84 (s, 2H), 7.36-7.43 (m, 1H), 6.96-7.04 (m, 2H), 4.84-4.88 (m, 1H), 4.29 (dd, J = 11.2, 2.1 Hz, 1H), 3.87 (d, J = 11.2 Hz, 1H), 3.11-3.16 (m, 1H), 2.93 (dd, J = 12.6, 4.2 Hz, 1H), 2.74 (dd, J = 12.7, 2.7 Hz, 1H), 1.89-2.02 (m, 2H); 363.3 |
| 25 | 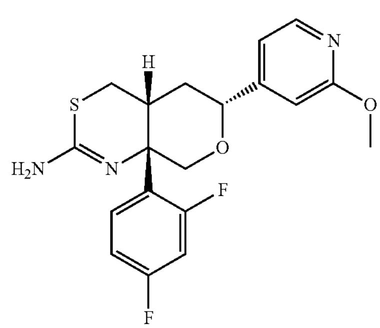 [SMILES: COc1cc([C@H]2C[C@H]3CSC(N)=N[C@@]3(c3ccc(F)cc3F)CO2)ccn1] | Method A | 1.79 minutes; 392.4 |
| 26 | 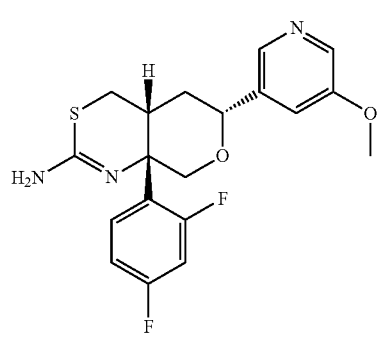 [SMILES: COc1cncc([C@H]2C[C@H]3CSC(N)=N[C@@]3(c3ccc(F)cc3F)CO2)c1] | Method A | 1.43 minutes; 392.4 |

TABLE 1-continued

Physical Data and Method of Preparation for Examples 23-29

| Example Number | Structure | Method of Preparation | $^1$H NMR (400 MHz, CD$_3$OD), δ (ppm); Mass spectrum, observed ion m/z [M + H]$^+$ or HPLC retention time$^1$ (minutes); Mass spectrum m/z [M + H]$^+$ (unless otherwise indicated) |
|---|---|---|---|
| 27 | 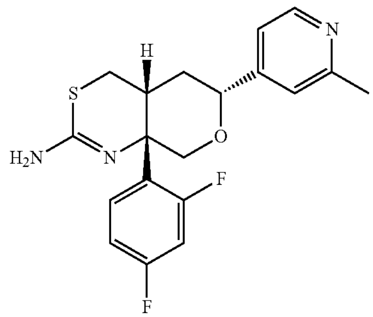 [SMILES: Cc1cc([C@H]2C[C@H]3CSC(N)=N[C@@]3(c3ccc(F)cc3F)CO2)ccn1] | Method A | 2.31 minutes; 376.4 |
| 28 | 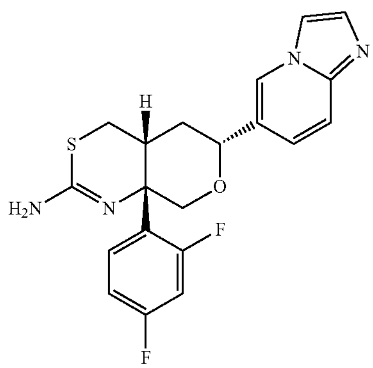 [SMILES: NC1=N[C@@]2(c3ccc(F)cc3F)CO[C@@H](c3ccc4nccn4c3)C[C@H]2CS1] | Method A | 2.21 minutes; 401.4 |
| 29 | 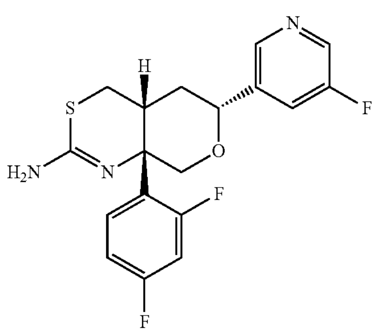 | Method A$^{2,3}$ | 8.39-8.45 (m, 2H), 7.57 (dtd, J = 9.3, 2.0, 1.3 Hz, 1H), 7.40 (td, J = 9.1, 6.7 Hz, 1H), 6.82-6.92 (m, 2H), 4.77 (dd, J = 11.6, 2.4 Hz, 1H), 4.26 (dd, J = 11.3, 2.2 Hz, 1H), 3.99 (d, J = 11.3 Hz, 1H), 3.11-3.15 (m, 1H), 3.04 (dd, J = 12.3, 4.1 Hz, 1H), 2.68 (dd, J = 12.5, 2.9 Hz, 1H), 2.00-2.10 (m, 1H), 1.81-1.85 (m, 1H); 380.1 |

$^1$HPLC conditions. Column: Waters Atlantis dC18, 4.6 × 50 mm, 5 µm; Mobile phase A: 0.05% trifluoroacetic acid in water (v/v); Mobile phase B: 0.05% trifluoroacetic acid in acetonitrile (v/v); Gradient: 5% to 95% B, linear over 4.0 minutes; Flow rate: 2 mL/minute.
$^2$In this case, the final deprotection was carried out with methylamine in ethanol.
$^3$In this case, trifluoroacetic acid (0.5 mL) was additionally added to the reduction conditions (second step) and the reaction mixture was stirred at room temperature under 50 psi hydrogen for 16 hours].

Biological Assays

BACE1 Cell-Free Assay:

Beta-secretase (BACE) is one of the enzymes involved in the generation of the amyloid beta peptide found in the amyloid plaques of Alzheimer's Disease patients. This assay measures the inhibition of the beta-secretase enzyme as it cleaves a non-native peptide.

A synthetic APP substrate that can be cleaved by beta-secretase having N-terminal biotin and made fluorescent by the covalent attachment of Oregon Green at the Cys residue is used to assay beta-secretase activity in the presence or absence of the inhibitory compounds. The substrate is Biotin-GLTNIKTEEISEISY^EVEFR-C[Oregon Green]KK-OH. The BACE1 enzyme is affinity purified material from conditioned media of CHO-K1 cells that have been transfected with a soluble BACE construct (BACE1deltaTM96His). Compounds are incubated in a ½ log dose response curve from a top concentration of 100 µM with BACE1 enzyme and the biotinylated fluorescent peptide in 384-well black plates (Thermo Scientific #4318). BACE1 is at a final concentration of 0.1 nM with a final concentration of peptide substrate of 150 nM in a reaction volume of 30 µL assay buffer [100 mM sodium acetate, pH 4.5 (brought to pH with acetic acid), and 0.001% Tween-20]. Plates are covered and incubated for 3 hours at 37° C. The reaction is stopped with the addition of 30

μL of 1.5 μM Streptavidin (Pierce, #21125). After a 10 minute incubation at room temperature, plates are read on a PerkinElmer EnVision for fluorescence polarization (Ex485 nm/Em530 nm). The activity of the beta-secretase enzyme is detected by changes in the fluorescence polarization that occur when the substrate is cleaved by the enzyme. Incubation in the presence of compound inhibitor demonstrates specific inhibition of beta-secretase enzymatic cleavage of the synthetic APP substrate.

Whole Cell Assay (In Vitro sAPPb Assay):

H4 human neuroglioma cells over-expressing the wild-type human APP$_{695}$ are treated for 18 hours with compound in a final concentration 1% DMSO. sAPPβ levels are measured using TMB-ELISA with capture APP N-terminal antibody (Affinity BioReagents, OMA1-03132), wild-type sAPPβ specific reporter p192 (Elan), and tertiary anti rabbit-HRP (GE Healthcare).

BACE2 Assay:

This assay measures the inhibition of the BACE2 enzyme as it cleaves a non-native peptide. A synthetic substrate that can be cleaved by BACE2 having N-terminal biotin and made fluorescent by the covalent attachment of Oregon Green at the Cys residue is used to assay BACE2 activity in the presence or absence of the inhibitory compounds. The substrate is Biotin-KEISEISYEVEFR-C(Oregon green)-KK-OH. The BACE2 enzyme is available from Enzo Life Sciences (Cat # BML-SE550). Compounds are incubated in a ½ log dose response curve from a top concentration of 100 μM with BACE2 enzyme and the biotinylated fluorescent peptide in 384-well black plates (Thermo Scientific #4318). BACE2 is at a final concentration of 2.5 nM with a final concentration of peptide substrate of 150 nM in a reaction volume of 30 μL assay buffer [100 mM sodium acetate, pH 4.5 (brought to pH with acetic acid), and 0.001% Tween-20]. Plates are covered and incubated for 3 hours at 37° C. The reaction is stopped with the addition of 30 μL of 1.5 μM Streptavidin (Pierce, #21125). After a 10 minute incubation at room temperature, plates are read on a PerkinElmer EnVision for fluorescence polarization (Ex485 nm/Em530 nm). The activity of the beta-secretase enzyme is detected by changes in the fluorescence polarization that occur when the substrate is cleaved by the enzyme. Incubation in the presence of compound inhibitor demonstrates specific inhibition of BACE2 enzymatic cleavage of the synthetic substrate.

TABLE 2

Biological Data for Examples 1-28

| Example Number | IUPAC Name | BACE1 Cell-free Assay IC$_{50}$ (μM)[a] | sAPPβ Whole-Cell Assay IC$_{50}$ (nM)[a] |
|---|---|---|---|
| 1 | (4aR,6R,8aS)-8a-(2,4-Difluorophenyl)-6-(5-fluoro-1-methyl-1H-pyrazol-3-yl)-4,4a,5,6,8,8a-hexahydropyrano[3,4-d][1,3]thiazin-2-amine | 0.0837[b] | 3.78[b] |
| 2 | (4aR,6R,8aS)-8a-(2,4-Difluorophenyl)-6-(5-fluoropyridin-2-yl)-4,4a,5,6,8,8a-hexahydropyrano[3,4-d][1,3]thiazin-2-amine | 0.233[b] | 18.2[b] |
| 3 | 5-[(4aR,6R,8aS)-2-Amino-8a-(2,4-difluorophenyl)-4,4a,5,6,8,8a-hexahydropyrano[3,4-d][1,3]thiazin-6-yl]-1-methylpyridin-2(1H)-one | 0.119 | 7.43[b] |
| 4 | (4aR,6R,8aS)-8a-(2,4-Difluorophenyl)-6-(imidazo[1,2-a]pyrimidin-2-yl)-4,4a,5,6,8,8a-hexahydropyrano[3,4-d][1,3]thiazin-2-amine, hydrochloride salt | 1.84 | 66.2 |
| 5 | (4aR,6R,8aS)-8a-(2,4-Difluorophenyl)-6-[1-(2,2,2-trifluoroethyl)-1H-pyrazol-4-yl]-4,4a,5,6,8,8a-hexahydropyrano[3,4-d][1,3]thiazin-2-amine | 0.0728 | 13.3 |
| 6 | (4aR,6R,8aS)-8a-(2,4-Difluorophenyl)-6-(5-methyl-1,2,4-oxadiazol-3-yl)-4,4a,5,6,8,8a-hexahydropyrano[3,4-d][1,3]thiazin-2-amine | 0.341[b] | 41.5[b] |
| 7 | rel-(4aR,6R,8aS)-8a-(2,4-Difluorophenyl)-6-(6-methylpyridin-3-yl)-4,4a,5,6,8,8a-hexahydropyrano[3,4-d][1,3]thiazin-2-amine, hydrochloride salt | 0.182 | 6.7 |
| 8 | (4aR,6R,8aS)-8a-(2,4-Difluorophenyl)-6-(4-fluoro-1-methyl-1H-pyrazol-3-yl)-4,4a,5,6,8,8a-hexahydropyrano[3,4-d][1,3]thiazin-2-amine, hydrochloride salt | 0.162[b] | 26.4[b] |
| 9 | (4R,4aR,6R,8aS)-8a-(2,4-Difluorophenyl)-4-methyl-6-(3-methyl-1,2-oxazol-5-yl)-4,4a,5,6,8,8a-hexahydropyrano[3,4-d][1,3]thiazin-2-amine | 0.0759[b] | 5.28[b] |
| 10 | (4aR,6R,8aS)-8a-(2,4-Difluorophenyl)-6-([1,3]oxazolo[4,5-c]pyridin-2-yl)-4,4a,5,6,8,8a-hexahydropyrano[3,4-d][1,3]thiazin-2-amine | 0.24 | 21.2 |
| 11 | (4aR,6R,8aS)-8a-(2,4-Difluorophenyl)-6-(5-methoxypyrimidin-2-yl)-4,4a,5,6,8,8a-hexahydropyrano[3,4-d][1,3]thiazin-2-amine, trifluoroacetate salt | 0.343 | 29.1 |

TABLE 2-continued

Biological Data for Examples 1-28

| Example Number | IUPAC Name | BACE1 Cell-free Assay IC$_{50}$ (μM)[a] | sAPPβ Whole-Cell Assay IC$_{50}$ (nM)[a] |
|---|---|---|---|
| 12 | (4aR,6R,8aS)-8a-(2,4-Difluorophenyl)-6-(2-methyl-2H-1,2,3-triazol-4-yl)-4,4a,5,6,8,8a-hexahydropyrano[3,4-d][1,3]thiazin-2-amine, hydrochloride salt | 0.466 | 41.3 |
| 13 | (4S,4aR,6R,8aS)-8a-(2,4-Difluorophenyl)-4-(fluoromethyl)-6-(3-methyl-1,2-oxazol-5-yl)-4,4a,5,6,8,8a-hexahydropyrano[3,4-d][1,3]thiazin-2-amine | 0.0548[b] | 13.1[b] |
| 14 | (4aR,6R,8aS)-6-[4-(Difluoromethyl)-1,3-oxazol-2-yl]-8a-(2,4-difluorophenyl)-4,4a,5,6,8,8a-hexahydropyrano[3,4-d][1,3]thiazin-2-amine | 0.231[b] | 20.8[b] |
| 15 | (4aR,6R,8aS)-8a-(2,4-Difluorophenyl)-6-[1-(²H$_3$)methyl-1H-pyrazol-4-yl]-4,4a,5,6,8,8a-hexahydropyrano[3,4-d][1,3]thiazin-2-amine | 0.0398 | 4.37[b] |
| 16 | (4R,4aR,6R,8aS)-8a-(2,4-Difluorophenyl)-4-methyl-6-(1-methyl-1H-pyrazol-4-yl)-4,4a,5,6,8,8a-hexahydropyrano[3,4-d][1,3]thiazin-2-amine | 0.0246[b] | 2.84[b] |
| 17 | (4aR,6R,8aS)-8a-(2,4-Difluorophenyl)-6-(2-methylpyrimidin-5-yl)-4,4a,5,6,8,8a-hexahydropyrano[3,4-d][1,3]thiazin-2-amine | 1.40[b] | 60.3[b] |
| 18 | (4aR,6R,8aS)-8a-(2,4-Difluorophenyl)-6-(1-methyl-1H-1,2,3-triazol-4-yl)-4,4a,5,6,8,8a-hexahydropyrano[3,4-d][1,3]thiazin-2-amine | 0.877[b] | 25.2[b] |
| 19 | 2-[(4aR,6R,8aS)-2-Amino-8a-(2,4-difluorophenyl)-4,4a,5,6,8,8a-hexahydropyrano[3,4-d][1,3]thiazin-6-yl]-1,3-oxazole-4-carbonitrile | 0.555[b] | 73.2[b] |
| 20 | (4aR,6R,8aS)-8a-(2,4-Difluorophenyl)-6-(5-methylpyrazin-2-yl)-4,4a,5,6,8,8a-hexahydropyrano[3,4-d][1,3]thiazin-2-amine | 0.389 | 20.2 |
| C89 | (4aS,6S,8aR)-8a-(2,4-Difluorophenyl)-6-(5-methylpyrazin-2-yl)-4,4a,5,6,8,8a-hexahydropyrano[3,4-d][1,3]thiazin-2-amine | 36.2 | 1,360 |
| 21 | (4aR,6R,8aS)-8a-(2,4-Difluorophenyl)-6-(5-ethoxy-1-methyl-1H-pyrazol-3-yl)-4,4a,5,6,8,8a-hexahydropyrano[3,4-d][1,3]thiazin-2-amine, trifluoroacetate salt | 5.4 | 123[b] |
| 22 | (4S,4aR,6R,8aS)-8a-(2,4-Difluorophenyl)-4-(fluoromethyl)-6-(1-methyl-1H-pyrazol-4-yl)-4,4a,5,6,8,8a-hexahydropyrano[3,4-d][1,3]thiazin-2-amine, hydrochloride salt | 0.054[b] | 6.28[b] |
| 23 | (4aR,6R,8aS)-8a-(2,4-Difluorophenyl)-6-([1,3]oxazolo[5,4-c]pyridin-2-yl)-4,4a,5,6,8,8a-hexahydropyrano[3,4-d][1,3]thiazin-2-amine | 5.02 | 40.8 |
| 24 | (4aR,6R,8aS)-8a-(2,4-Difluorophenyl)-6-(pyrimidin-5-yl)-4,4a,5,6,8,8a-hexahydropyrano[3,4-d][1,3]thiazin-2-amine | 1.55 | 141 |
| 25 | (4aR,6R,8aS)-8a-(2,4-Difluorophenyl)-6-(2-methoxypyridin-4-yl)-4,4a,5,6,8,8a-hexahydropyrano[3,4-d][1,3]thiazin-2-amine | 0.384 | 40.5[b] |
| 26 | (4aR,6R,8aS)-8a-(2,4-Difluorophenyl)-6-(5-methoxypyridin-3-yl)-4,4a,5,6,8,8a-hexahydropyrano[3,4-d][1,3]thiazin-2-amine | 1.25 | 62.6 |
| 27 | (4aR,6R,8aS)-8a-(2,4-Difluorophenyl)-6-(2-methylpyridin-4-yl)-4,4a,5,6,8,8a-hexahydropyrano[3,4-d][1,3]thiazin-2-amine | 0.221 | 4.73[b] |
| 28 | (4aR,6R,8aS)-8a-(2,4-Difluorophenyl)-6-(imidazo[1,2-a]pyridin-6-yl)-4,4a,5,6,8,8a-hexahydropyrano[3,4-d][1,3]thiazin-2-amine | 2.15 | 15.5[b] |
| 29 | (4aR,6R,8aS)-8a-(2,4-difluorophenyl)-6-(5-fluoropyridin-3-yl)-4,4a,5,6,8,8a-hexahydropyrano[3,4-d][1,3]thiazin-2-amine | 0.0379 | 2.70 |

[a]Reported IC$_{50}$ values are the average of 2 determinations, unless otherwise indicated.
[b]Reported IC$_{50}$ values are the geometric mean of 3-9 determinations.

We claim:
1. A method of treating Alzheimer's disease in a patient, the method comprising administering a therapeutically effective amount of a-compound of Formula I

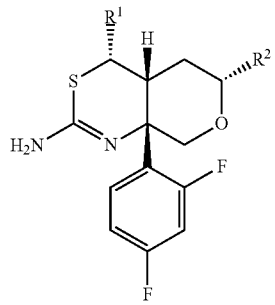

wherein
R$^1$ is hydrogen or methyl, wherein said methyl is optionally substituted with one to three fluoro;
R$^2$ is a 5- to 10-membered heteroaryl, having one to four heteroatoms independently selected from N, O or S, wherein at least one of the heteroatoms is N and wherein said N is optionally substituted with R$^4$; and wherein said 5- to 10-membered heteroaryl is optionally substituted on carbon with one to three R$^3$;
R$^3$ at each occurrence is independently selected from the group consisting of halogen, hydroxy, cyano, C$_{1-6}$alkyl, C$_{1-6}$alkoxy, C$_{1-6}$alkoxy-C$_{1-6}$alkyl, C$_{3-6}$cycloalkoxy, C$_{3-6}$cycloalkoxy-(CR$^{5a}$R$^{5b}$)$_m$—, C$_{3-6}$cycloalkyl-(CR$^{5a}$R$^{5b}$)$_n$—O—, —(CR$^{5a}$R$^{5b}$)$_m$—C$_{3-6}$cycloalkyl or —(CR$^{5a}$R$^{5b}$)$_m$-(4- to 6-membered heterocycloalkyl); wherein said C$_{1-6}$alkyl, C$_{1-6}$alkoxy or C$_{1-6}$alkoxy-C$_{1-6}$alkyl are each optionally substituted with one to three fluoro and wherein said C$_{3-6}$cycloalkyl, C$_{3-6}$cycloalkoxy and (4- to 6-membered heterocycloalkyl) moieties are optionally substituted with one to three substituents independently selected from the group consisting of fluoro, methyl, fluoromethyl, difluoromethyl or trifluoromethyl;
R$^4$ is hydrogen, C$_{1-6}$alkyl, —(CR$^{5a}$R$^{5b}$)$_m$—C$_{3-6}$cycloalkyl or —(CR$^{5a}$R$^{5b}$)$_m$-(4- to 6-membered heterocycloalkyl); wherein said C$_{1-6}$alkyl, C$_{3-6}$cycloalkyl and -(4- to 6-membered heterocycloalkyl) moieties are each optionally substituted with one to three substituents independently selected from fluoro, methyl, trifluoromethyl, methoxy or trifluoromethoxy;
R$^{5a}$ and R$^{5b}$ are independently hydrogen, methyl, fluoromethyl, difluoromethyl, trifluoromethyl or methoxy;
m at each occurrence is independently 0, 1 or 2; and
n is 1, 2 or 3;
or a tautomer thereof or a pharmaceutically acceptable salt of said compound or tautomer;
to a patient in need of treatment thereof.
2. The method of claim 1 wherein
R$^2$ is a 5-membered heteroaryl selected from the group consisting of pyrazolyl, oxazolyl, isoxazolyl, triazolyl and oxadiazolyl; each optionally substituted on carbon with one to two R$^3$; and wherein said pyrazolyl and triazolyl
are substituted on N with R$^4$;
R$^3$ at each occurrence is independently selected from the group consisting of halogen, cyano, C$_{1-6}$alkyl, and C$_{1-6}$alkoxy; wherein said alkyl is optionally substituted with one to three fluoro; and R$^4$ is hydrogen, methyl or trifluoroethyl;
or a tautomer thereof or a pharmaceutically acceptable salt of said compound or tautomer.
3. The method of claim 2 wherein R$^2$ is selected from the group consisting of

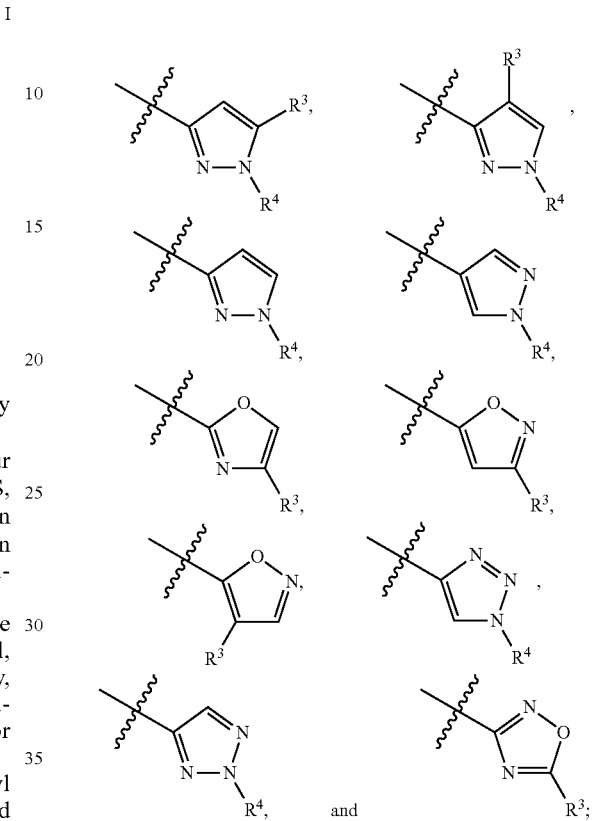

R$^3$ is selected from the group consisting of fluoro, cyano, methyl, fluoromethyl, difluoromethyl, trifluoromethyl, methoxy and ethoxy; and
R$^4$ is methyl or trifluoroethyl;
or a tautomer thereof or a pharmaceutically acceptable salt of said compound or tautomer.
4. The method according to claim 3 wherein R$^1$ is hydrogen;
or a tautomer thereof or a pharmaceutically acceptable salt of said compound or tautomer.
5. The method according to claim 3 wherein R$^1$ is methyl or fluoromethyl;
or a tautomer thereof or a pharmaceutically acceptable salt of said compound or tautomer.
6. The method according to claim 5 wherein
R$^2$ is

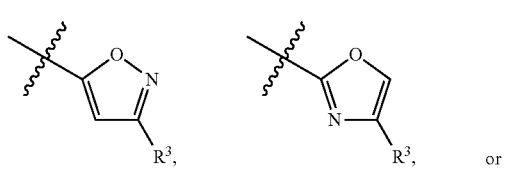

or

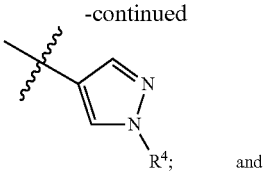

R³ is methyl;
or a tautomer thereof or a pharmaceutically acceptable salt of said compound or tautomer.

7. The method according to claim 4 wherein the compound is selected from the group consisting of
(4aR,6R,8aS)-8a-(2,4-Difluorophenyl)-6-(5-fluoro-1-methyl-1H-pyrazol-3-yl)-4,4a,5,6,8,8a-hexahydropyrano[3,4-d][1,3]thiazin-2-amine;
(4aR,6R,8aS)-8a-(2,4-Difluorophenyl)-6-[1-(2,2,2-trifluoroethyl)-1H-pyrazol-4-yl]-4,4a,5,6,8,8a-hexahydropyrano[3,4-d][1,3]thiazin-2-amine;
(4aR,6R,8aS)-8a-(2,4-Difluorophenyl)-6-(5-methyl-1,2,4-oxadiazol-3-yl)-4,4a,5,6,8,8a-hexahydropyrano[3,4-d][1,3]thiazin-2-amine;
(4aR,6R,8aS)-8a-(2,4-Difluorophenyl)-6-(4-fluoro-1-methyl-1H-pyrazol-3-yl)-4,4a,5,6,8,8a-hexahydropyrano[3,4-d][1,3]thiazin-2-amine;
(4aR,6R,8aS)-8a-(2,4-Difluorophenyl)-6-(2-methyl-2H-1,2,3-triazol-4-yl)-4,4a,5,6,8,8a-hexahydropyrano[3,4-d][1,3]thiazin-2-amine;
(4aR,6R,8aS)-6-[4-(Difluoromethyl)-1,3-oxazol-2-yl]-8a-(2,4-difluorophenyl)-4,4a,5,6,8,8a-hexahydropyrano[3,4-d][1,3]thiazin-2-amine;
(4aR,6R,8aS)-8a-(2,4-Difluorophenyl)-6-[1-(²H₃)methyl-1H-pyrazol-4-yl]-4,4a,5,6,8,8a-hexahydropyrano[3,4-d][1,3]thiazin-2-amine;
(4aR,6R,8aS)-8a-(2,4-Difluorophenyl)-6-(1-methyl-1H-1,2,3-triazol-4-yl)-4,4a,5,6,8,8a-hexahydropyrano[3,4-d][1,3]thiazin-2-amine;
2-[(4aR,6R,8aS)-2-Amino-8a-(2,4-difluorophenyl)-4,4a,5,6,8,8a-hexahydropyrano[3,4-d][1,3]thiazin-6-yl]-1,3-oxazole-4-carbonitrile;
(4aR,6R,8aS)-8a-(2,4-Difluorophenyl)-6-(5-methyl pyrazin-2-yl)-4,4a,5,6,8,8a-hexahydropyrano[3,4-d][1,3]thiazin-2-amine;
(4aS,6S,8aR)-8a-(2,4-Difluorophenyl)-6-(5-methyl pyrazin-2-yl)-4,4a,5,6,8,8a-hexahydropyrano[3,4-d][1,3]thiazin-2-amine; and
(4aR,6R,8aS)-8a-(2,4-Difluorophenyl)-6-(5-ethoxy-1-methyl-1H-pyrazol-3-yl)-4,4a,5,6,8,8a-hexahydropyrano[3,4-d][1,3]thiazin-2-amine;
or a tautomer thereof or a pharmaceutically acceptable salt of said compound or tautomer.

8. The method according to claim 5 wherein the compound is selected from the group consisting of
(4S,4aR,6R,8aS)-8a-(2,4-Difluorophenyl)-4-(fluoromethyl)-6-(3-methyl-1,2-oxazol-5-yl)-4,4a,5,6,8,8a-hexahydropyrano[3,4-d][1,3]thiazin-2-amine;
(4R,4aR,6R,8aS)-8a-(2,4-Difluorophenyl)-4-methyl-6-(3-methyl-1,2-oxazol-5-yl)-4,4a,5,6,8,8a-hexahydropyrano[3,4-d][1,3]thiazin-2-amine;
(4R,4aR,6R,8aS)-8a-(2,4-Difluorophenyl)-4-methyl-6-(1-methyl-1H-pyrazol-4-yl)-4,4a,5,6,8,8a-hexahydropyrano[3,4-d][1,3]thiazin-2-amine;
(4S,4aR,6R,8aS)-8a-(2,4-Difluorophenyl)-4-(fluoromethyl)-6-(1-methyl-1H-pyrazol-4-yl)-4,4a,5,6,8,8a-hexahydropyrano[3,4-d][1,3]thiazin-2-amine;
or a tautomer thereof or a pharmaceutically acceptable salt of said compound or tautomer.

9. The method of claim 1 wherein
R² is a 6-membered heteroaryl selected from the group consisting of pyridinyl, pyridonyl, pyrimidinyl and pyrazinyl; each optionally substituted on carbon with one to two R³; and wherein said pyridonyl is substituted on N with R⁴;
R³ at each occurrence is independently selected from the group consisting of halogen, cyano, $C_{1-6}$alkyl, and $C_{1-6}$alkoxy; wherein said alkyl is optionally substituted with one to three fluoro; and
R⁴ is hydrogen, methyl or trifluoroethyl;
or a tautomer thereof or a pharmaceutically acceptable salt of said compound or tautomer.

10. The method of claim 9 wherein
R² is selected from the group consisting of

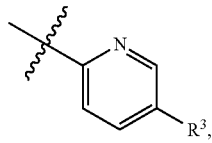 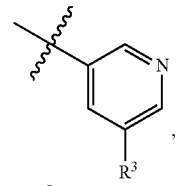

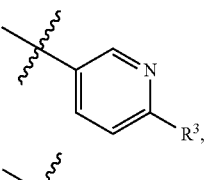 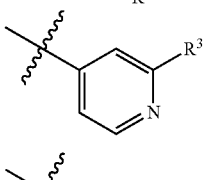

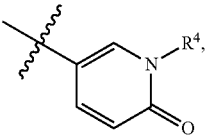 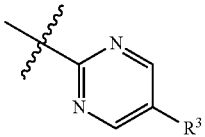

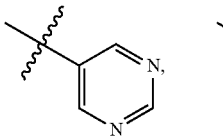 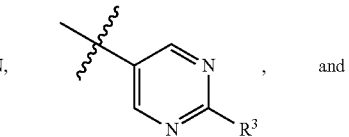 and

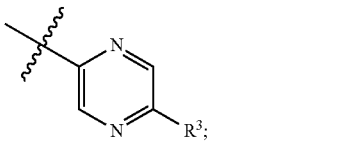

R³ is selected from fluoro, methyl, and methoxy;
R⁴ is methyl;
or a tautomer thereof or pharmaceutically acceptable salt of said compound or tautomer.

11. The method of claim 10 wherein
R¹ is hydrogen;
or a tautomer thereof or a pharmaceutically acceptable salt of said compound
or tautomer.

12. The method of claim 11 wherein the compound is selected from the group consisting of
(4aR,6R,8aS)-8a-(2,4-Difluorophenyl)-6-(5-fluoropyridin-2-yl)-4,4a,5,6,8,8a-hexahydropyrano[3,4-d][1,3]thiazin-2-amine;
5-[(4aR,6R,8aS)-2-Amino-8a-(2,4-difluorophenyl)-4,4a,5,6,8,8a-hexahydropyrano[3,4-d][1,3]thiazin-6-yl]-1-methylpyridin-2(1H)-one;
rel-(4aR,6R,8aS)-8a-(2,4-Difluorophenyl)-6-(6-methylpyridin-3-yl)-4,4a,5,6,8,8a-hexahydropyrano[3,4-d][1,3]thiazin-2-amine;

(4aR,6R,8aS)-8a-(2,4-Difluorophenyl)-6-(5-methoxypyrimidin-2-yl)-4,4a,5,6,8,8a-hexahydropyrano[3,4-d][1,3]thiazin-2-amine;

(4aR,6R,8aS)-8a-(2,4-Difluorophenyl)-6-(2-methylpyrimidin-5-yl)-4,4a,5,6,8,8a-hexahydropyrano[3,4-d][1,3]thiazin-2-amine;

(4aR,6R,8aS)-8a-(2,4-Difluorophenyl)-6-(pyrimidin-5-yl)-4,4a,5,6,8,8a-hexahydropyrano[3,4-d][1,3]thiazin-2-amine;

(4aR,6R,8aS)-8a-(2,4-Difluorophenyl)-6-(2-methoxypyridin-4-yl)-4,4a,5,6,8,8a-hexahydropyrano[3,4-d][1,3]thiazin-2-amine;

(4aR,6R,8aS)-8a-(2,4-Difluorophenyl)-6-(5-methoxypyridin-3-yl)-4,4a,5,6,8,8a-hexahydropyrano[3,4-d][1,3]thiazin-2-amine;

(4aR,6R,8aS)-8a-(2,4-Difluorophenyl)-6-(2-methylpyridin-4-yl)-4,4a,5,6,8,8a-hexahydropyrano[3,4-d][1,3]thiazin-2-amine; and (4aR,6R,8aS)-8a-(2,4-Difluorophenyl)-6-(5-fluoropyridin-3-yl)-4,4a,5,6,8,8a-hexahydropyrano[3,4-d][1,3]thiazin-2-amine;

or a tautomer thereof or a pharmaceutically acceptable salt of said compound or tautomer.

13. The method of claim 1 wherein $R^1$ is hydrogen; and $R^2$ is selected from the group consisting of oxazolopyridinyl, imidazopyridinyl and imidazopyrimidinyl;

or a tautomer thereof or a pharmaceutically acceptable salt of said compound or tautomer.

14. The method of claim 13 wherein $R^2$ is selected from the group consisting of

[1,3]oxazolo[4,5-c]pyridinyl, [1,3]oxazolo[5,4-c]pyridinyl, imidazo[1,2-a]pyridinyl and imidazo[1,2-a]pyrimidinyl;

or a tautomer thereof or a pharmaceutically acceptable salt of said compound or tautomer.

15. The method of claim 14 wherein the compound is selected from the group consisting of (4aR,6R,8aS)-8a-(2,4-Difluorophenyl)-6-(imidazo[1,2-a]pyrimidin-2-yl)-4,4a,5,6,8,8a-hexahydropyrano[3,4-d][1,3]thiazin-2-amine;

(4aR,6R,8aS)-8a-(2,4-Difluorophenyl)-6-([1,3]oxazolo[4,5-c]pyridin-2-yl)-4,4a,5,6,8,8a-hexahydropyrano[3,4-d][1,3]thiazin-2-amine;

(4aR,6R,8aS)-8a-(2,4-Difluorophenyl)-6-([1,3]oxazolo[5,4-c]pyridin-2-yl)-4,4a,5,6,8,8a-hexahydropyrano[3,4-d][1,3]thiazin-2-amine; and (4aR,6R,8aS)-8a-(2,4-Difluorophenyl)-6-(imidazo[1,2-a]pyridin-6-yl)-4,4a,5,6,8,8a-hexahydropyrano[3,4-d][1,3]thiazin-2-amine;

or a tautomer thereof or a pharmaceutically acceptable salt of said compound or tautomer.

16. A pharmaceutical composition comprising a therapeutically effective amount of the compound (4S,4aR,6R,8aS)-8a-(2,4-Difluorophenyl)-4-(fluoromethyl)-6-(3-methyl-1,2-oxazol-5-yl)-4,4a,5,6,8,8a-hexahydropyrano[3,4-d][1,3]thiazin-2-amine; or a tautomer thereof or a pharmaceutically acceptable salt of said compound or tautomer, and a pharmaceutically acceptable vehicle, diluent or carrier.

17. A method of treating Alzheimer's disease in a patient, the method comprising administering a therapeutically effective amount of the compound (4S,4aR,6R,8aS)-8a-(2,4-Difluorophenyl)-4-(fluoromethyl)-6-(3-methyl-1,2-oxazol-5-yl)-4,4a,5,6,8,8a-hexahydropyrano[3,4-d][1,3]thiazin-2-amine; or a tautomer thereof or a pharmaceutically acceptable salt of said compound or tautomer, to a patient in need of treatment thereof.

* * * * *